(12) United States Patent
Tan et al.

(10) Patent No.: US 12,167,682 B2
(45) Date of Patent: Dec. 10, 2024

(54) MULTI-COMPONENT COMPOSITION

(71) Applicant: Guangzhou Chinaray Optoelectronic Materials Ltd., Guangdong (CN)

(72) Inventors: Jiahui Tan, Guangdong (CN); Yusheng Chen, Guangdong (CN); Junyou Pan, Guangdong (CN)

(73) Assignee: Guangzhou Chinaray Optoelectronic Materials Ltd., Guangzhou (CN)

( * ) Notice: Subject to any disclaimer, the term of this patent is extended or adjusted under 35 U.S.C. 154(b) by 250 days.

(21) Appl. No.: 17/638,867

(22) PCT Filed: Sep. 15, 2020

(86) PCT No.: PCT/CN2020/115414
§ 371 (c)(1),
(2) Date: Feb. 28, 2022

(87) PCT Pub. No.: WO2021/052339
PCT Pub. Date: Mar. 25, 2021

(65) Prior Publication Data
US 2023/0006142 A1    Jan. 5, 2023

(30) Foreign Application Priority Data
Sep. 20, 2019    (CN) .......................... 201910889812.9

(51) Int. Cl.
*C07C 13/72* (2006.01)
*C07D 251/24* (2006.01)
(Continued)

(52) U.S. Cl.
CPC ........... *H10K 85/624* (2023.02); *C07C 13/72* (2013.01); *C07D 251/24* (2013.01); *C09K 11/06* (2013.01);
(Continued)

(58) Field of Classification Search
CPC ............... H10K 85/624; H10K 85/626; H10K 85/654; H10K 50/15; H10K 50/16;
(Continued)

(56) References Cited

FOREIGN PATENT DOCUMENTS

| CN | 106103428 | 11/2016 |
|---|---|---|
| CN | 109638171 | 4/2019 |

(Continued)

OTHER PUBLICATIONS

International Search Report and the Written Opinion Dated Dec. 16, 2020 From the International Searching Authority Re. Application No. PCT/CN2020/115414 and Its Translation Into English (20 Pages).

(Continued)

*Primary Examiner* — Mark Kopec
*Assistant Examiner* — Jaison P Thomas

(57) ABSTRACT

A composition for manufacturing an organic electronic device includes at least three organic functional materials H1, H2, and H3, and at least one organic solvent. The organic functional materials H1 and H2 can form a type II semiconductor heterojunction structure. A LUMO value of the organic functional material H3 is greater than or equal to that of the organic functional materials H1 and H2, and a HOMO value thereof is less than or equal to that of the organic functional materials H1 and H2.

20 Claims, 1 Drawing Sheet

(51) Int. Cl.
  *C09K 11/06* (2006.01)
  *H10K 85/60* (2023.01)
  *H10K 50/15* (2023.01)
  *H10K 50/16* (2023.01)
  *H10K 101/00* (2023.01)
  *H10K 101/30* (2023.01)

(52) U.S. Cl.
  CPC ......... *H10K 85/626* (2023.02); *H10K 85/654* (2023.02); *C07C 2603/97* (2017.05); *C09K 2211/1007* (2013.01); *C09K 2211/1011* (2013.01); *C09K 2211/1018* (2013.01); *H10K 50/15* (2023.02); *H10K 50/16* (2023.02); *H10K 2101/30* (2023.02); *H10K 2101/90* (2023.02)

(58) Field of Classification Search
  CPC ........... H10K 2101/30; H10K 2101/90; H10K 85/60; H10K 85/615; H10K 85/6572; H10K 50/11; H10K 85/342; H10K 2101/10; H10K 2101/40; C07C 13/72; C07C 2603/97; C07C 2603/40; C07C 15/14; C07C 15/38; C07C 2603/18; C07C 2603/54; C07C 15/20; C07C 15/27; C07D 251/24; C09K 11/06; C09K 2211/1007; C09K 2211/1011; C09K 2211/1018; Y02E 10/549; C09D 11/30
  See application file for complete search history.

(56) References Cited

FOREIGN PATENT DOCUMENTS

| | | | |
|---|---|---|---|
| CN | 109659448 | 4/2019 | |
| WO | WO-2018095390 A1 * | 5/2018 | ........... C07D 209/86 |
| WO | WO 2019/120085 | 6/2019 | |
| WO | WO 2019/120177 | 6/2019 | |
| WO | WO-2019120263 A1 * | 6/2019 | ........... C07C 211/54 |

OTHER PUBLICATIONS

Notification of Office Action and Search Report Dated Mar. 7, 2023 From the State Intellectual Property Office of the People's Republic of China Re. Application No. 202080056366.4 and Its Translation Into English. (17 Pages).

* cited by examiner

MULTI-COMPONENT COMPOSITION

RELATED APPLICATIONS

This application is a National Phase of PCT Patent Application No. PCT/CN2020/115414 having International filing date of Sep. 15, 2020, which claims the benefit of priority of Chinese Patent Application No. 201910889812.9 filed on Sep. 20, 2019. The contents of the above applications are all incorporated by reference as if fully set forth herein in their entirety.

FIELD AND BACKGROUND OF THE INVENTION

The present disclosure relates to the field of organic electroluminescent device materials, and in particular to a multi-component composition and an application thereof to an organic electronic device, particularly to an organic light-emitting diode.

With the characteristics properties of light weight, active emitting, wide viewing angle, high contrast, high emitting efficiency, low energy consumption, easy preparation for flexible and large-sized panels, etc., organic light-emitting diodes (OLEDs) are regarded as the most promising next-generation display technology in the industry. In order to improve luminous efficiency of the organic light-emitting diodes and promote processes of large-scale industrialization of the organic light-emitting diodes, at present, the luminescence properties and lifetime of the organic light-emitting diodes is a key issue that needs to be solved urgently.

The host material is the key element for obtaining high-performance organic light-emitting diodes. At present, OLED light-emitting devices are generally manufactured by using single-host or co-host materials with light-emitting material. However, the single-host materials will cause different carrier transmission rates, resulting in serious roll-off of device efficiency at high brightness, thereby causing the devices to have shortened lifespan. Use of the co-host materials can alleviate some of the problems caused by the single-host materials, especially matching with appropriate materials, and selected co-host materials can effectively form an exciplex, thereby greatly improving the luminous efficiency and lifetime of the devices. (See Kim et al. in Adv. Func. Mater. 2013) However, in prior art, the co-host materials are generally used in vacuum evaporation devices, and the lifetime thereof still needs to be further improved. Vacuum evaporation processes have high cost and high processing requirements, such as requiring fine masks, etc., thus limiting applications of the organic light-emitting diodes as large-area and low-cost display and lighting devices. In contrast, solution processing processes such as inkjet printing and roll-to-roll have become a very promising technique for preparing organic optoelectronic devices, especially organic light-emitting diode displays, due to their outstanding advantages such as no need for fine masks, room temperature processes, high material utilization, and good scalability. In order to realize the processes, suitable printing inks and materials are the key. At present, regarding inkjet printing process, there are still no effective solutions to problems of providing efficient multi-host material system, film drying process, and ink printability.

Therefore, new materials suitable for printing processes, especially host material systems, need to be developed.

SUMMARY OF INVENTION

In view of deficiencies of the prior art mentioned above, a purpose of the present disclosure is to provide a multi-component composition and an application thereof to provide a new material suitable for printing processes, thereby improving efficiency and lifetime of printed devices.

Technical solutions of the present disclosure are as follows:

a composition, which includes at least three organic functional materials H1, H2, and H3, and at least one organic solvent; wherein, 1) H1 and H2 form a type II semiconductor heterojunction structure, and min (LUMO(H1)−HOMO(H2), LUMO(H2)−HOMO(H1)) ≤min($E_T$(H1), $E_T$(H2))+0.1 eV; and 2) LUMO(H3) ≥max(LUMO(H1), LUMO(H2)) and HOMO(H3)≤min (HOMO(H1), HOMO(H2)); wherein, LUMO(H1) represents a lowest unoccupied molecular orbital energy level of H1, HOMO(H1) represents a highest occupied molecular orbital energy level of H1, and $E_T$(H1) represents a triplet state energy level of H1; LUMO(H2) represents a lowest unoccupied molecular orbital energy level of H2, HOMO(H2) represents a highest occupied molecular orbital energy level of H2, and $E_T$(H2) represents a triplet state energy level of H2; and LUMO(H3) represents a lowest unoccupied molecular orbital energy level of H3, and HOMO(H3) represents a highest occupied molecular orbital energy level of H3.

The present disclosure further relates to an organic electronic device, which includes a functional layer manufactured by the composition mentioned above. Particularly, the functional layer is a light-emitting layer.

Beneficial effect: the composition of the present disclosure includes at least three organic functional materials H1, H2, and H3 and at least one organic solvent. By restricting relationships of energy levels among H1, H2 and H3, it has better printing performance and film-forming performance when used as a host material, thereby realizing high-performance organic electronic devices by solution processing, especially printing processes. In particular, the lifetime of the device is improved to a certain extent, thereby providing a low-cost and high-efficiency manufacturing technical solution.

DESCRIPTION OF SPECIFIC EMBODIMENTS OF THE INVENTION

Figure 1:
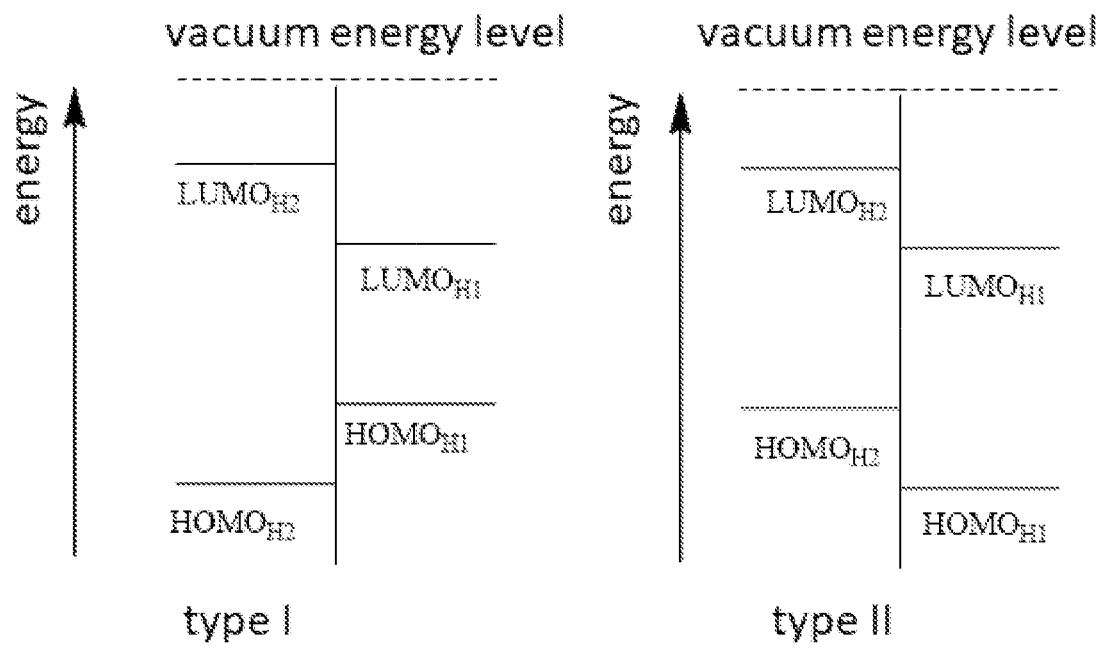
FIG. 1 is a schematic diagram of energy level relationships of a type I semiconductor heterojunction and a type II semiconductor heterojunction.
Figure 2:
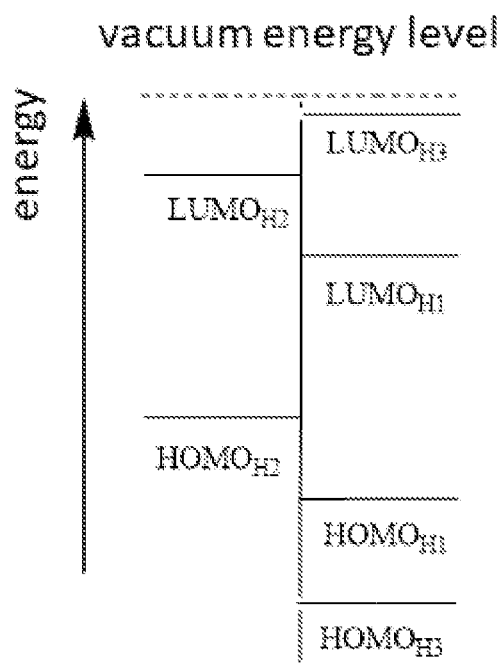
FIG. 2 is a schematic diagram of an energy level relationship of LUMO and HOMO between organic functional materials H1, H2, and H3 in a composition.

The present disclosure provides a multi-component composition and an application thereof to an organic electronic device. In order to make the purpose, technical solutions, and effects of the present disclosure clearer and more definite, the following further describes the present disclosure in detail. It should be understood that the specific embodiments described herein are only used to explain the disclosure, and are not used to limit the disclosure.

In the present disclosure, "substituted" means that a hydrogen atom in the substituted group is replaced by a substituent.

In the present disclosure, "number of ring atoms" means a number of atoms that are bonded to each other and constitute a ring of a structural compound (such as a monocyclic compound, a fused ring compound, a cross-linked compound, a carbocyclic compound, and a heterocyclic compound). When the ring is substituted by a substituent, atoms of the substituent are not included in the ring atoms. The same applies to the "number of ring atoms" described below unless otherwise specified. For example, the number of ring atoms of a benzene ring is 6, the number of ring atoms of a naphthalene ring is 10, and the number of ring atoms of a thienyl group is 5.

An aromatic group refers to a hydrocarbon group containing at least one aromatic ring. A heteroaromatic group refers to an aromatic hydrocarbon group containing at least one heteroatom. The heteroatom is preferably selected from Si, N, P, O, S, and/or Ge, and more preferably from Si, N, P, O, and/or S. A fused cyclic aromatic group means that an aromatic group has two or more rings, in which two carbon atoms are shared by two adjacent rings, that is, a fused ring. A fused heterocyclic aromatic group refers to a fused cyclic aromatic hydrocarbon group containing at least one heteroatom. For the objective of the present disclosure, an aromatic group or heteroaromatic group includes not only aromatic ring systems, but also non-aromatic ring systems. Therefore, for the objective of the present disclosure, similarly, systems, such as pyridine, thiophene, pyrrole, pyrazole, triazole, imidazole, oxazole, oxadiazole, thiazole, tetrazole, pyrazine, pyridazine, pyrimidine, triazine, and carbene, are also considered as an aromatic group or a heterocyclic aromatic group. For the objective of the present disclosure, fused cyclic aromatic groups or fused cyclic heteroaromatic groups include not only systems of aromatic groups or heteroaromatic groups, but also groups in which a plurality of aromatic groups or heteroaromatic groups may also be interrupted by short non-aromatic units (less than 10% of non-hydrogen atoms, preferably less than 5% of non-hydrogen atoms, such as C, N, or O). Therefore, systems such as 9,9'-spirobifluorene, 9,9-diarylfluorene, triarylamine, diarylether, etc., are also considered to be fused cyclic aromatic systems for the objective of the present disclosure.

In the embodiments of the present disclosure, energy level structures of organic materials, triplet energy levels $E_T$, HOMO, and LUMO play a key role. These energy levels are described below.

HOMO and LUMO energy levels can be measured by photoelectric effects, such as XPS (X-ray Photoelectron Spectroscopy) and UPS (Ultraviolet Photoelectron Spectroscopy) or by Cyclic Voltammetry (hereinafter referred to as CV). Recently, quantum chemical methods, such as density functional theory (hereinafter referred to as DFT), have also become effective methods for calculating molecular orbital energy levels.

Triplet energy levels $E_{T1}$ of organic materials can be measured by low-temperature time-resolved luminescence spectroscopy, or by quantum simulation calculation (such as time-dependent DFT), such as by commercial software Gaussian 09W (Gaussian Inc.), and a specific simulation method can refer to WO2011141110 or is as described in the examples below.

It should be noted that absolute values of HOMO, LUMO, and $E_{T1}$ depend on a measurement or calculation method that is used, even for a same method but different evaluation methods, for example, onset and peak points on a CV curve can give different HOMO/LUMO values. Therefore, reasonably meaningful comparisons should be made using the same measurement method and the same evaluation method. In the description of the embodiments of the present disclosure, the values of HOMO, LUMO, and $E_{T1}$ are based on time-dependent DFT simulation, but do not affect application of other measurement or calculation methods.

In the present disclosure, (HOMO−1) is defined as a second highest occupied orbital energy level, (HOMO−2) is defined as a third highest occupied orbital energy level, and so on. (LUMO+1) is defined as a second lowest unoccupied orbital energy level, (LUMO+2) is defined as a third lowest unoccupied orbital energy level, and so on.

The present disclosure relates to a composition, which includes at least three organic functional materials H1, H2, and H3, and at least one organic solvent. Wherein, 1) H1 and H2 form a type II semiconductor heterojunction structure, and min(LUMO(H1)−HOMO(H2), LUMO(H2)−HOMO(H1))≤min($E_T$(H1), $E_T$(H2))+0.1 eV; and 2) LUMO(H3)≥max(LUMO(H1), LUMO(H2)) and HOMO(H3)≤min(HOMO(H1), HOMO(H2)); wherein, LUMO(H1) represents a lowest unoccupied molecular orbital energy level of H1, HOMO(H1) represents a highest occupied molecular orbital energy level of H1, and $E_T$(H1) represents a triplet state energy level of H1; LUMO(H2) represents a lowest unoccupied molecular orbital energy level of H2, HOMO(H2) represents a highest occupied molecular orbital energy level of H2, and $E_T$(H2) represents a triplet state energy level of H2; and LUMO(H3) represents a lowest unoccupied molecular orbital energy level of H3, and HOMO(H3) represents a highest occupied molecular orbital energy level of H3.

The organic functional materials H1 and H2 form the type II semiconductor heterojunction structure and an exciplex, which can make a composition thereof have better stability.

In an embodiment, in the composition, min(LUMO(H1)−HOMO(H2), LUMO(H2)−HOMO(H1))≤min($E_T$(H1), $E_T$(H2)).

In another embodiment, in the composition, min(LUMO(H1)−HOMO(H2), LUMO(H2)−HOMO(H1))≤min($E_T$(H1), $E_T$(H2))−0.1 eV.

In another embodiment, in the composition, min(LUMO(H1)−HOMO(H2), LUMO(H2)−HOMO(H1))≤min($E_T$(H1), $E_T$(H2))−0.2 eV.

In an embodiment, LUMO(H2)≥LUMO(H1) and HOMO(H2)≥HOMO(H1).

In an embodiment, LUMO(H2)−LUMO(H1)≥0.1 eV; further, LUMO(H2)−LUMO(H1)≥0.2 eV; and still further, LUMO(H2)−LUMO(H1)≥0.5 eV.

In an embodiment, HOMO(H2)−HOMO(H1)≥0.1 eV; further, HOMO(H2)−HOMO(H1)≥0.3 eV; and still further, HOMO(H2)−HOMO(H1)≥0.5 eV.

In an embodiment, LUMO(H3)−max(LUMO(H1), LUMO(H2))≥0.1 eV; and further, LUMO(H3)−max(LUMO(H1), LUMO(H2))≥0.2 eV.

In an embodiment, HOMO(H3)−min(HOMO(H1), HOMO(H2))≤0.1 eV; further, HOMO(H3)−min(HOMO(H1), HOMO(H2))≤0.3 eV; and still further, HOMO(H3)−min(HOMO(H1), HOMO(H2))≤0.5 eV.

In an embodiment, a viscosity at 25° C. of the composition ranges from 1 cPs to 100 cPs, and/or a surface tension at 25° C. thereof ranges from 19 dyne/cm to 50 dyne/cm. The composition so formulated would be particularly suitable for inkjet printing.

In an embodiment, the viscosity thereof at 25° C. ranges from 1 cPs to 50 cPs, further 1 cPs to 30 cPs, and still further 1.5 cps to 20 cps.

In an embodiment, the surface tension thereof ranges from 22 dyne/cm to 35 dyne/cm at 25° C., and preferably 25 dyne/cm to 33 dyne/cm at 25° C.

In an embodiment, in the three organic functional materials H1, H2, and H3 of the composition, at least one organic functional material has a molecular weight greater than or equal to 600 g/mol, particularly greater than or equal to 700 g/mol.

In an embodiment, in the three organic functional materials H1, H2, and H3 of the composition of the present disclosure, at least two organic functional materials have a molecular weight greater than or equal to 600 g/mol, particularly greater than or equal to 700 g/mol.

In an embodiment, in the composition of the present disclosure, a difference in molecular weights between any two of H1, H2, and H3 is greater than or equal to 50 g/mol, further greater than or equal to 70 g/mol, and particularly greater than or equal to 90 g/mol.

In an embodiment, in the composition of the present disclosure, a difference in sublimation temperatures between two of H1, H2, and H3 is greater than or equal to 30K, further greater than or equal to 40K, still further greater than or equal to 50K, and particularly greater than or equal to 60K.

Co-hosts in vapor deposition typed OLEDs preferably require that two host materials have similar chemical properties or physical properties, such as molecular weight and sublimation temperature. In the present disclosure, applicants find that multiple host materials with different properties in solution-processed OLEDs may improve film-forming performance, thereby improving performance of devices. The properties mentioned above, may also be others, such as glass transition temperature, different molecular volumes, etc., in addition to molecular weight and sublimation temperature. Thus, the following conditions can be substituted for the above conditions:
  a) a difference in glass transition temperatures between two of H1, H2, and H3 is greater than or equal to 20K, further greater than or equal to 30K, still further greater than or equal to 40K, and particularly greater than or equal to 45K.
  b) a difference in molecular volumes between two of H1, H2, and H3 is greater than or equal to 20%, further greater than or equal to 30%, still further greater than or equal to 40%, and particularly greater than or equal to 45%.

In an embodiment, in the composition of the present disclosure, solubilities of the three organic functional materials H1, H2, and H3 in the organic solvent are all greater than or equal to 0.5 wt %, and differences of solubilities between H1, H2, and H3 in the organic solvent are less than or equal to 0.2 wt %.

In an embodiment, in the composition, the solubilities of the three organic functional materials H1, H2, and H3 in the organic solvent are all greater than or equal to 0.5 wt %, further the solubility of at least one organic functional material in the organic solvent is greater than or equal to 1 wt %, still further the solubility of at least one organic functional material in the organic solvent is greater than or equal to 1.5 wt %, and particularly the solubility of at least one organic functional material in the organic solvent is greater than or equal to 3 wt %.

In an embodiment, a difference of the solubilities between any two of H1, H2, and H3 in the organic solvent is less than or equal to 0.2 wt %, further less than or equal to 0.15 wt %, and still further less than or equal to 0.1 wt %.

In an embodiment, in the composition of the present disclosure, a weight ratio of the organic functional materials to the composition ranges from 0.3 wt % to 30 wt %, further 0.5 wt % to 20 wt %, still further 0.5 wt % to 15 wt %, and particularly 1 wt % to 5 wt %.

In an embodiment, at least one of the organic functional materials H1, H2, and H3 has a glass transition temperature greater than or equal to 100° C., further greater than or equal to 120° C., still further greater than or equal to 140° C., and particularly greater than or equal to 160° C.

In an embodiment, all the organic functional materials H1, H2, and H3 have a glass transition temperature greater than or equal to 100° C., further greater than or equal to 120° C., still further greater than or equal to 140° C., and particularly greater than or equal to 160° C.

In an embodiment, in the composition, a molar ratio of the third organic functional material H3 to the organic functional materials H1, H2, and H3 ranges from 1% to 60%.

In an embodiment, a molar ratio of the first organic functional material H1 to the second organic functional material H2 ranges from 1:9 to 9:1, further 3:7 to 7:3, still further 4:6 to 6:4, and particularly is 5:5.

In an embodiment, in the composition of the present disclosure, H1 is an electron transport material, and H2 is a hole transport material.

Further, the organic functional material H1 contains F, CN, or any of the following groups:

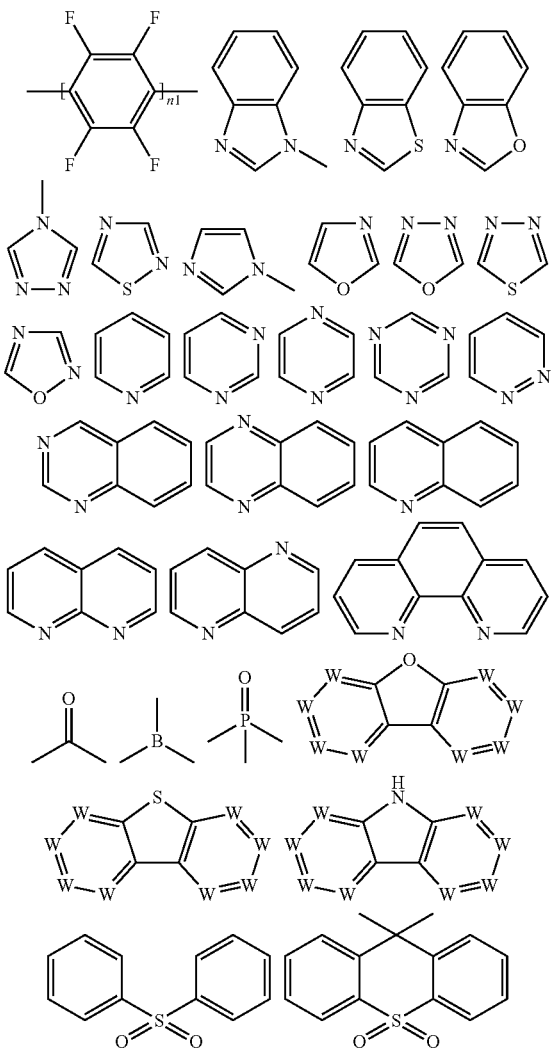

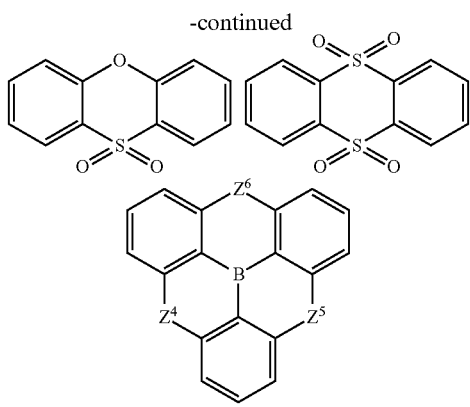

Wherein, hydrogen atoms in the above groups may be further substituted by R;

each W independently represents CR or N, and particularly at least one W is N;

$Z^4$ to $Z^6$ is a single bond, $C(R)_2$, O, S, or none;

n1 is an integer ranging from 1 to 3; and each R is independently selected from the group consisting of H, D, a linear alkyl group with 1 to 20 carbon atoms, a linear alkoxy group with 1 to 20 carbon atoms, a linear thioalkoxy group with 1 to 20 carbon atoms, a branched or cyclic alkyl group with 3 to 20 carbon atoms, a branched or cyclic alkoxy group with 3 to 20 carbon atoms, a branched or cyclic thioalkoxy group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, $CF_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a heteroaryloxy group with 5 to 60 ring atoms, or a combination thereof.

In an embodiment, the organic functional material H1 is a structure of general formula (1):

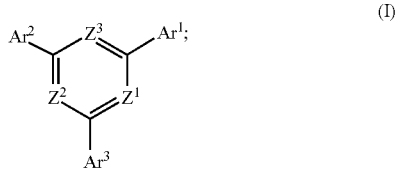

wherein, $Ar^1$ to $Ar^3$ are independently selected from a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms; and $Z^1$ to $Z^3$ each independently represent $CR_1$ or N, and at least one of $Z^1$ to $Z^3$ is N; and in an embodiment $Z^1$ to $Z^3$ are N;

each $R_1$ is independently selected from the group consisting of H, D, a linear alkyl group with 1 to 20 carbon atoms, a linear alkoxy group with 1 to 20 carbon atoms, a linear thioalkoxy group with 1 to 20 carbon atoms, a branched or cyclic alkyl group with 3 to 20 carbon atoms, a branched or cyclic alkoxy group with 3 to 20 carbon atoms, a branched or cyclic thioalkoxy group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, $CF_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a heteroaryloxy group with 5 to 60 ring atoms, or a combination thereof.

In an embodiment, at least one of $Ar^1$ to $Ar^3$ contains the following groups:

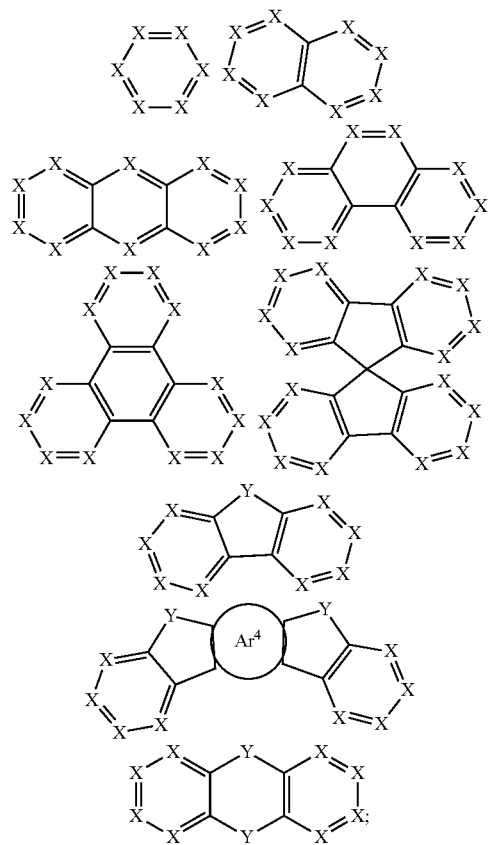

wherein, each X independently represents $CR_2$ or N;

each Y independently represents $CR_3R_4$, $NR_3$, $BR_3$, O, S, $SiR_3R_4$, $PR_3$, $P(=O)R_3$, $S=O$, $S(=O)_2$, or $C=O$;

$Ar^4$ is independently a substituted or unsubstituted phenyl group;

$R_2$ to $R_4$ are each independently selected from the group consisting of H, D, a linear alkyl group with 1 to 20 carbon atoms, an alkoxy group with 1 to 20 carbon atoms, a thioalkoxy group with 1 to 20 carbon atoms, a branched alkyl group with 3 to 20 carbon atoms, a cyclic alkyl group with 3 to 20 carbon atoms, an alkoxy group with 3 to 20 carbon atoms, a thioalkoxy group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, $CF_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a heteroaryloxy group with 5 to 60 ring atoms, or a combination thereof.

In an embodiment, H1 has a structure selected from general formulas (1-1) to (1-4):

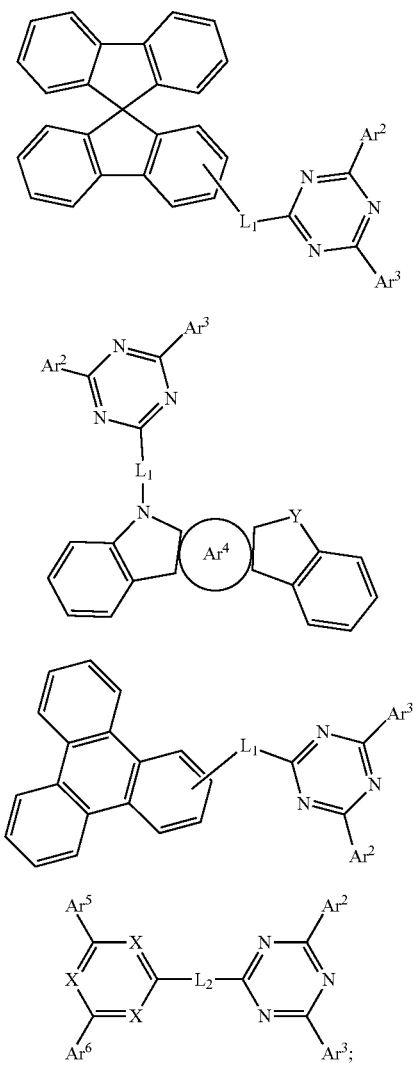

wherein, $Ar^5$ to $Ar^6$ are independently selected from a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms; and $L_1$ and $L_2$ are each independently selected from a single bond, a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms; and In an embodiment, at least one of $Ar_2$ to $Ar^3$ in the general formulas (1-1) to (1-2) or

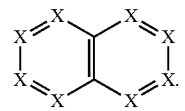

Ar4 to Ar5 in the general formula (1-4) is selected from the following groups:

In an embodiment, $L_1$ and $L_2$ are each independently selected from following groups:

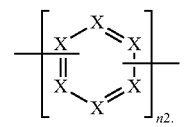

Wherein, n2 is an integer ranging from 1 to 3.

Further, H1 is a structure selected from general formulas (A-1) to (A-3):

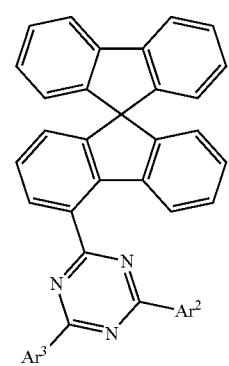

(A-1)

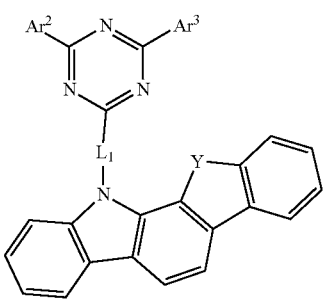

(A-2)

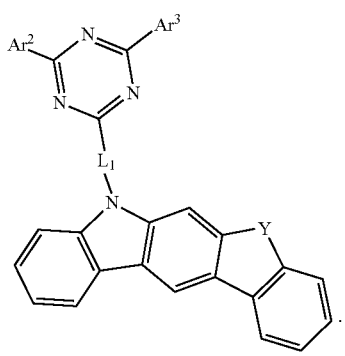

(A-3)

In an embodiment, $Ar^2$, $Ar^3$, $Ar^5$, and $Ar^6$ are each independently selected from an aromatic group containing 6a ring atoms, wherein, a is 1, 2, 3, 4, 5, 6, or 7.

In one embodiment, $Ar^2$, $Ar^3$, $Ar^5$, and $Ar^6$ are each independently selected from following groups:

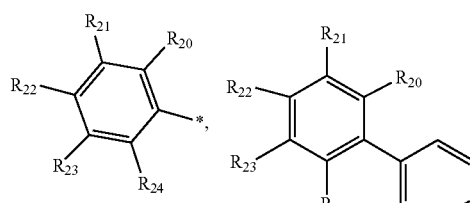

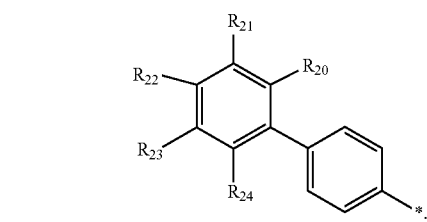

Wherein, $R_{20}$ to $R_{24}$ are each independently selected from H or phenyl group.

In an embodiment, $Ar^2$, $Ar^3$, $Ar^5$, and $Ar^6$ are each independently selected from following groups:

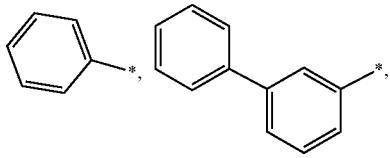

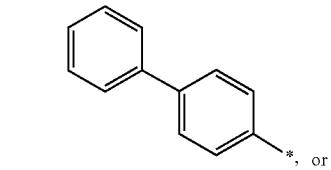

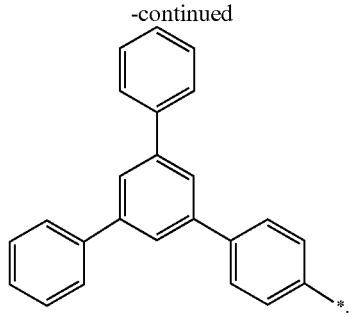

In an embodiment, the organic functional material H2 is a hole transport material, and especially, H2 has a structure selected from general formulas (2-1) to (2-4):

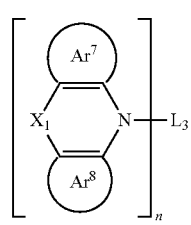

(2-1)

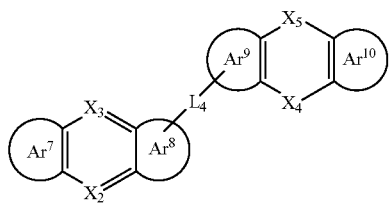

(2-2)

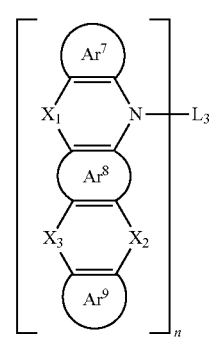

(2-3)

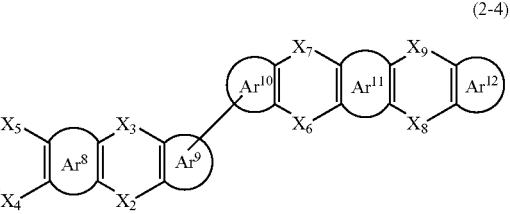

(2-4)

wherein, $X_1$ to $X_9$ each independently represent a single bond, $CR_5R_6$, $NR_5$, O, S, $SiR_5R_6$, $PR_5$, $P(=O)R_5$, S=O, $S(=O)_2$, or C=O, $X_2$ and $X_3$ are not a single bond at a same time, $X_4$ and $X_5$ are not a single bond at a same time, $X_6$ and $X_7$ are not a single bond at a same time, and $X_8$ and $X_9$ are not a single bond at a same time;

$Ar^7$ to $Ar^{12}$ are each independently selected from a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms; and $L_3$ and $L_4$ are each independently selected from a single bond, a triarylamino group, a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms;

n is an integer ranging from 1 to 4; and $R_5$ to $R_6$ are each independently selected from the group consisting of H, D, a linear alkyl group with 1 to 20 carbon atoms, an alkoxy group with 1 to 20 carbon atoms, a thioalkoxy group with 1 to 20 carbon atoms, a branched alkyl group with 3 to 20 carbon atoms, a cyclic alkyl group with 3 to 20 carbon atoms, an alkoxy group with 3 to 20 carbon atoms, a thioalkoxy group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, $CF_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a heteroaryloxy group with 5 to 60 ring atoms, or a combination thereof.

In an embodiment, $X_1$ is selected from a single bond, $CR_5R_6$, $NR_5$, O, or S, and especially $X_1$ is a single bond.

In an embodiment, $\lambda_2$ to $X_9$ each independently represent a single bond, $CR_5R_6$, NR5, O, or S. Particularly, one of $X_2$ to $X_3$ is a single bond, one of $X_4$ to $X_5$ is a single bond, one of $X_6$ to $X_7$ is a single bond, and one of $X_8$ to $X_9$ is a single bond.

In an embodiment, $Ar^7$ to $Ar^{12}$ are selected from the following groups:

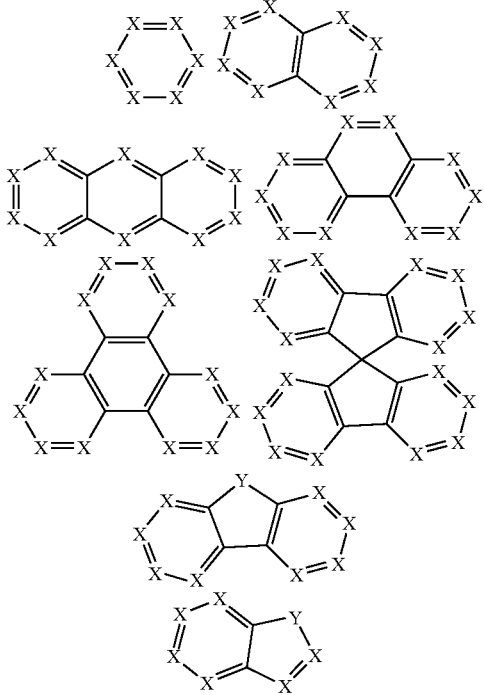

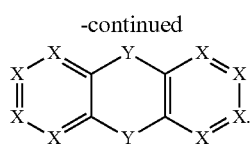

Wherein, definitions of X and Y are same as above.

In some embodiments, $Ar^7$ to $Ar^{12}$ are phenyl groups unsubstituted or substituted by $R_2$.

In an embodiment, $L_3$ and $L_4$ are each independently selected from a single bond, triarylamino group, or following groups:

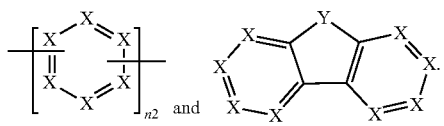

Wherein, n2 is an integer ranging from 1 to 3, and X and Y are as defined above.

In an embodiment, the general formula (2-1) has a structure of the general formula (3-1):

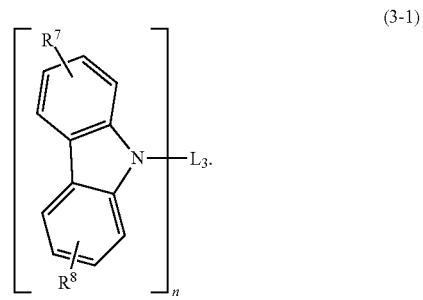

(3-1)

Wherein, $R^7$ to $R^8$ are each independently selected from the group consisting of H, D, a linear alkyl group with 1 to 20 carbon atoms, an alkoxy group with 1 to 20 carbon atoms, a thioalkoxy group with 1 to 20 carbon atoms, a branched alkyl group with 3 to 20 carbon atoms, a cyclic alkyl group with 3 to 20 carbon atoms, an alkoxy group with 3 to 20 carbon atoms, a thioalkoxy group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, $CF_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a heteroaryloxy group with 5 to 60 ring atoms, or a combination thereof.

In an embodiment, in the general formula (3-1), $L_3$ is a triarylamine group, further, $L_3$ is a triphenylamine group, and even further, $L_3$ is

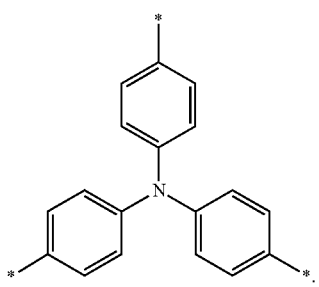

In an embodiment, the general formula (3-1) is a structure of the following general formula:

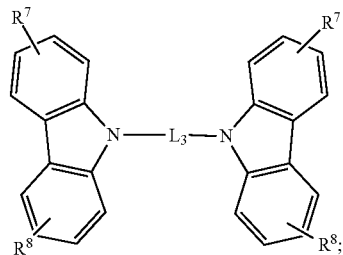

Further, $L_3$ is a biphenyl group, and even further, $L_3$ is

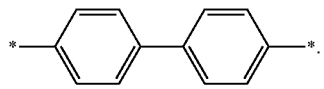

In an embodiment, the general formula (2-2) has a structure of following general formula:

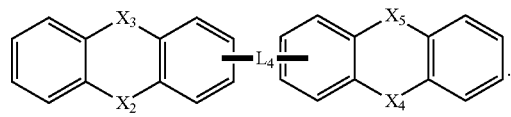

Further, the general formula (2-2) has a structure of the general formula (3-2):

(3-2)

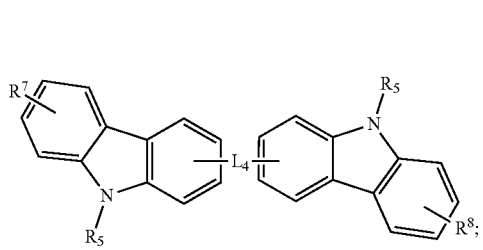

Further, $L_4$ is a single bond; still further, $R_5$ is selected from

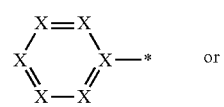

or

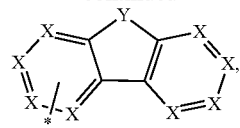

wherein, X and Y are as defined above. Particularly, $R_5$ is selected from

 or 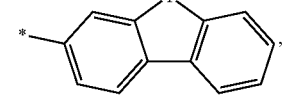

and further Y is —$(CH_3)_2$.

In some embodiments, the general formula (2-3) has a structure selected from the following general formulas:

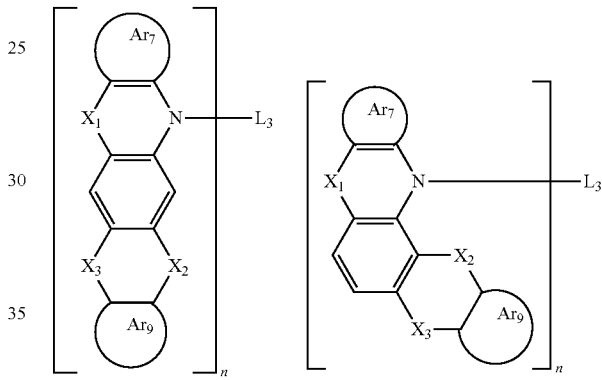

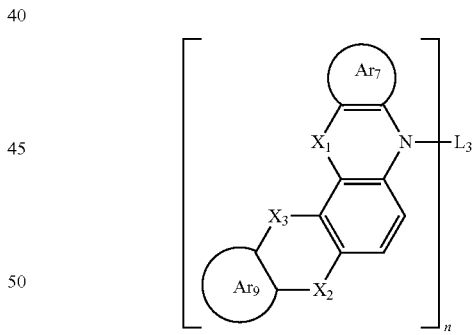

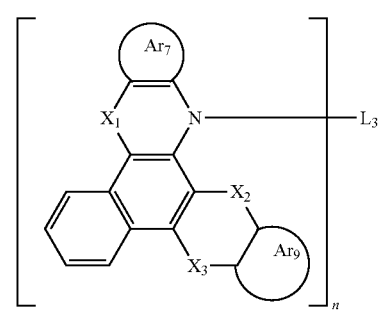

-continued

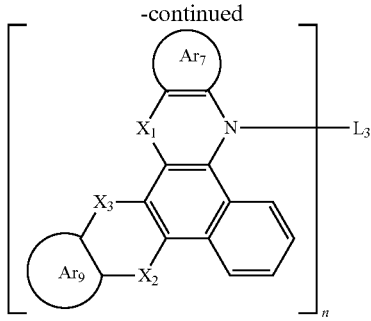

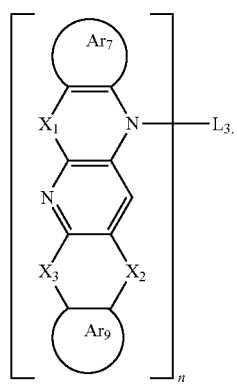

In an embodiment, the general formula (2-3) has a structure of the general formula (3-3):

(3-3)

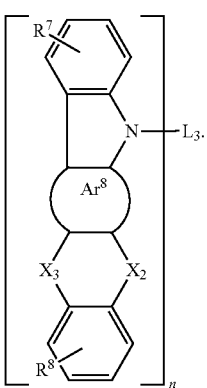

Further, the general formula (3-3) has a following structure:

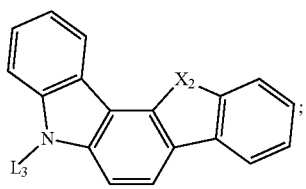

wherein, each $L_3$ is independently selected from

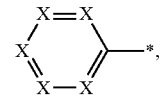

and further, each $L_3$ is independently selected from

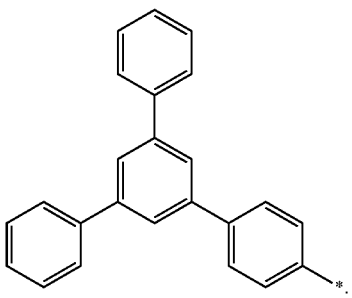

Further, $X_2$ is N-Ph.

In some embodiments, the general formula (2-4) has a structure of the general formula (3-4):

(3-4)

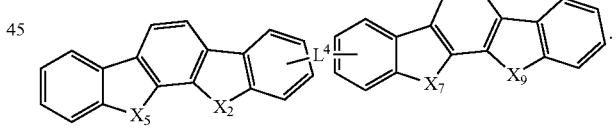

In an embodiment, the general formula (2-4) has a structure of the following general formula:

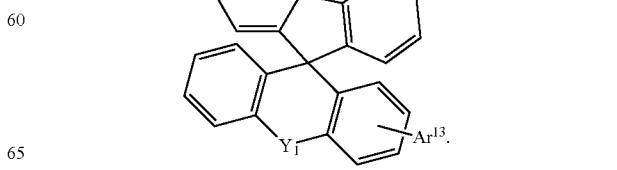

In one embodiment, H2 is selected from general formulas (3-2) or (3-4), further, $L_4$ is a single bond.

In one embodiment, the organic functional material H3 has a structure of general formula (4):

(4)

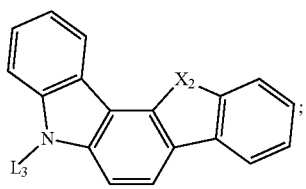

wherein, $Y_1$ independently represents nonexistence, a single bond, $CR_9R_{10}$, $NR_9$, O, S, $SiR_9R_{10}$, $PR_9$, P(=O)$R_9$, S=O, S(=O)2, or C=O;

$Ar^{13}$ is independently selected from a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms; and $R_9$ and $R_{10}$ are each independently selected from the group consisting of H, D, a linear alkyl group with 1 to 20 carbon atoms, an alkoxy group with 1 to 20 carbon atoms, a thioalkoxy group with 1 to 20 carbon atoms, a branched alkyl group with 3 to 20 carbon atoms, a cyclic alkyl group with 3 to 20 carbon atoms, an alkoxy group with 3 to 20 carbon atoms, a thioalkoxy group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, $CF_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a heteroaryloxy group with 5 to 60 ring atoms, or a combination thereof.

Further, $Ar^{13}$ is selected from the following groups:

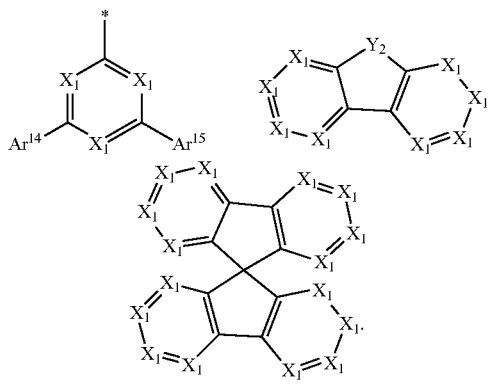

wherein, each $X_1$ independently represents $CR_{11}$ or N;
each $Y_2$ independently represents $CR_{11}R_{12}$, $NR_{11}$, O, S, $SiR_{11}R_{12}$, $PR_{11}$, P(=O)$R_{11}$, S=O, S(=O)$_2$, or C=O;

$Ar^{14}$ and $Ar^{15}$ are each independently selected from a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms; and $R_{11}$ to $R_{12}$ are each independently selected from the group consisting of H, D, a linear alkyl group with 1 to 20 carbon atoms, an alkoxy group with 1 to 20 carbon atoms, a thioalkoxy group with 1 to 20 carbon atoms, a branched alkyl group with 3 to 20 carbon atoms, a cyclic alkyl group with 3 to 20 carbon atoms, an alkoxy group with 3 to 20 carbon atoms, a thioalkoxy group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, $CF_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a heteroaryloxy group with 5 to 60 ring atoms, or a combination thereof.

In one embodiment, $Ar^{14}$ to $Ar^{15}$ are each independently

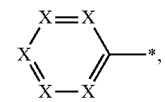

wherein, X is as defined above. Further, $Ar^{14}$ to $Ar^{15}$ are each independently selected from:

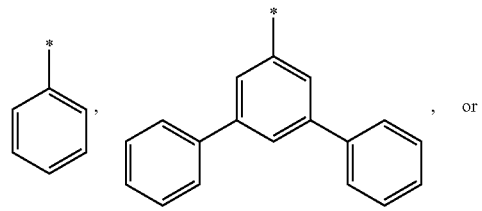

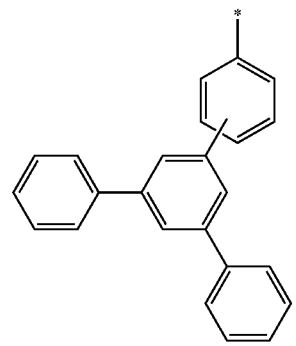

In an embodiment, $Ar^{13}$ is

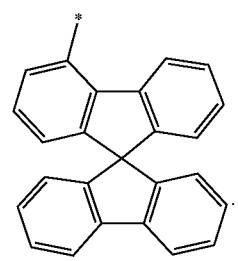 [SMILES: *c1cccc2c1-c1ccccc1C21c2ccccc2-c2ccccc21]

In one embodiment, in the composition of the present disclosure, the organic functional material H3 has a following structure:

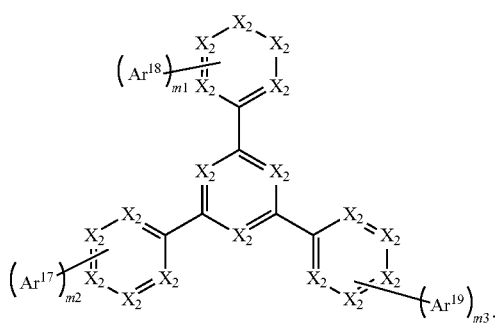

wherein, each $X_2$ independently represents $CR_{13}$ or N;

$Ar^{17}$ to $Ar^{19}$ are each independently selected from a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms; and m1, m2, and m3 are each independently an integer ranging from 0 to 3, and m1+m2+m3≥2;

each $R_{13}$ is independently selected from the group consisting of H, D, a linear alkyl group with 1 to 20 carbon atoms, an alkoxy group with 1 to 20 carbon atoms, a thioalkoxy group with 1 to 20 carbon atoms, a branched alkyl group with 3 to 20 carbon atoms, a cyclic alkyl group with 3 to 20 carbon atoms, an alkoxy group with 3 to 20 carbon atoms, a thioalkoxy group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, $CF_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a heteroaryloxy group with 5 to 60 ring atoms, or a combination thereof.

Further, H3 has a structure selected from general formulas (B-1) or (B-2):

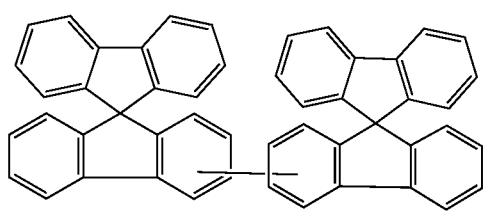

(B-1)

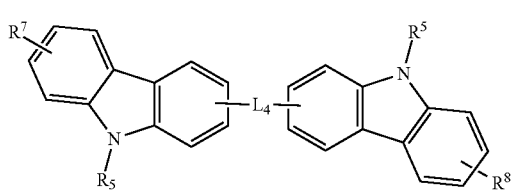

(B-2)

In an embodiment, H1 has the structure of the general formula (1-2), H2 has the structure selected from the general formulas (3-1) or (3-2), and H3 has the structure of the general formula (4).

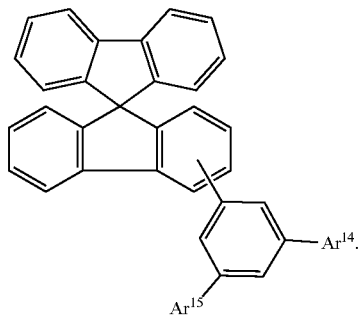

(1-1)

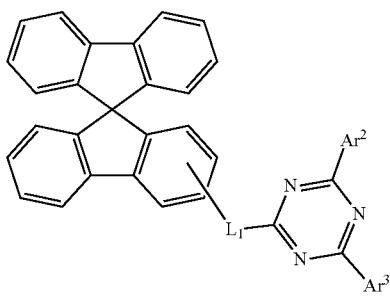

(1-2)

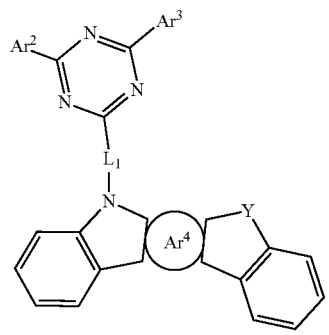

(3-1)

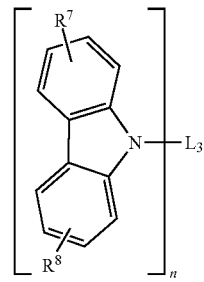

(3-2)

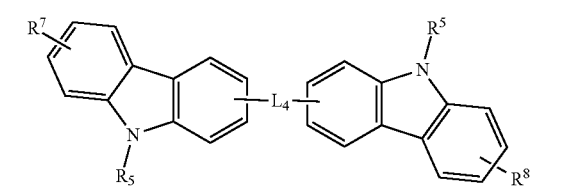

(4)

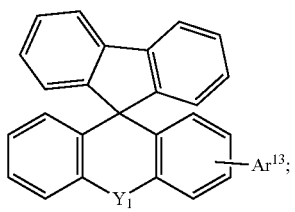

Wherein, $Ar_2$, $Ar_3$, $Ar^4$, Y, $L_3$, $R_5$, $R^7$ to $R^8$, $Y_1$, and $Ar^{13}$ have the same definitions as above.

In one embodiment, H1 has the structure of the general formulas (1-1) or (1-2), H2 has the structure of the general formulas (3-1) or (3-2), and H3 has the structure of the general formulas (B-1) or (B-2). The general formulas are as defined above, and will not be repeated here.

In one embodiment, H1 has the structure of the general formula (1-1), H2 has the structure of the general formulas (3-1) or (3-2), and H3 has the structure of the general formula (B-1).

In one embodiment, H1 has the structure of the general formula (1-2), H2 has the structure of the general formulas (3-1) or (3-2), and H3 has the structure of the general formula (B-1).

In one embodiment, H1 has the structure of the general formula (1-2), H2 has the structure of the general formulas (3-1) or (3-2), and H3 has the structure of the general formula (B-2).

In one embodiment, H1 has the structure of the general formula (1-2), H2 has the structure of the general formula (3-2), and H3 has the structure of the general formula (B-1). The general formulas are as defined above, and will not be repeated here.

In one embodiment, H1 has the structure of the general formula (1-2), H2 has the structure of the general formula (3-2), and H3 has the structure of the general formula (B-2). The general formulas are as defined above, and will not be repeated here.

Specific examples that can be used as H1 are listed below, but are not limited to:

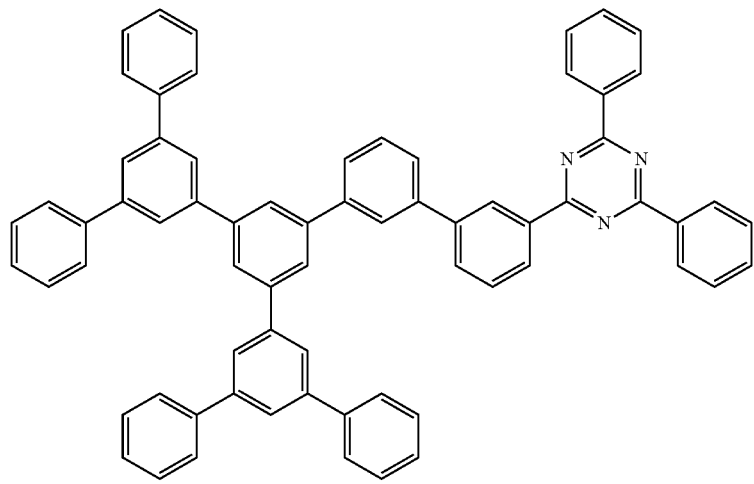

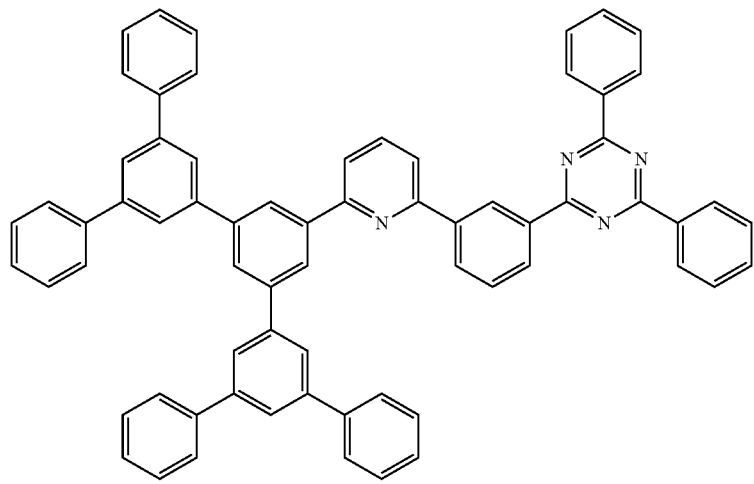

-continued
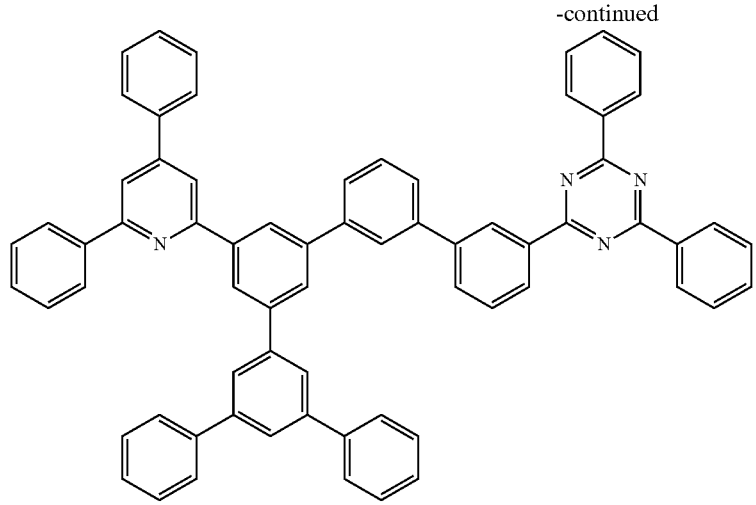
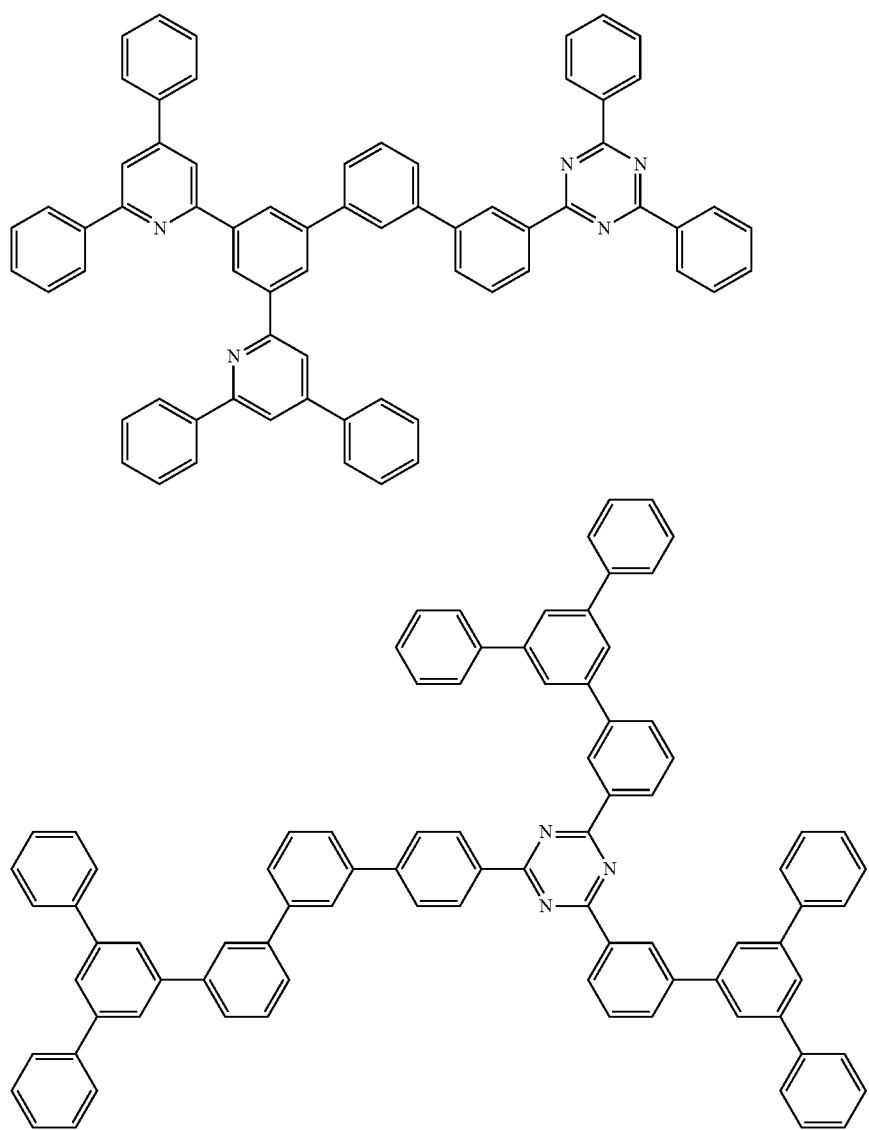

-continued
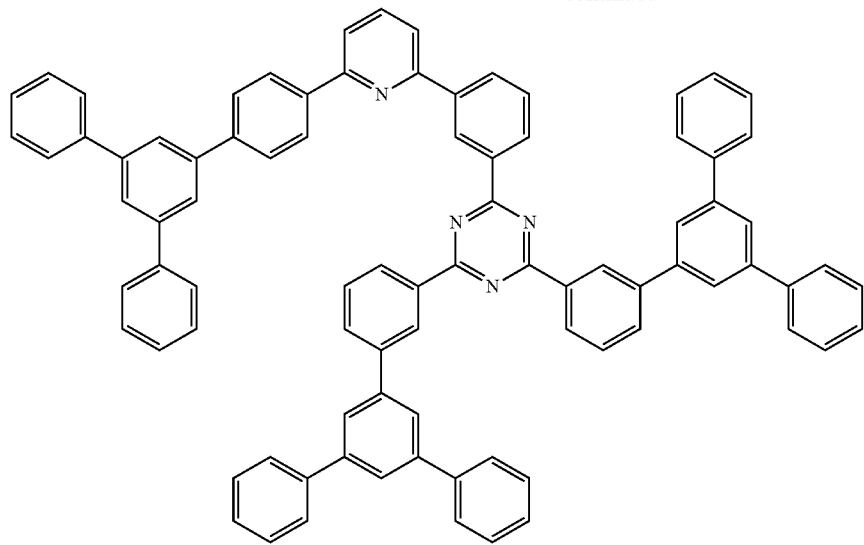
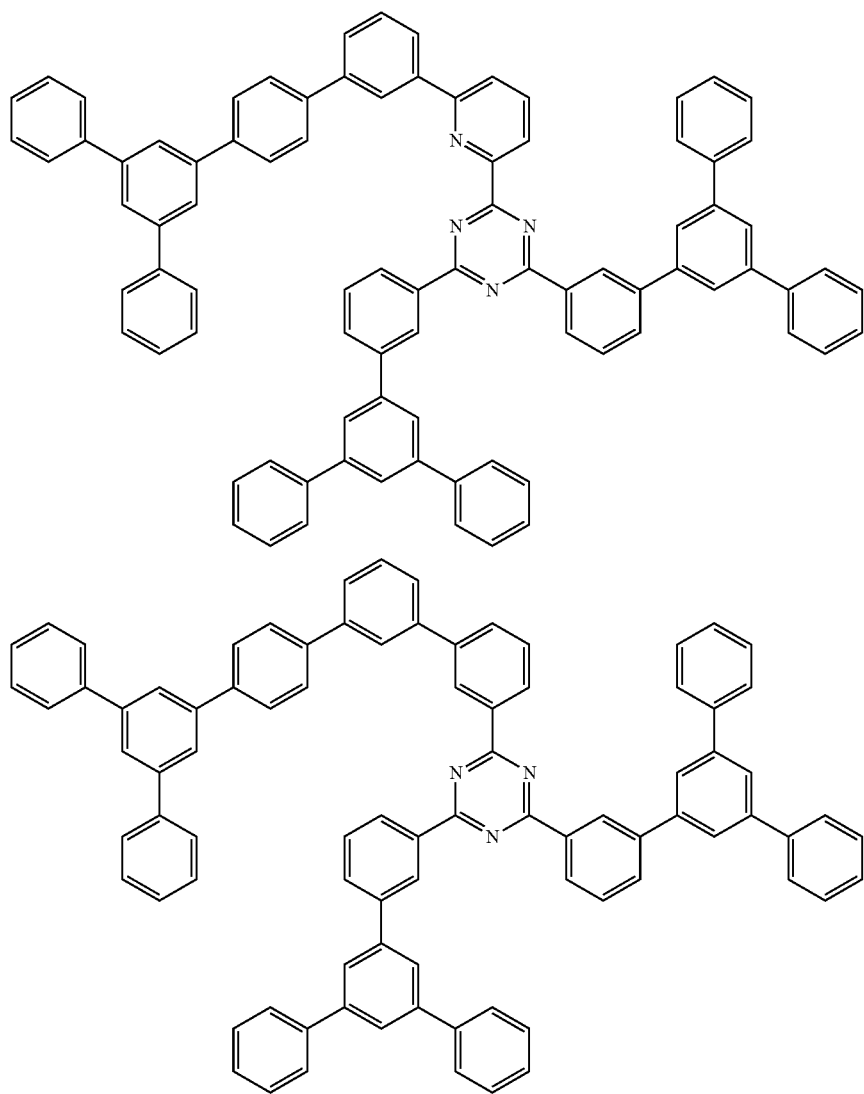

-continued
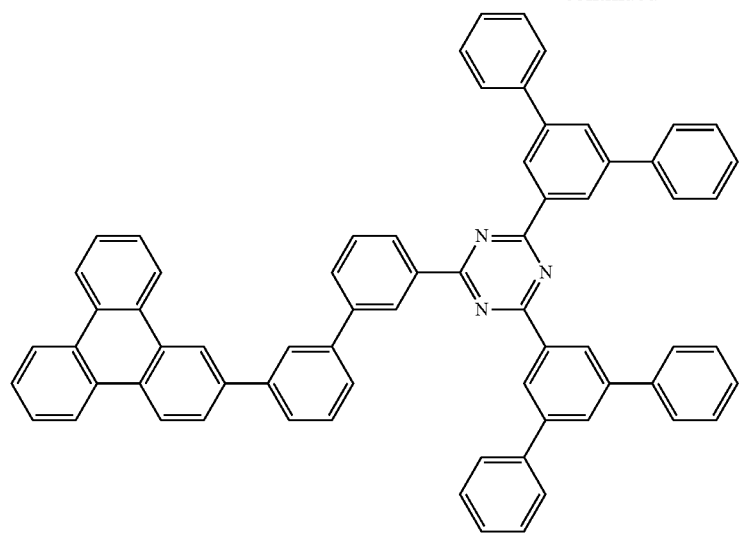
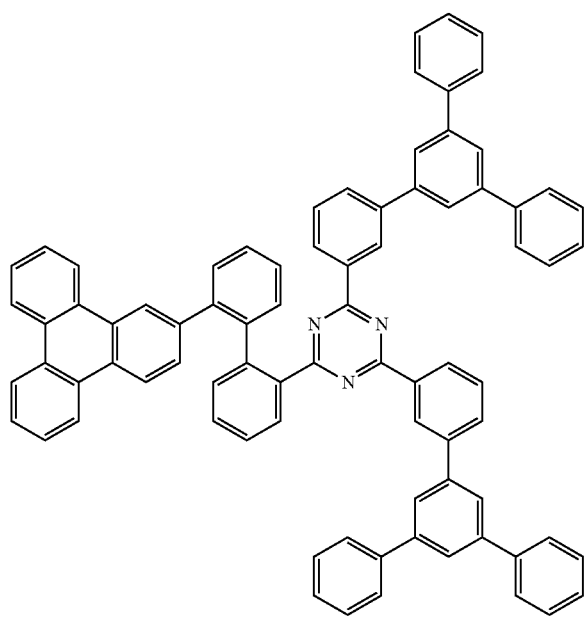

-continued
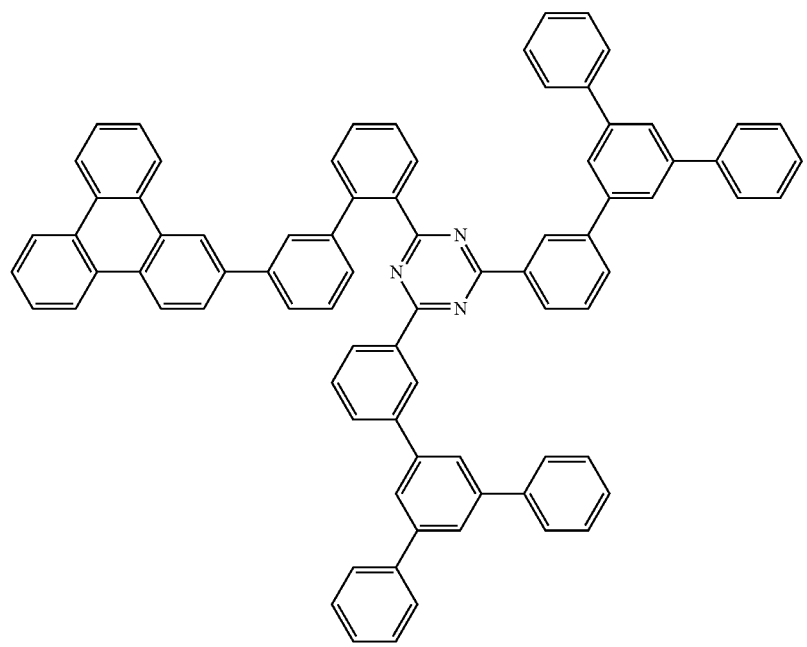
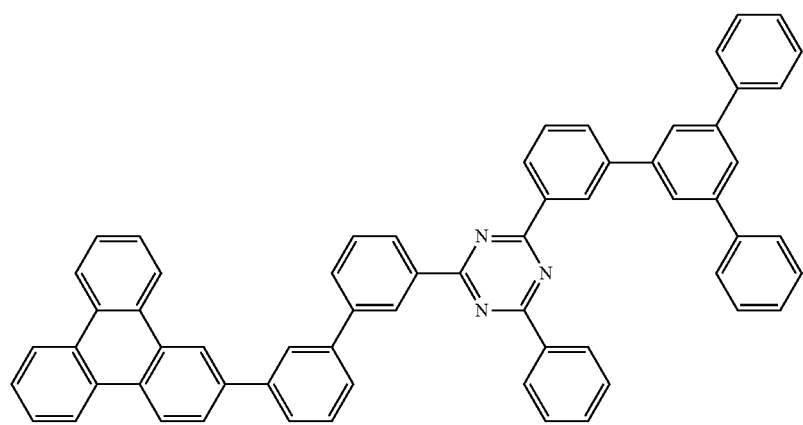
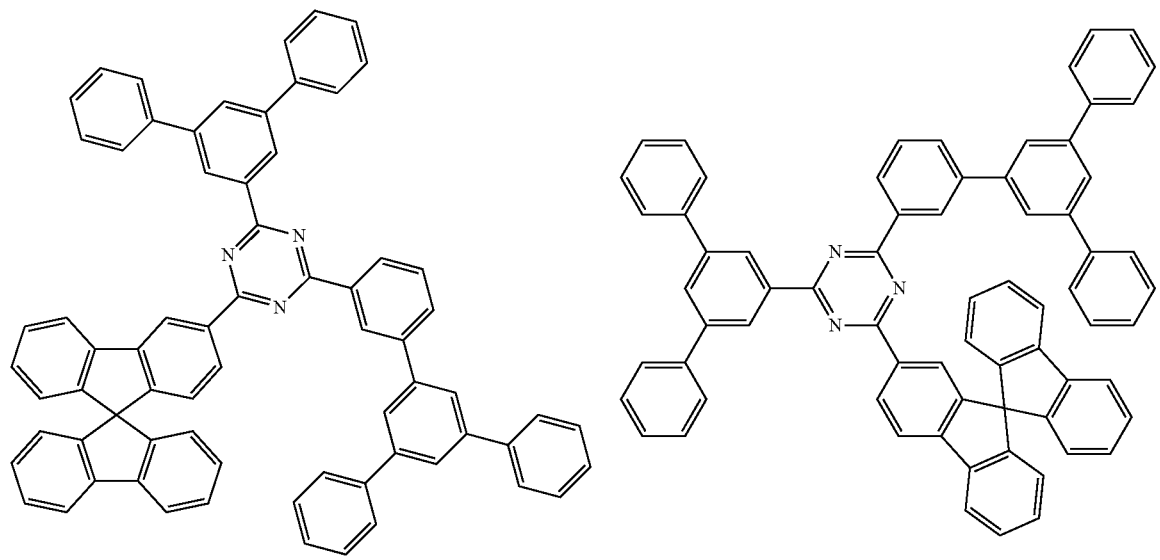

-continued
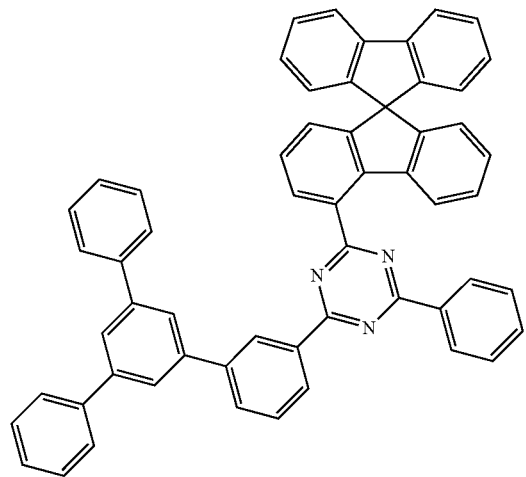

-continued
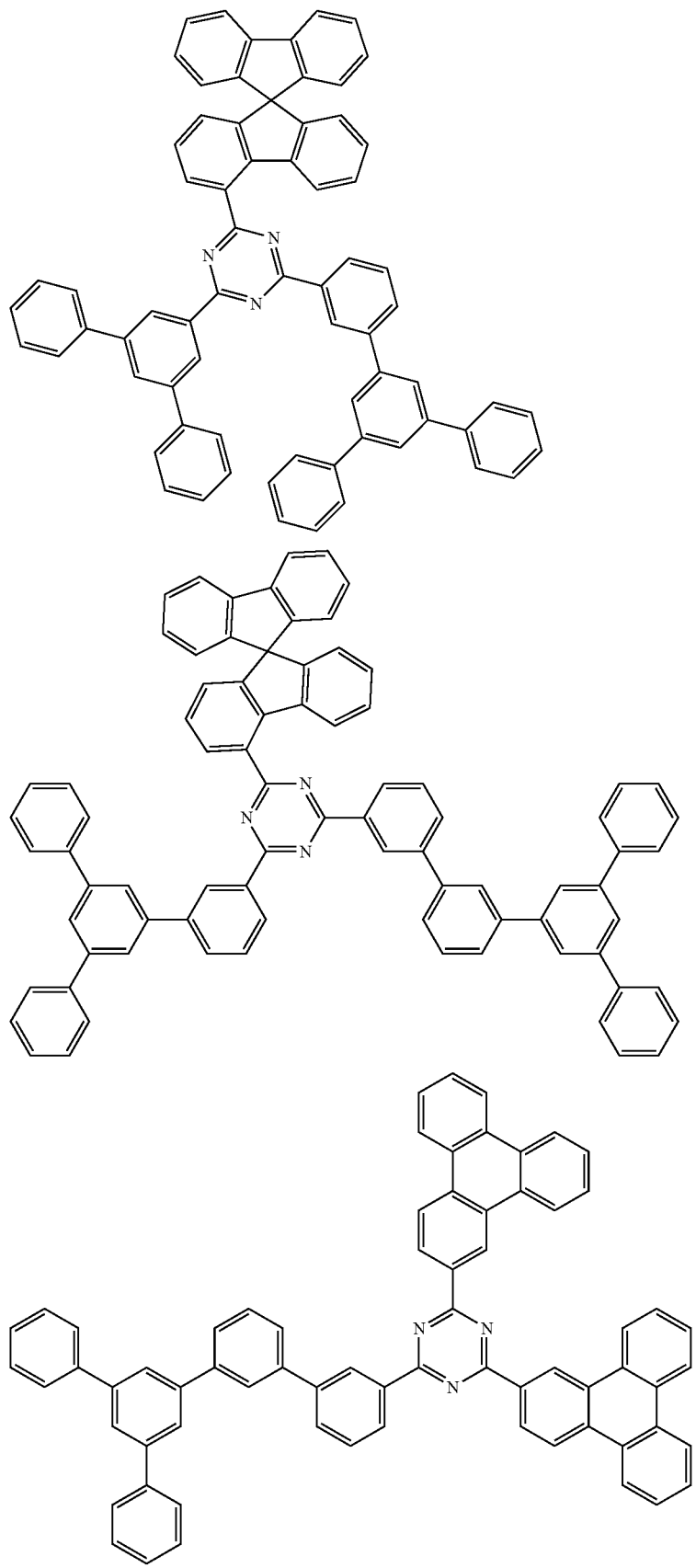

-continued
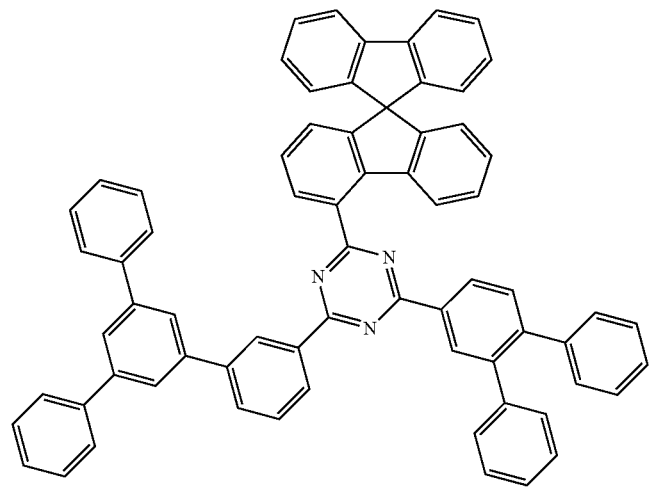
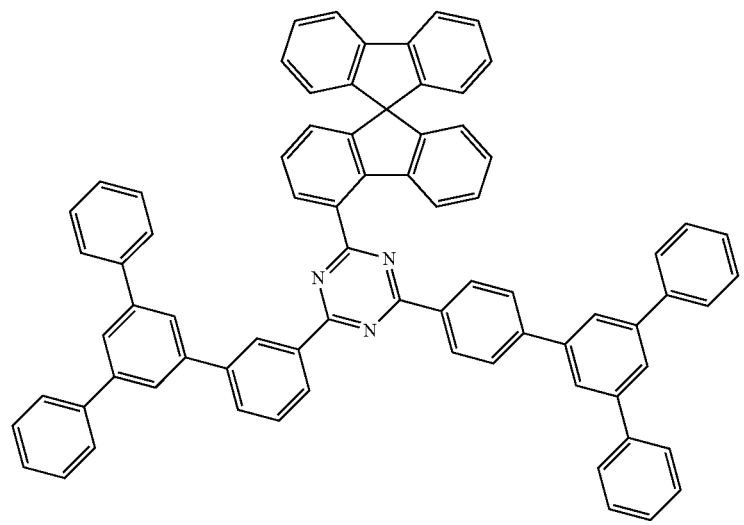
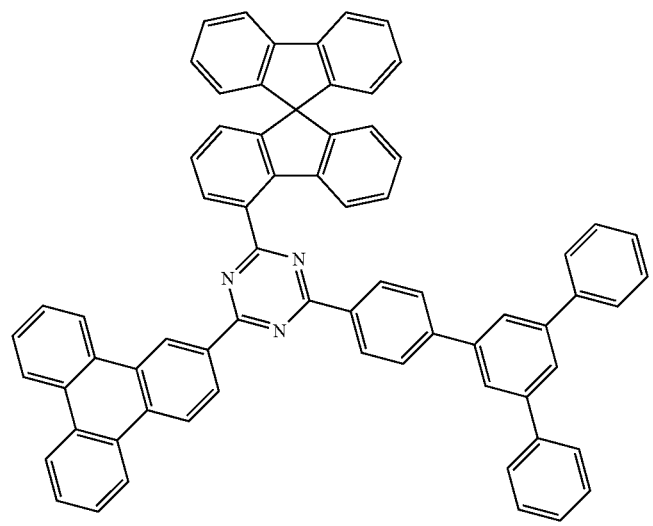

-continued
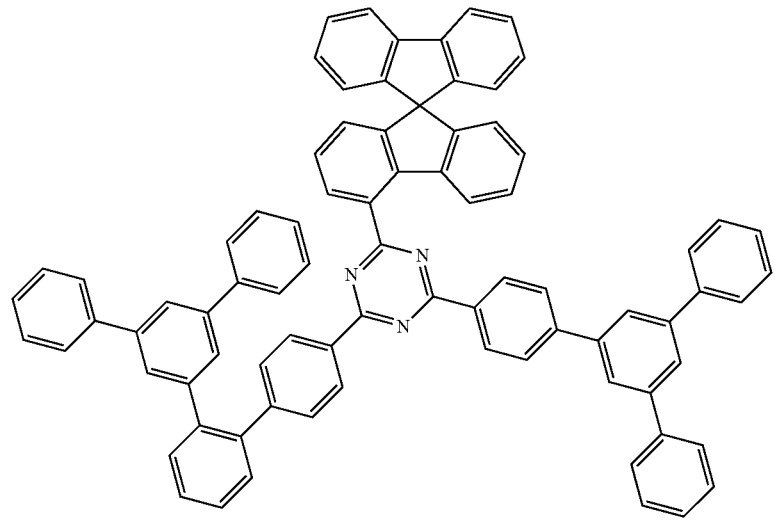
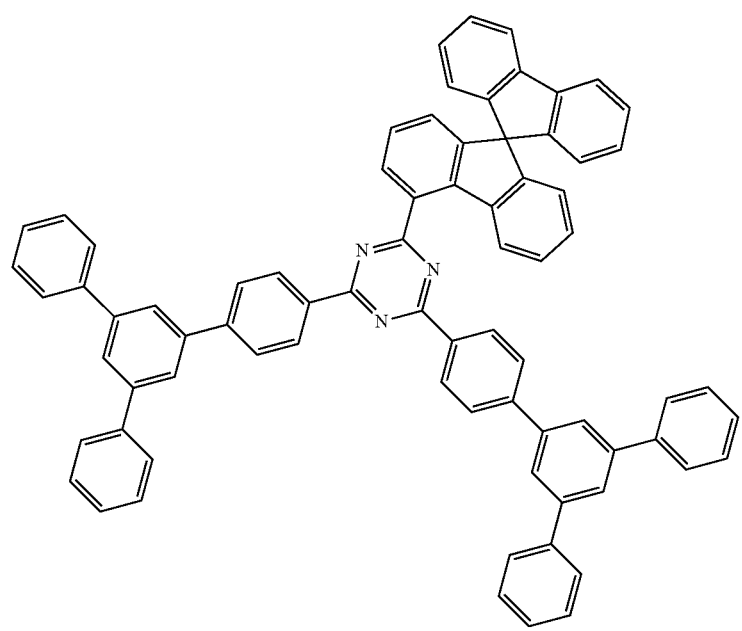
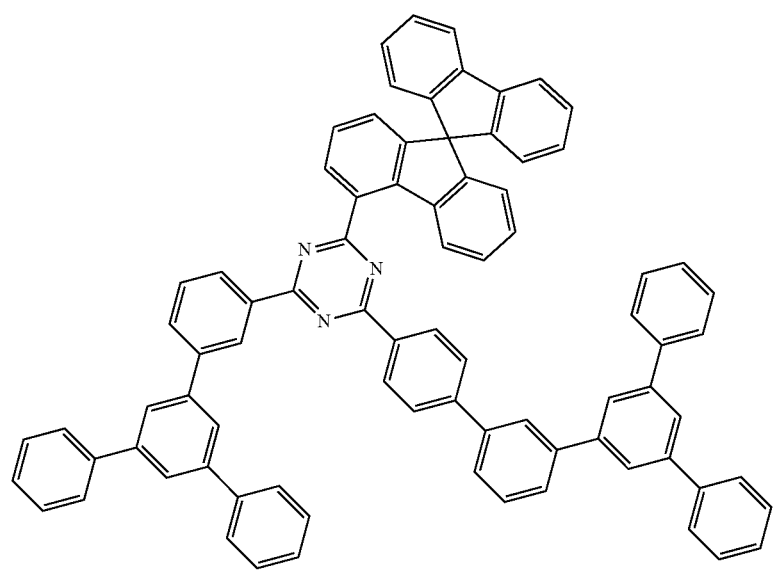

-continued
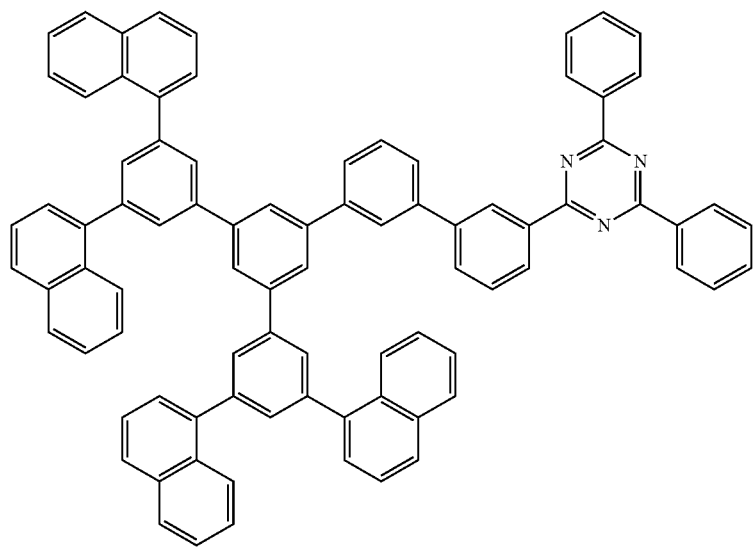
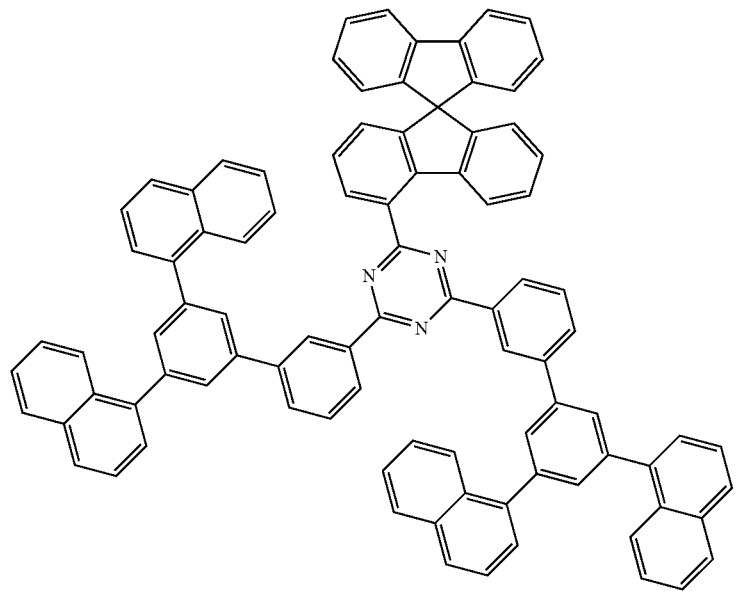
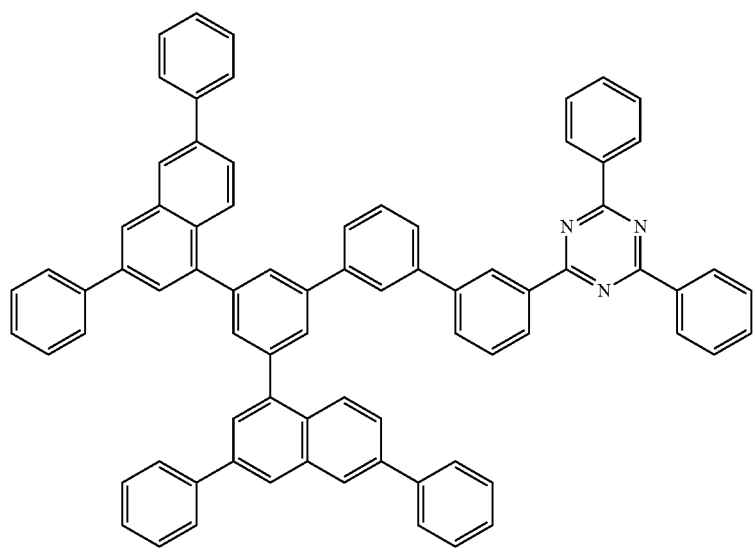

-continued
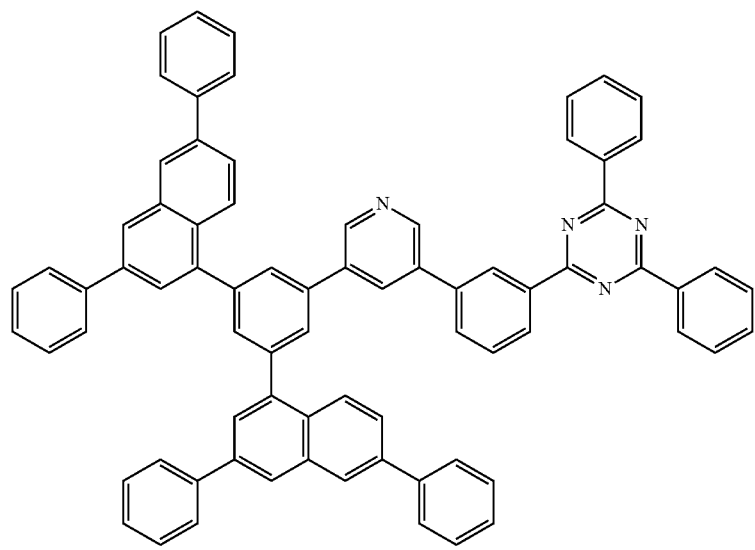
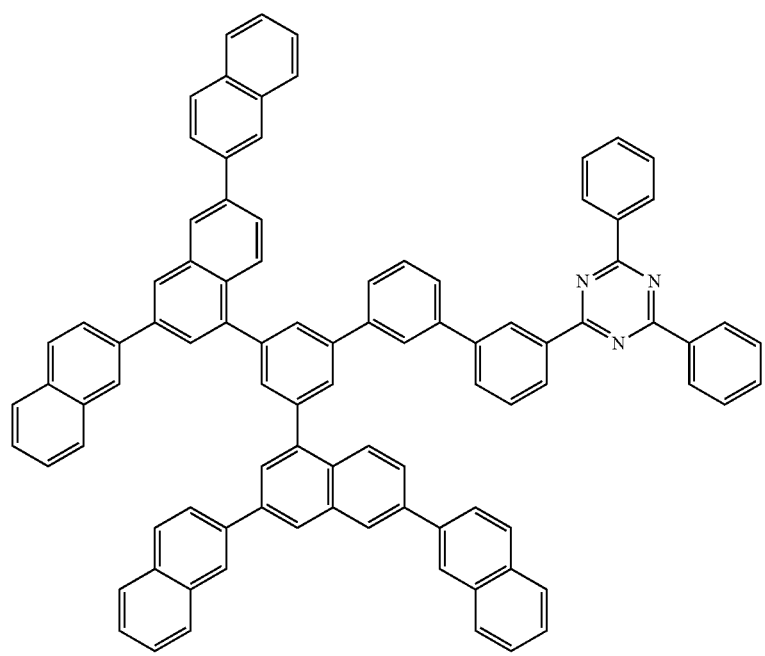

-continued
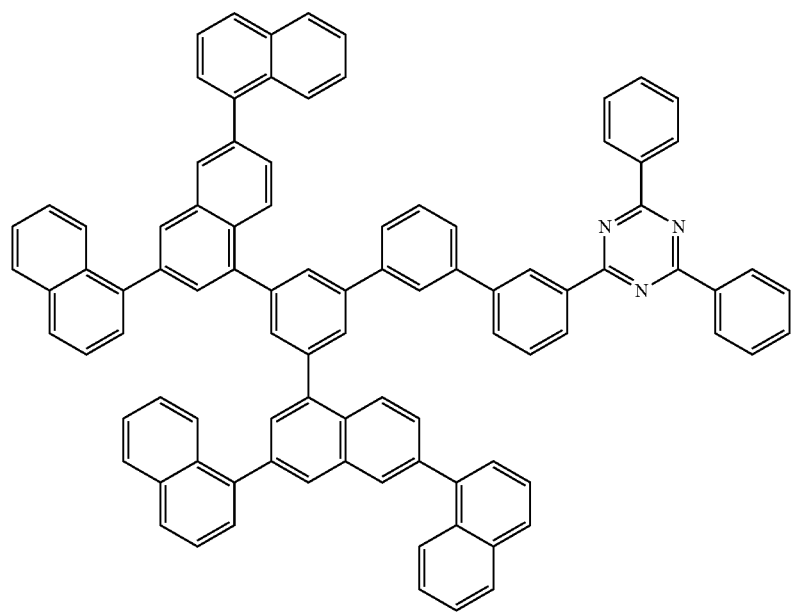
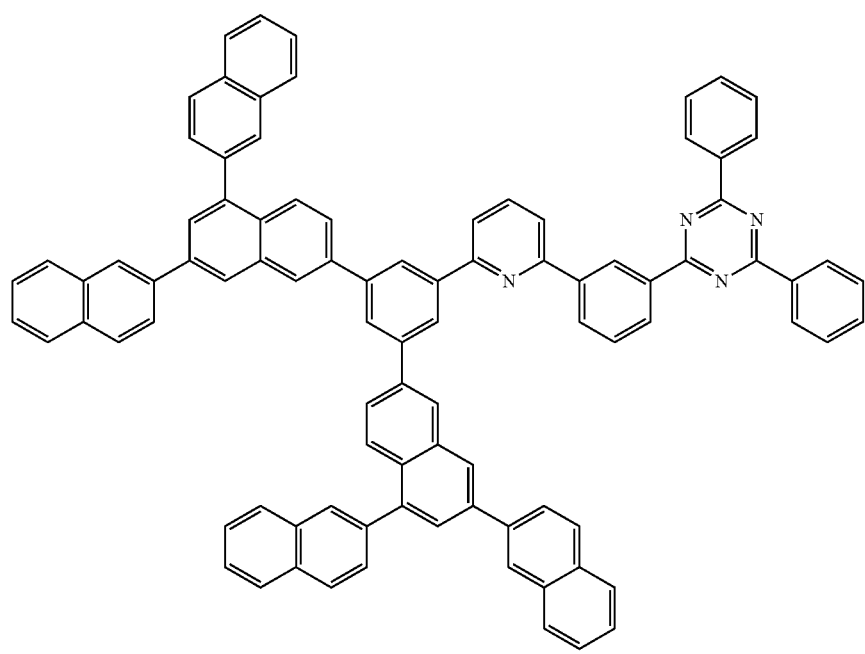

-continued
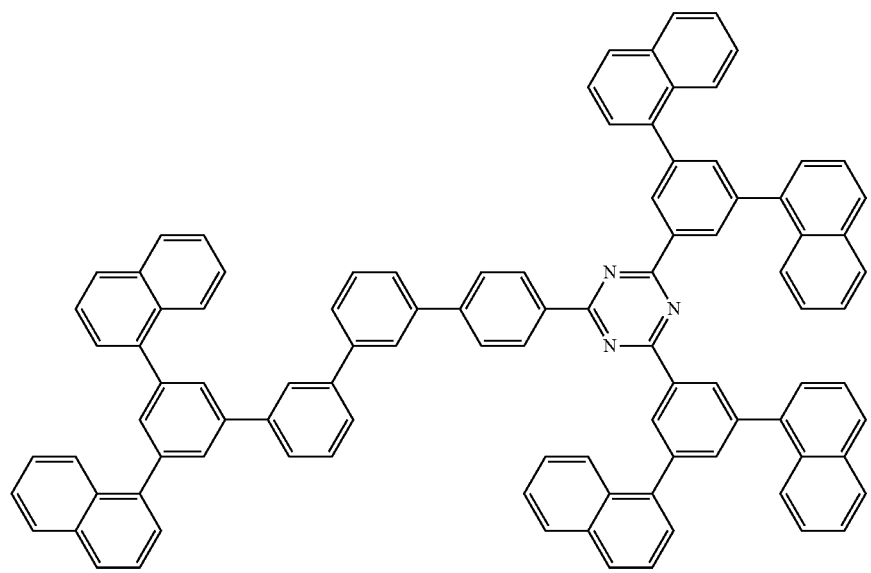
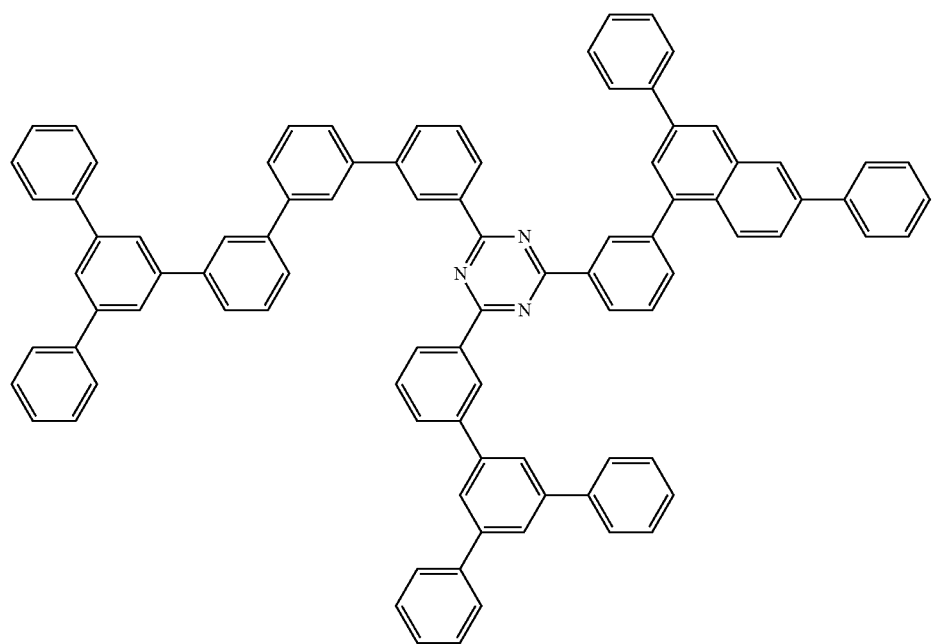

-continued
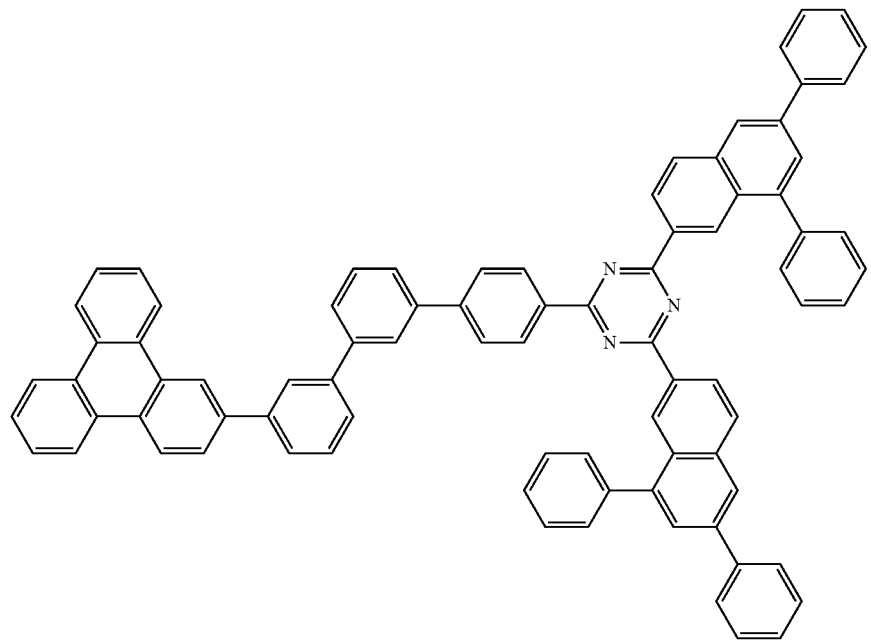
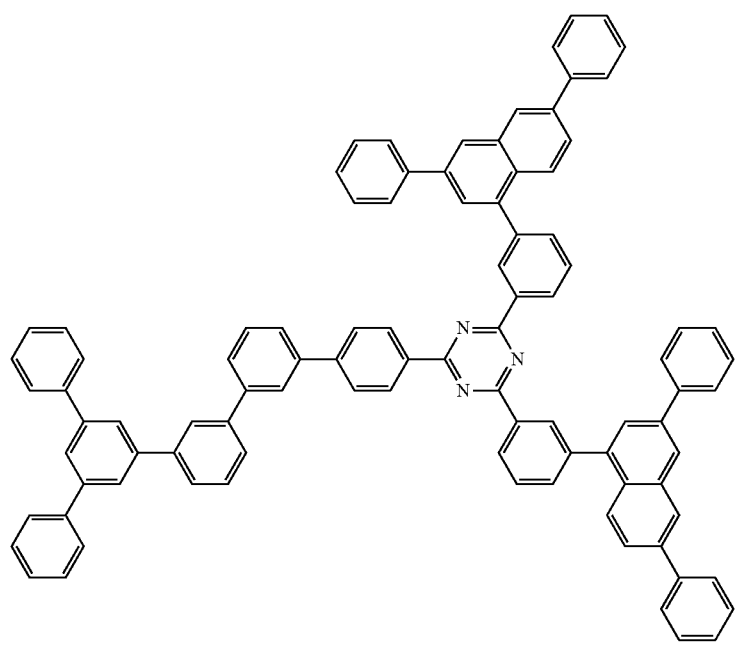

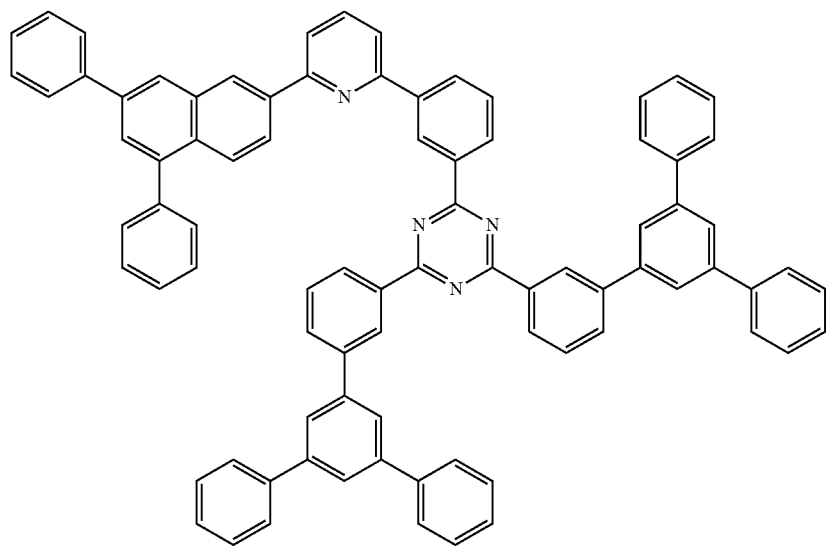
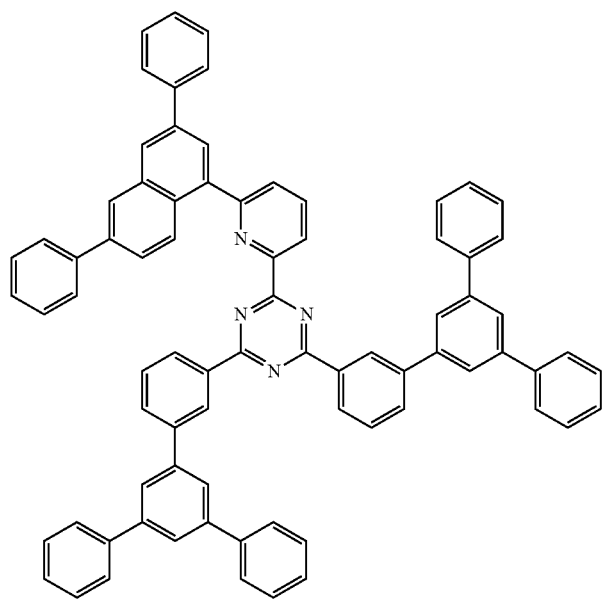

-continued
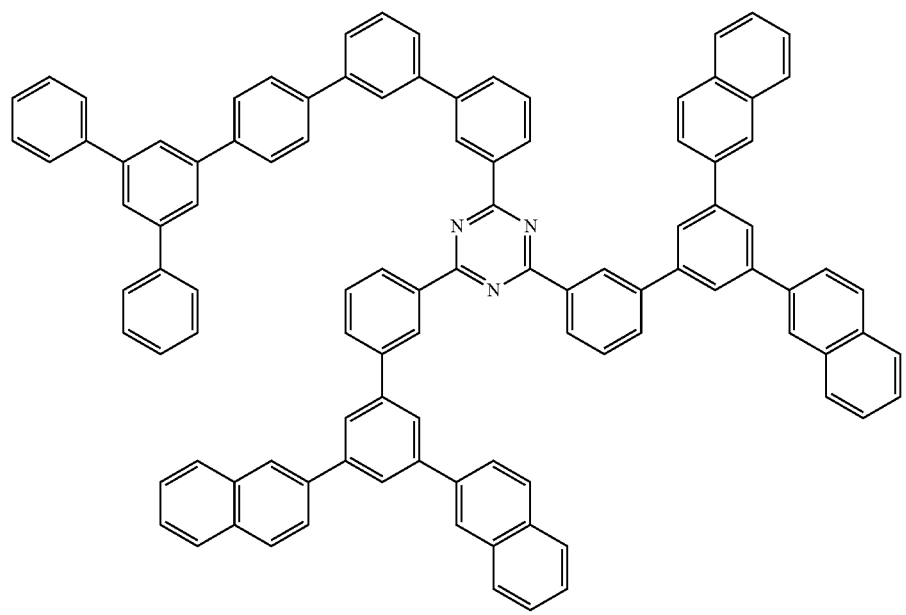
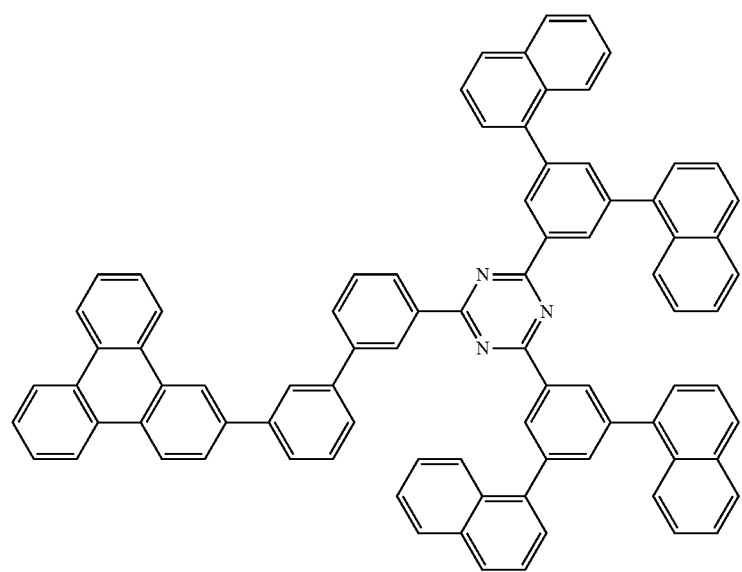

-continued
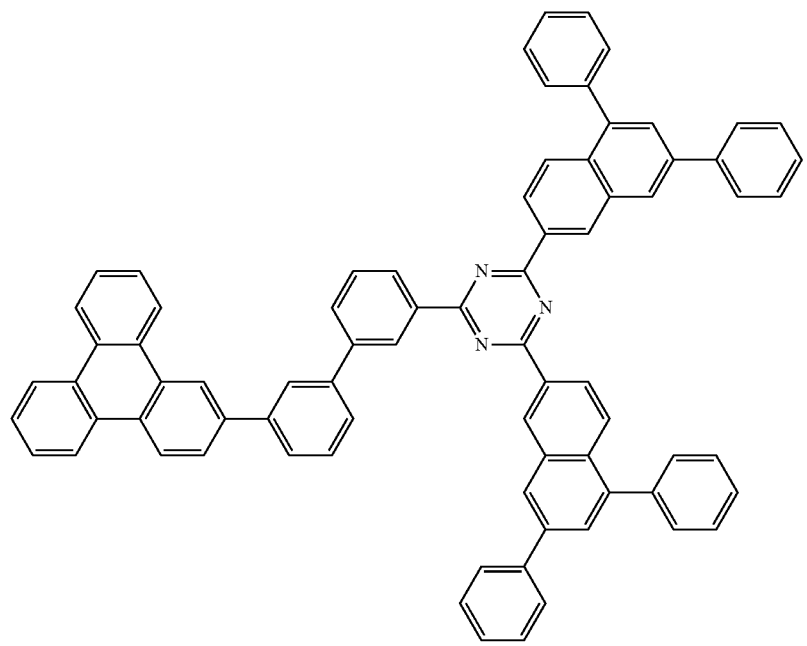
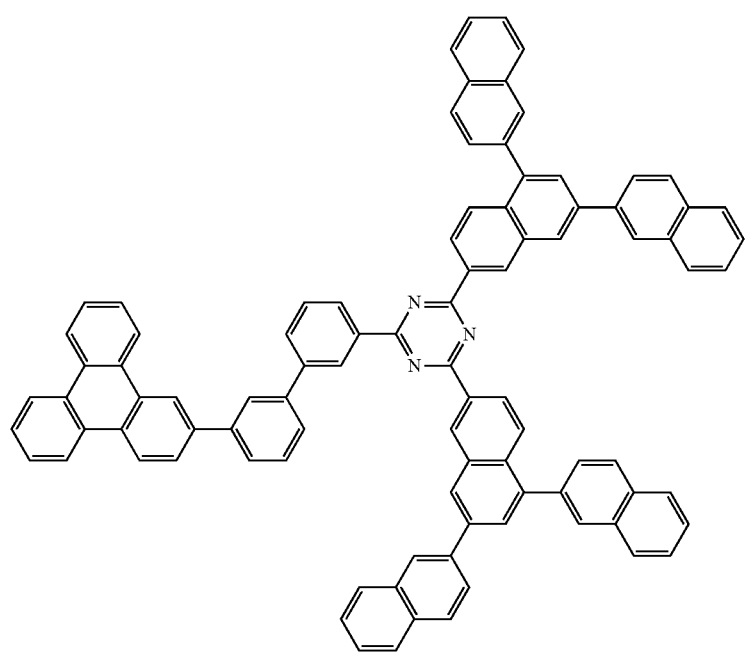

-continued
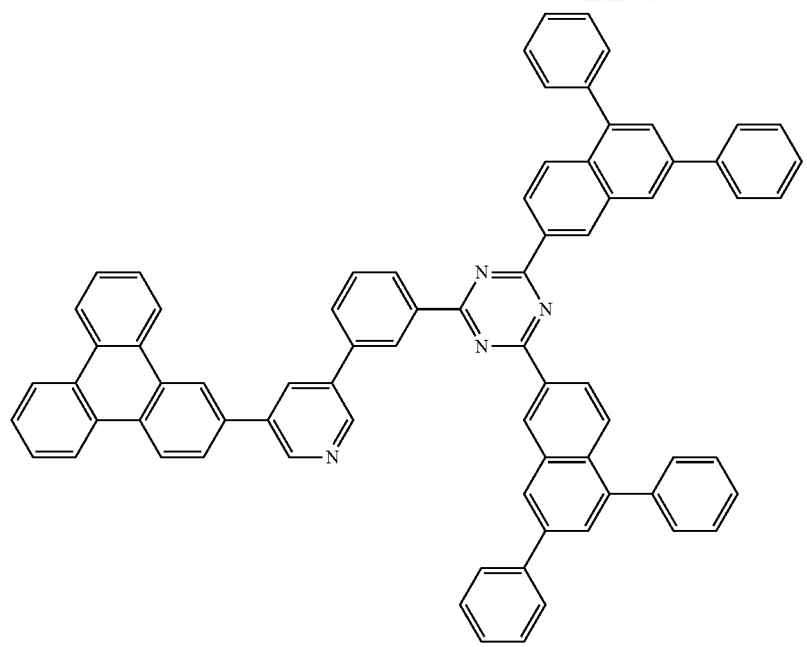
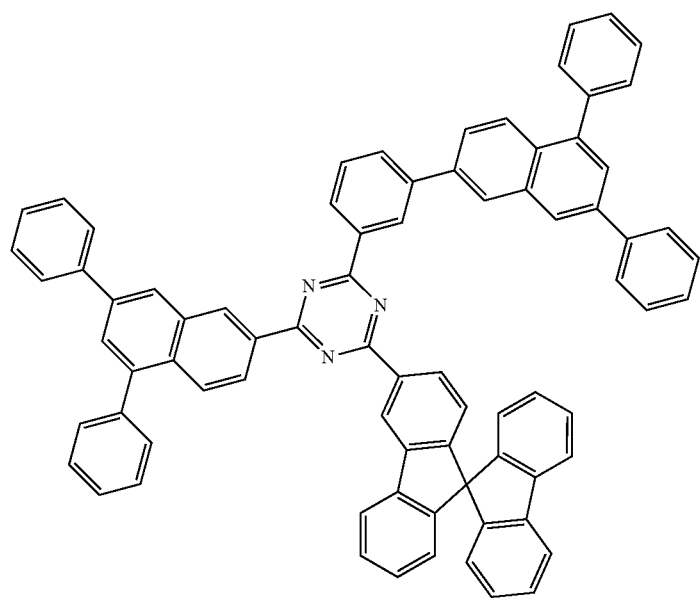

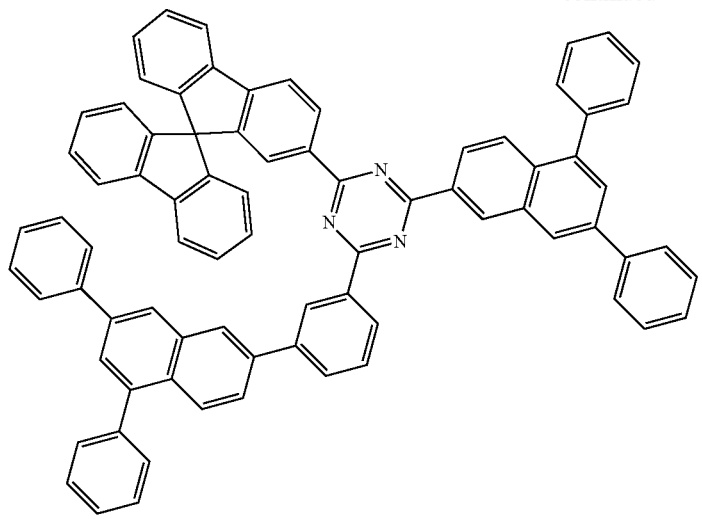
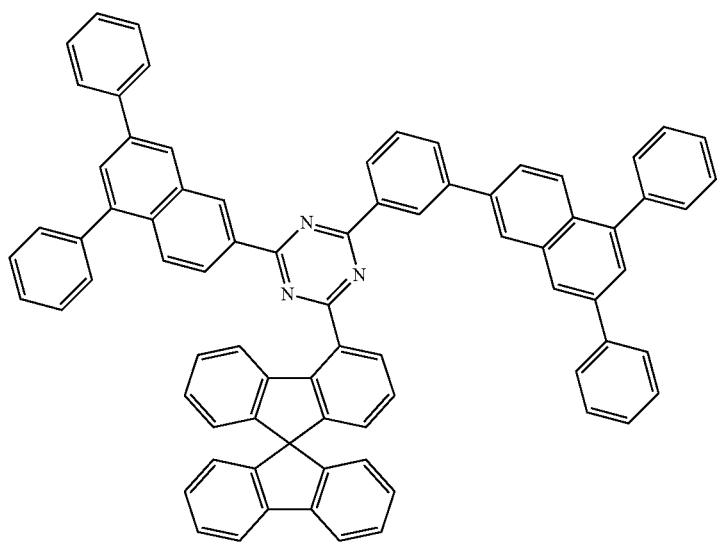
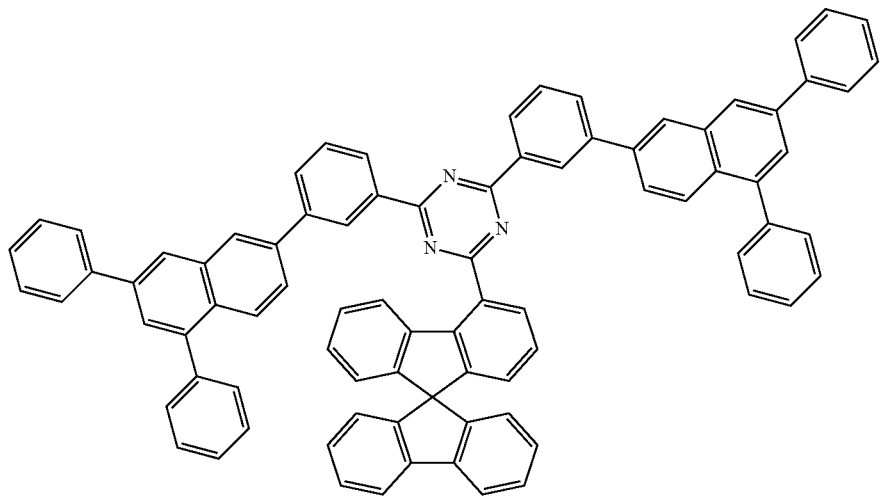

61 62
-continued
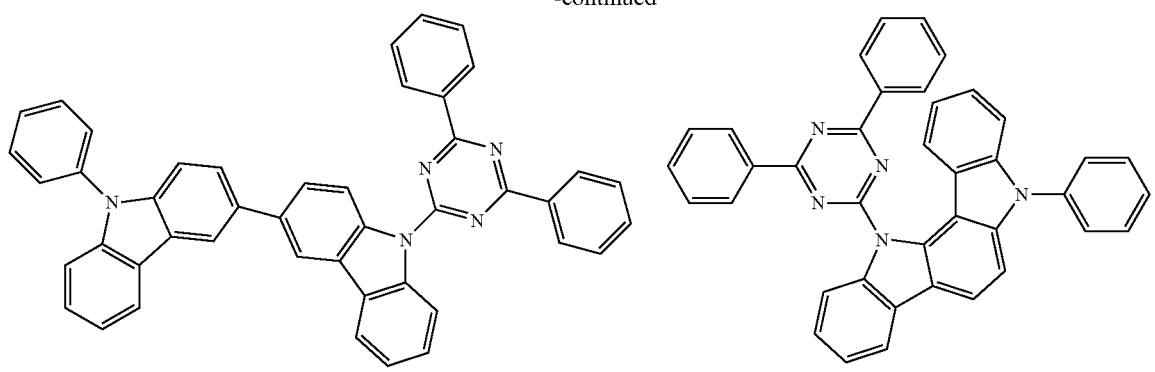
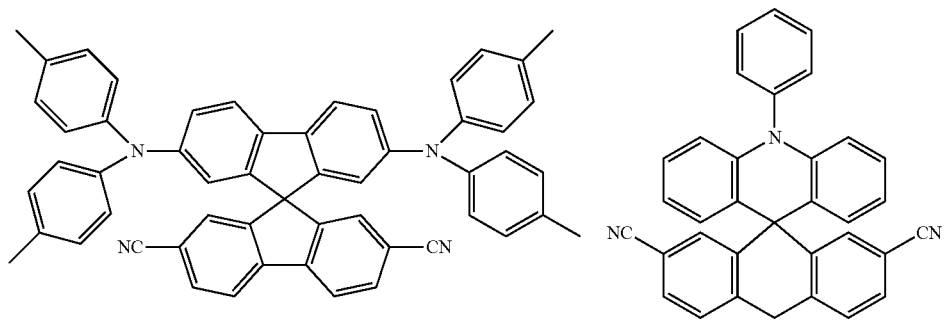
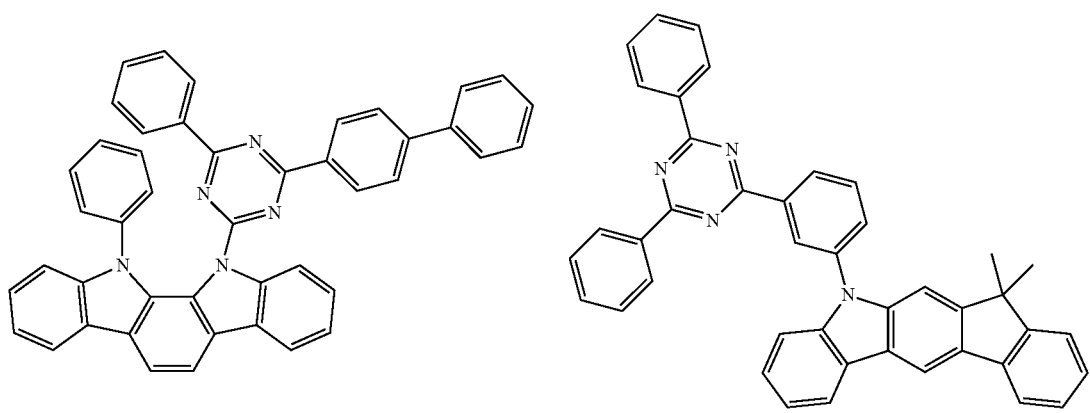
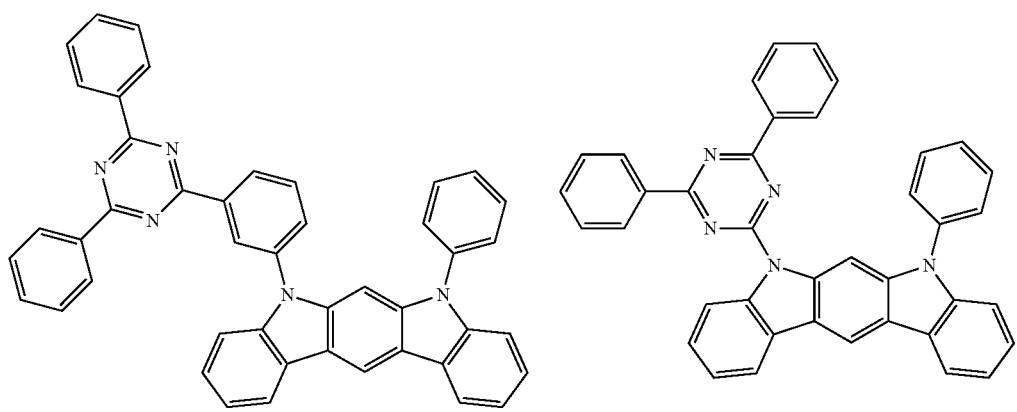

-continued
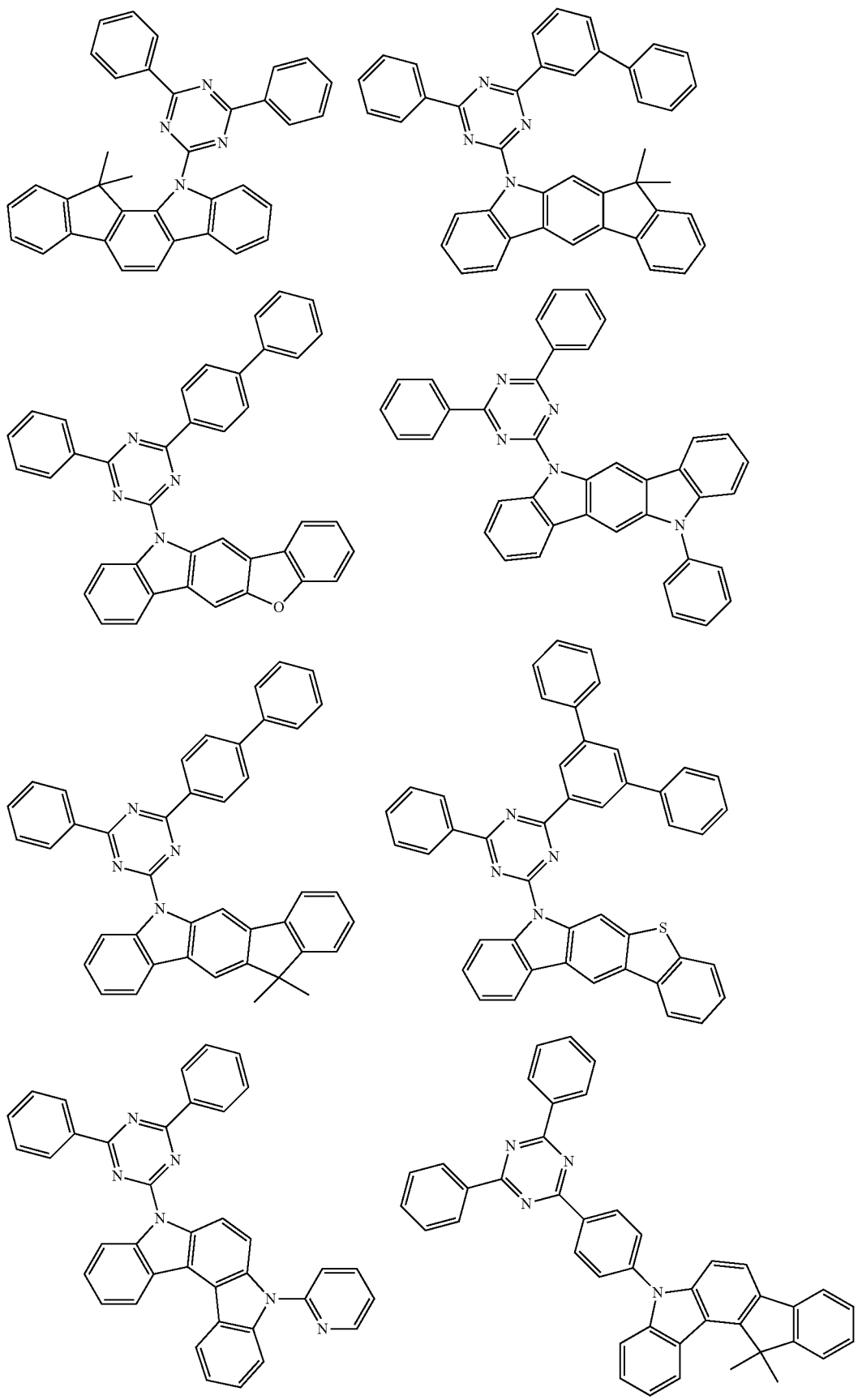

-continued
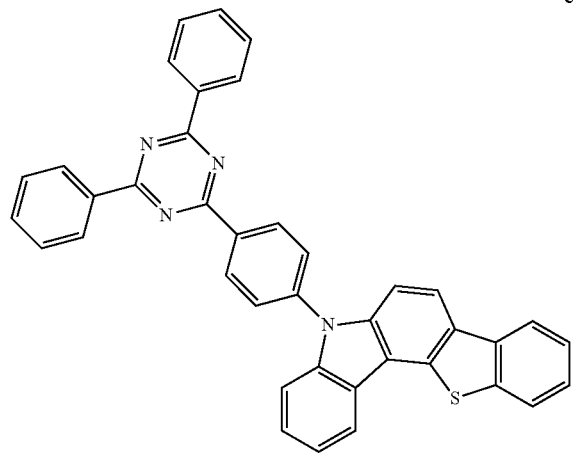
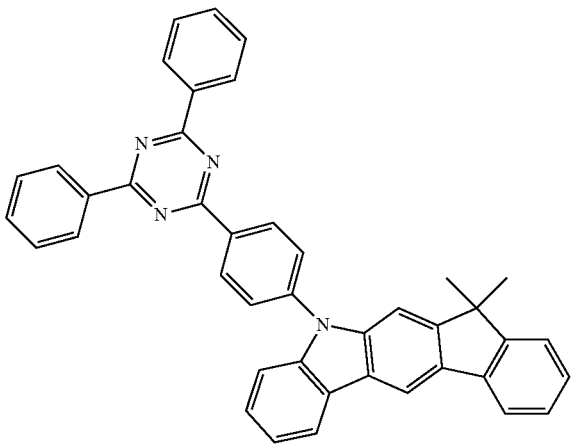
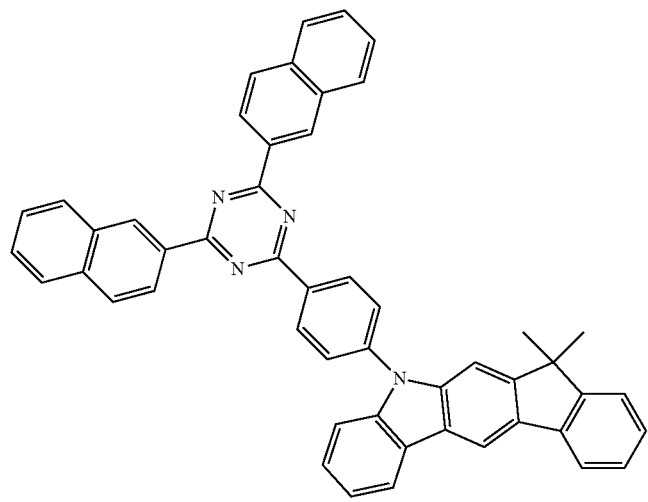
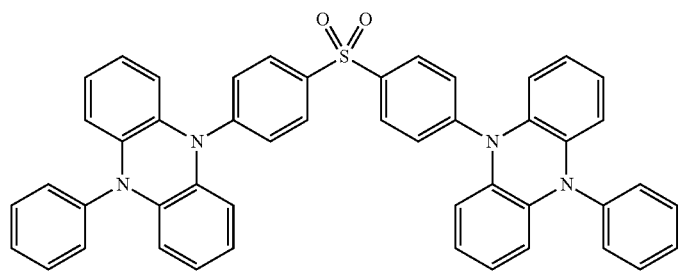
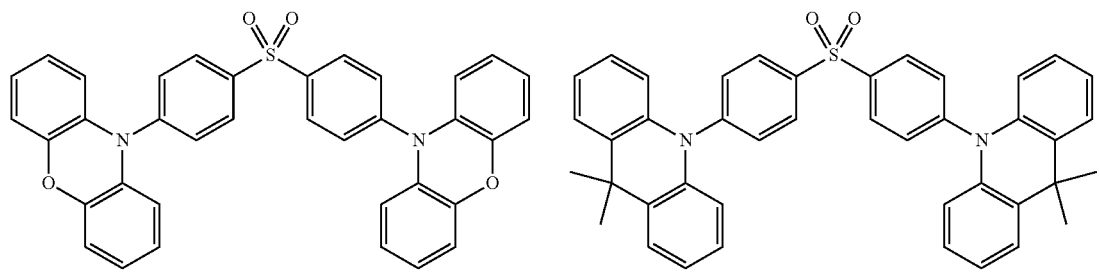

-continued
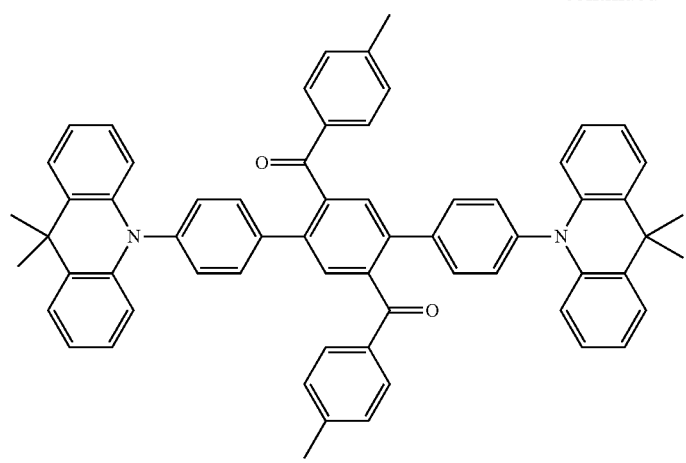
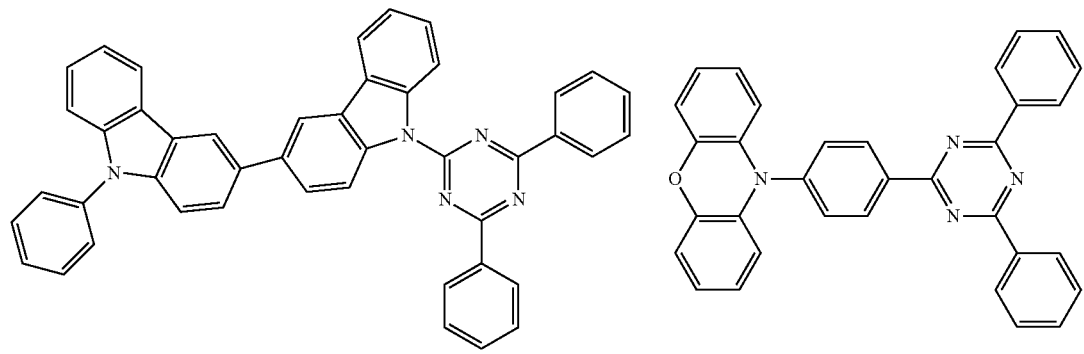
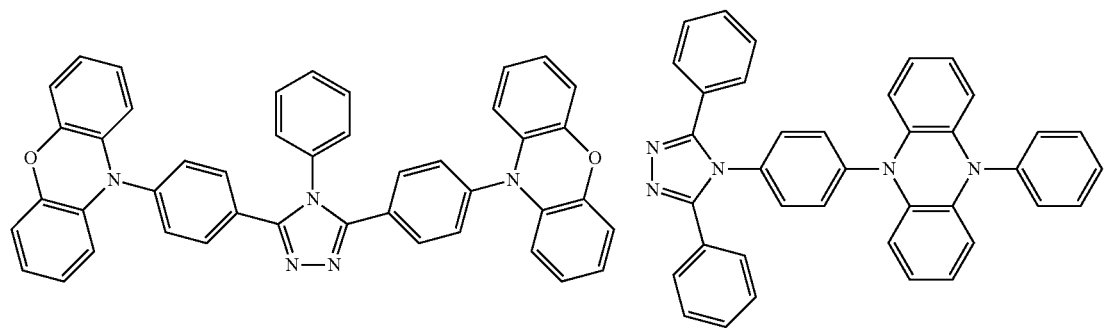
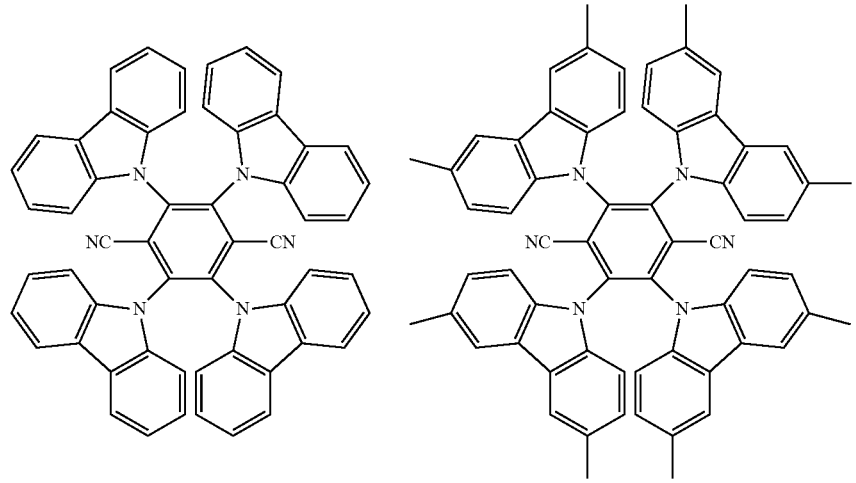

-continued
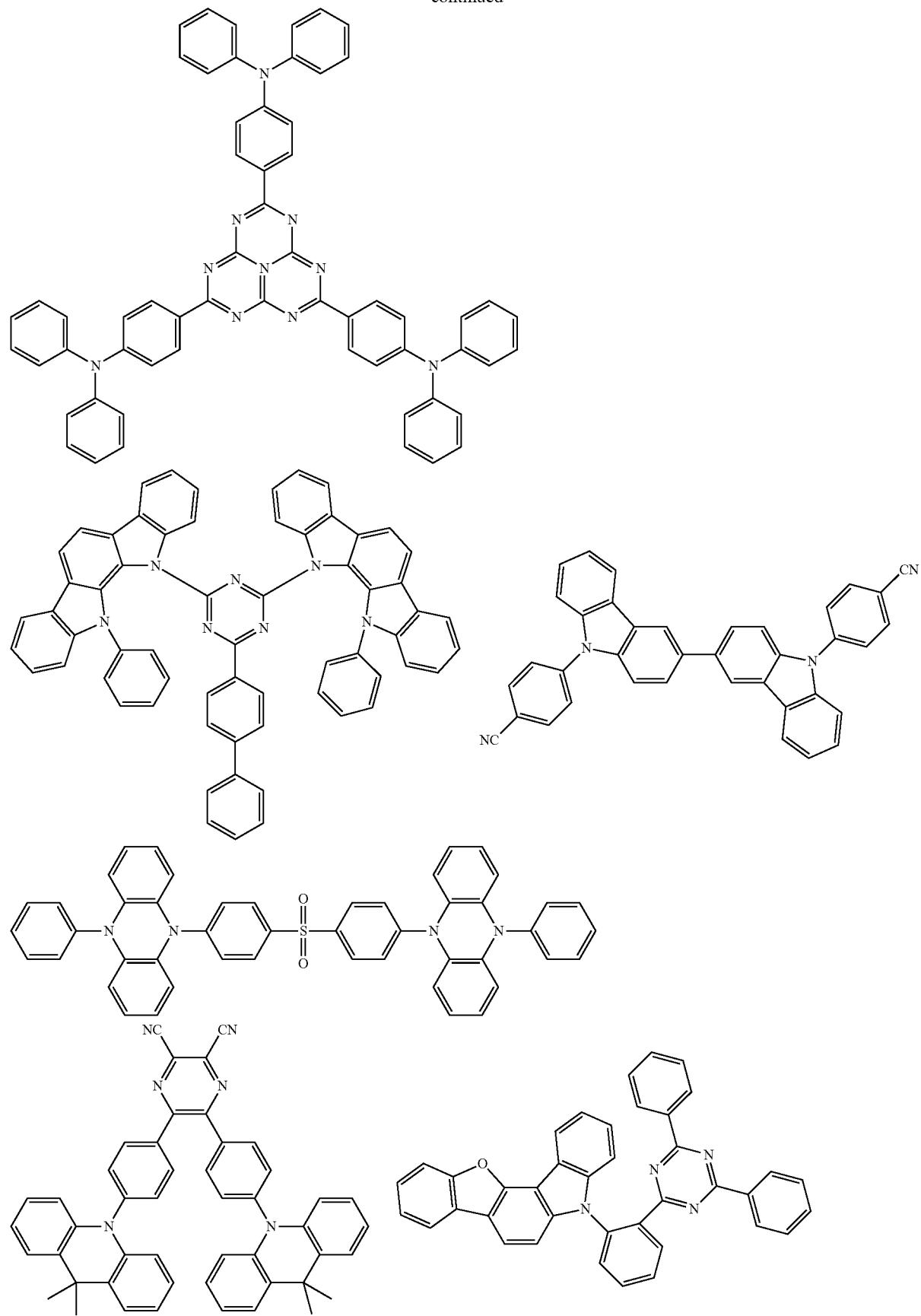

-continued
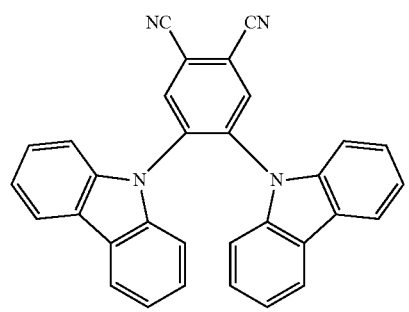
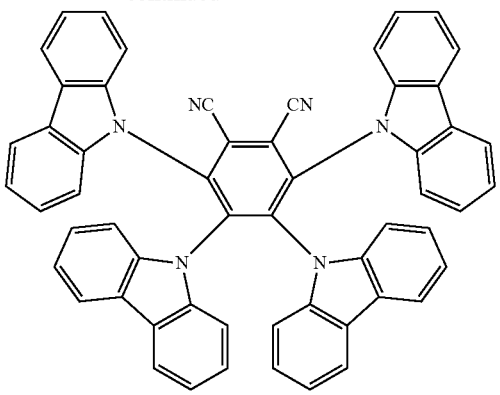
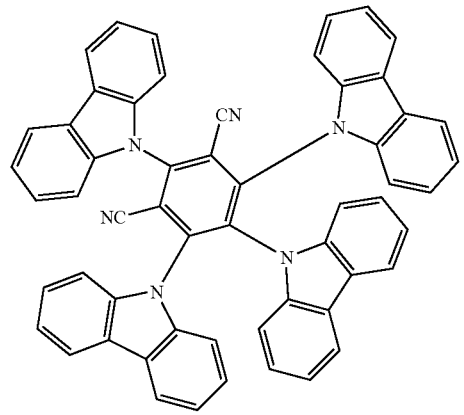
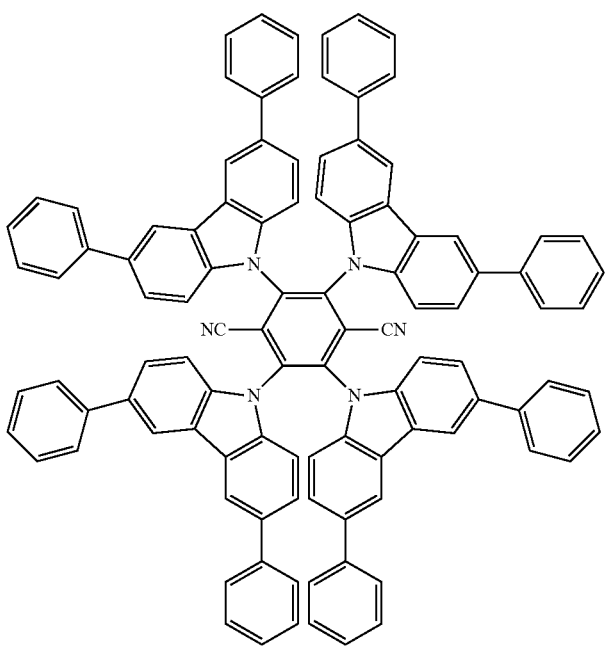
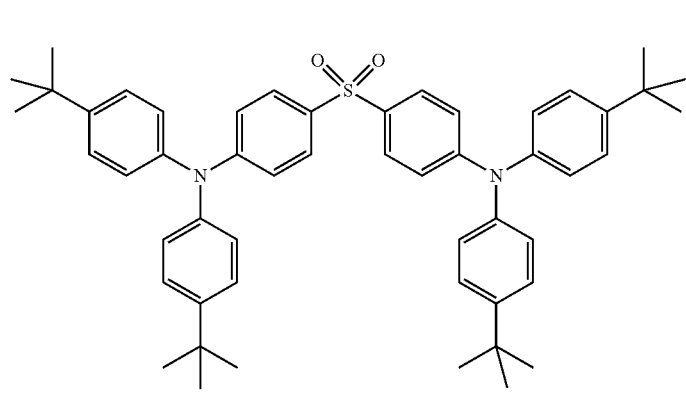
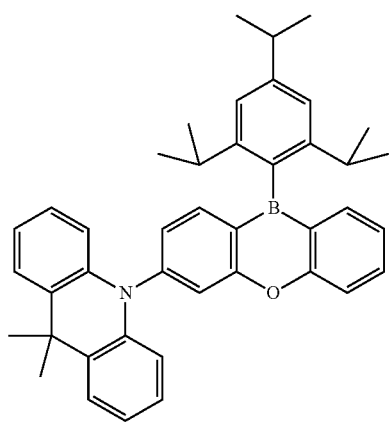

-continued
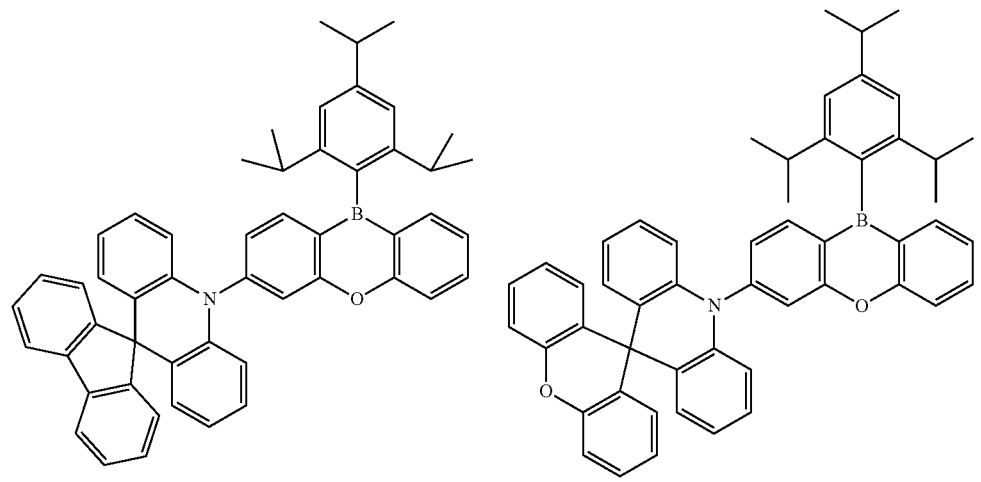
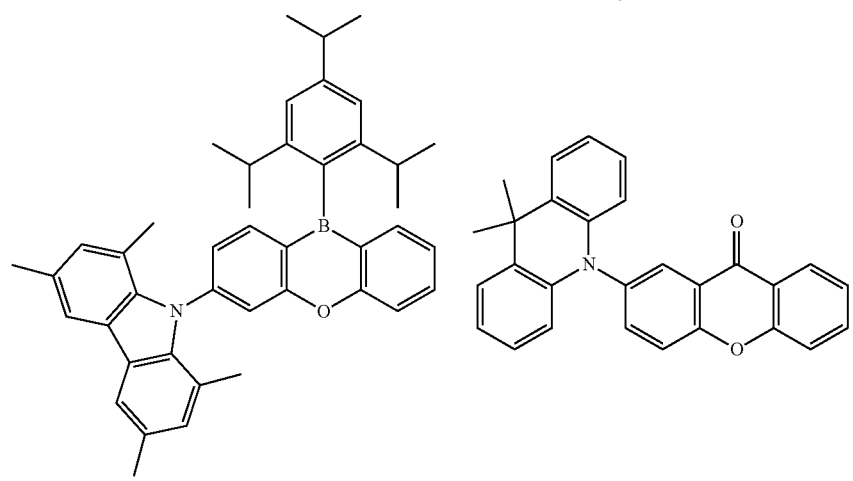
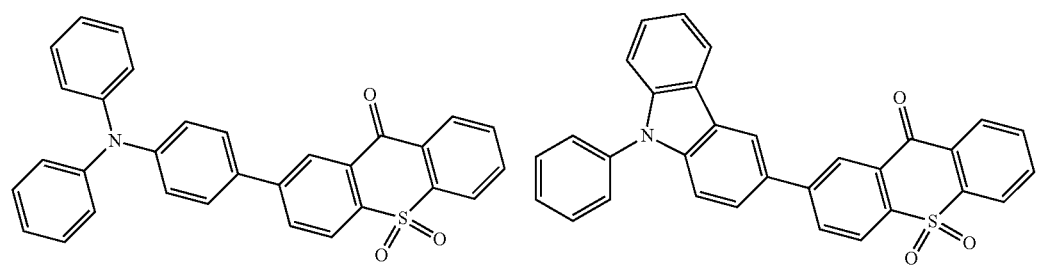
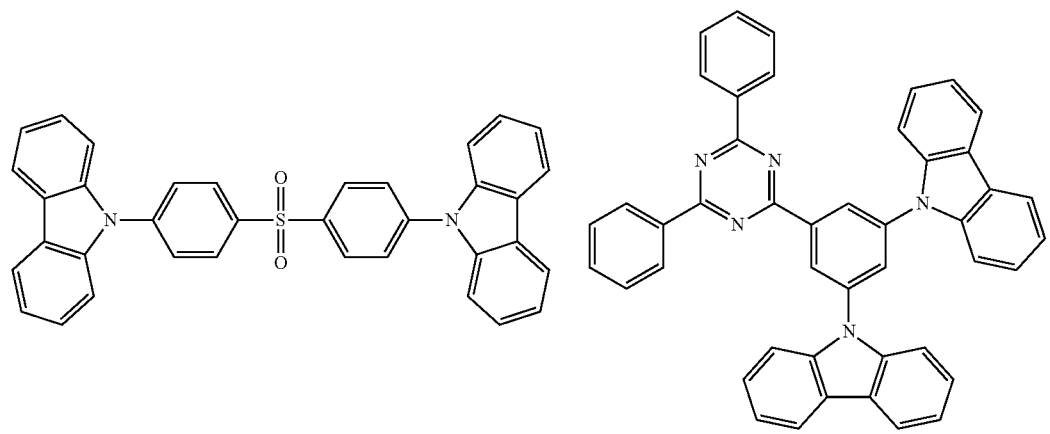

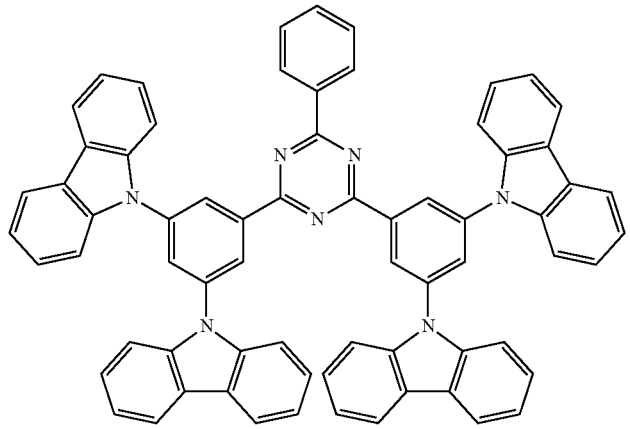
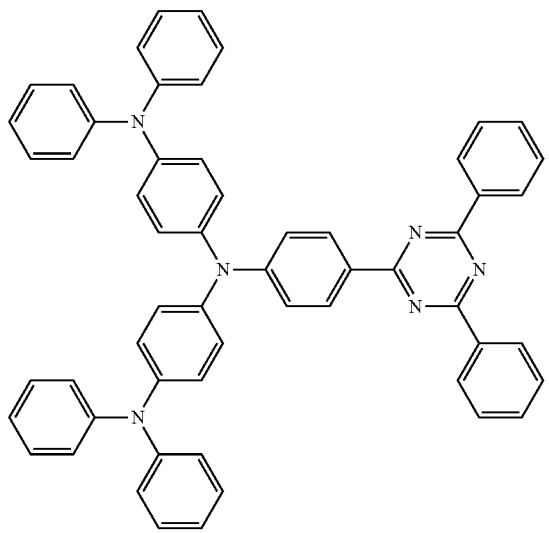
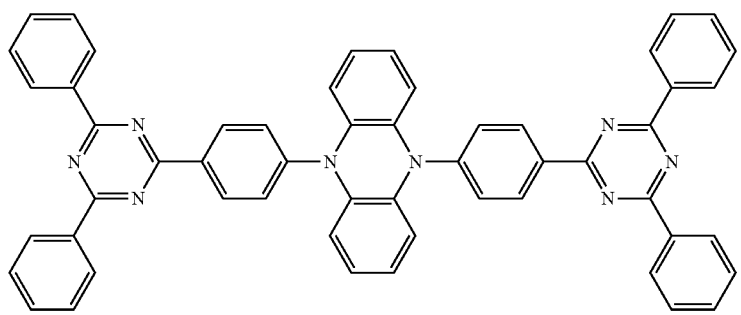
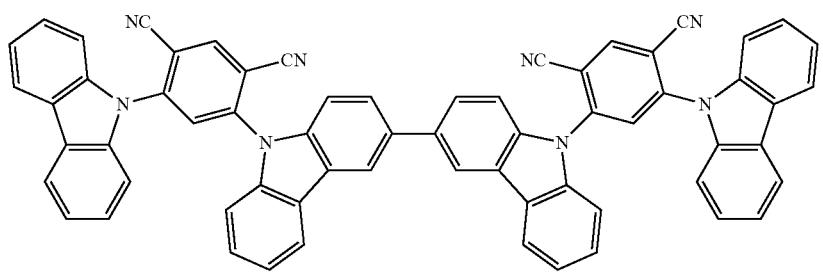
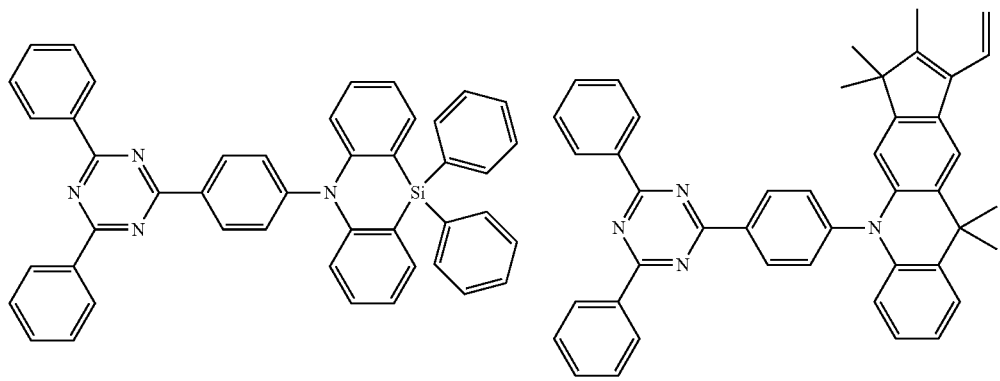

-continued
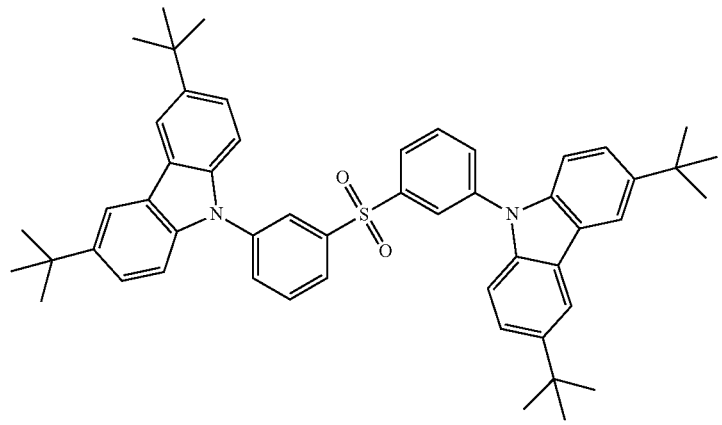
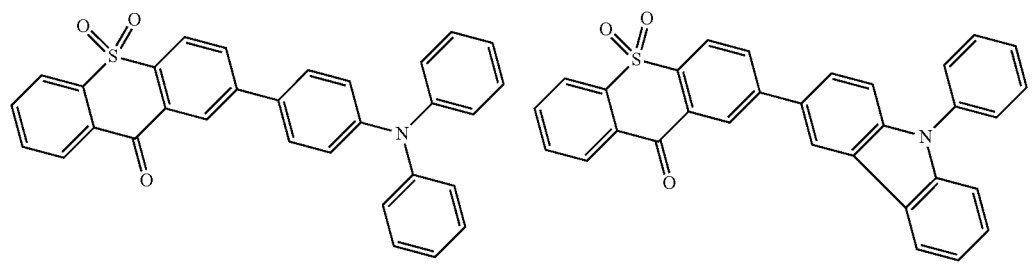
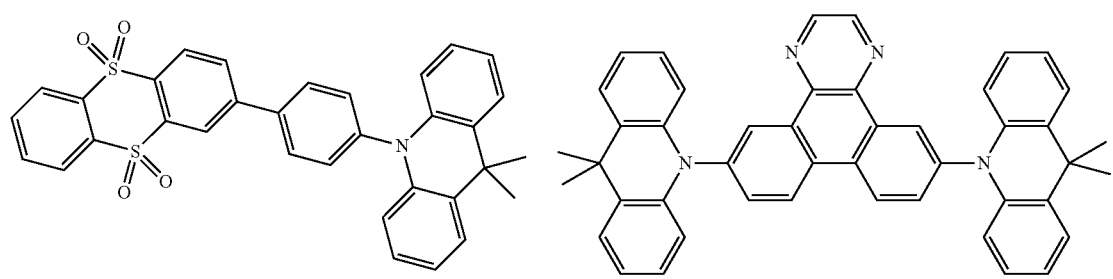
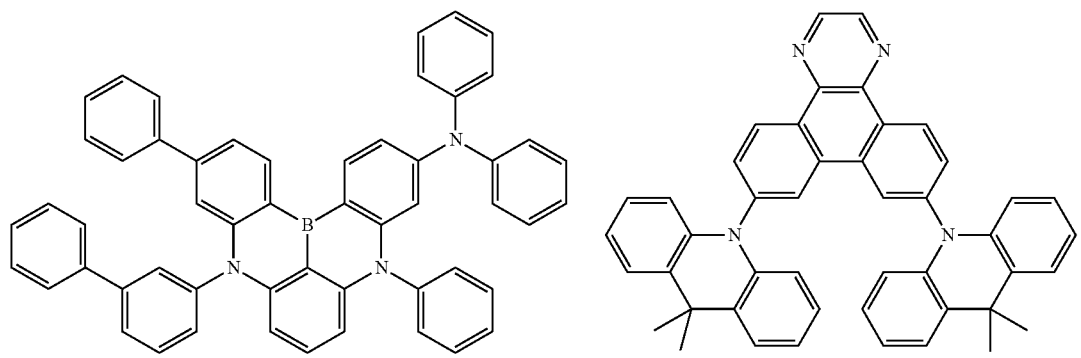

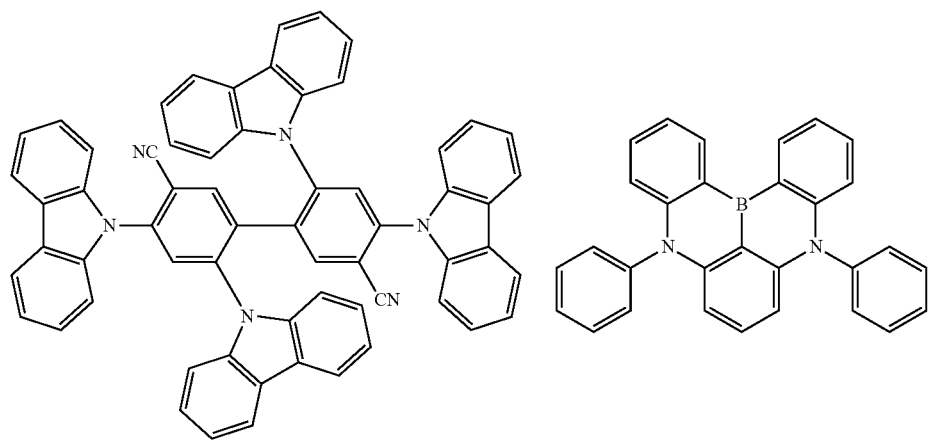
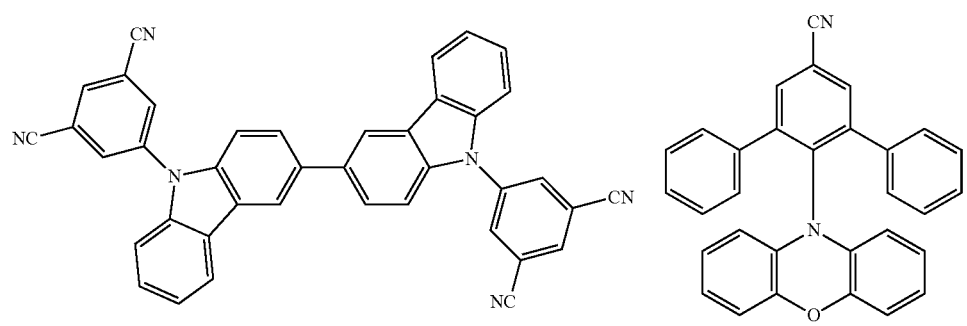
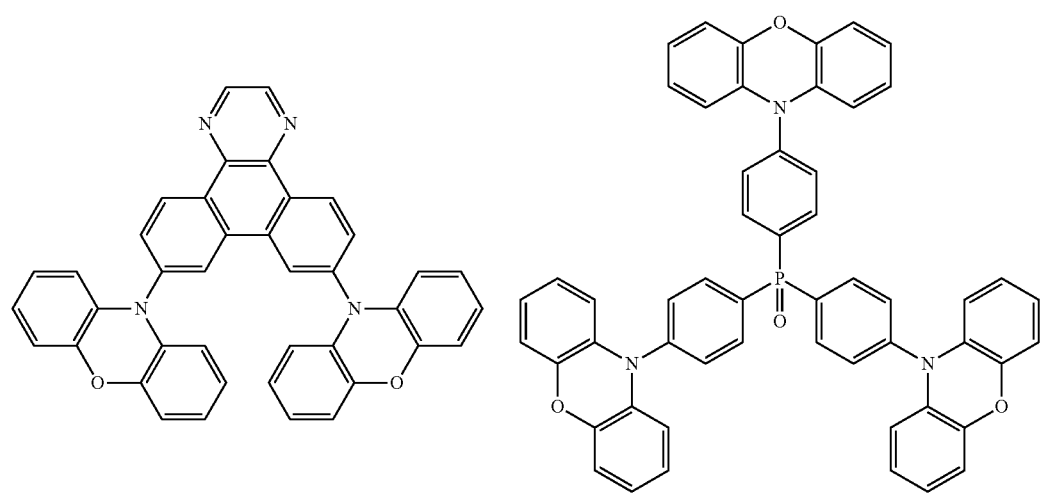

81
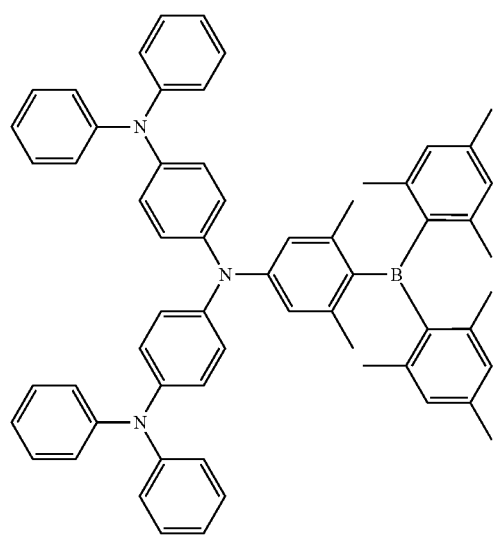
82
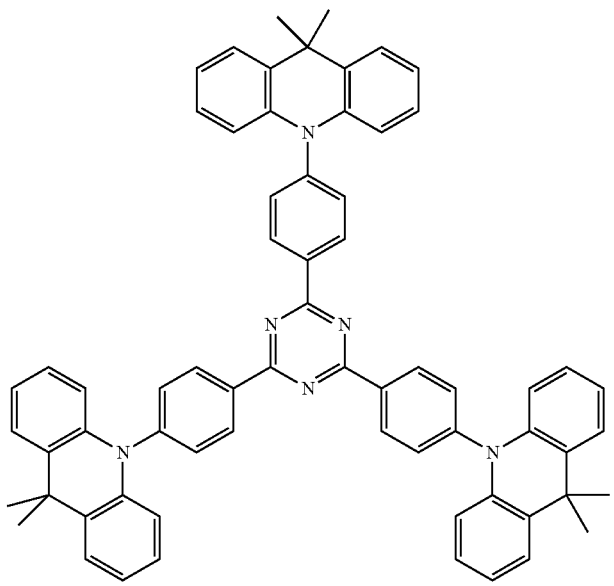
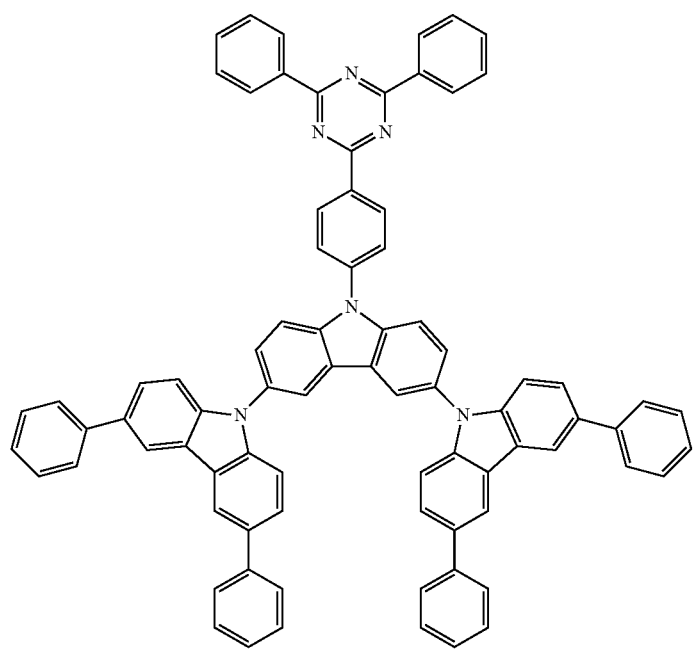

-continued
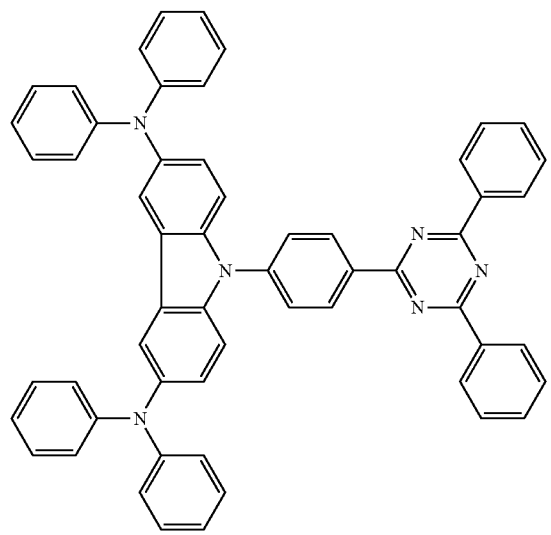
Specific examples that can be used as H2 are listed below, but are not limited to:
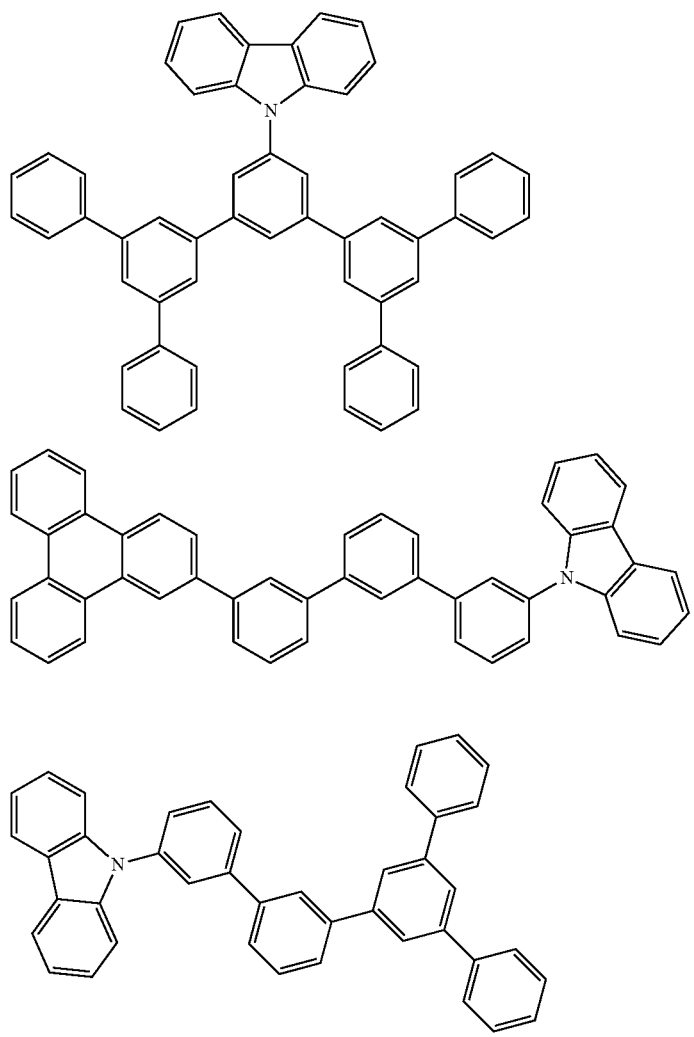

-continued
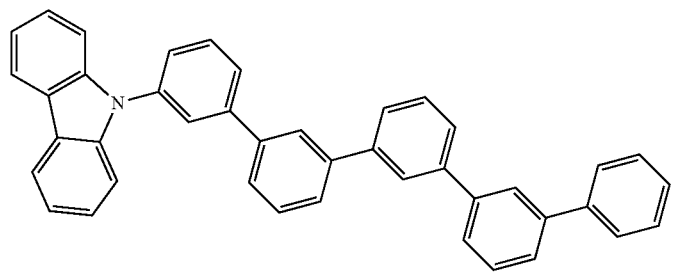
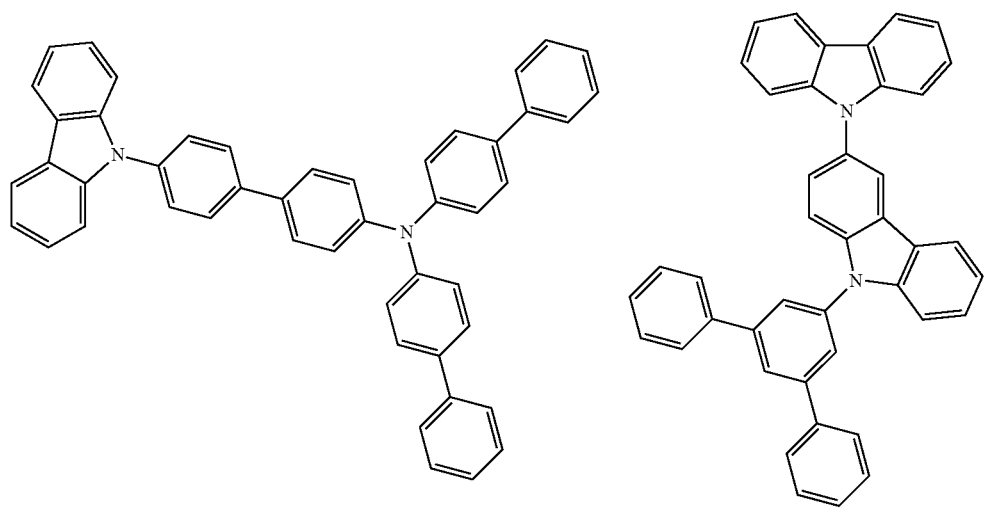
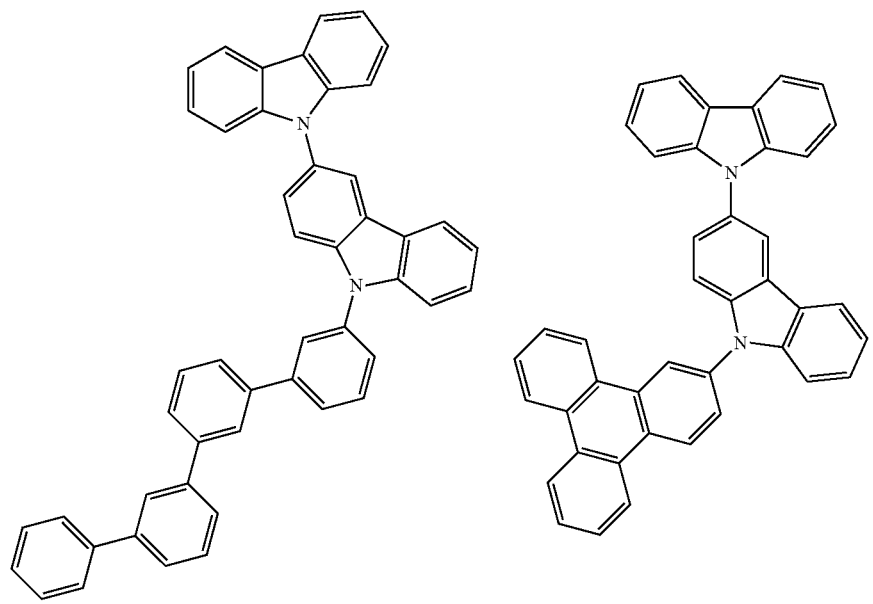

-continued
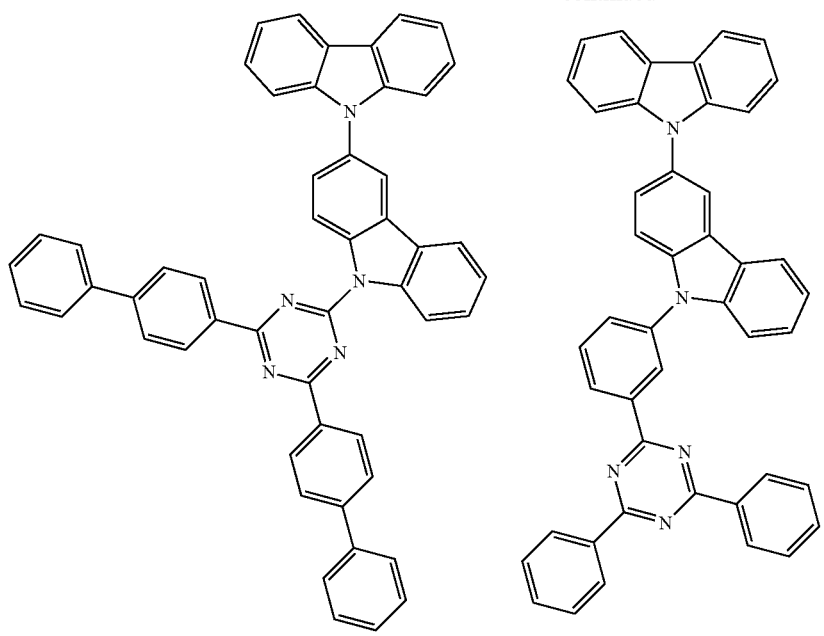
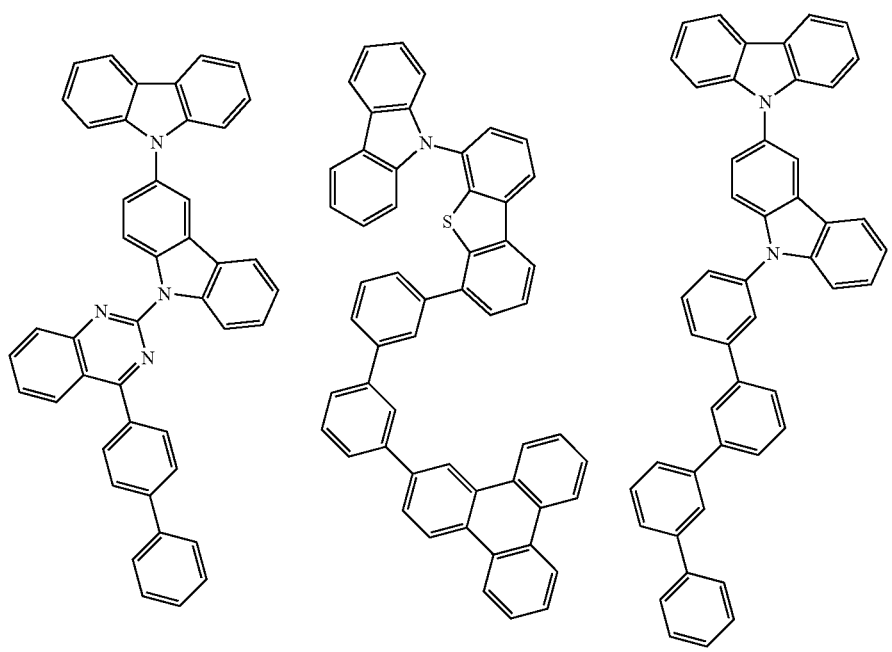

-continued
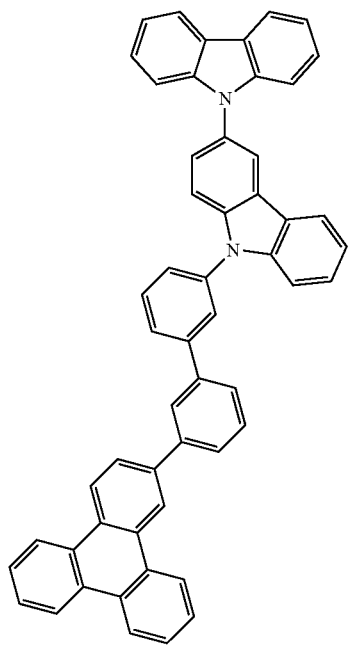
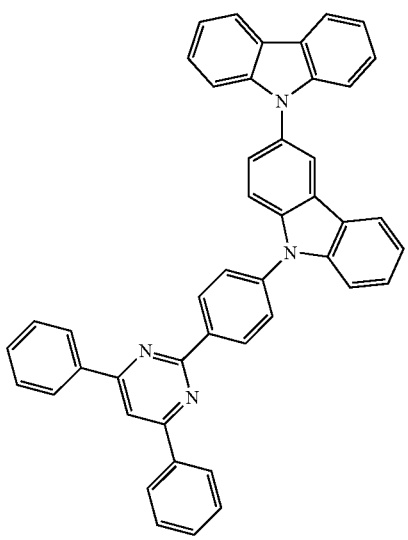
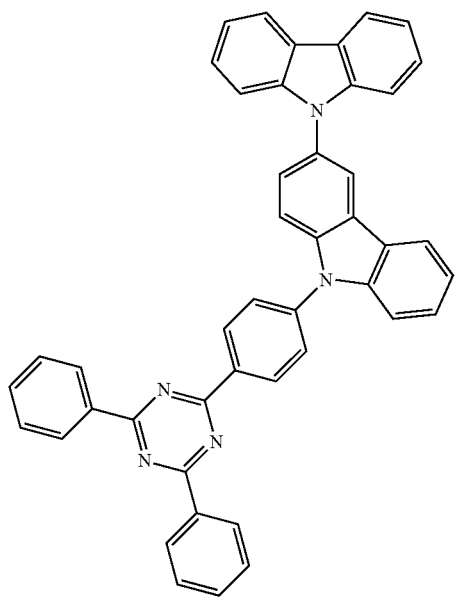
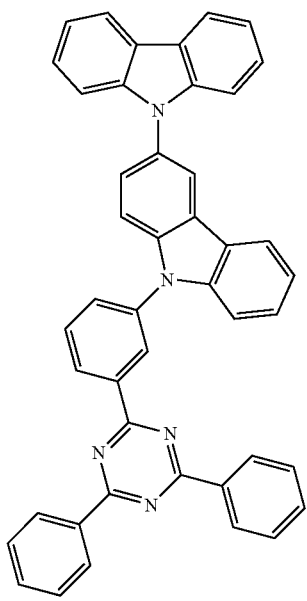

-continued
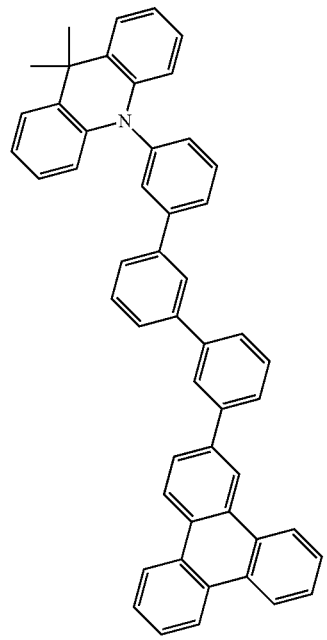 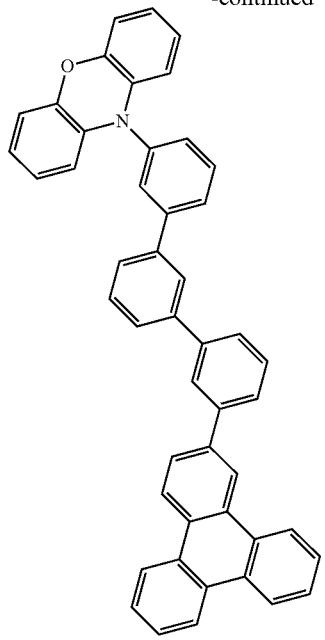 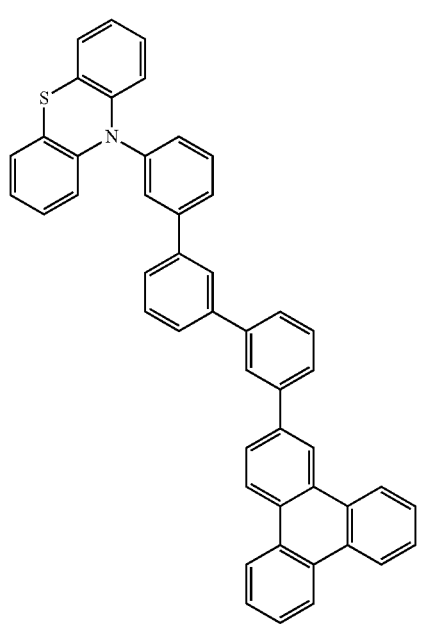
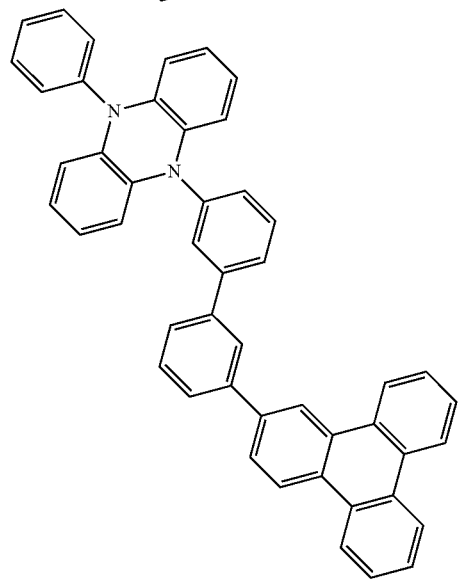 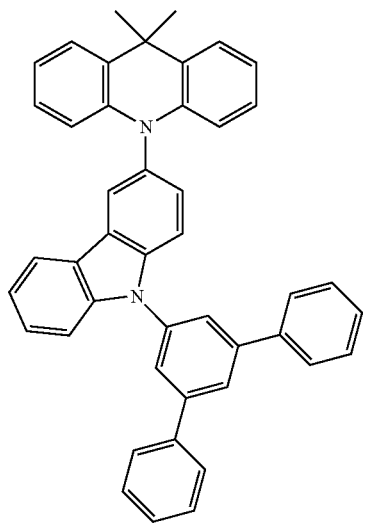
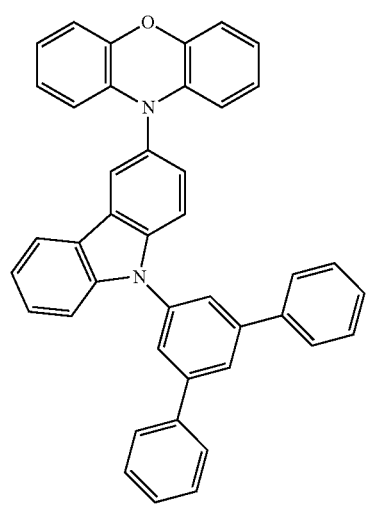 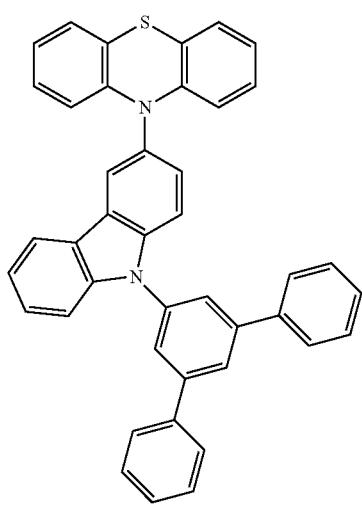 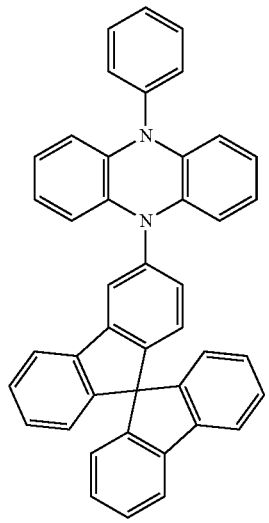

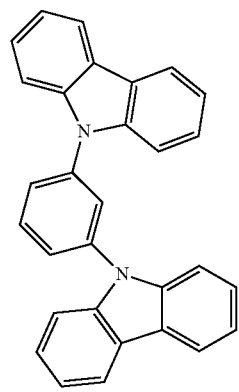
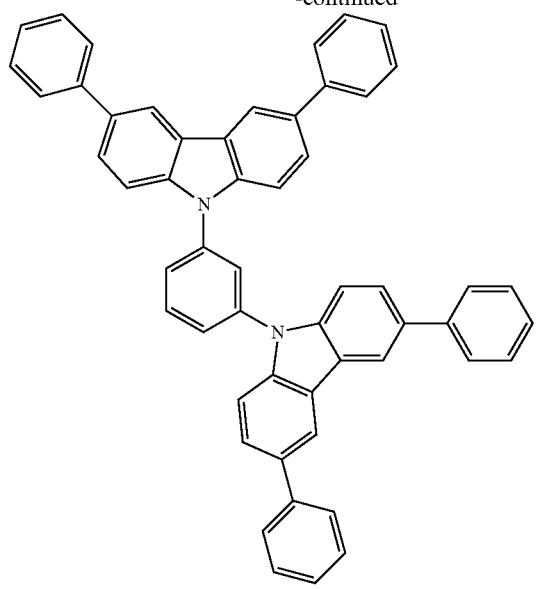
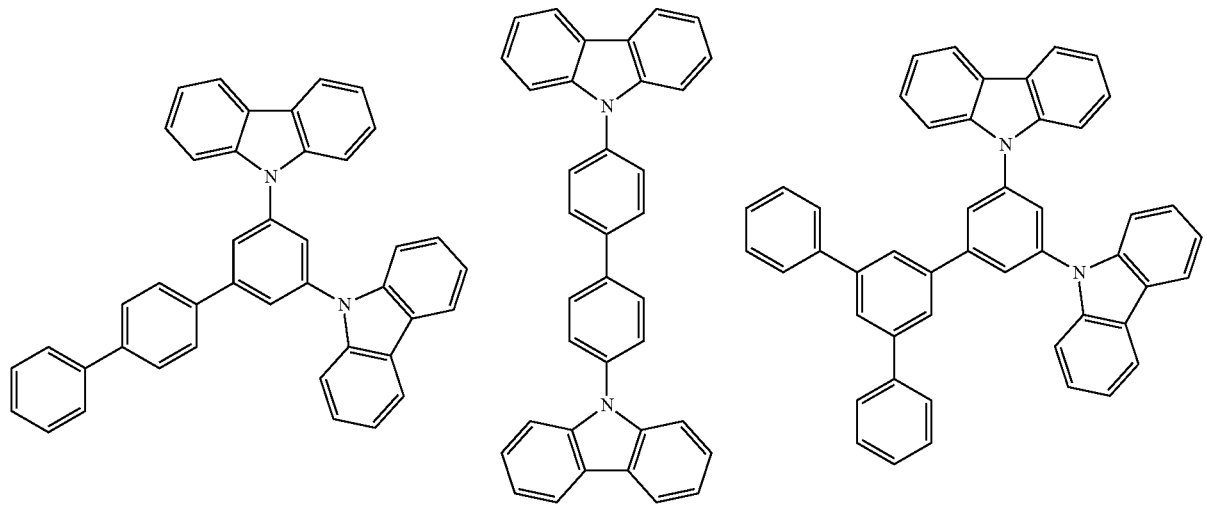
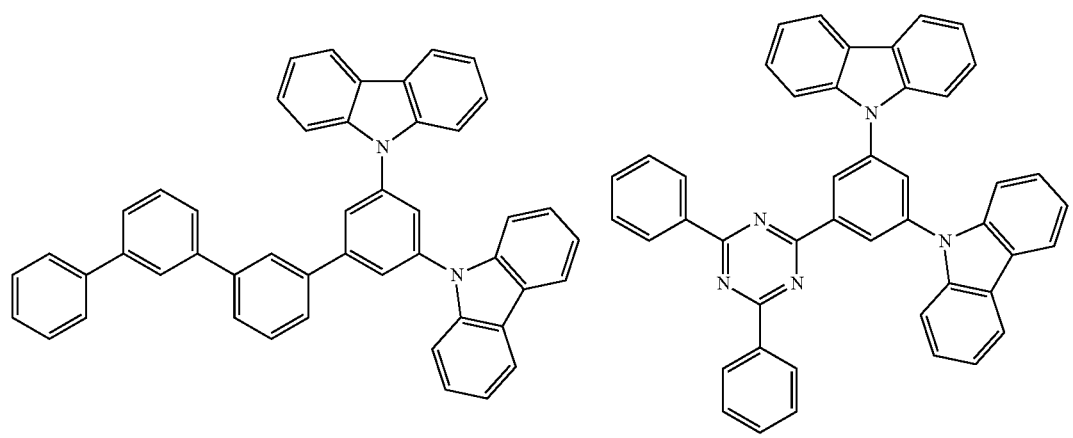

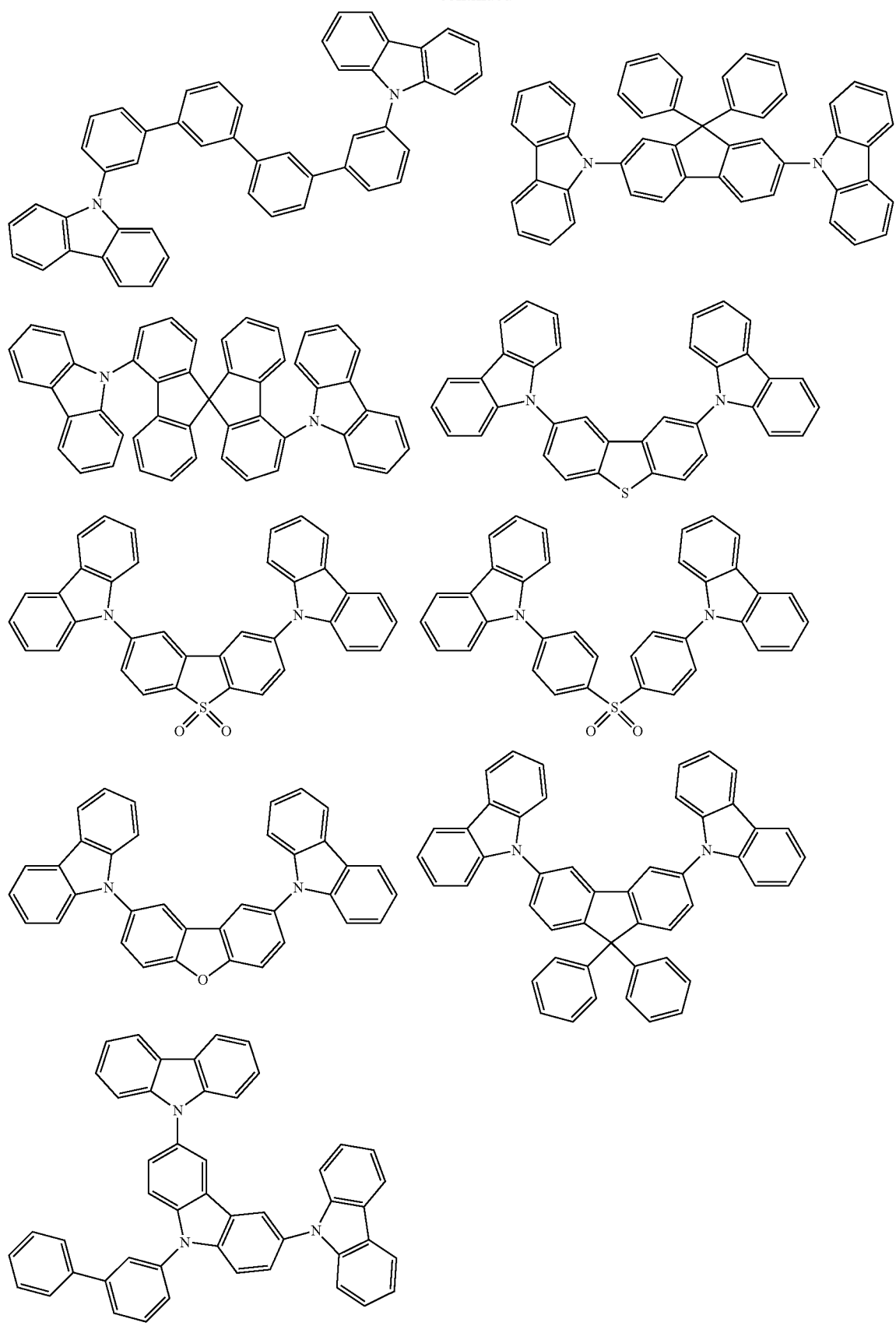

-continued
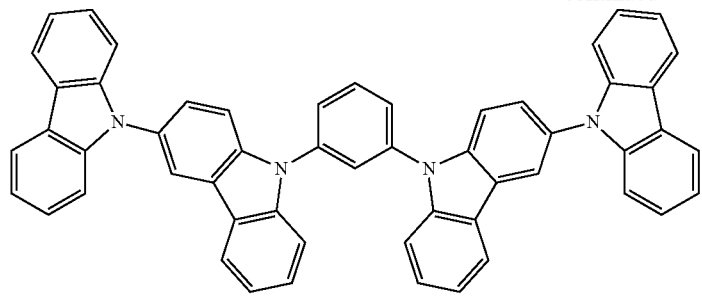
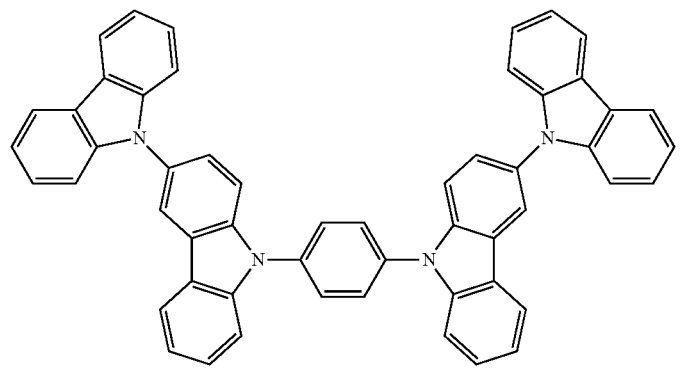
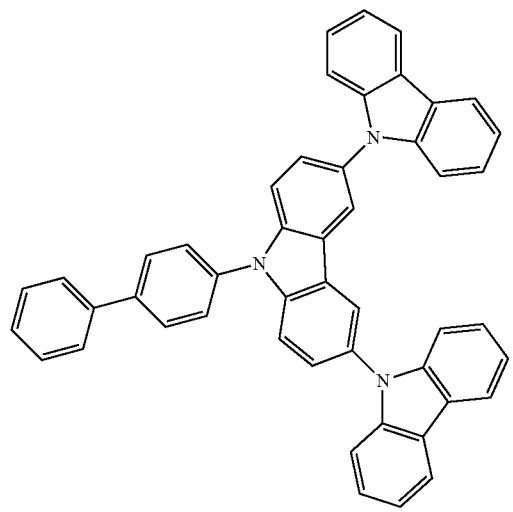
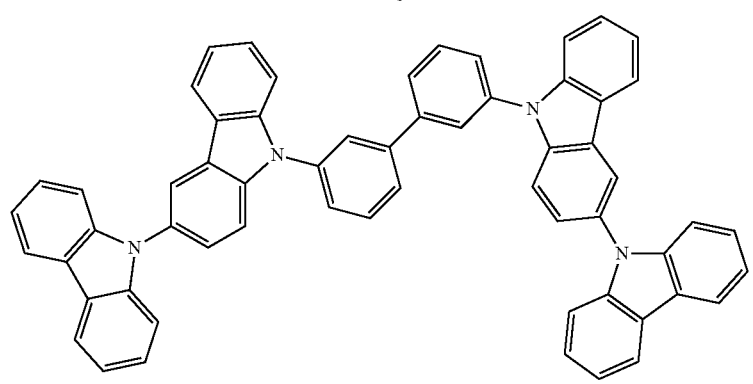

-continued
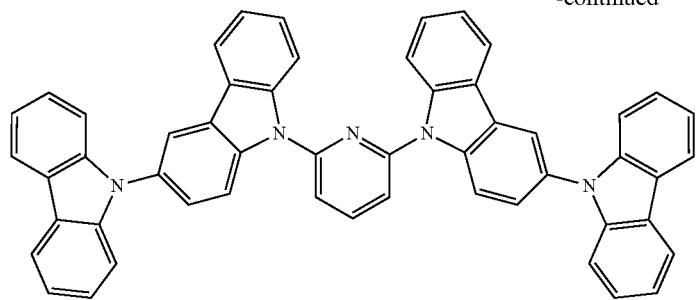
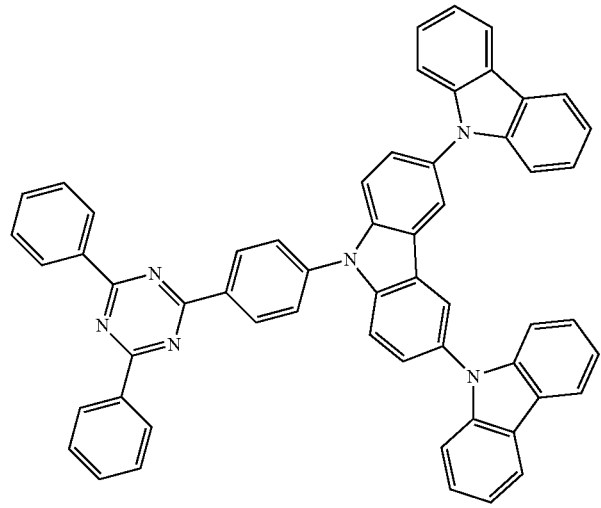
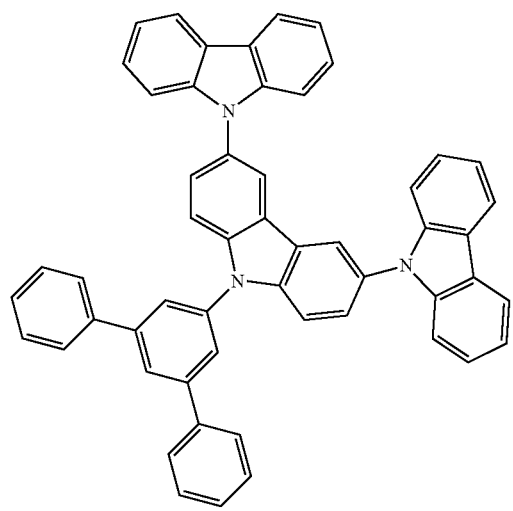
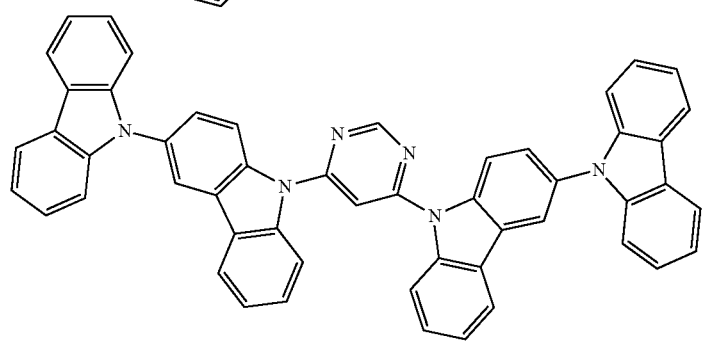

-continued
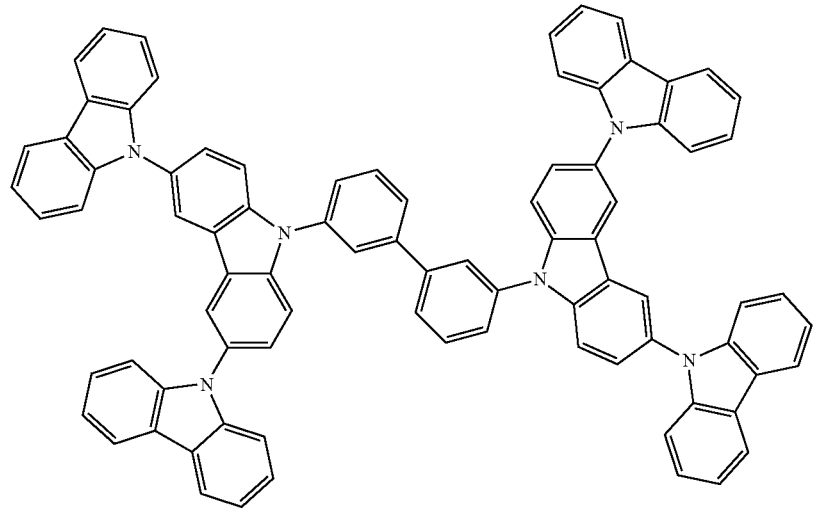
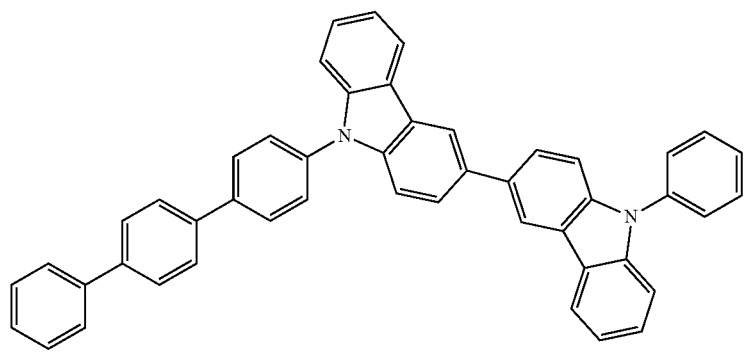
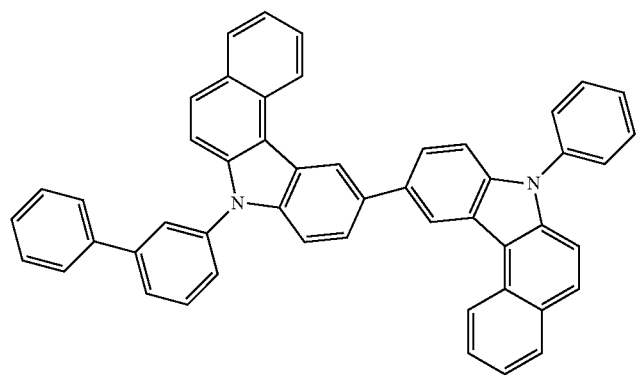
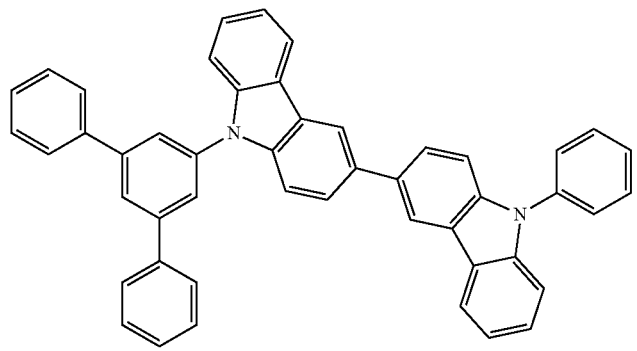

-continued
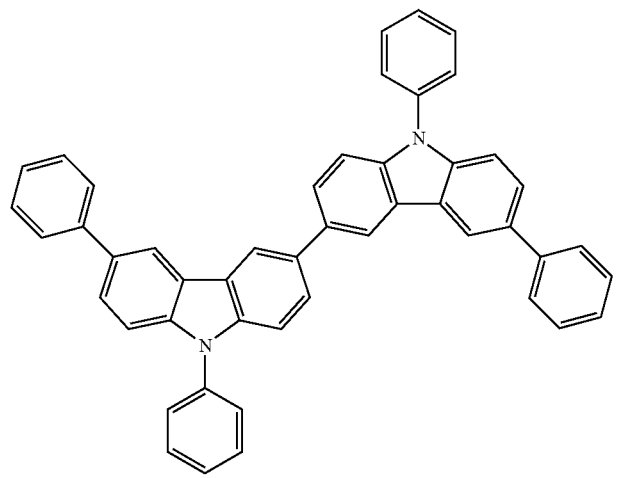
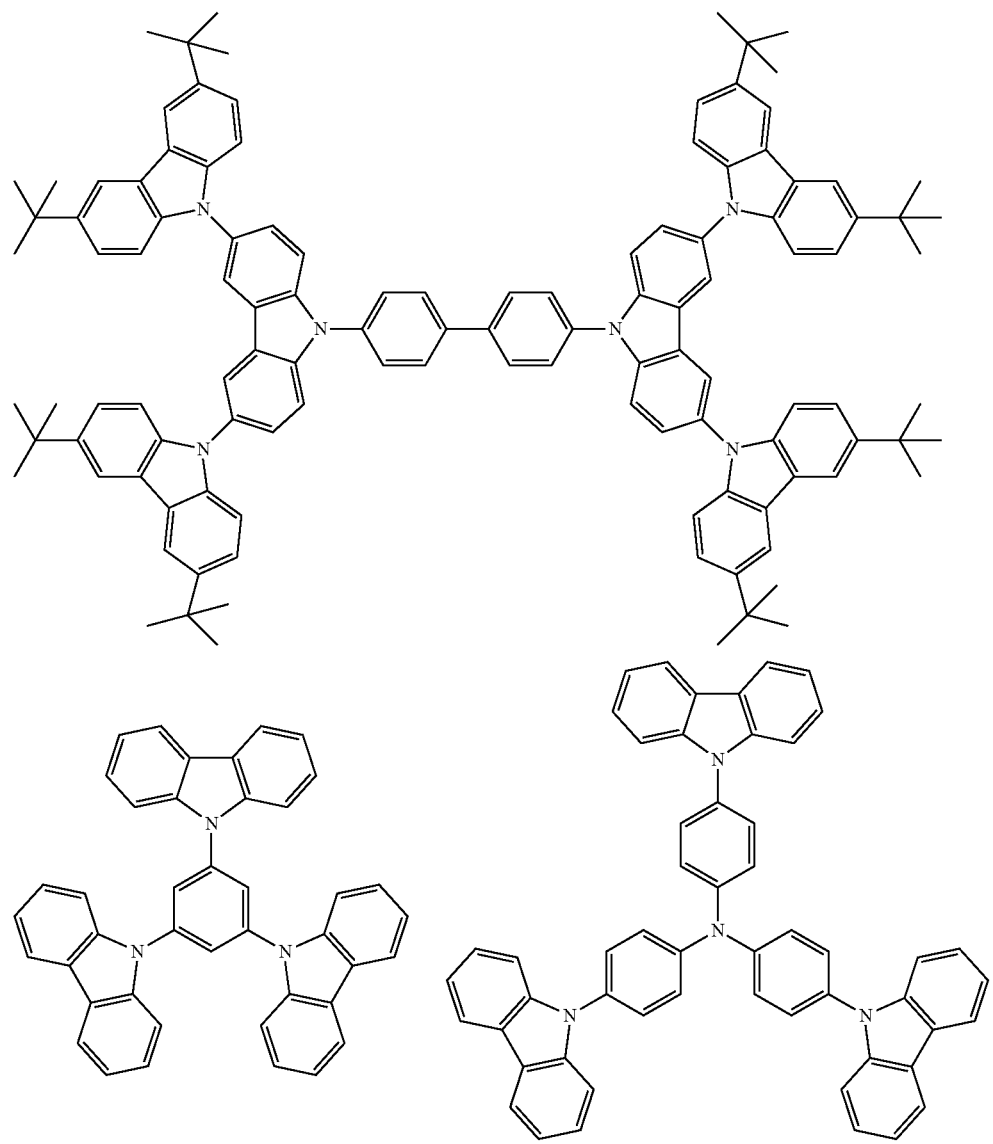

-continued
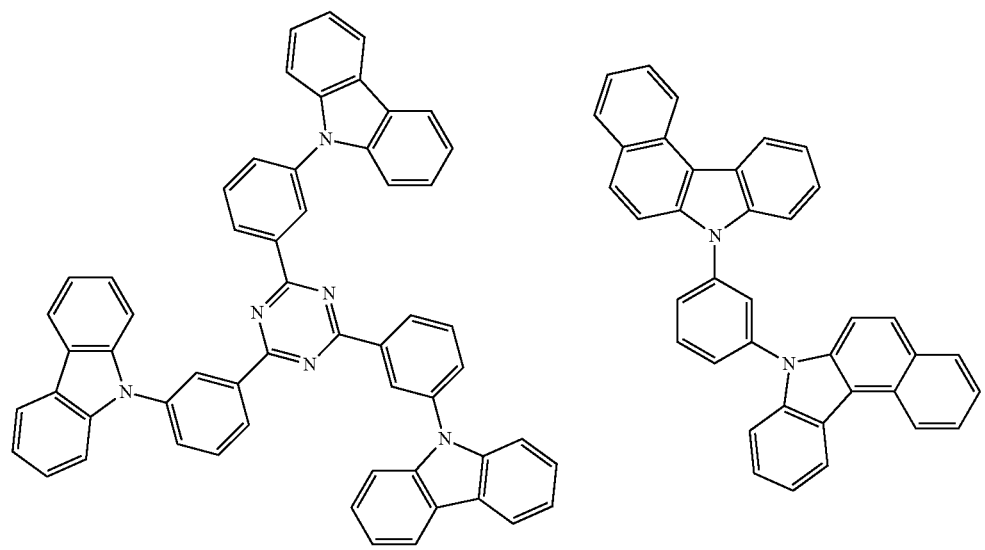
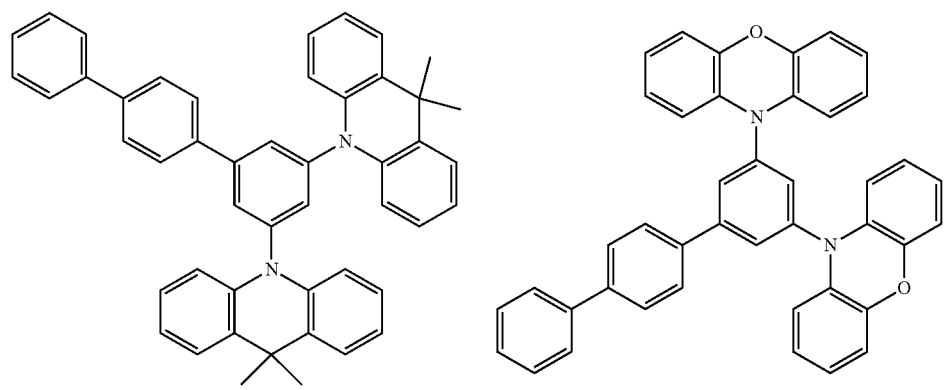
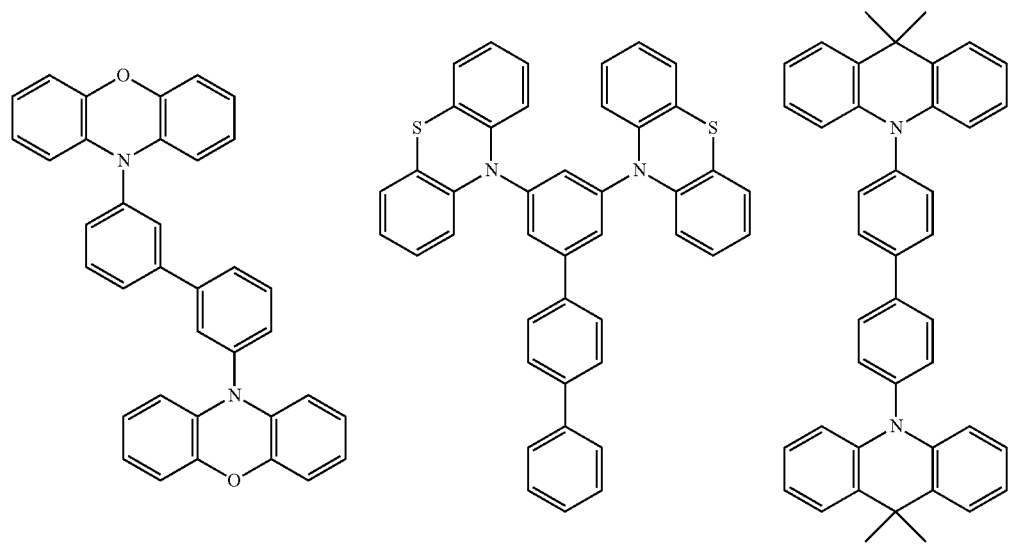

-continued
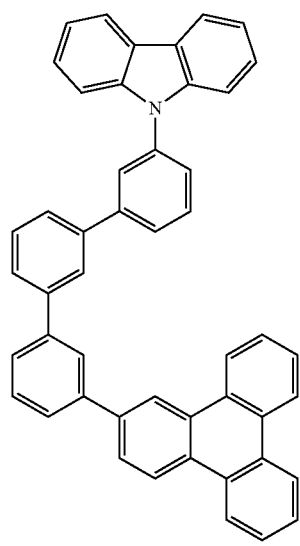
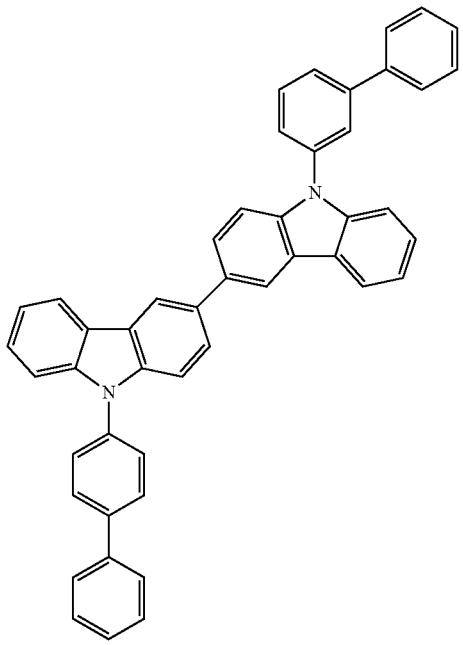
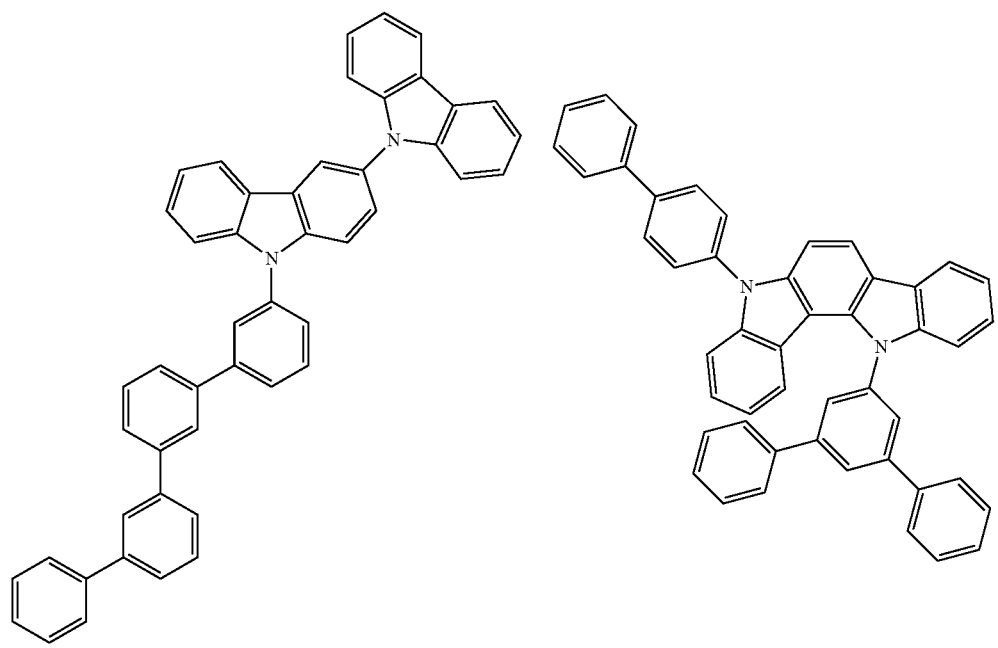
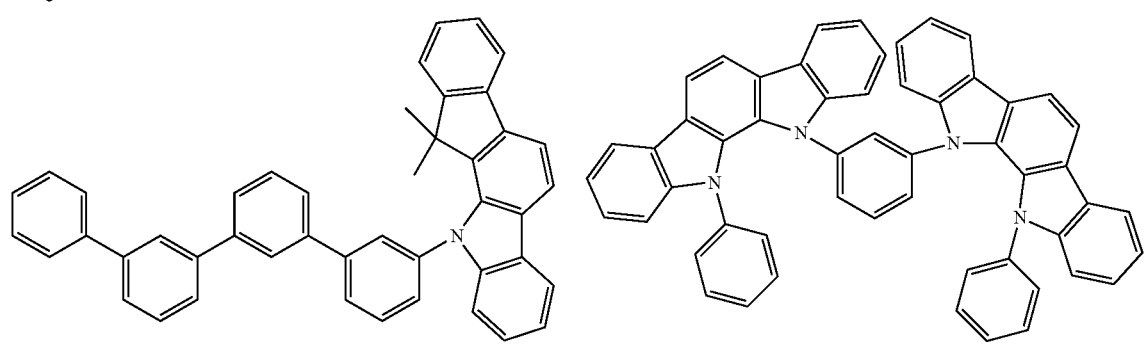

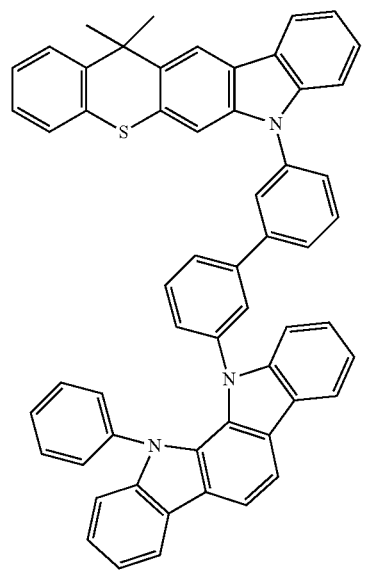
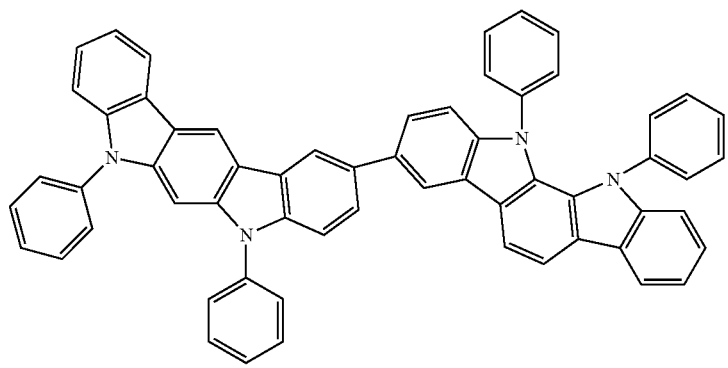
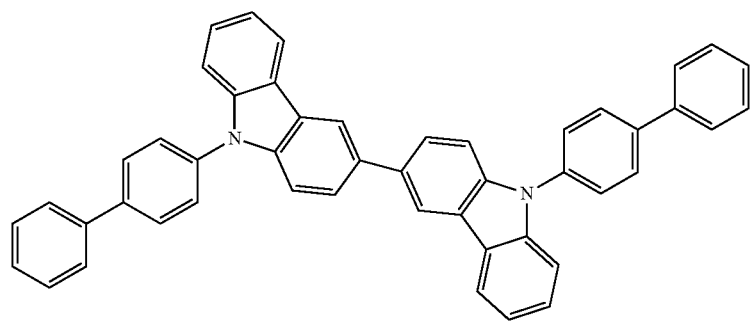
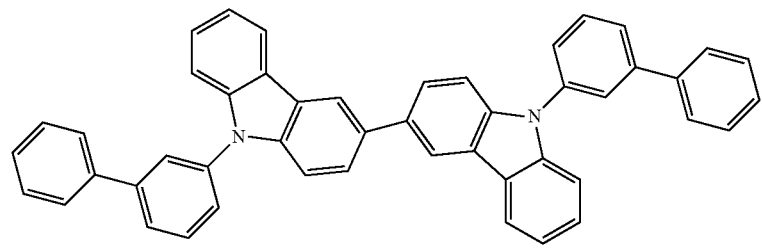
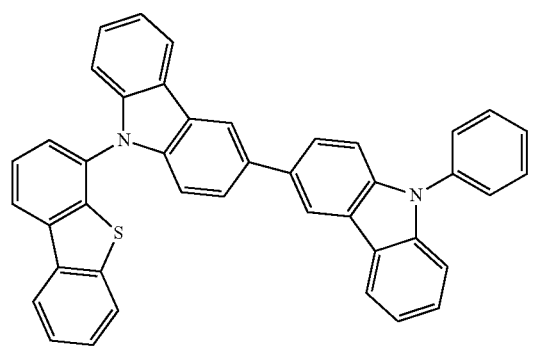
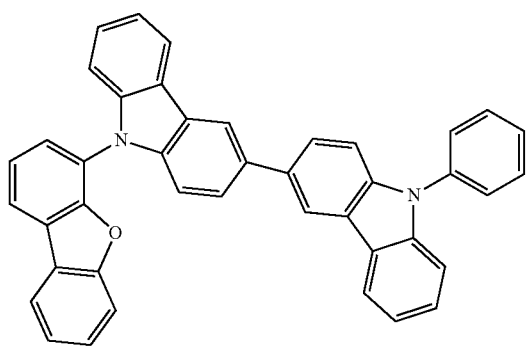

-continued
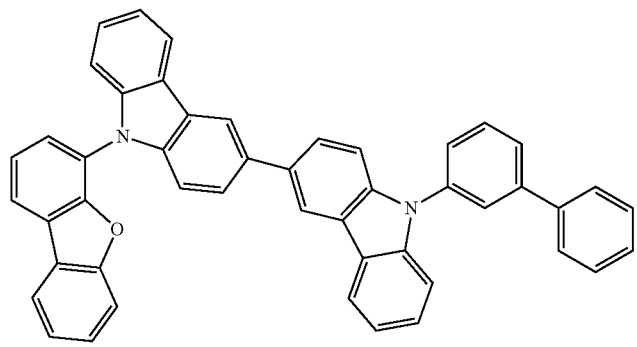
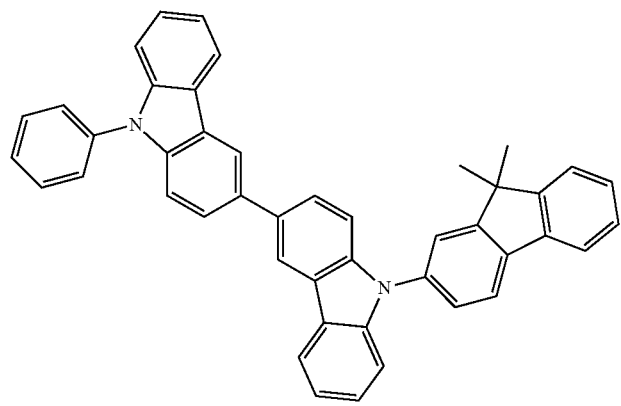
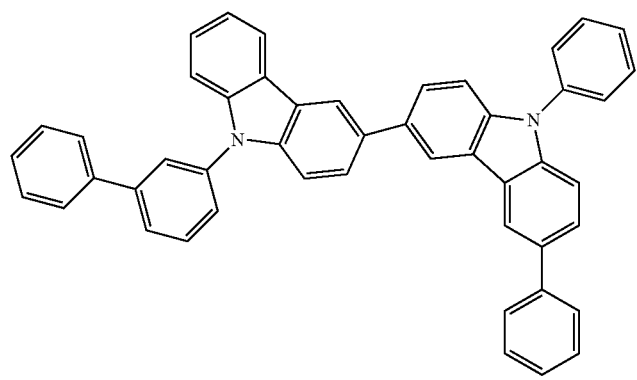
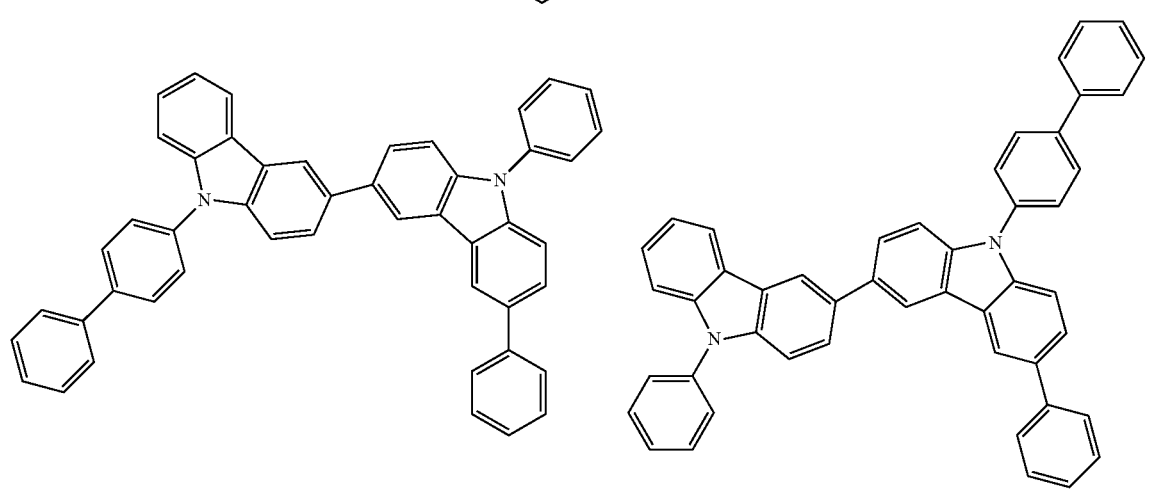

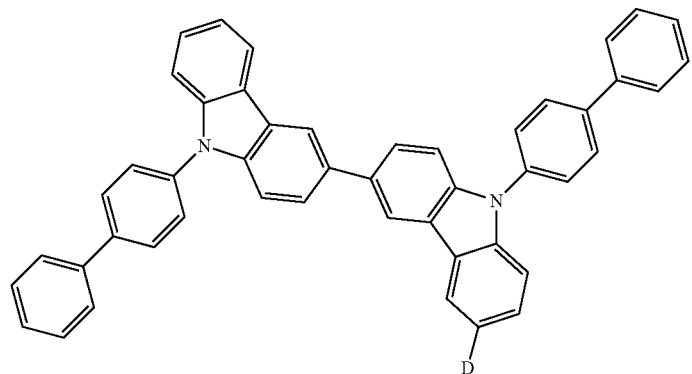
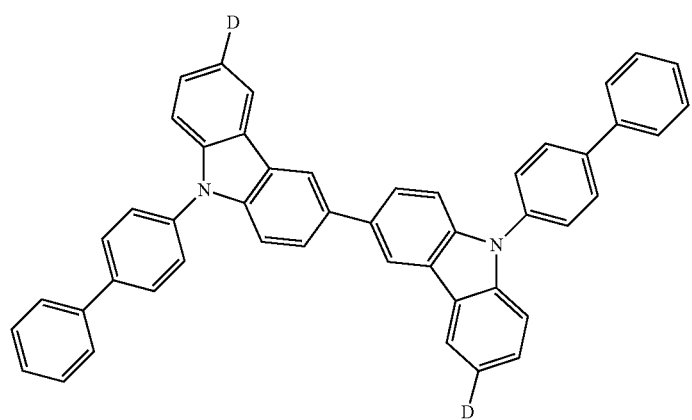
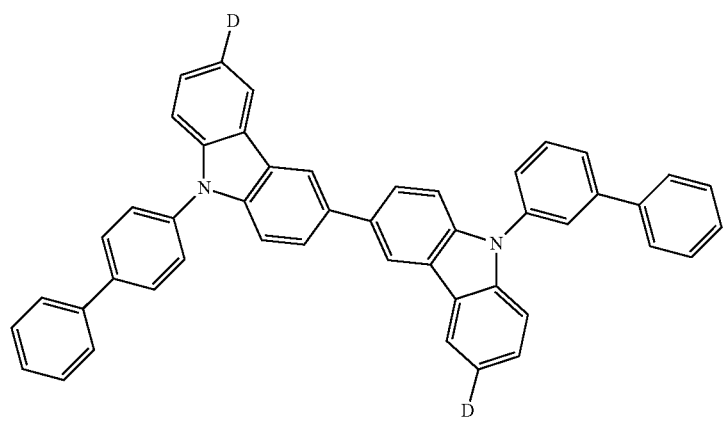

-continued
115
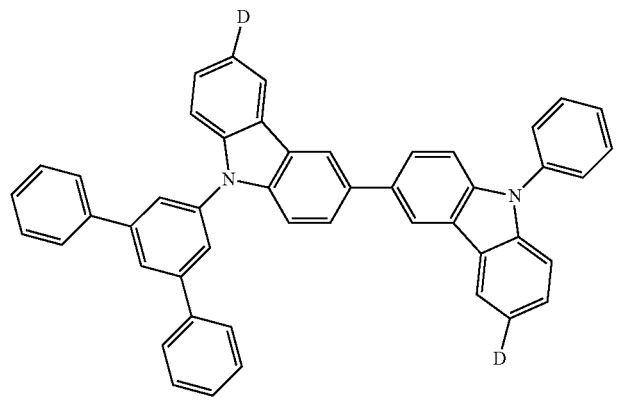
116
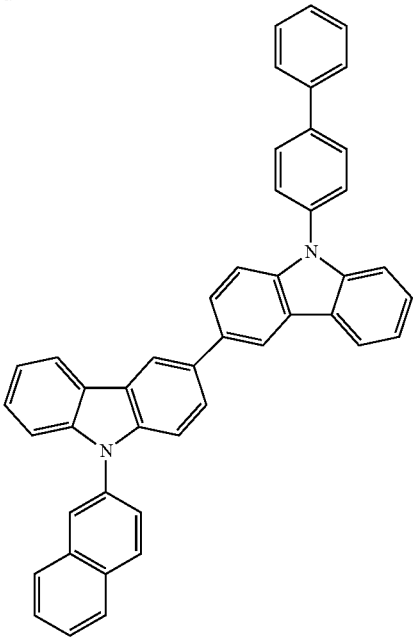
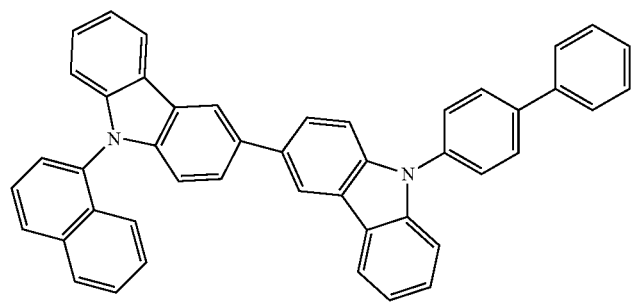
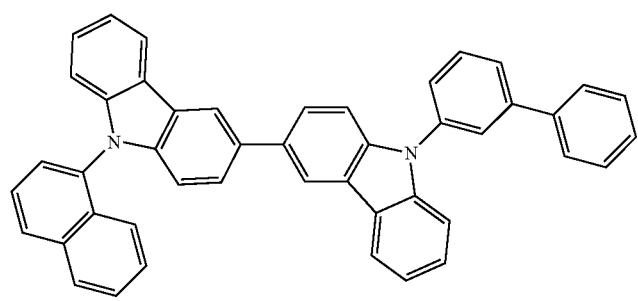
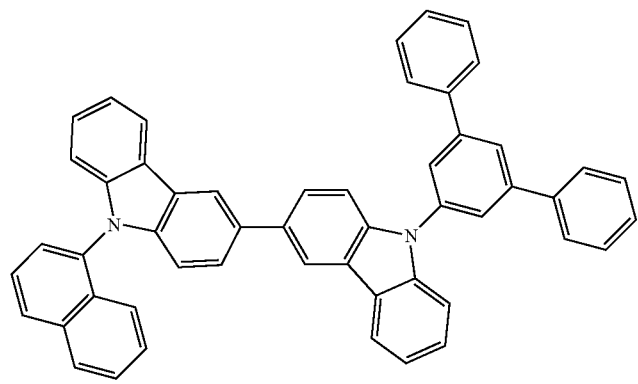

-continued
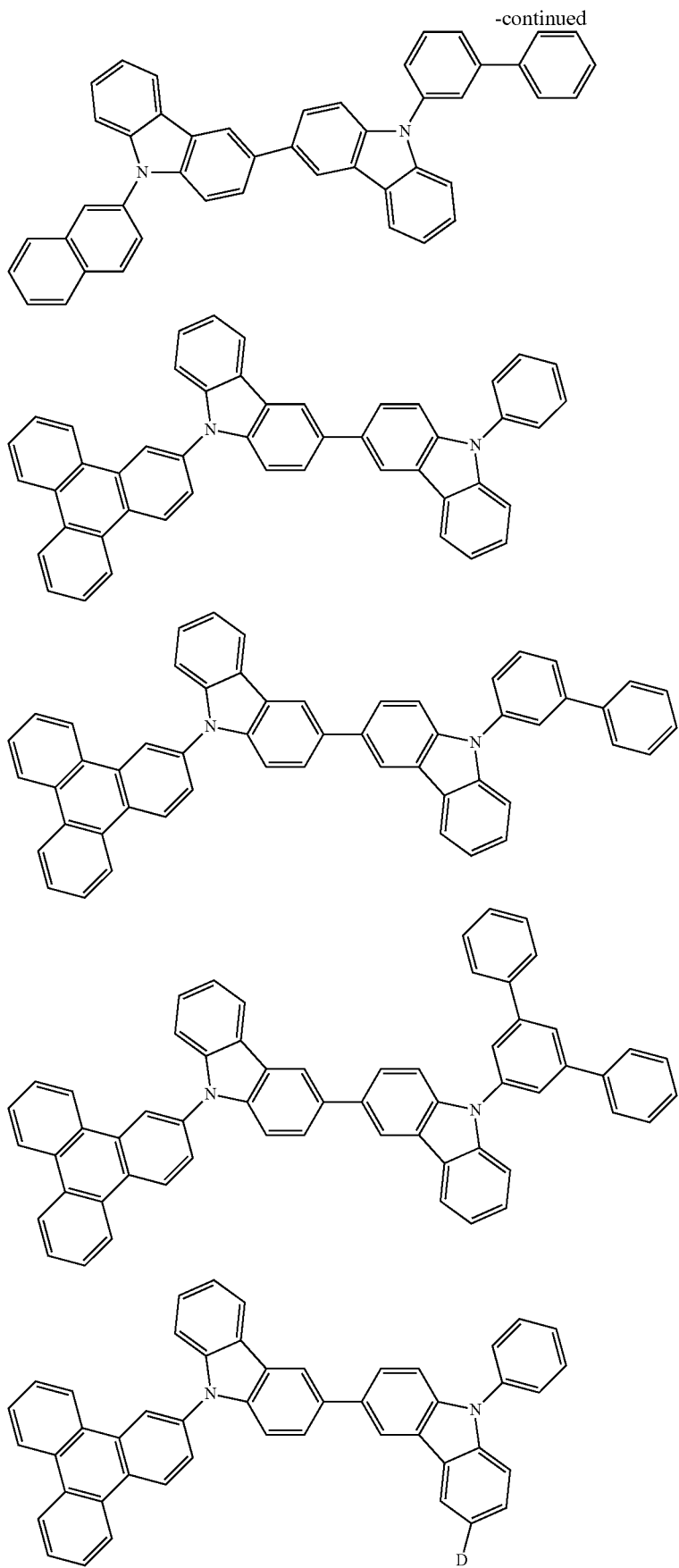

-continued
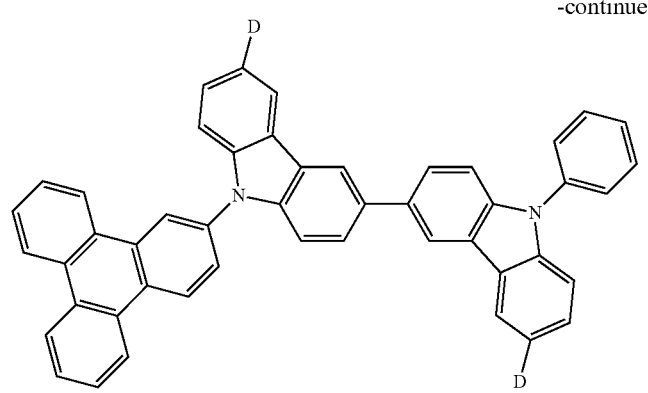
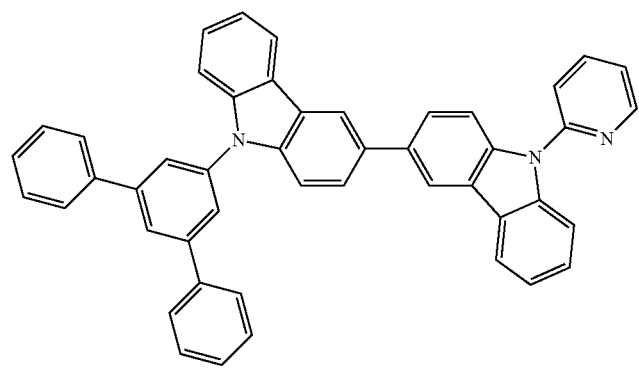
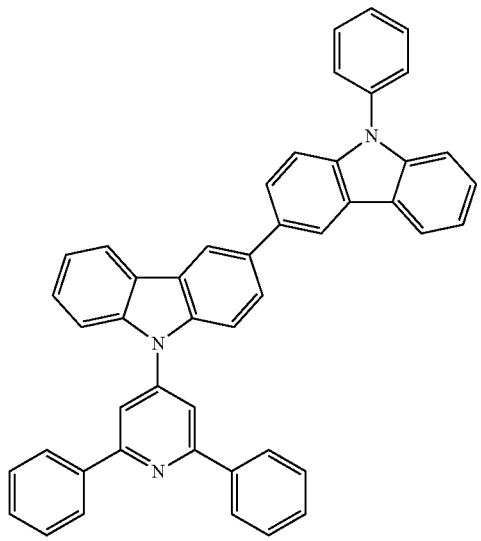
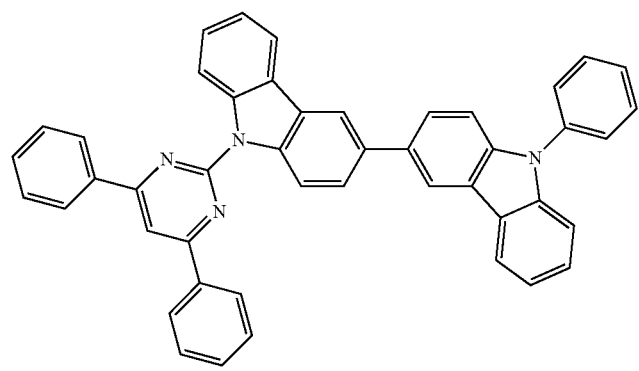
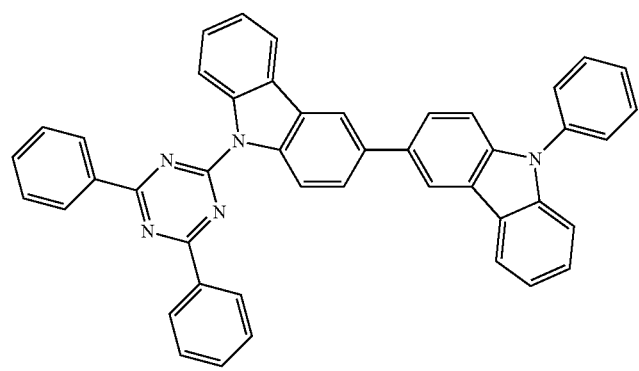

121 122
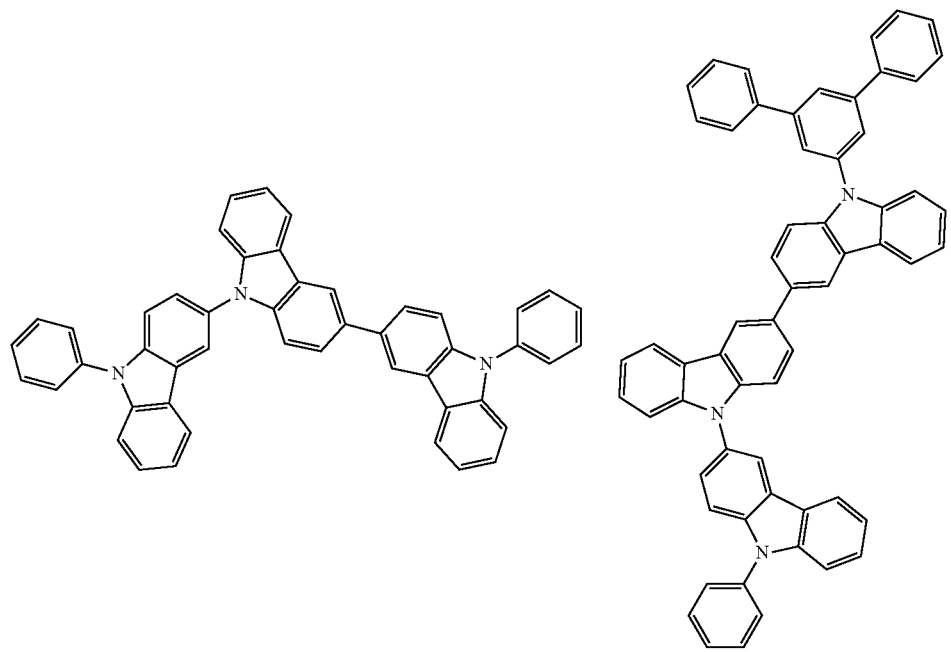
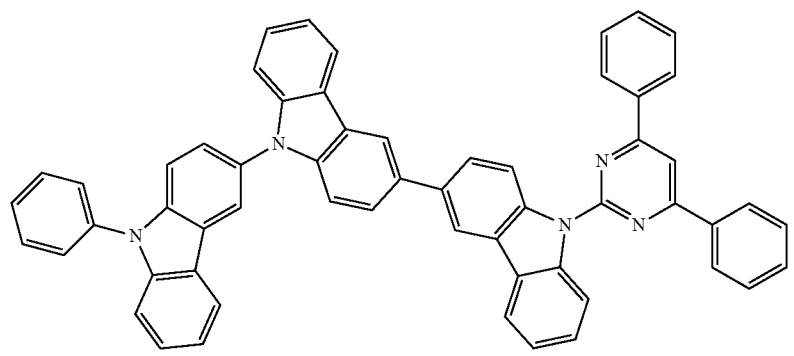
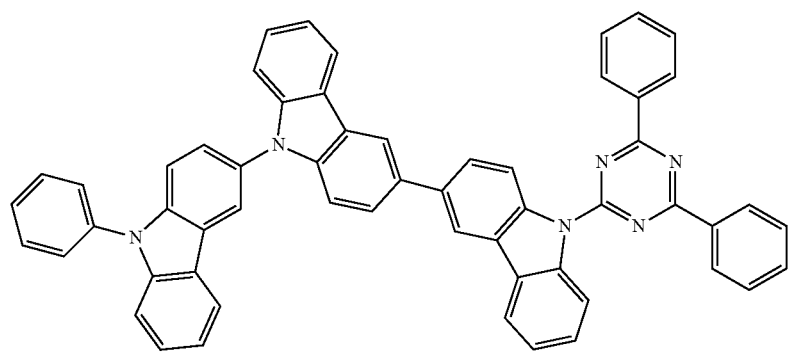

123 124
-continued
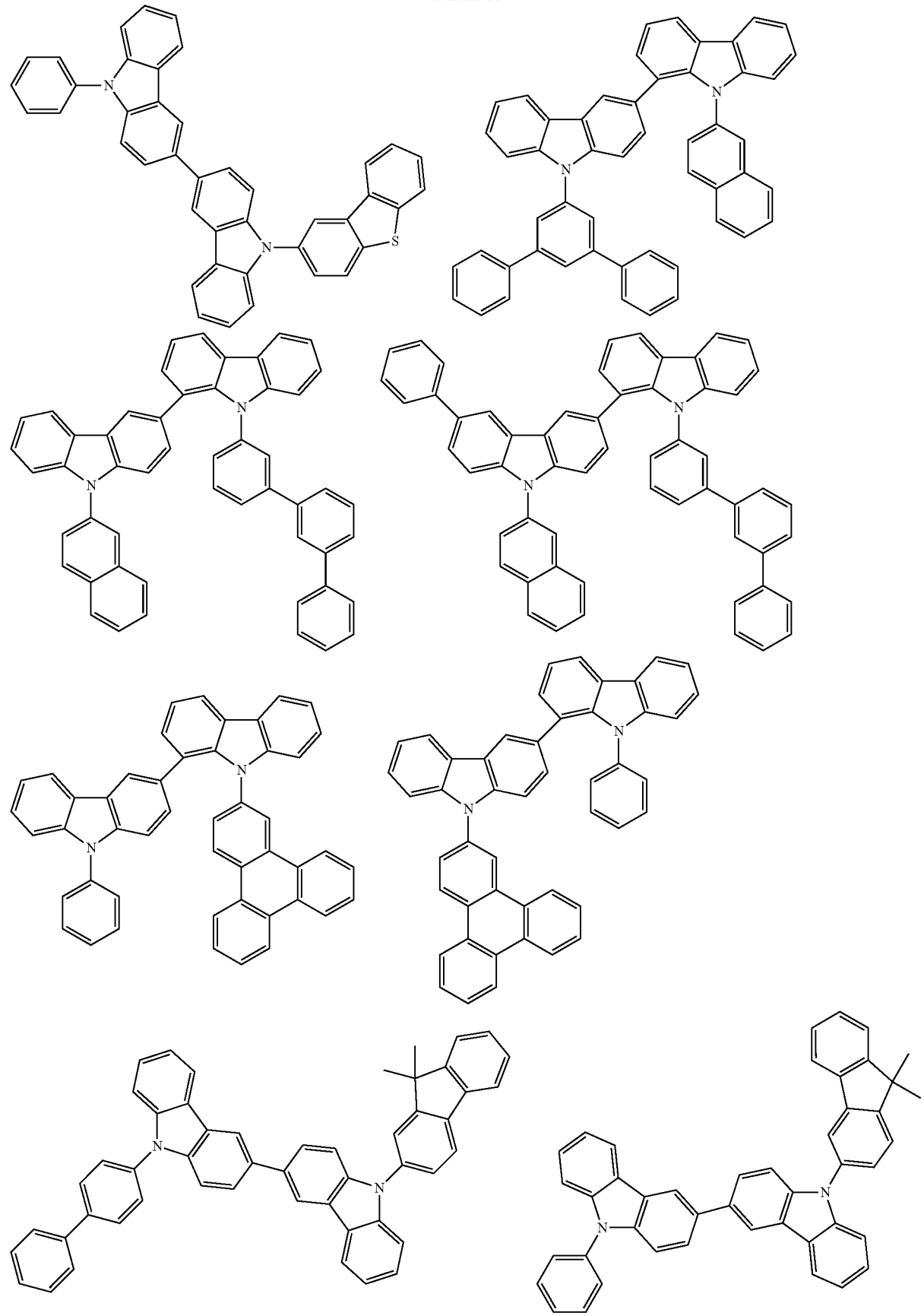

-continued
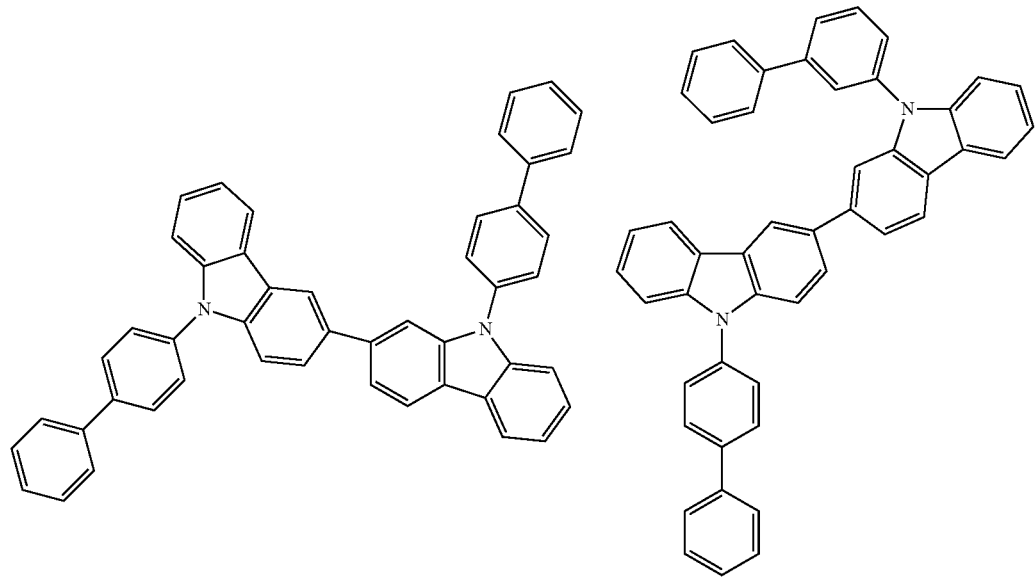
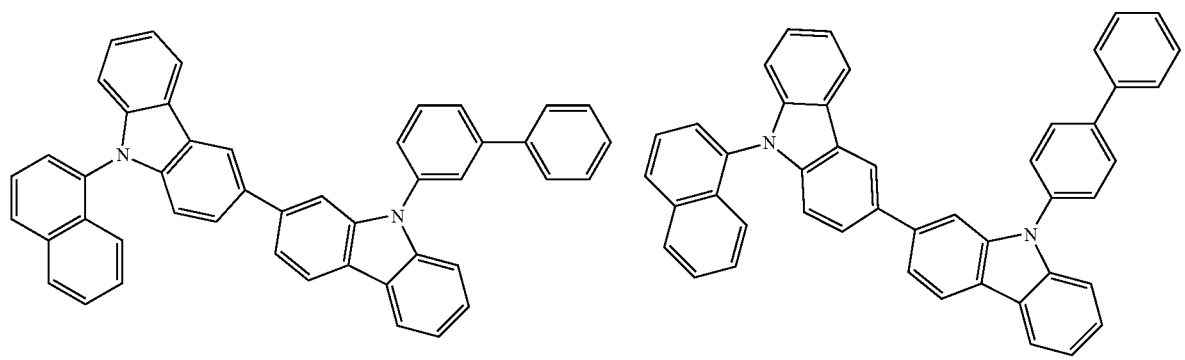
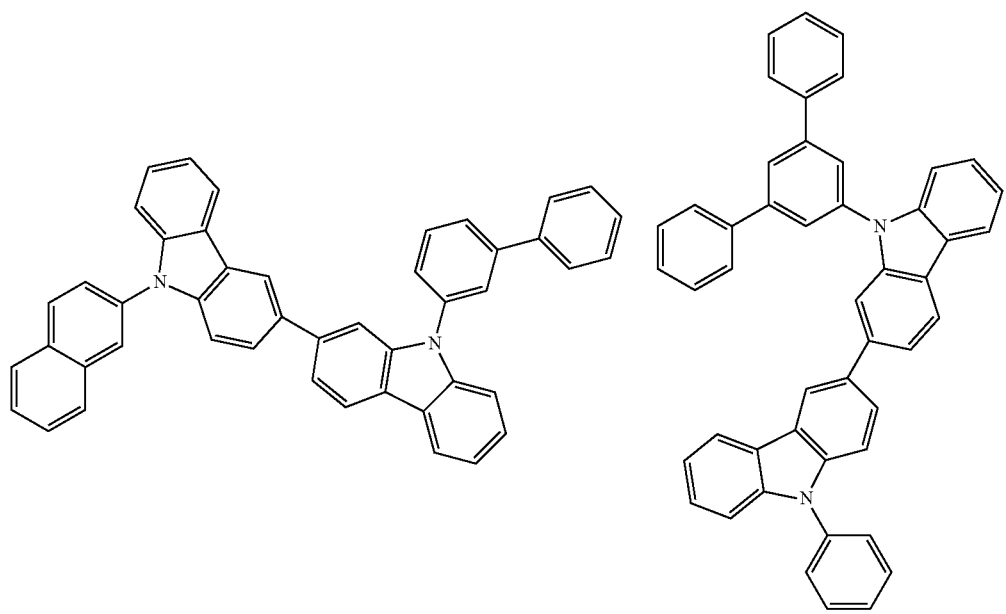

127
128
-continued
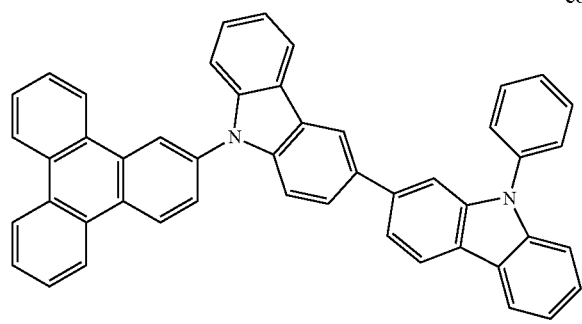
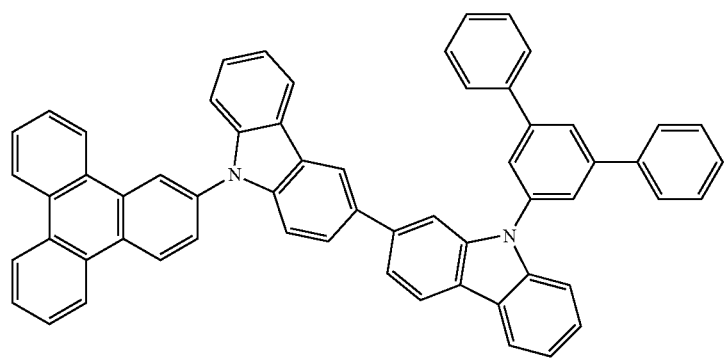
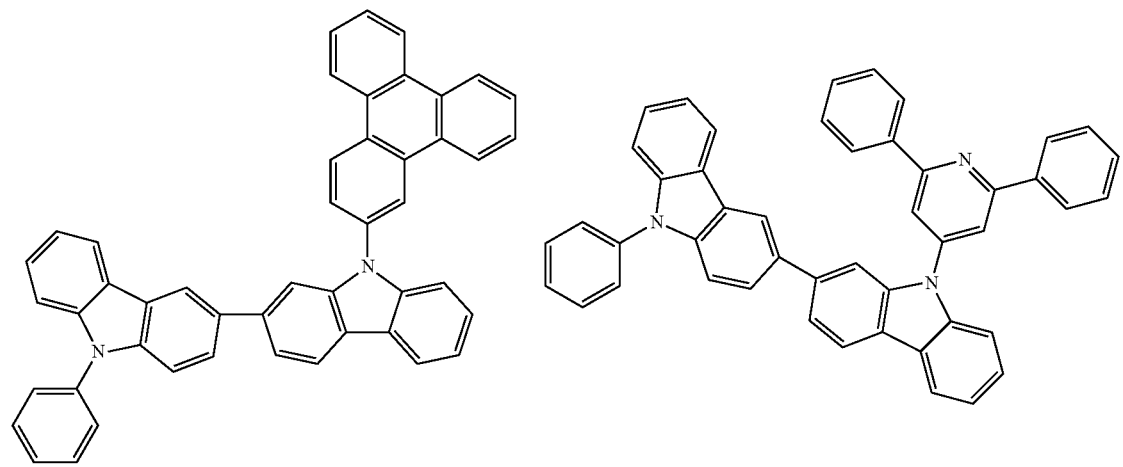
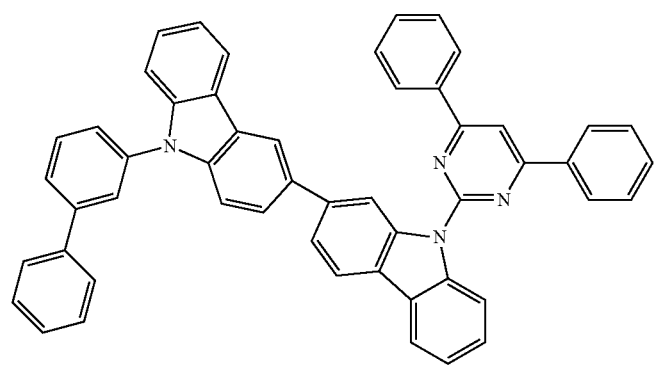

129
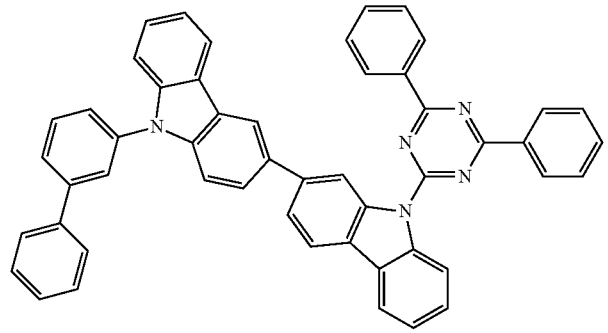
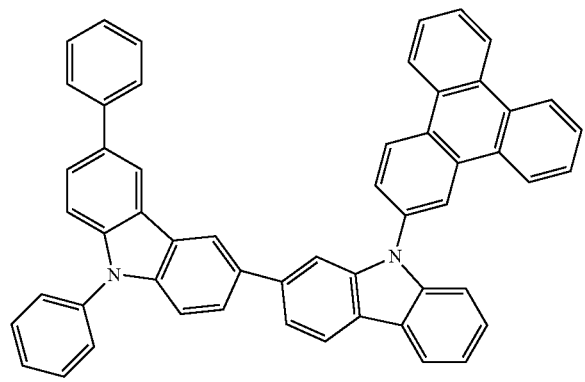
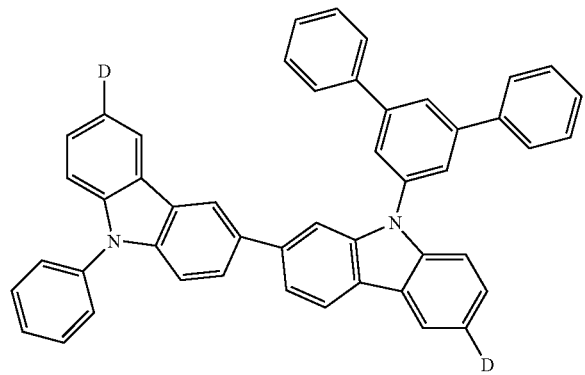
130
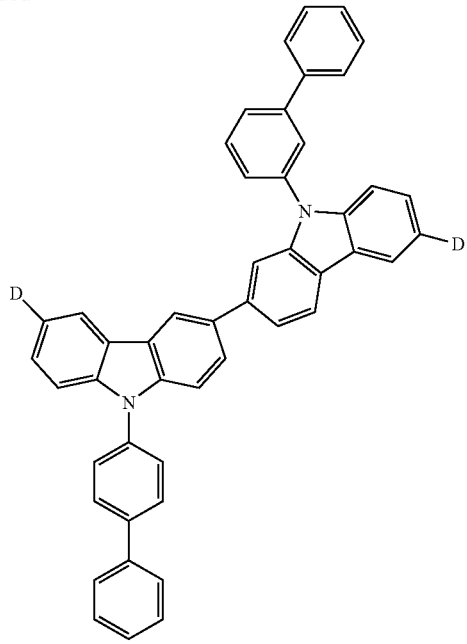
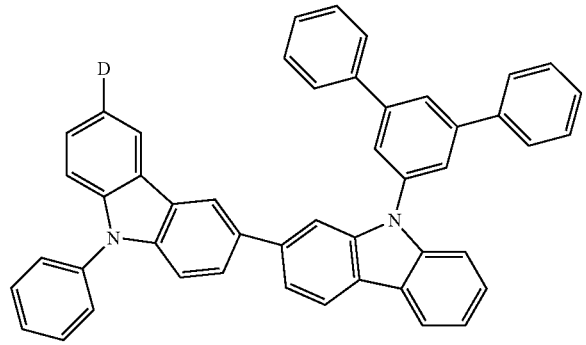
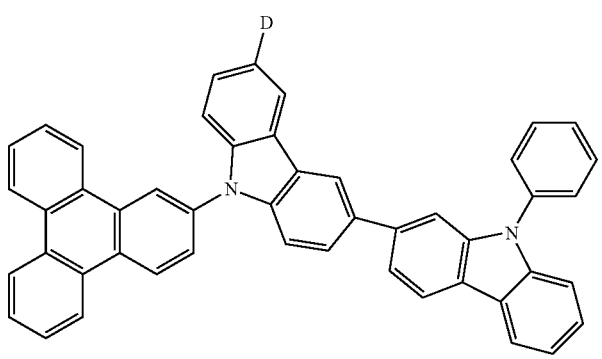

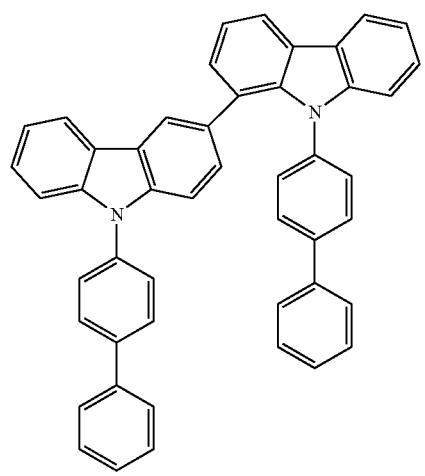
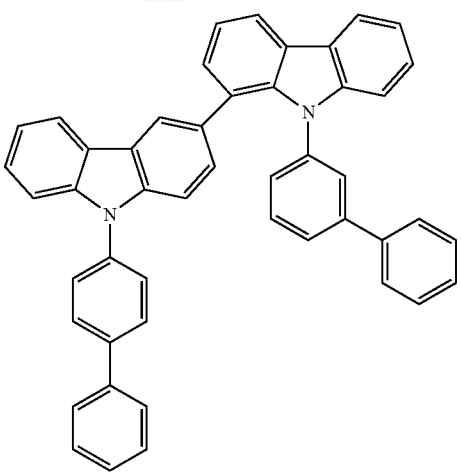
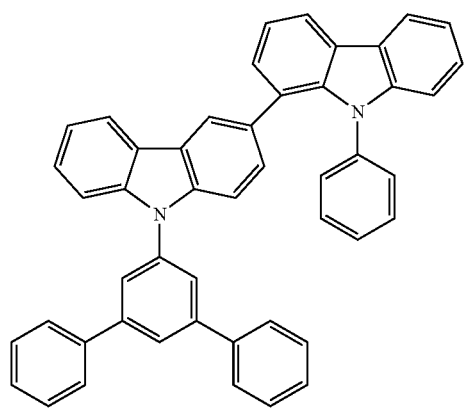
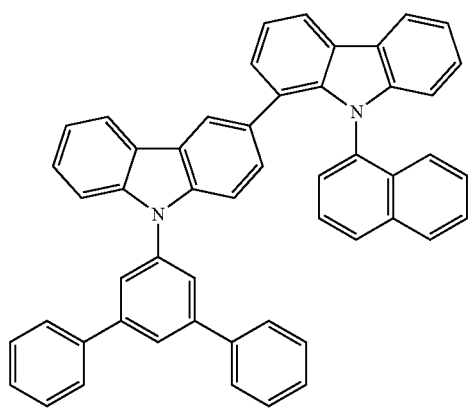
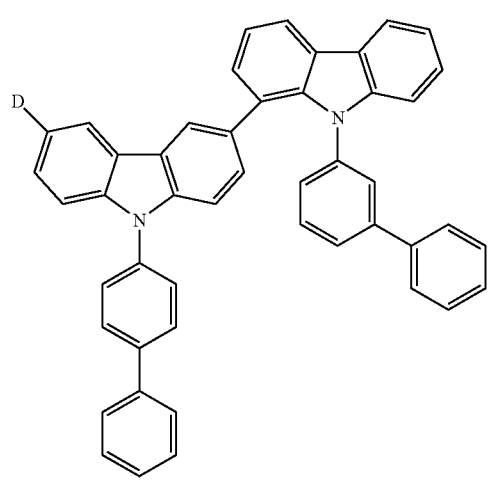
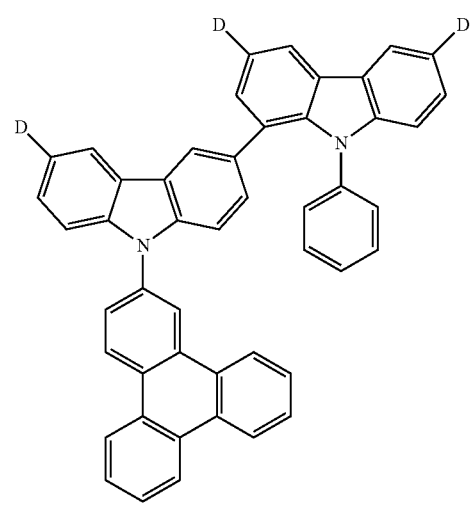

-continued
133
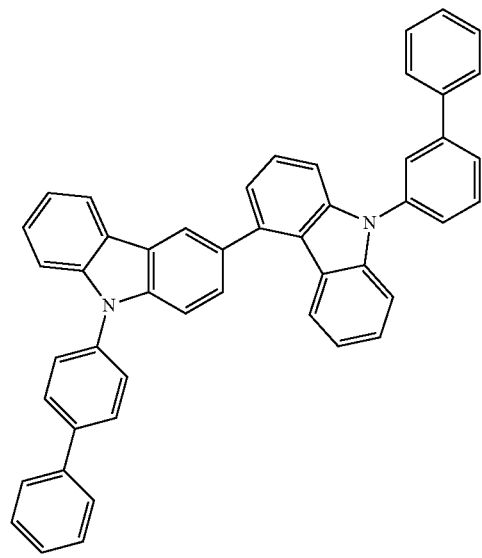
134
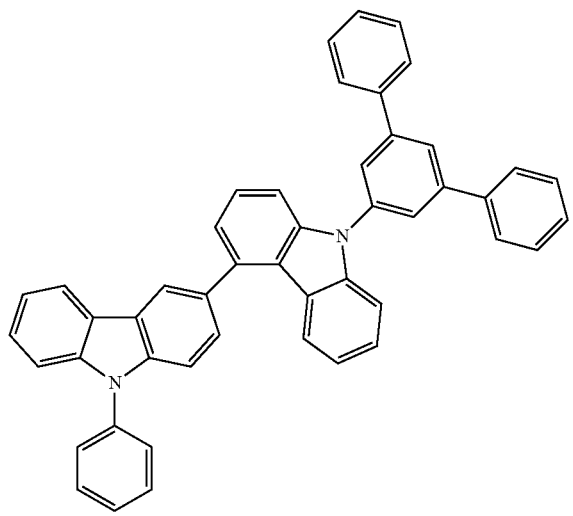
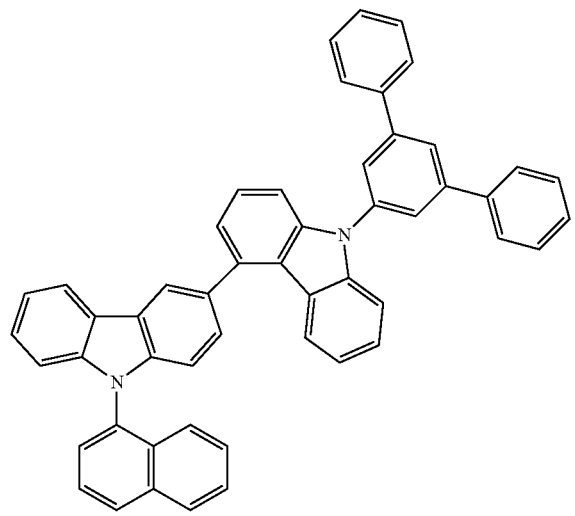
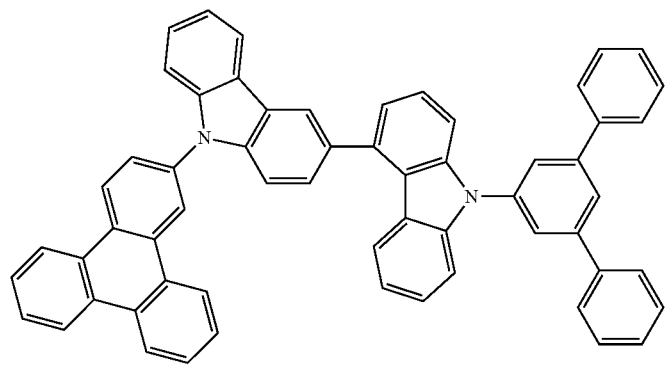

-continued
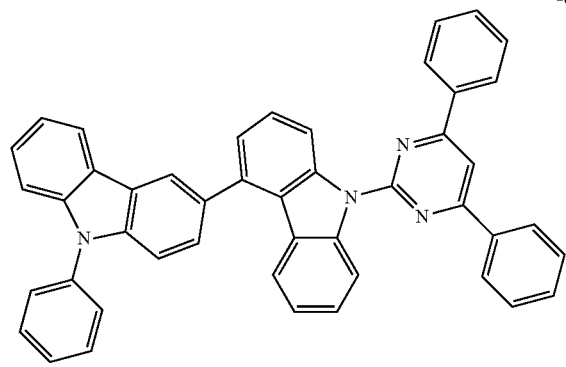
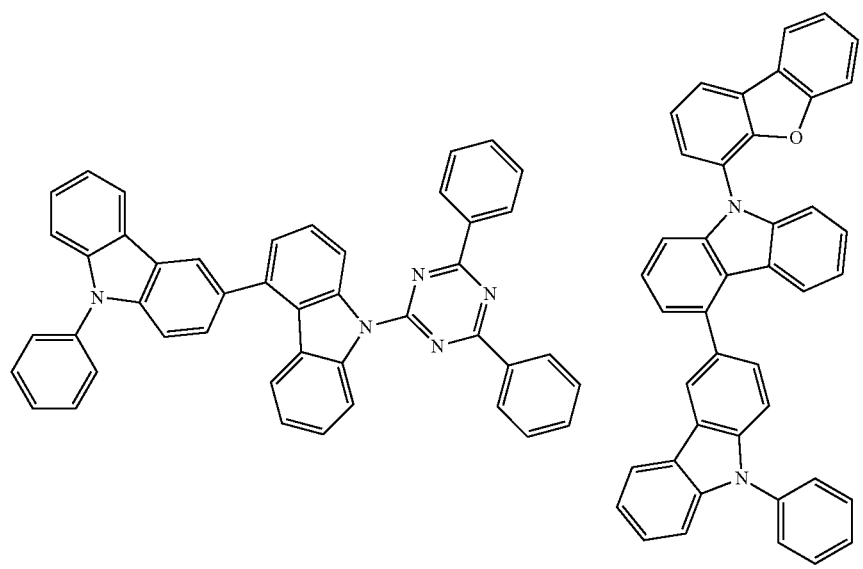
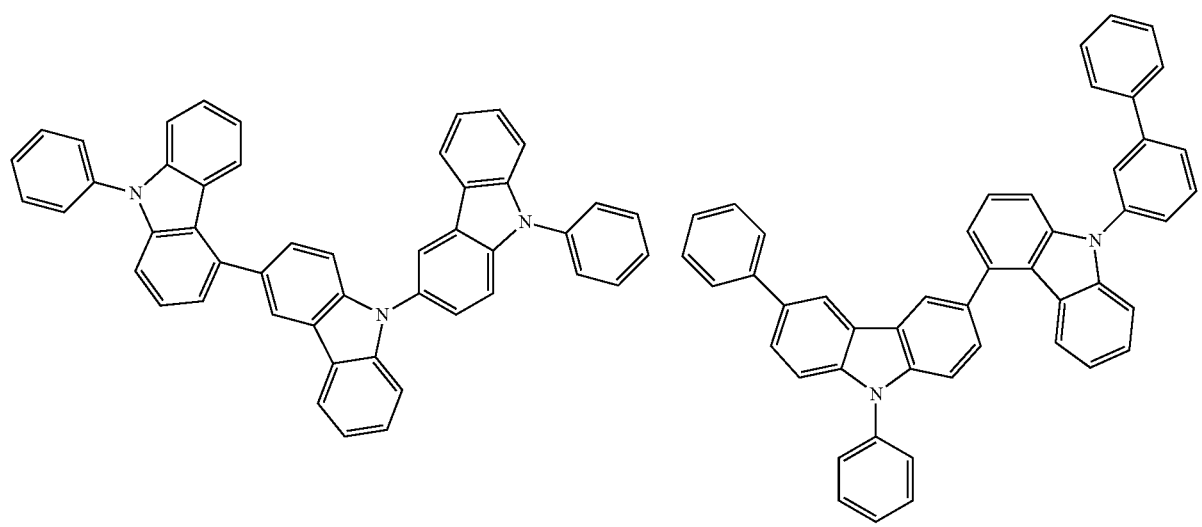

-continued
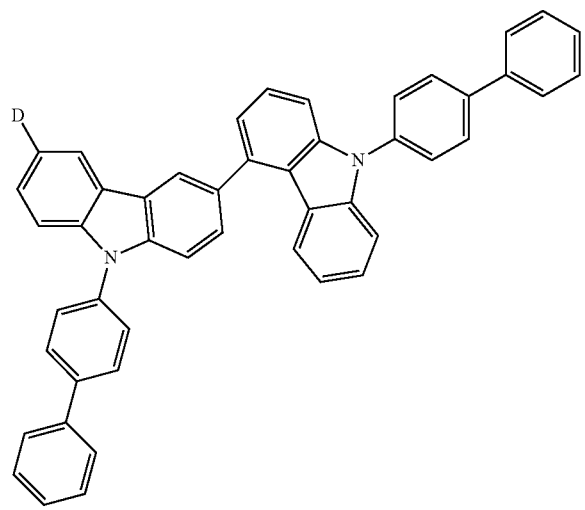
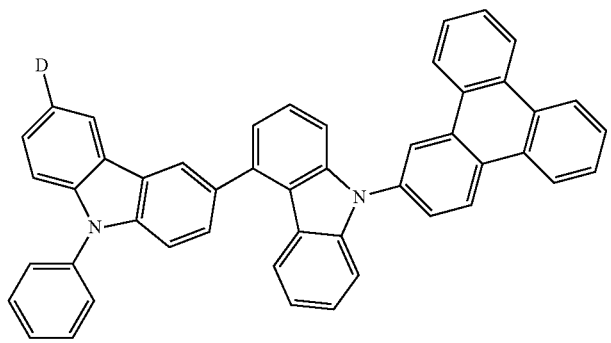
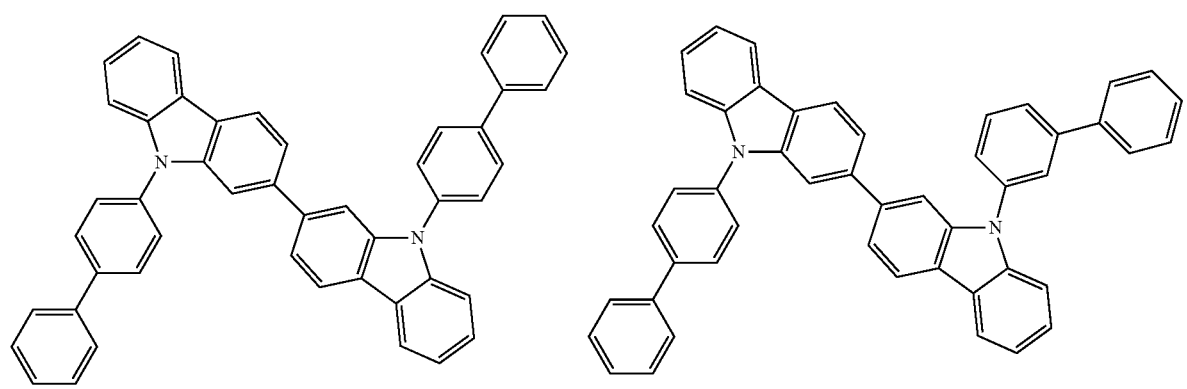
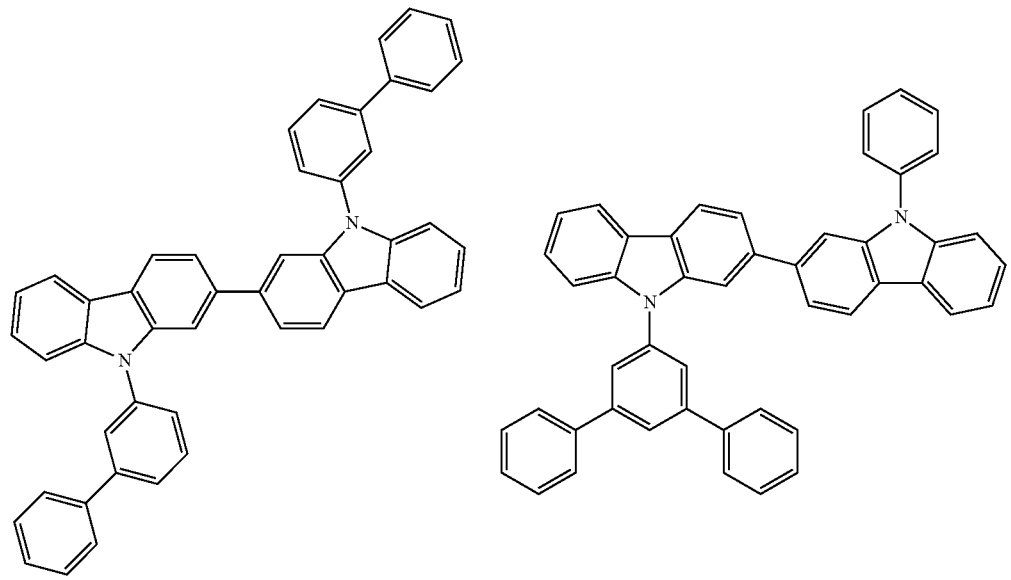

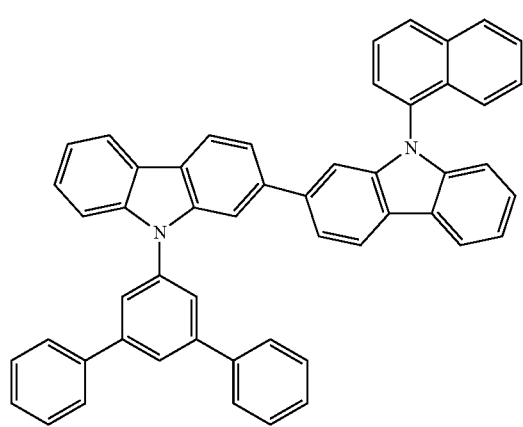
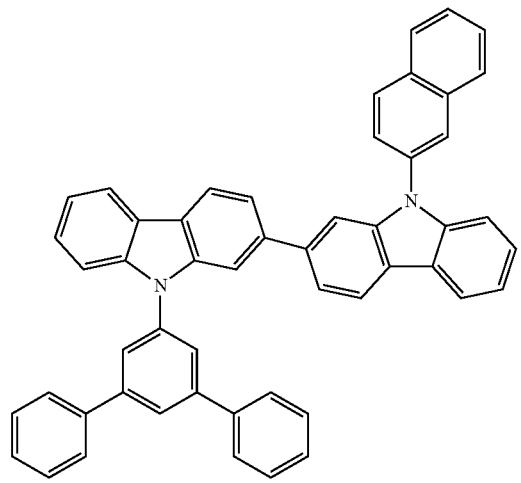
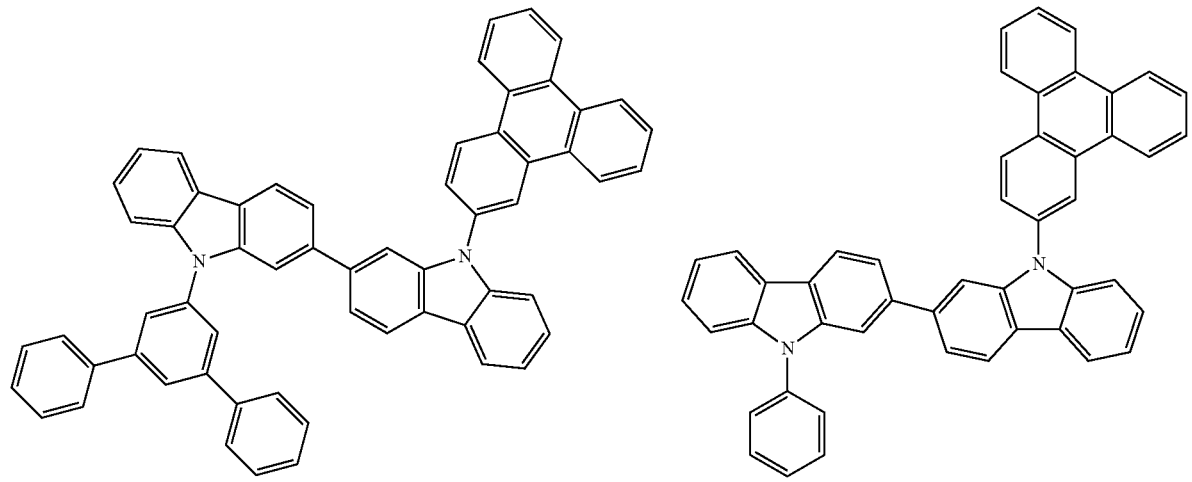
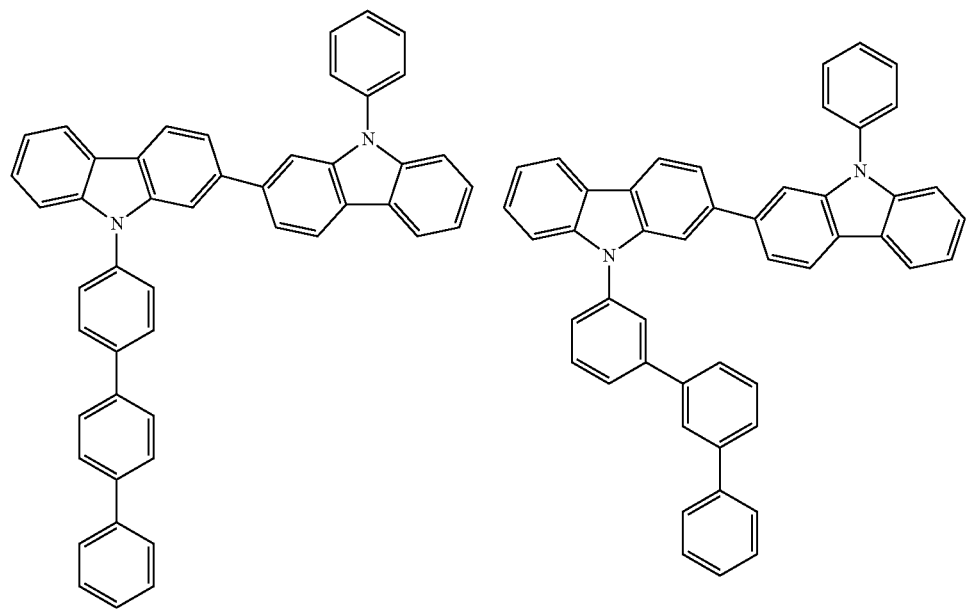

141
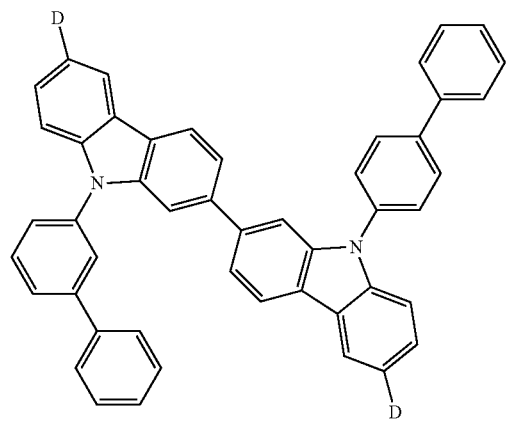
-continued
142
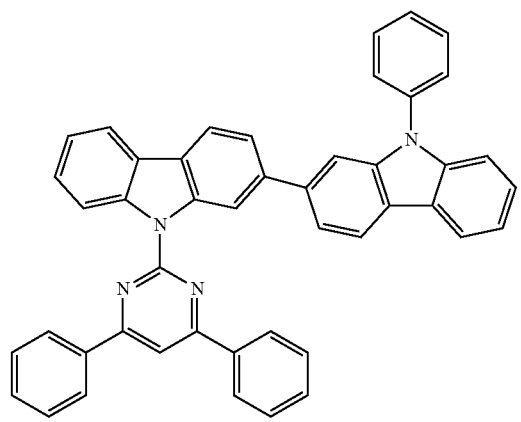
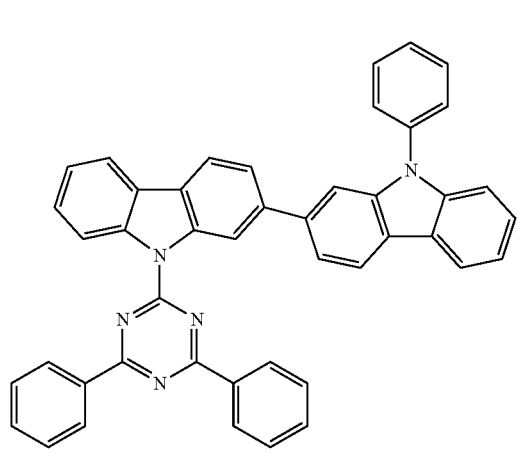
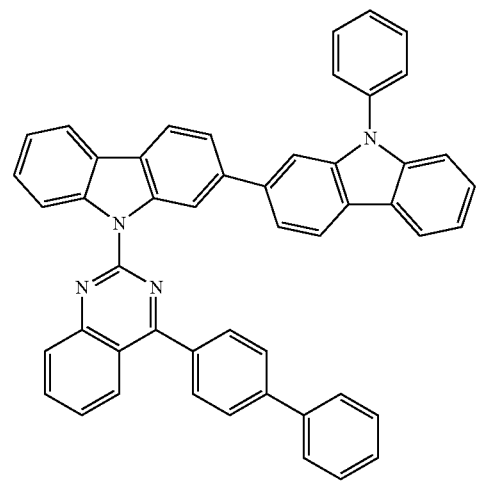
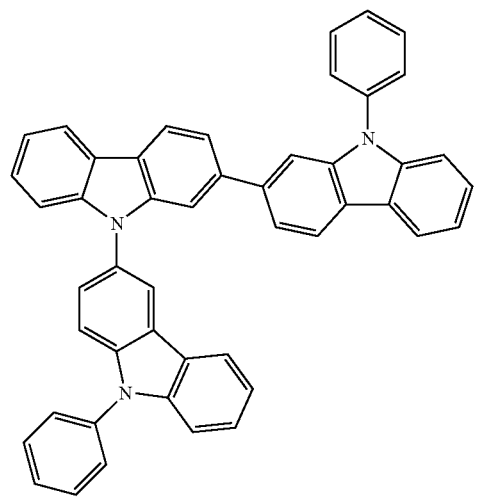
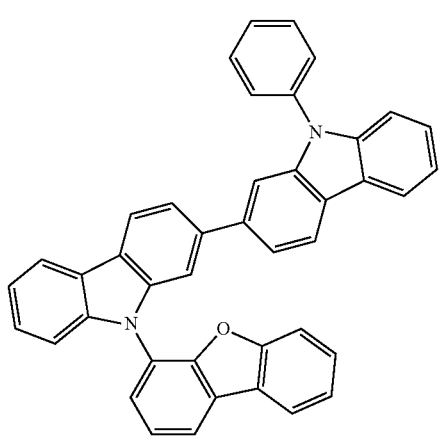

-continued
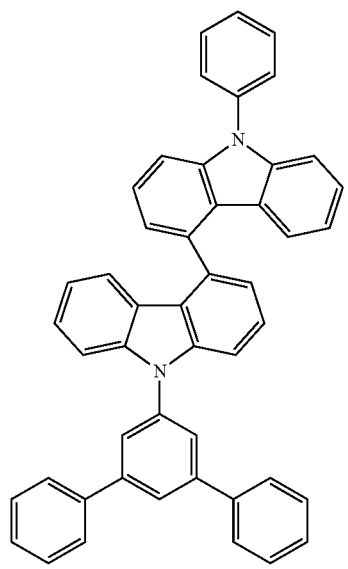
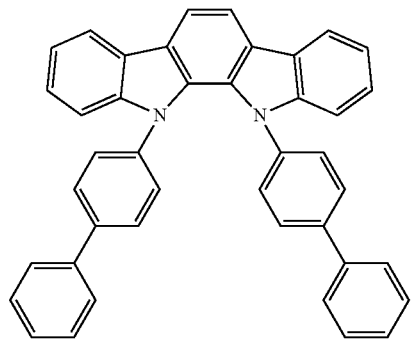
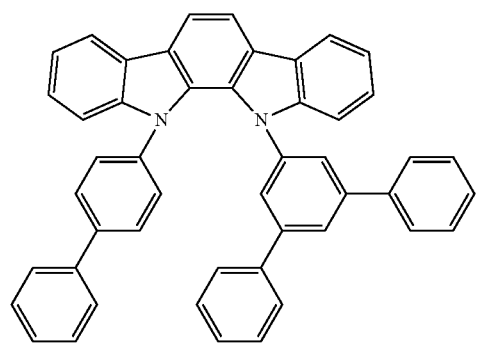
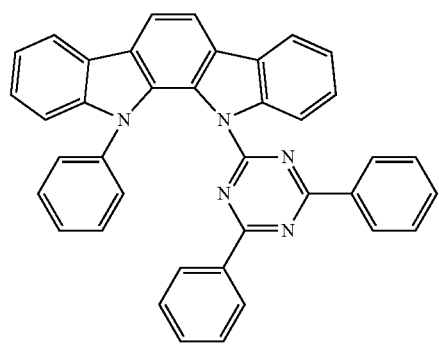
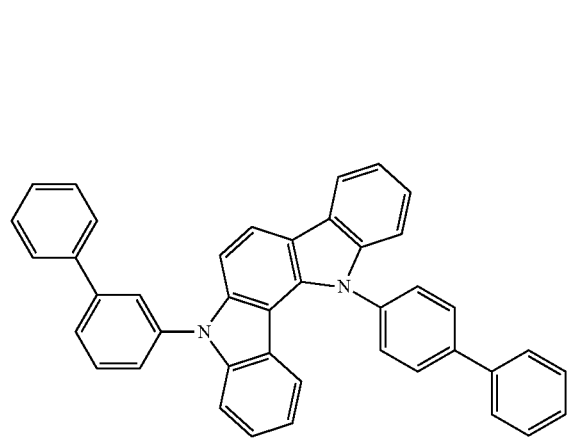
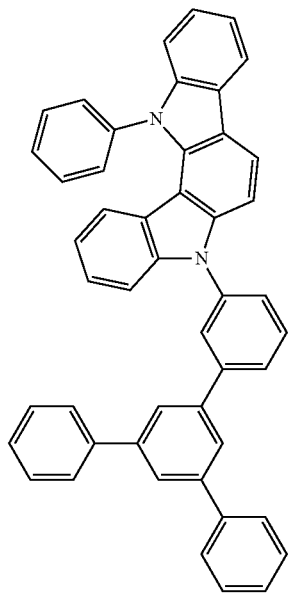

-continued
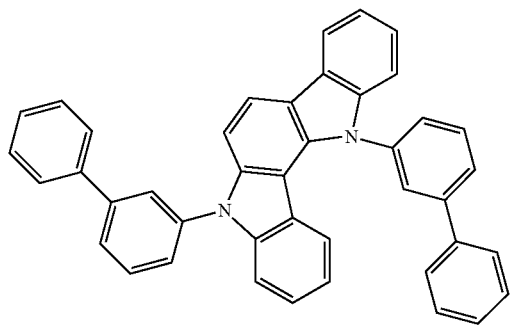
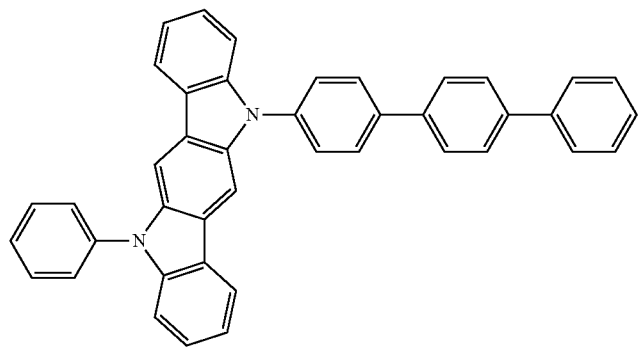
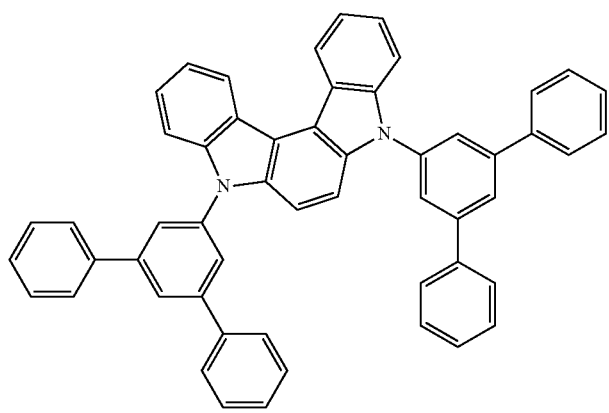
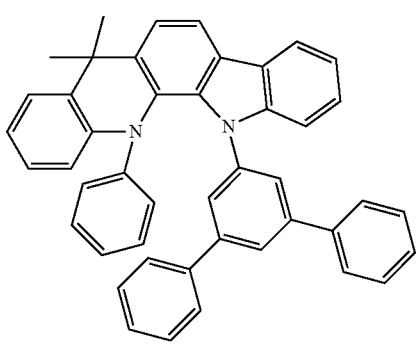
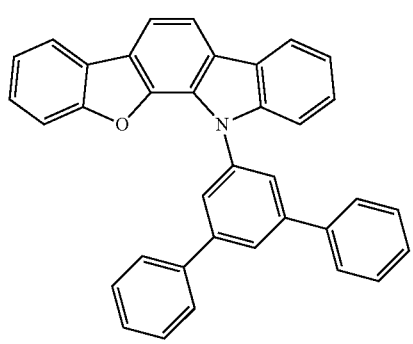
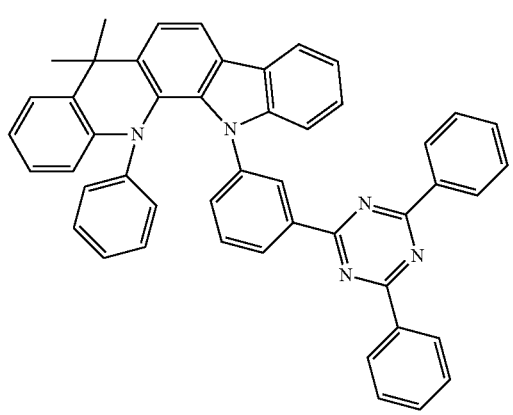
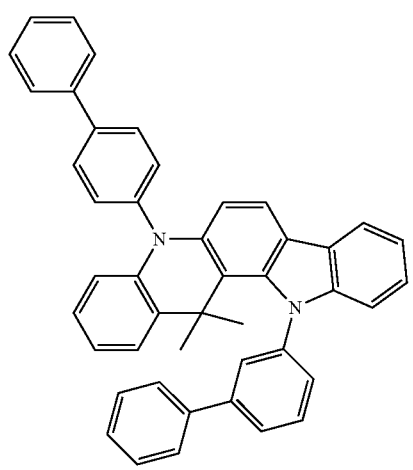
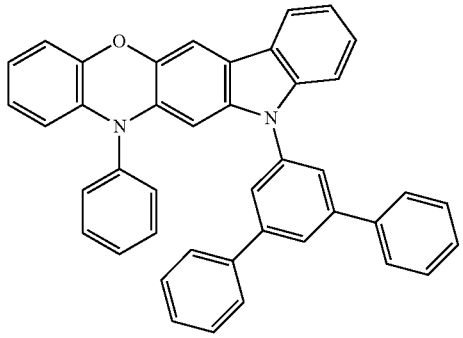

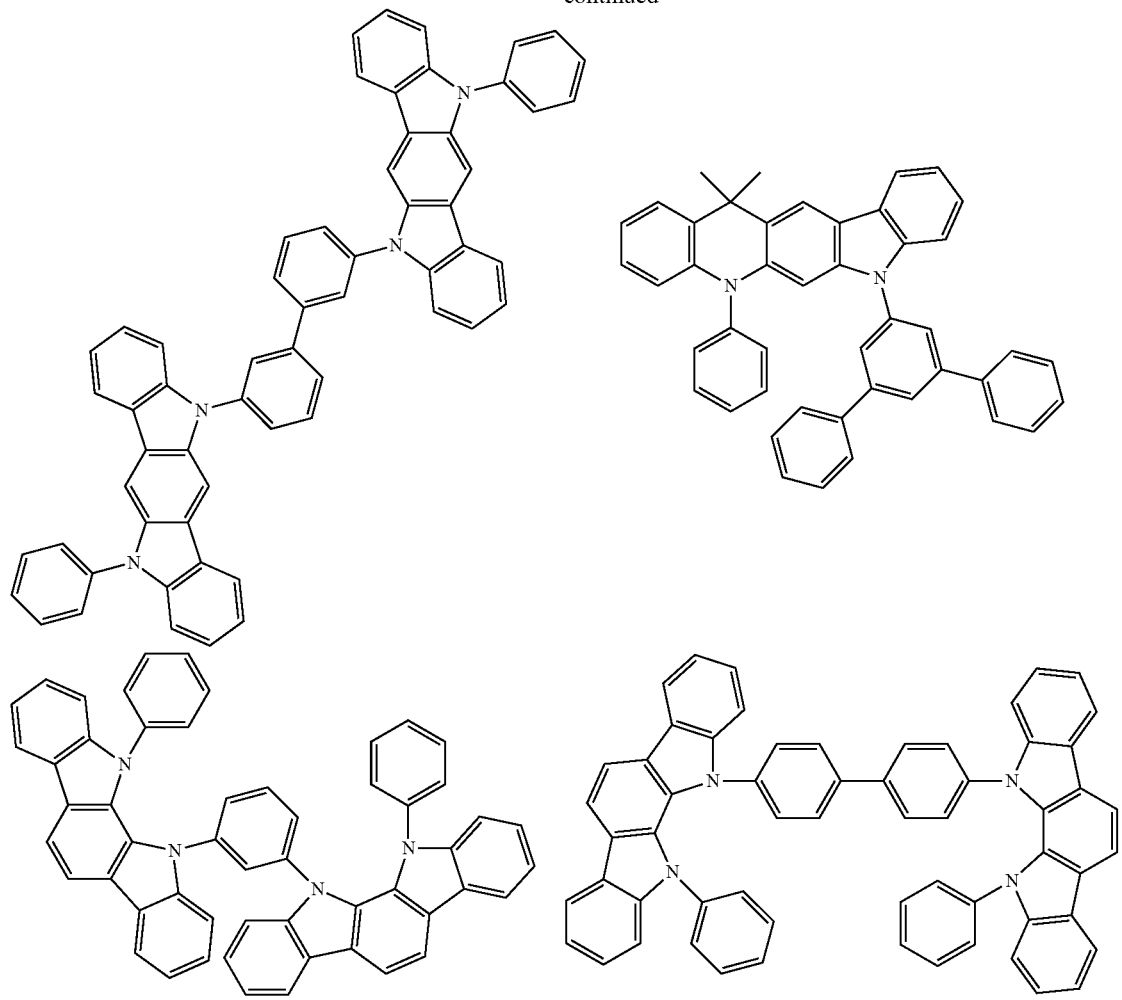
Specific examples that can be used as H3 are listed below, but are not limited to:
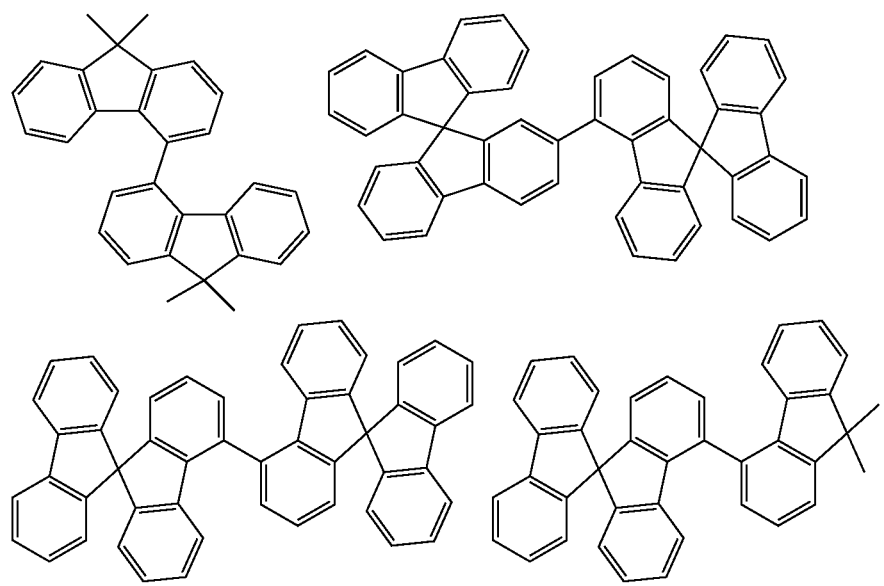

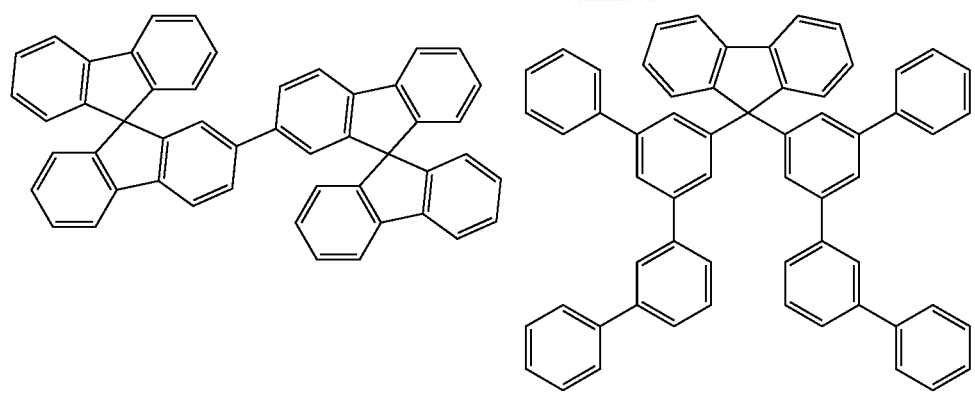
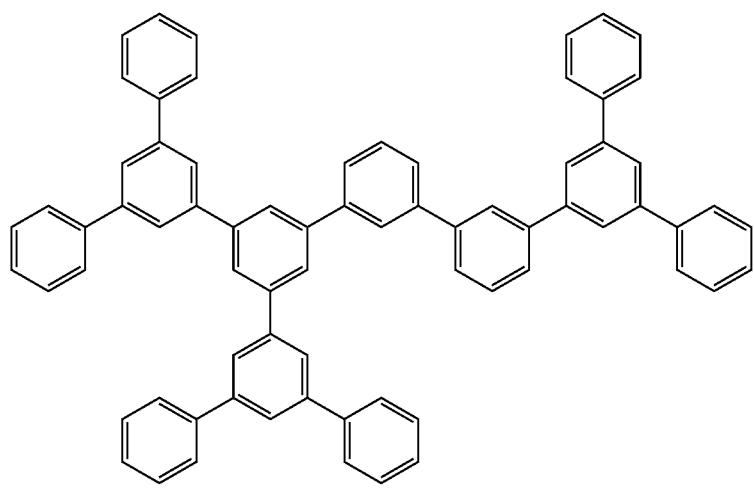
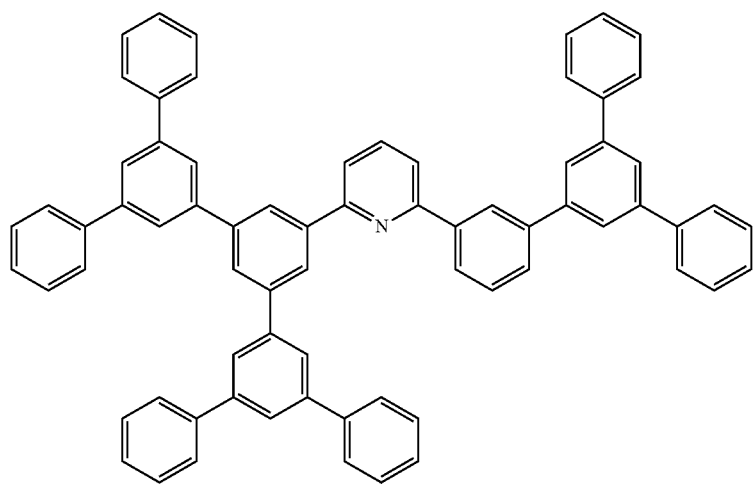

-continued
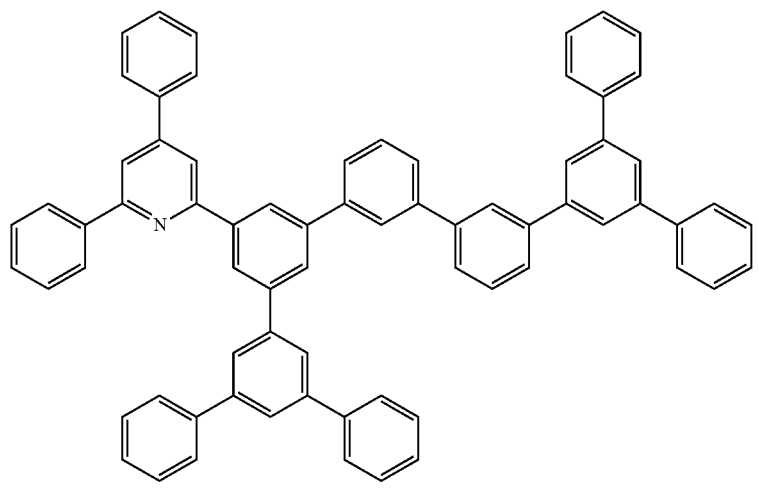
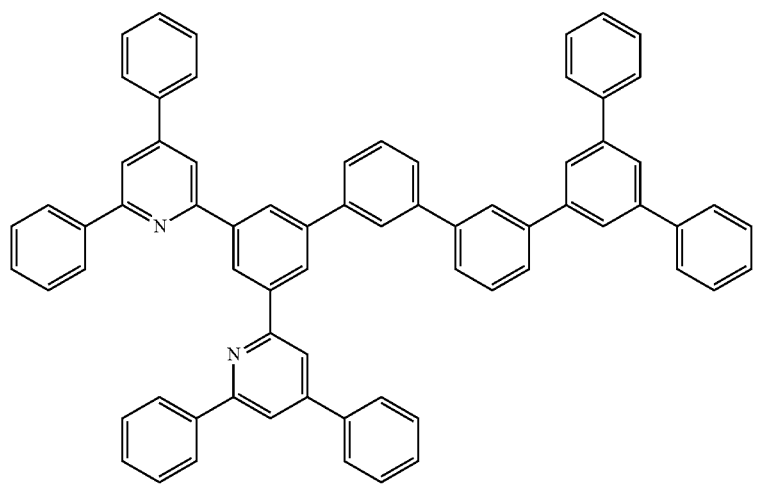
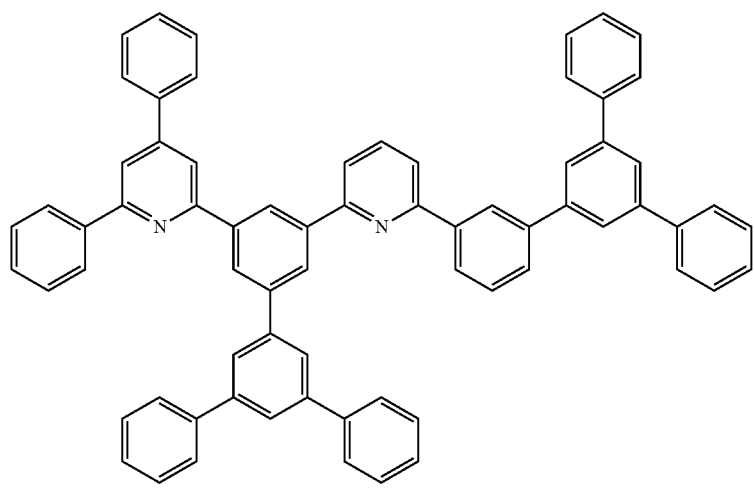

-continued
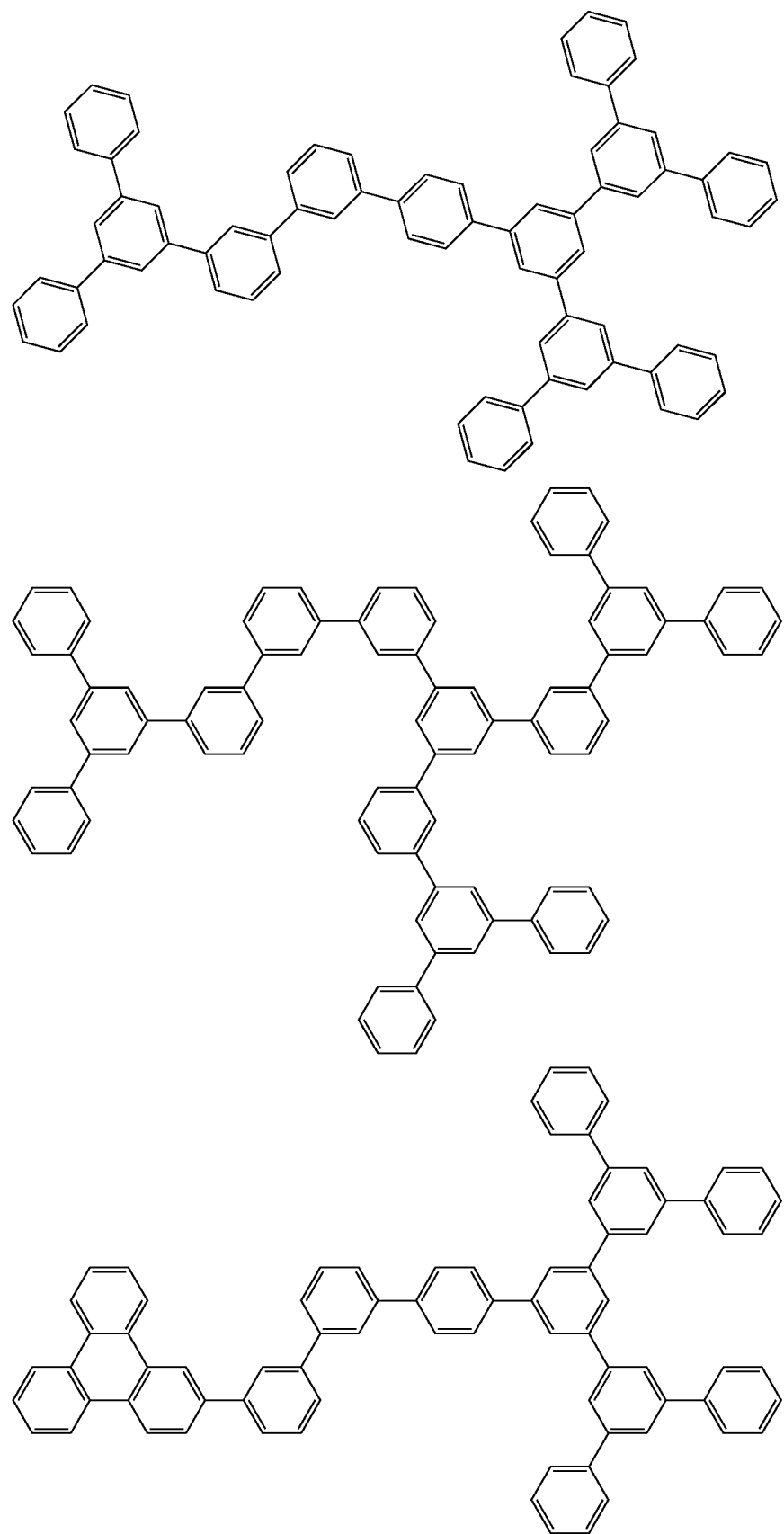

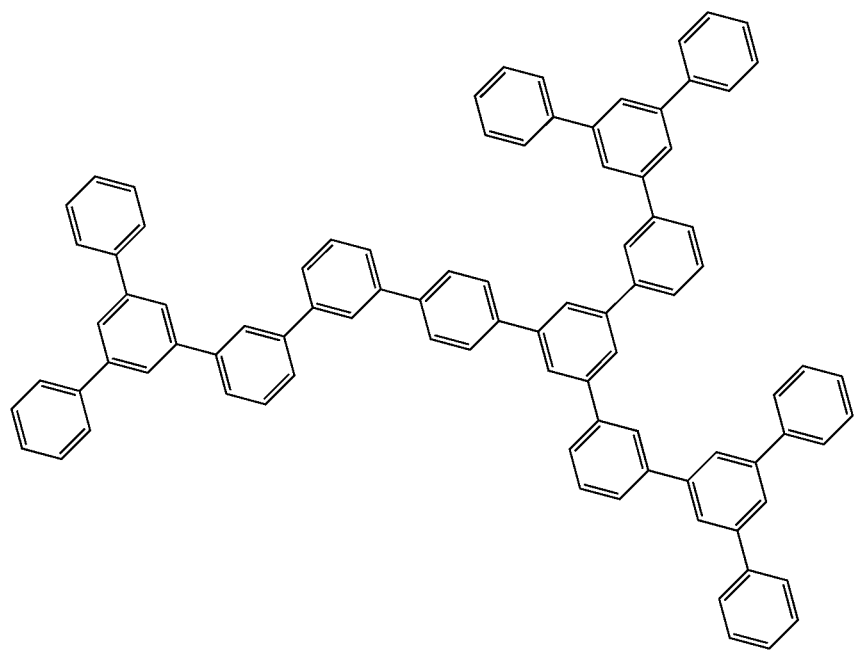

-continued
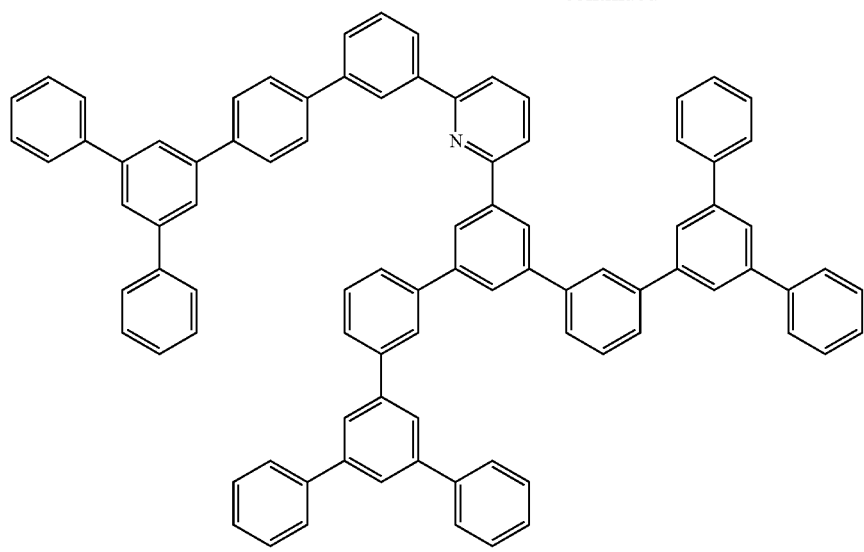
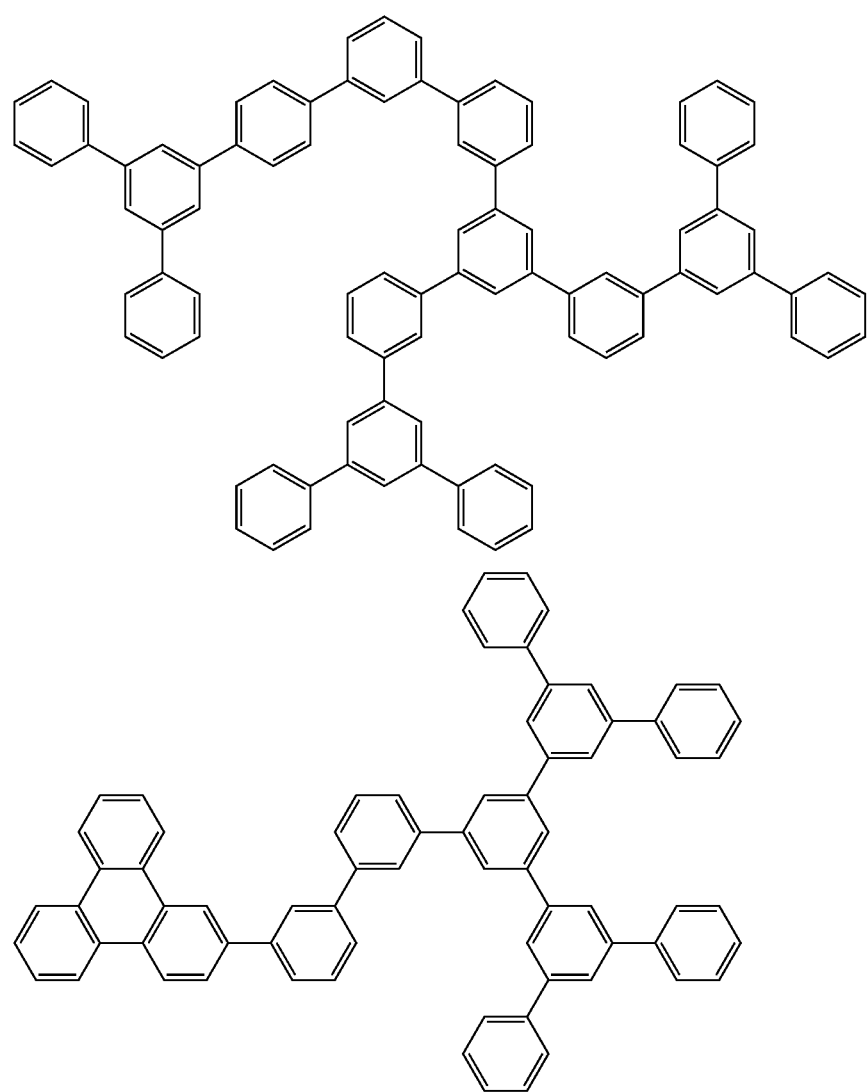

-continued
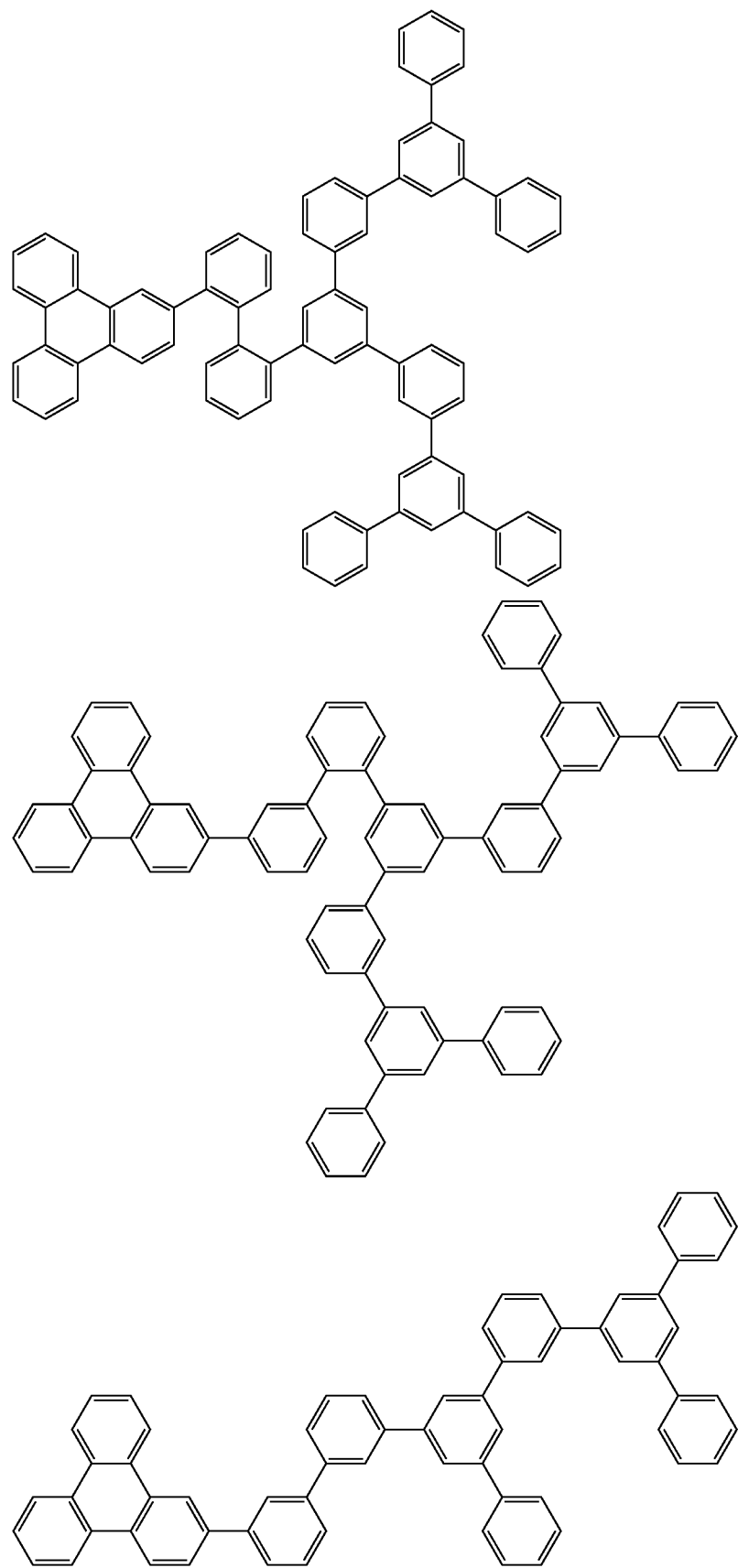

-continued
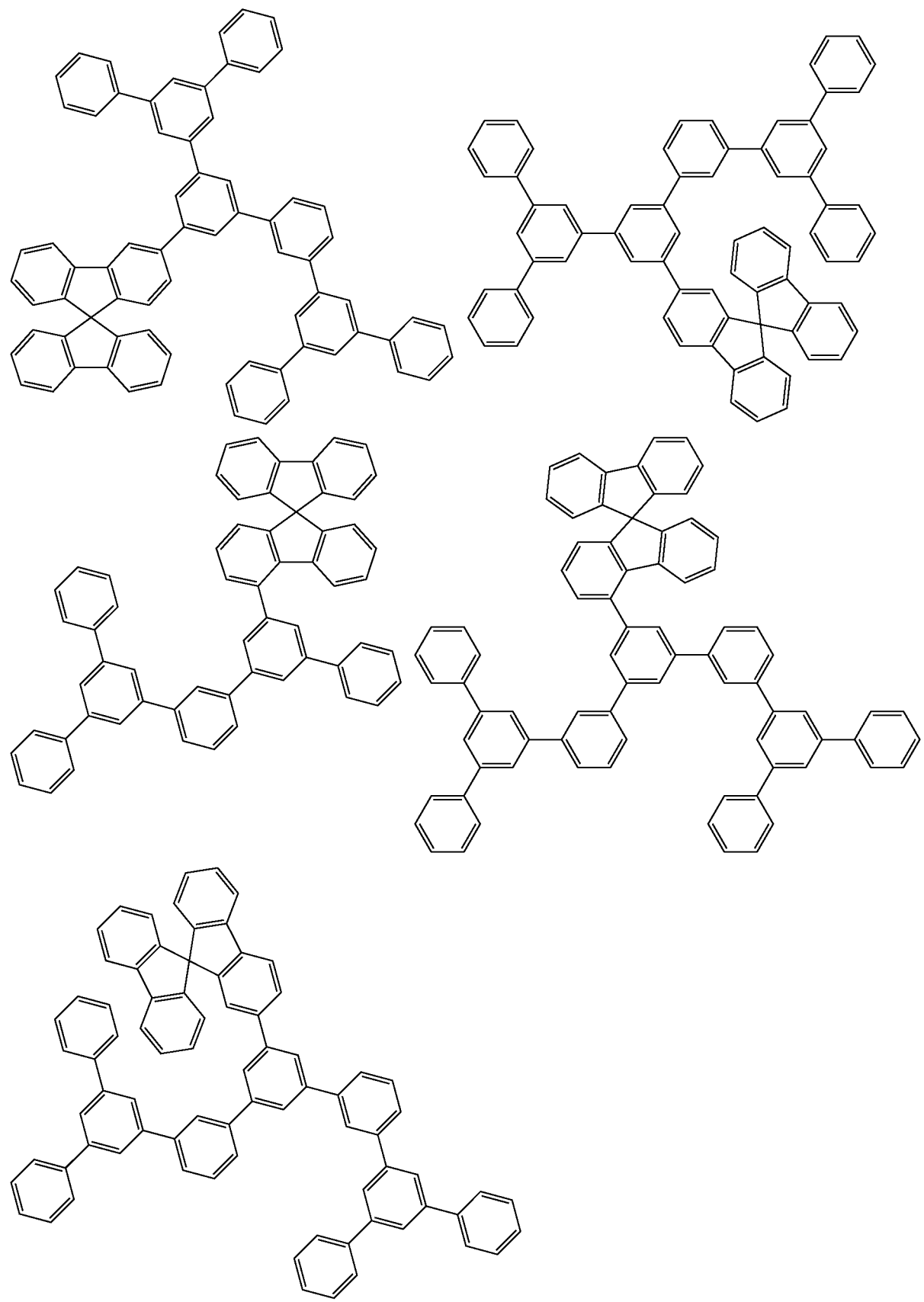

-continued
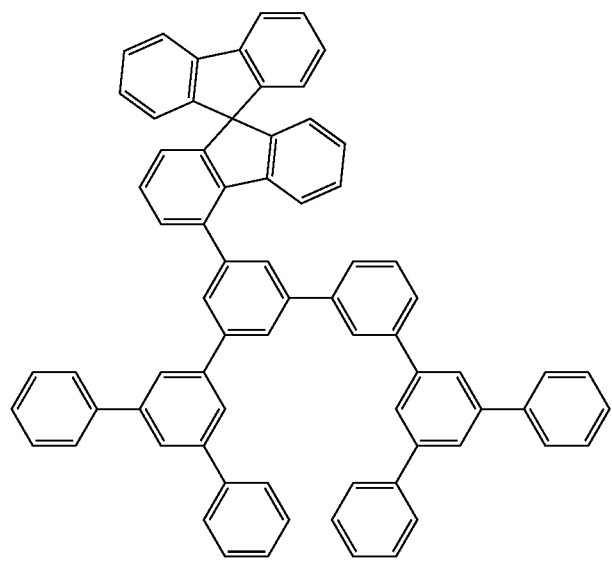
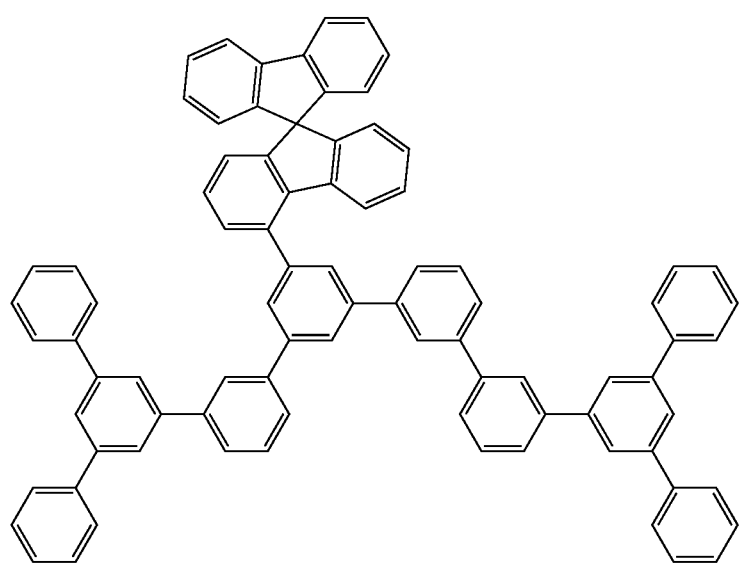

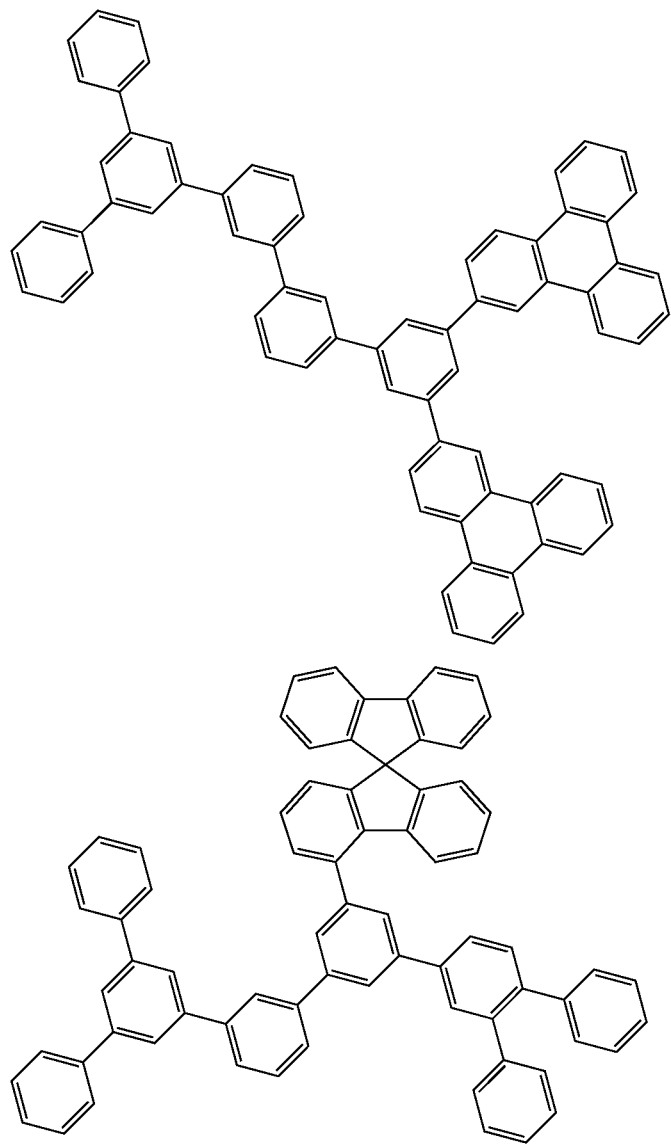
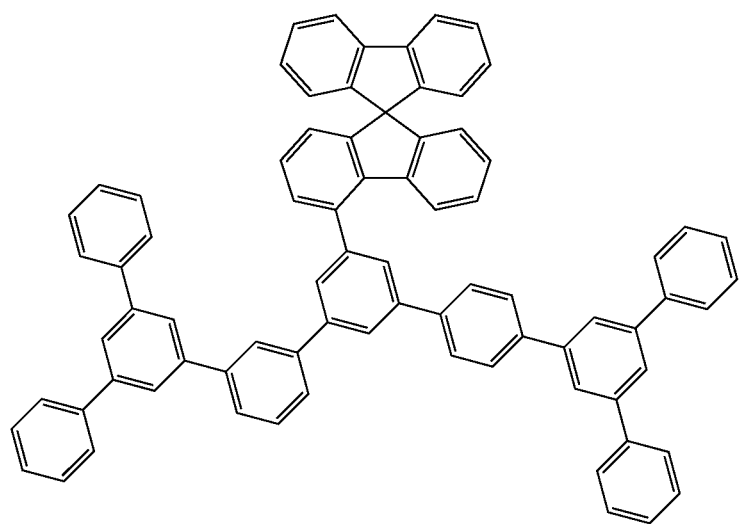

-continued
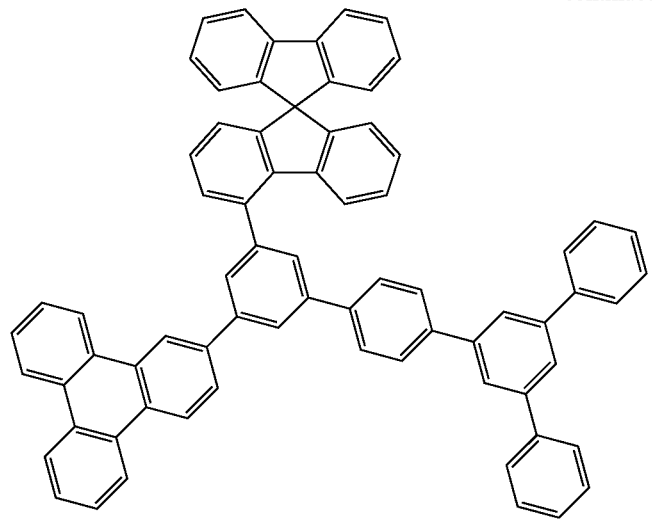
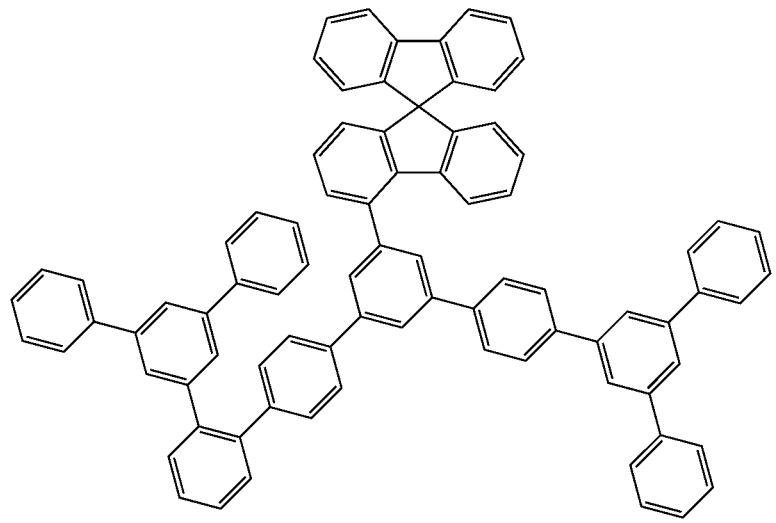
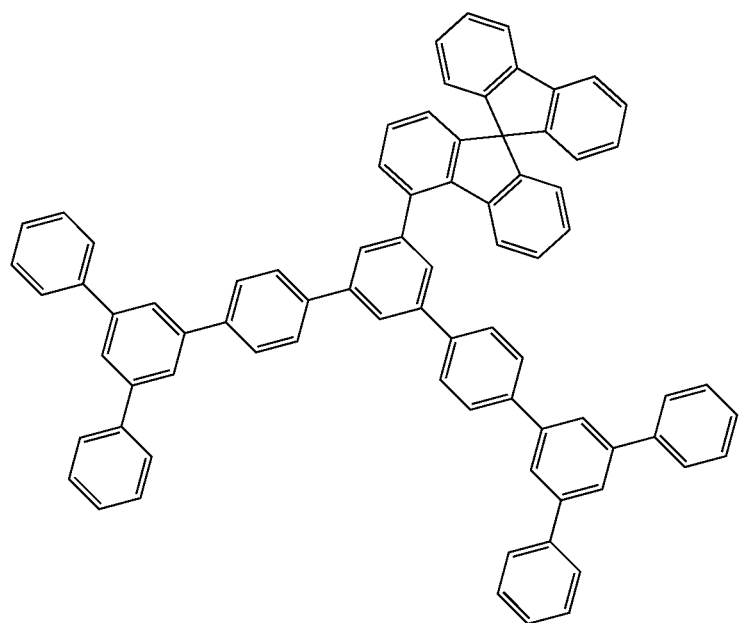

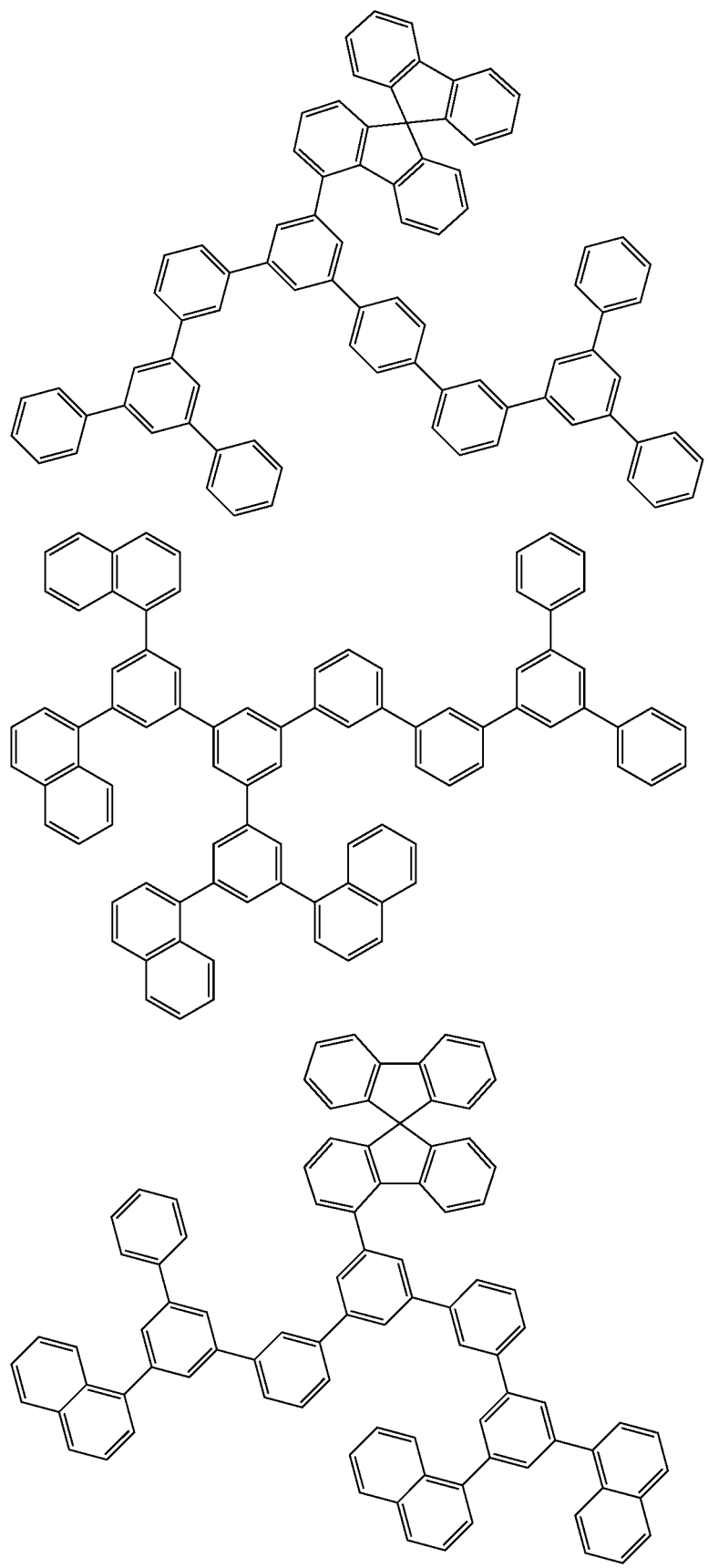

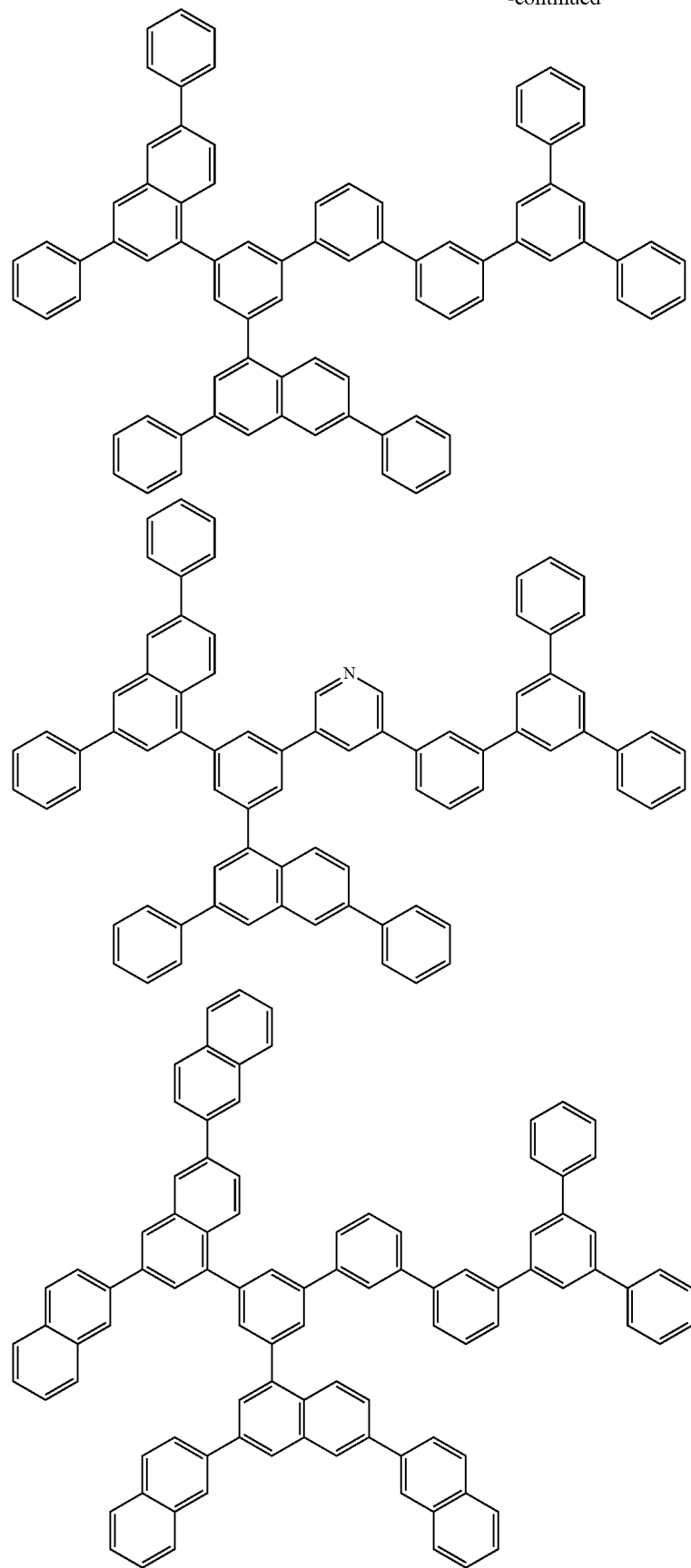

-continued
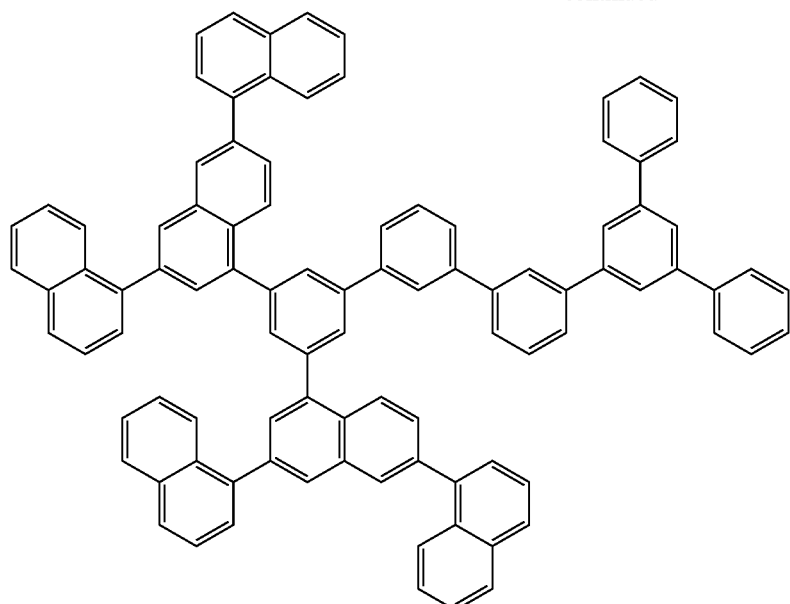
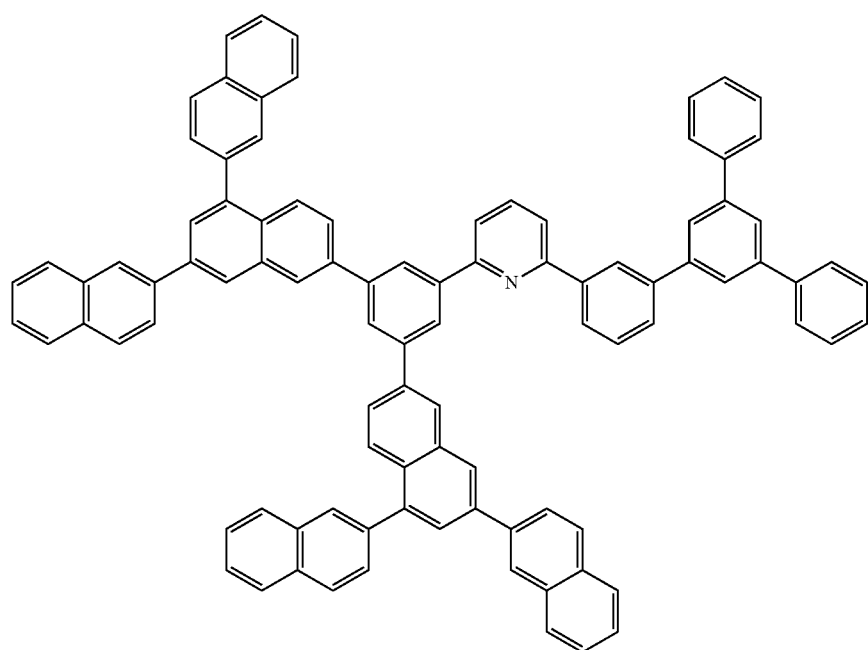

-continued
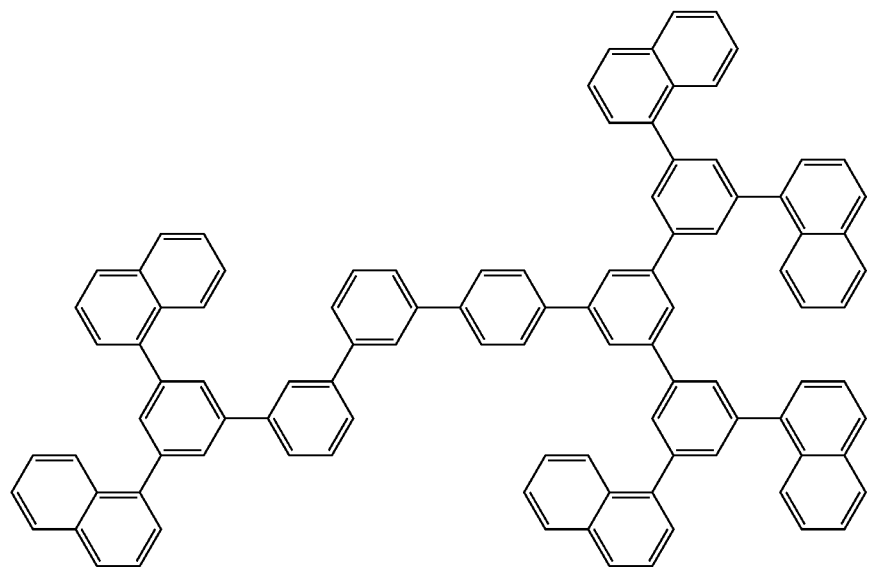
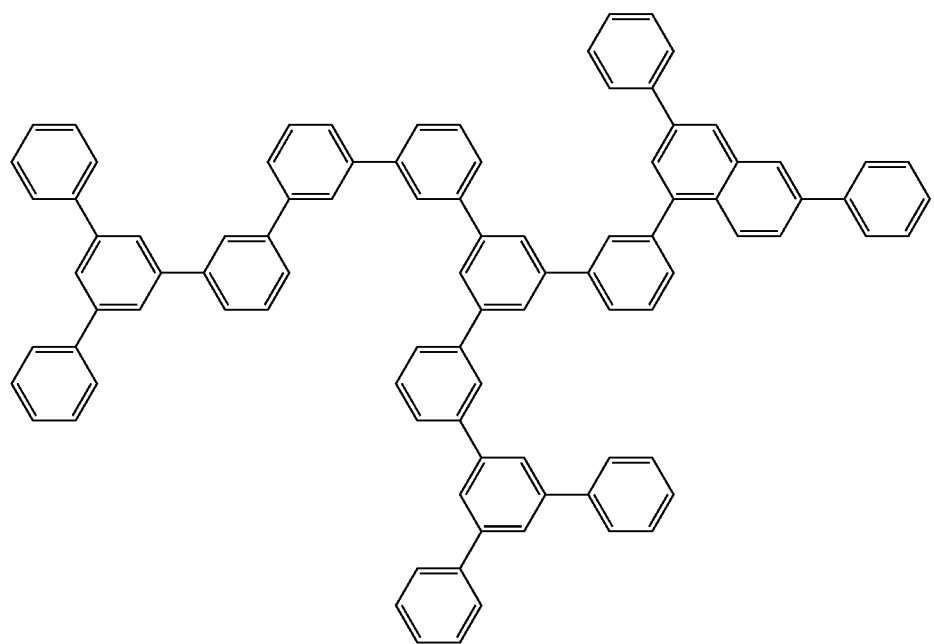

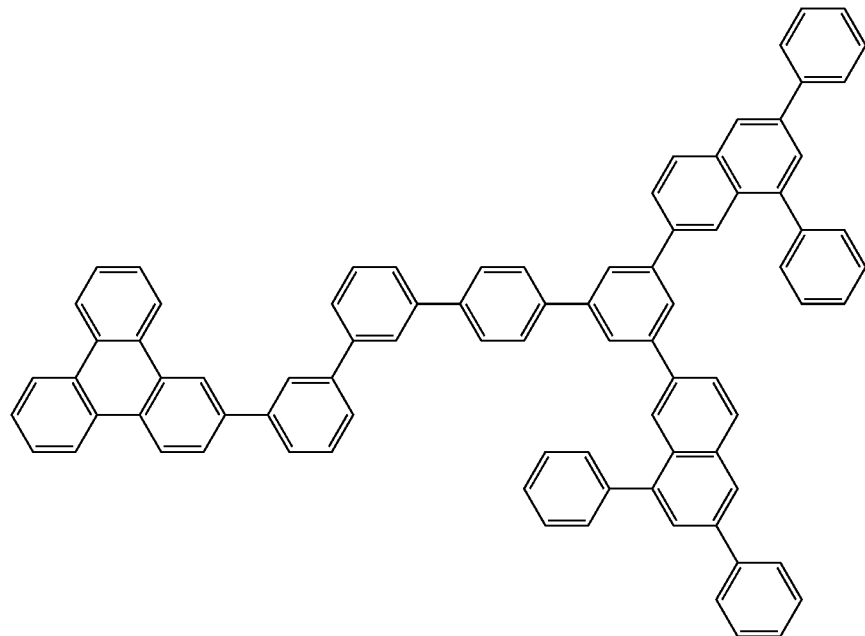
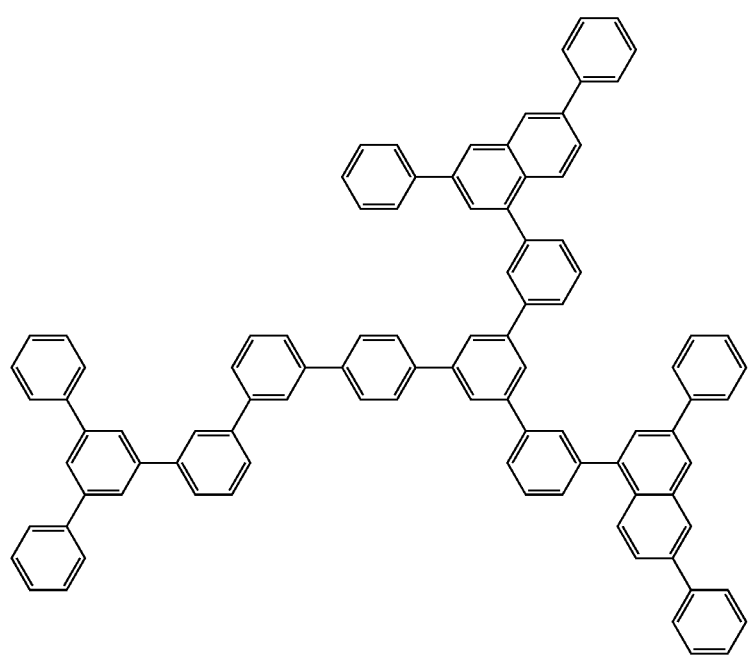

-continued
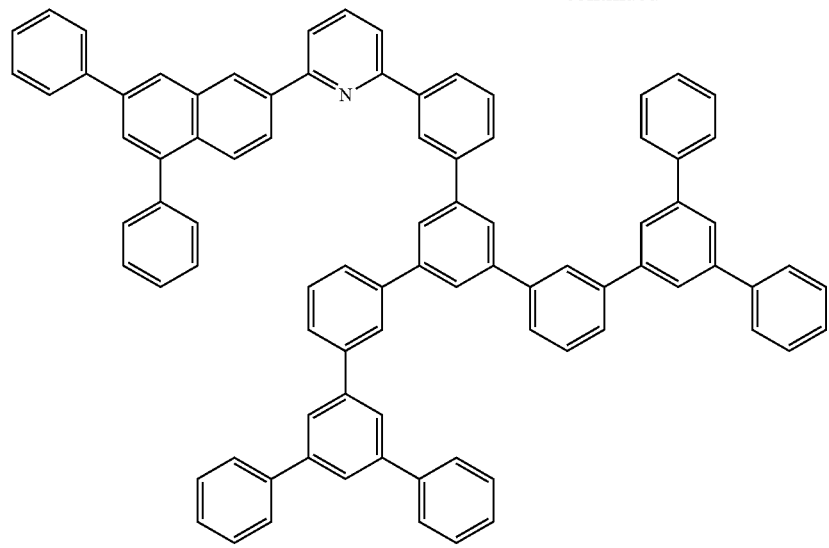
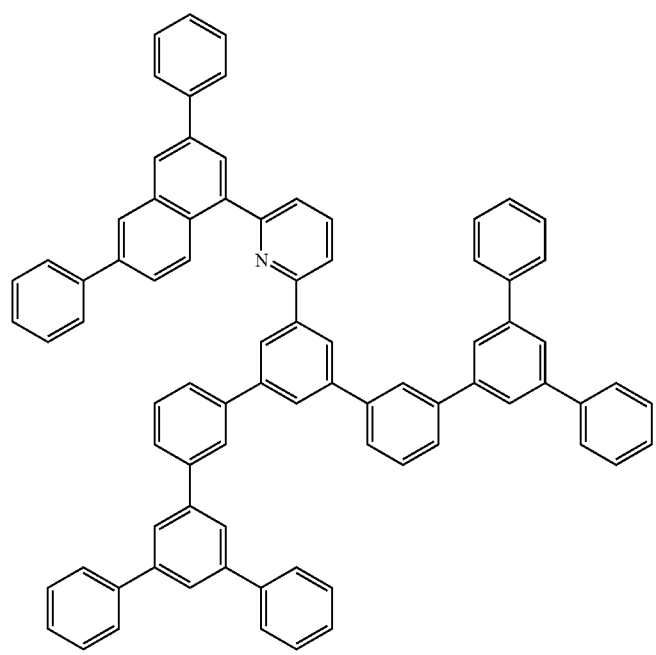

-continued
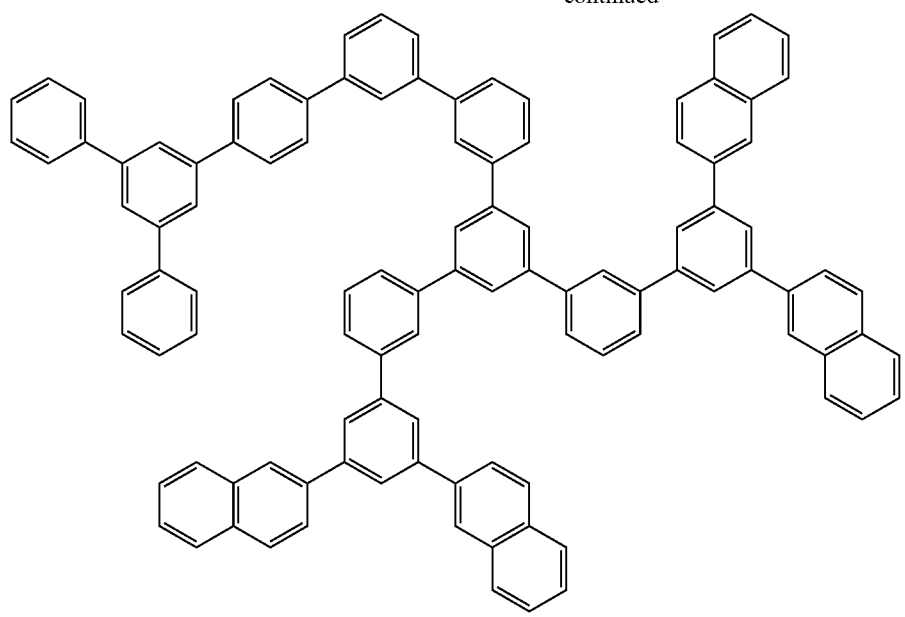
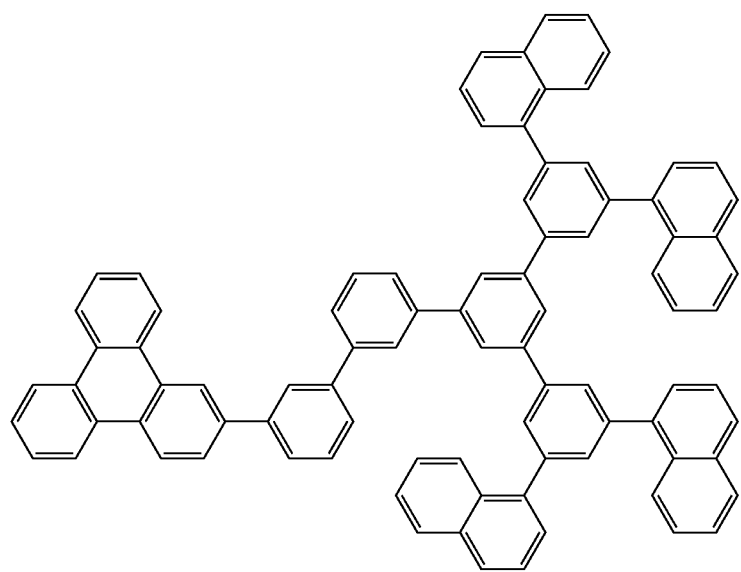

-continued
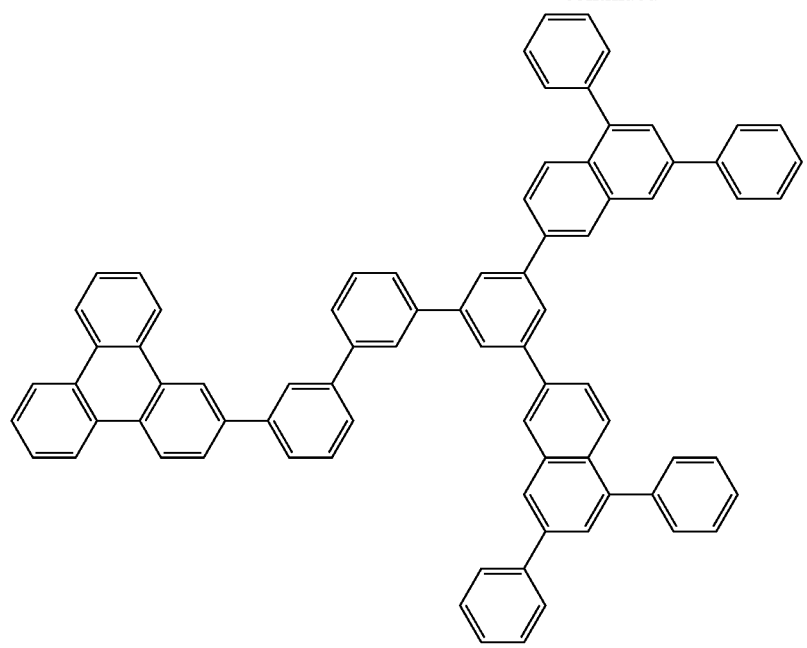
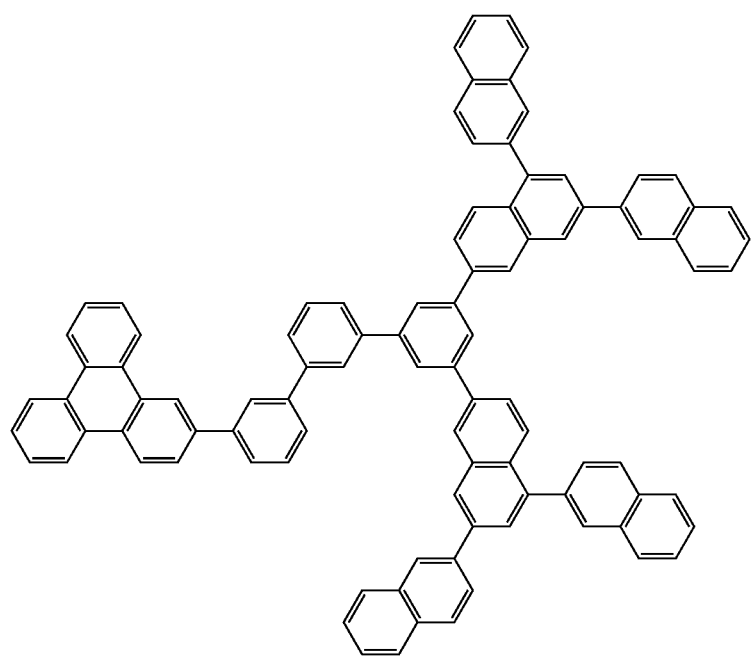

-continued

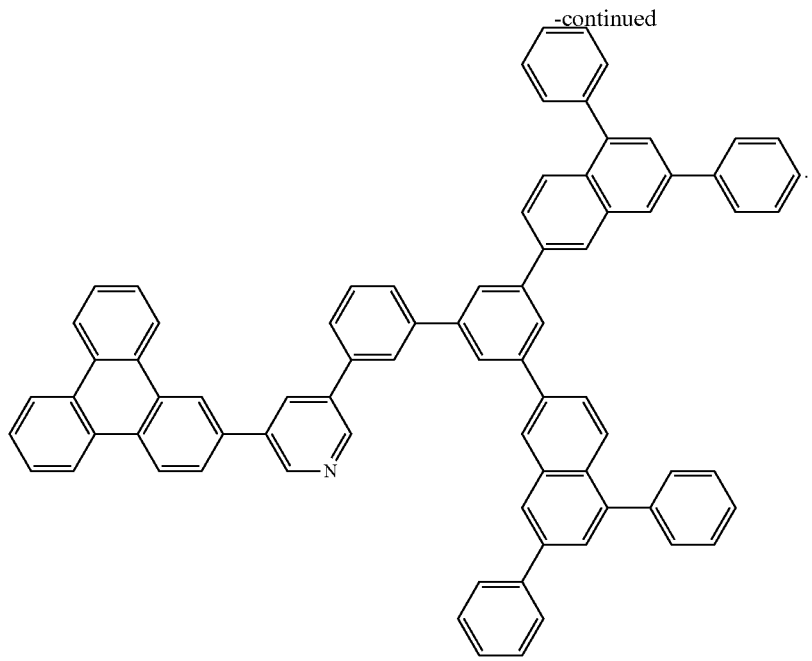

In an embodiment, the composition of the present disclosure may further include a fourth organic functional material. The fourth organic functional material may be one selected from the group consisting of: a hole injection materials (HIM), a hole transport materials (HTM), a hole blocking materials (HBM), an electron injection materials (EIM), an electron transport materials (ETM), an electron blocking materials (EBM), an organic host materials (Host), a singlet emitters (fluorescence emitters), a triplet emitters (phosphorescence emitters), a thermally activated delayed fluorescent materials (TADFs), and an organic dyes. For example, various organic functional materials are described in detail in WO 2010135519 A1, US 20090134784 A1, and WO 2011110277 A1, and the entire contents of these three patent documents are hereby incorporated by reference.

In an embodiment, the composition of the present disclosure only includes the three organic functional materials H1, H2, and H3 and at least one organic solvent.

In an embodiment, the at least one organic solvent is selected from aromatic, heteroaromatic, ester, aromatic ketone, aromatic ether, aliphatic ketone, aliphatic ether, alicyclic or olefinic compound, borate ester, phosphate ester compounds, and a mixture thereof.

In an embodiment, in the composition of the present disclosure, a surface tension of the organic solvent at 25° C. ranges from 20 dyne/cm to 45 dyne/cm, further from 22 dyne/cm to 35 dyne/cm, and particularly from 25 dyne/cm to 33 dyne/cm.

In an embodiment, the at least one organic solvent is selected from aromatic or heteroaromatic based solvents.

Examples of the aromatic or heteroaromatic based solvents that are suitable for the present disclosure are as follows, but are not limited to: p-diisopropylbenzene, pentylbenzene, tetrahydronaphthalene, cyclohexylbenzene, chloronaphthalene, 1,4-dimethylnaphthalene, 3-isopropylbiphenyl, p-methylcumene, dipentylbenzene, tripentylbenzene, amyltoluene, o-diethylbenzene, m-diethylbenzene, p-diethylbenzene, 1,2,3,4-tetramethylbenzene, 1,2,3,5-tetramethylbenzene, 1,2,4,5-tetramethylbenzene, butylbenzene, dodecylbenzene, dihexylbenzene, dibutylbenzene, p-diisopropylbenzene, cyclohexylbenzene, benzylbutylbenzene, dimethylnaphthalene, 3-isopropyl biphenyl, p-methylcumene, 1-methylnaphthalene, 1,2,4-trichlorobenzene, 4,4-difluorodiphenylmethane, 1,2-dimethoxy-4-(1-propenyl) benzene, diphenylmethane, 2-phenyl pyridine, 3-phenyl pyridine, N-methyl diphenylamine, 4-isopropyl biphenyl, α, α-dichlorodiphenylmethane, 4-(3-phenylpropyl)pyridine, benzyl benzoate, 1,1-bis(3,4-dimethylphenyl)ethane, 2-isopropylnaphthalene, quinoline, isoquinoline, methyl 2-furoate, and ethyl 2-furancarboxylate.

Examples of the aromatic ketone based solvents that are suitable for the present disclosure are as follows, but are not limited to: 1-tetralone, 2-tetralone, 2-(phenylepoxy)tetralone, 6-(methoxy)tetralone, acetophenone, propiophenone, benzophenone, and their derivatives, such as 4-methylacetophenone, 3-methylacetophenone, 2-methylacetophenone, 4-methylpropiophenone, 3-methylpropiophenone, and 2-methylpropiophenone.

Examples of the aromatic ether based solvents that are suitable for the present disclosure are as follows, but are not limited to: 3-phenoxytoluene, butoxybenzene, p-anisaldehyde dimethylacetal, tetrahydro-2-phenoxy-2H-pyran, 1,2-dimethoxy-4-(1-propenyl) benzene, 1,4-benzodioxane, 1,3-dipropylbenzene, 2,5-dimethoxytoluene, 4-ethyl phenethyl ether, 1,3-dipropoxybenzene, 1,2,4-trimethoxybenzene, 4-(1-propenyl)-1,2-dimethoxybenzene, 1,3-dimethoxybenzene, glycidyl phenyl ether, dibenzyl ether, 4-tert-butyl anisole, trans-p-propenyl anisole, 1,2-dimethoxybenzene, 1-methoxynaphthalene, diphenyl ether, 2-phenoxymethyl ether, 2-phenoxytetrahydrofuran, and ethyl-2-naphthyl ether.

In an embodiment, in the composition of the present disclosure, the at least one organic solvent may selected from aliphatic ketones, for example, 2-nonanone, 3-nonanone, 5-nonanone, 2-decanone, 2,5-hexanedione, 2,6,8-trimethyl-4-nonanone, fenone, phorone, isophorone, and di-n-amyl ketone, or aliphatic ethers, for example, amyl ether, hexyl ether, dioctyl ether, ethylene glycol dibutyl ether, diethylene glycol diethyl ether, diethylene glycol butyl methyl ether, diethylene glycol dibutyl ether, triethylene glycol dimethyl ether, triethylene glycol ethyl methyl ether, triethylene glycol butyl methyl ether, tripropylene glycol dimethyl ether, and tetraethylene glycol dimethyl ether.

In some preferred embodiments, in the composition of the present disclosure, the at least one organic solvent may be selected from ester-based solvents: alkyl octanoate, alkyl sebacate, alkyl stearate, alkyl benzoate, alkyl phenylacetate, alkyl cinnamate, alkyl oxalate, alkyl maleate, alkyl lactone, and alkyl oleate. Preferably, the at least one organic solvent may be octyl octanoate, diethyl sebacate, diallyl phthalate, or isononyl isononanoate.

The solvents mentioned above may be used alone or as a mixture of two or more organic solvents.

In some embodiments, in addition to the above-mentioned organic functional materials and the at least one organic solvent, the composition of the present disclosure may further include another organic solvent. Examples of another organic solvent includes but is not limited to: methanol, ethanol, 2-methoxyethanol, dichloromethane, chloroform, chlorobenzene, o-dichlorobenzene, tetrahydrofuran, anisole, morpholine, toluene, o-xylene, m-xylene, p-xylene, 1,4-dioxane, acetone, methyl ethyl ketone, 1,2 dichloroethane, 3-phenoxytoluene, 1,1,1-trichloroethane, 1,1,2,2-tetrachloroethane, ethyl acetate, butyl acetate, dimethylformamide, dimethylacetamide, dimethylsulfoxide, tetrahydronaphthalene, decalin, indene, and/or a mixture thereof.

In an embodiment, solvents that are particularly suitable for the composition of the present disclosure are those having a Hansen solubility parameter in following ranges:
- $\delta_d$ (dispersion force) in a range of 17.0 to 23.2 $MPa^{1/2}$, especially 18.5 to 21.0 $mpa^{1/2}$;
- $\delta_p$ (polar force) in a range of 0.2 to 12.5 $MPa^{1/2}$, especially 2.0 to 6.0 $MPa^{1/2}$; and
- $\delta_h$ (hydrogen bonding force) in a range of 0.9 to 14.2 $MPa^{1/2}$, especially 2.0 to 6.0 $MPa^{1/2}$.

In the composition of the present disclosure, a boiling point parameter of the organic solvent should be considered when selecting. The boiling point of the organic solvent of the present disclosure is greater than or equal to 150° C., further greater than or equal to 180° C., still further greater than or equal to 200° C., even further greater than or equal to 250° C., and particularly greater than or equal to 300° C. The boiling point in these ranges is beneficial for preventing nozzle clogging in inkjet printheads. The organic solvent can be evaporated from a solvent system to form a functional material thin film.

The present disclosure also relates to a use of the composition as a printing ink when preparing an organic electronic device by printing or coating.

Suitable printing or coating techniques include, but are not limited to, inkjet printing, typography, screen printing, dip coating, spin coating, blade coating, roller printing, torsion roller printing, lithography, flexographic printing, rotary printing, spraying coating, brushing coating, pad printing, slot die coating, etc. Preferred are gravure printing, screen printing, and inkjet printing. Gravure printing and ink jet printing will be applied in the embodiments of the present disclosure. The solution or suspension may additionally include one or more components such as surfactants, lubricants, wetting agents, dispersing agents, hydrophobic agents, binders, etc., to adjust viscosity, film-forming properties, improve adhesion, and the like.

According to the preparation method mentioned above, a functional layer formed has a thickness ranging from 5 nm to 1000 nm.

The present disclosure further relates to an organic electronic device, which includes the functional layer prepared by the composition mentioned above. The organic electronic device may be, but is not limited to, organic-light emitting diodes (OLEDs), organic photovoltaic cells (OPV), organic light-emitting electrochemical cells (OLEEC), organic field-effect transistors (OFET), organic light-emitting field effect transistors, organic lasers, organic spintronics, organic sensors, and organic plasmon emitting diodes, etc., and preferably organic electroluminescent devices, such as OLED, OLEEC, and organic light-emitting field effect transistors.

In some embodiments, the organic electroluminescent devices at least include a light-emitting layer prepared by the composition mentioned above.

The light-emitting devices, particularly the OLEDs, include a substrate, an anode, at least one light-emitting layer, and a cathode.

The substrate may be opaque or transparent. A transparent substrate can be used to fabricate a transparent light-emitting device. For example, refer to Bulovic et al., Nature 1996, 380, p29, and Gu et al., Appl. Phys. Lett. 1996, 68, p2606. The substrate may be rigid or flexible. The substrate may be plastics, metals, semiconductor wafers, or glass. Preferably, the substrate has a smooth surface. Substrates without surface defects are particularly desirable. In an embodiment, the substrate is flexible and may be made of polymer film or plastics, A glass transition temperature Tg is greater than or equal to 150° C., further greater than 200° C., still further greater than 250° C., and especially greater than 300° C. Examples of suitable flexible substrates are polyethylene terephthalate (PET) and polyethylene glycol(2,6-naphthalene) (PEN).

The anode may include a conductive metal or metal oxide, or a conductive polymer. The anode can easily inject holes into a hole injection layer (HIL), a hole transport layer (HTL), or a light-emitting layer. In an embodiment, an absolute value of a difference between a work function of the anode and a HOMO energy level or valence band energy level of an emitter in the light-emitting layer or a p-type semiconductor material as an HIL, HTL, or electron blocking layer (EBL) is less than 0.5 eV, further less than 0.3 eV, and still further less than 0.2 eV. Examples of anode materials include, but are not limited to, Al, Cu, Au, Ag, Mg, Fe, Co, Ni, Mn, Pd, Pt, ITO, aluminum-doped zinc oxide (AZO), etc. Other suitable anode materials are known and can be readily selected for use by those of ordinary skill in the art. The anode materials may be deposited using any suitable techniques, such as a suitable physical vapor deposition method, which includes radio frequency magnetron sputtering, vacuum thermal evaporation, electron beam (e-beam), etc. In some embodiments, the anode is patterned. Patterned ITO conductive substrates are commercially available and can be used to fabricate devices of the present disclosure.

The cathode may include a conductive metal or metal oxide. The cathode can easily inject electrons into an EIL or ETL, or directly into the light-emitting layer. In an embodiment, an absolute value of a difference between a work function of the cathode and a LUMO energy level or conduction band energy level of the emitter in the light-emitting layer or an N-type semiconductor material as an electron injection layer (EIL), an electron transport later (ETL), or a hole blocking layer (HBL) is less than 0.5 eV, further less than 0.3 eV, and still further less than 0.2 eV. In principle, all materials that can be used as cathodes for OLEDs are possible as cathode materials for the devices of the disclosure. Examples of anode materials include, but are not limited to, Al, Au, Ag, Ca, Ba, Mg, LiF/Al, Mg/Ag alloy, BaF2/Al, Cu, Fe, Co, Ni, Mn, Pd, Pt, ITO, etc. The cathode materials may be deposited using any suitable techniques, such as a suitable physical vapor deposition method, which includes radio frequency magnetron sputtering, vacuum thermal evaporation, electron beam (e-beam), etc.

The OLEDs may include other functional layers, such as a hole injection layer (HIL), a hole transport layer (HTL), an electron blocking layer (EBL), an electron injection layer (EIL), an electron transport layer (ETL), and a hole blocking layer (HBL). Materials suitable for use in these functional layers are described in detail above and in WO 2010135519 A1, US 20090134784 A1, and WO 2011110277 A1, and the entire contents of these three patent documents are hereby incorporated by reference.

The light-emitting devices of the present disclosure has a light-emitting wavelength ranging from 300 nm to 1000 nm, preferably from 350 nm to 900 nm, and more preferably from 400 nm to 800 nm.

The present disclosure also relates to applications of the light-emitting devices of the present disclosure on various electronic devices, which include, but are not limited to, display devices, lighting devices, light sources, sensors, etc.

The present disclosure will be described below with reference to the preferred embodiments, but is not limited to the following embodiments. It should be understood that the appended claims summarize the scope of the present disclosure. Under the guidance of the inventive concept, those skilled in the art should recognize that certain changes made to the various embodiments of the present disclosure will be covered by the spirit and scope of the claims of the present disclosure.

SPECIFIC EMBODIMENT

1. Selection of Organic Functional Materials

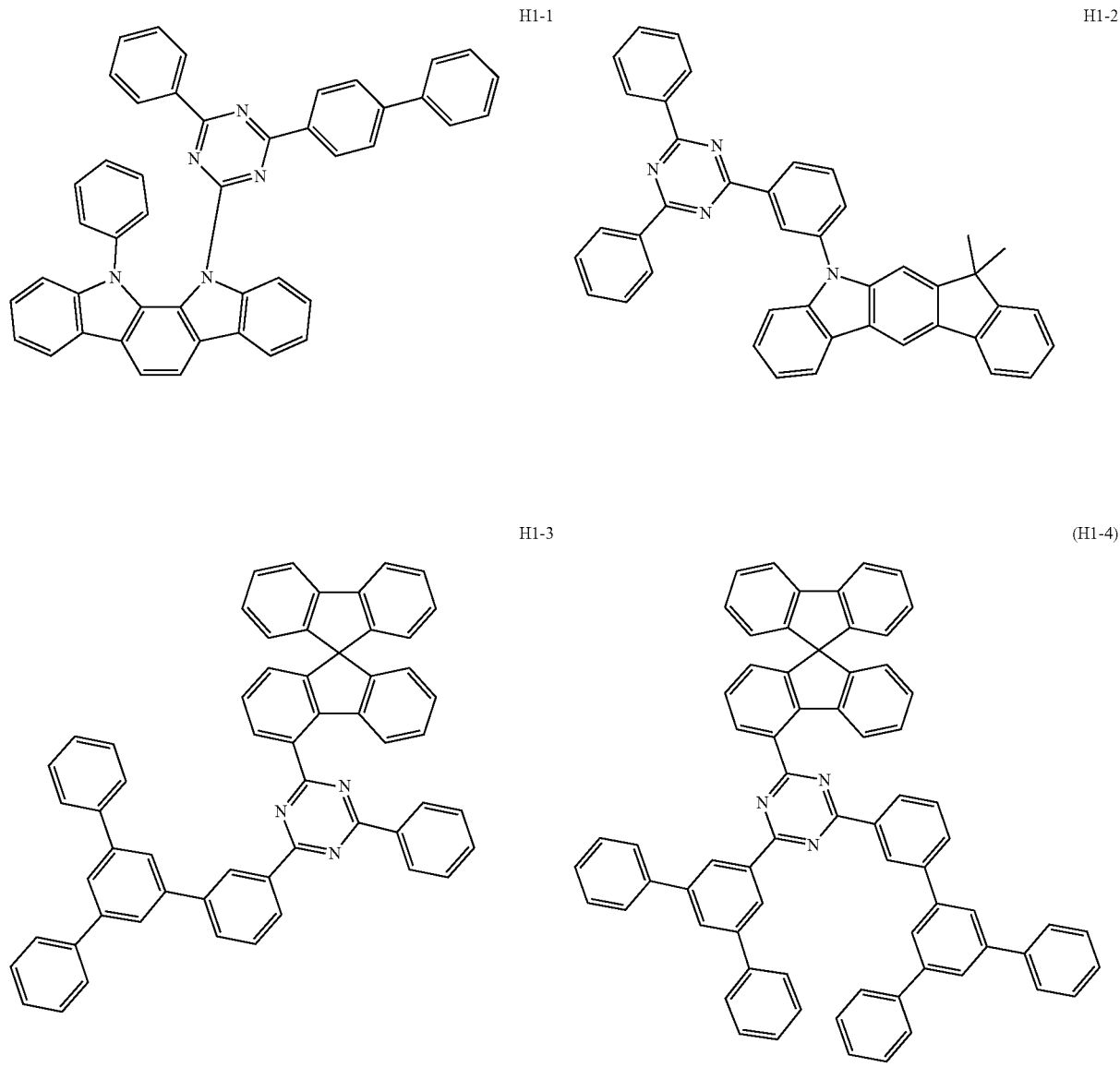

H2-1
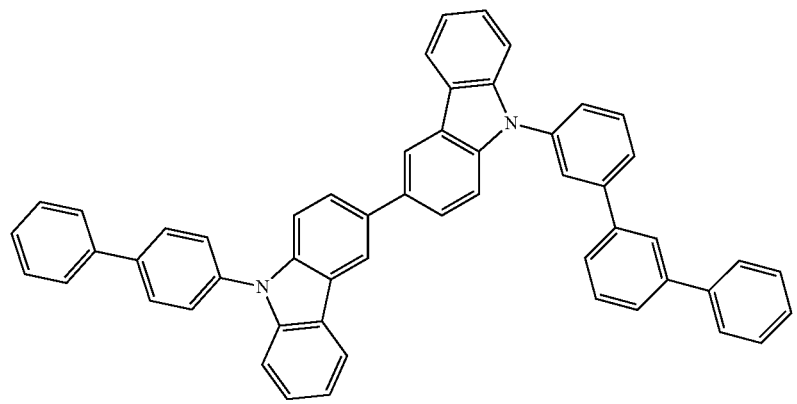
H2-2 H2-3
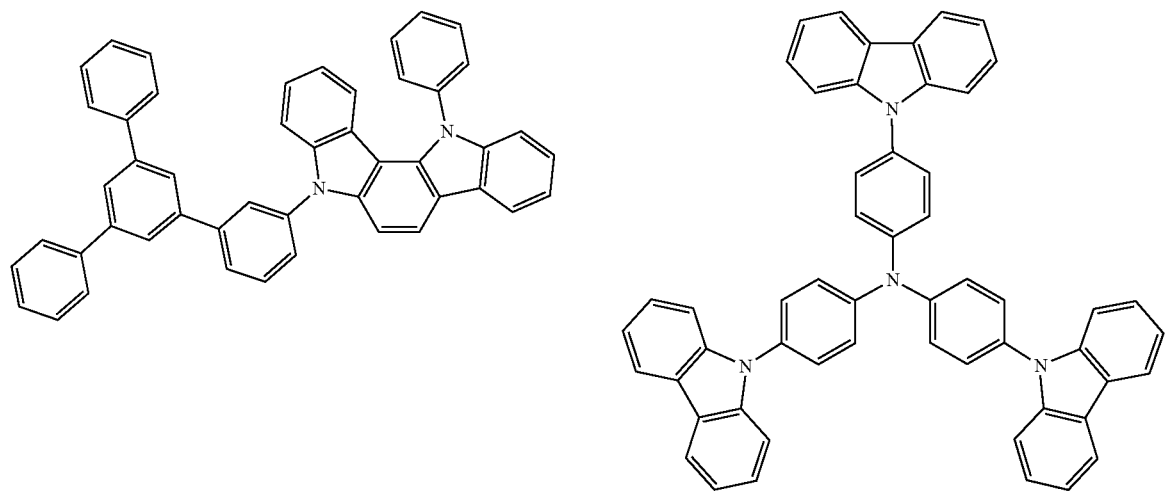
(H2-4) (H2-5)
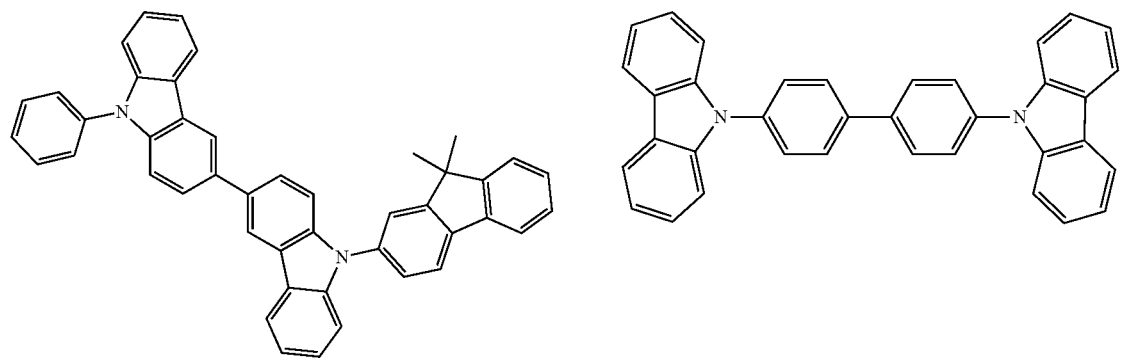

H3-1
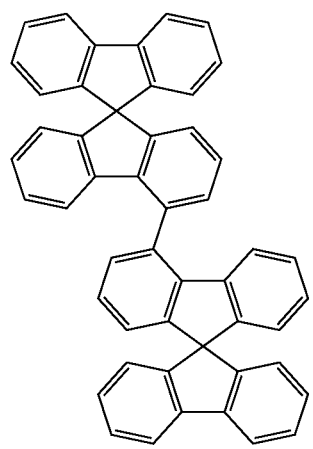
H3-2
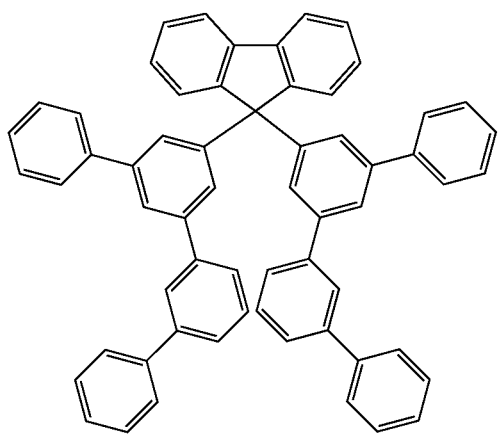
H3-3
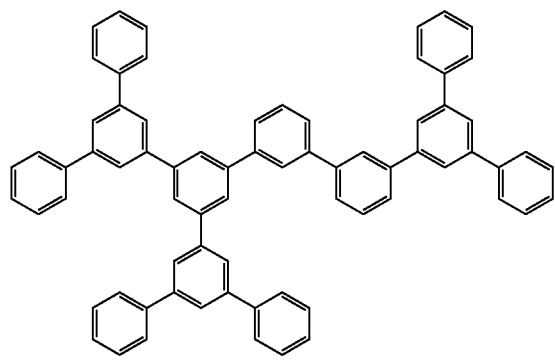
(H3-4)
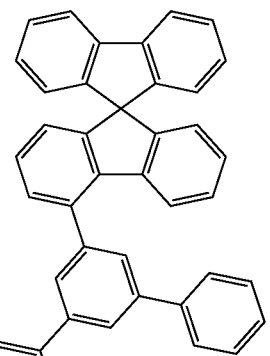
(H3-5)
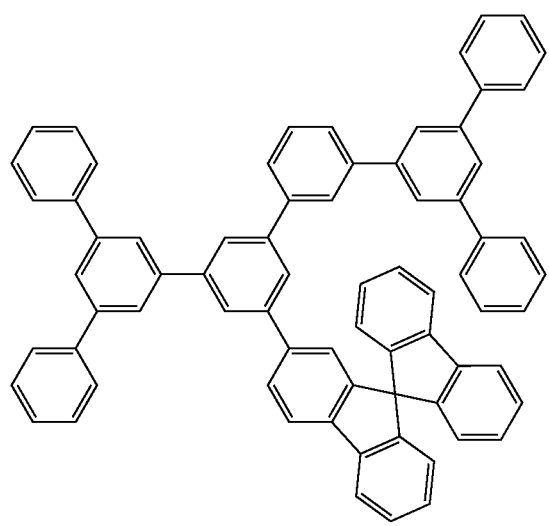
(H3-6)
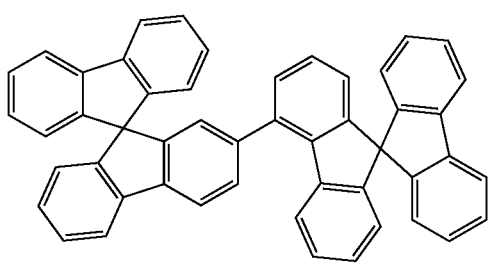
Wherein, compounds H1-1, H1-2, H1-3, and H1-4 are used as the first organic functional material.
Compounds H2-1, H2-2, H2-3, H2-4, and H2-5 are used as the second organic functional material.
Compounds H3-1, H3-2, H3-3, H3-4, H3-5, and H3-6 are used as the third organic functional material.
For the synthesis reaction of H1-1, see WO 2008056746 A; for the synthesis reaction of H1-2, see US 2012238105 A;

and for the synthesis reaction of H1-3, see WO 2014023388 A. For the synthesis reaction of H2-1, see WO 2015156449 A; for the synthesis reaction of H2-2, see WO 2007063796 A; for the synthesis reaction of H2-3, see Adv. Funct. Mater. 2007, 17, 1028-1036; for the synthesis reaction of H2-4, see WO 2014030872 A; and for the synthesis reaction of H2-5, see WO 2003074628 A. For the synthesis reaction of H3-1, see Org. Lett. 2009, 11, 2607-2610A; and for the synthesis reaction of H3-2 and H3-3, see WO 2009124627 A.

2. Synthesis of Organic Materials

Synthesis Example 1

Synthesis of H1-4

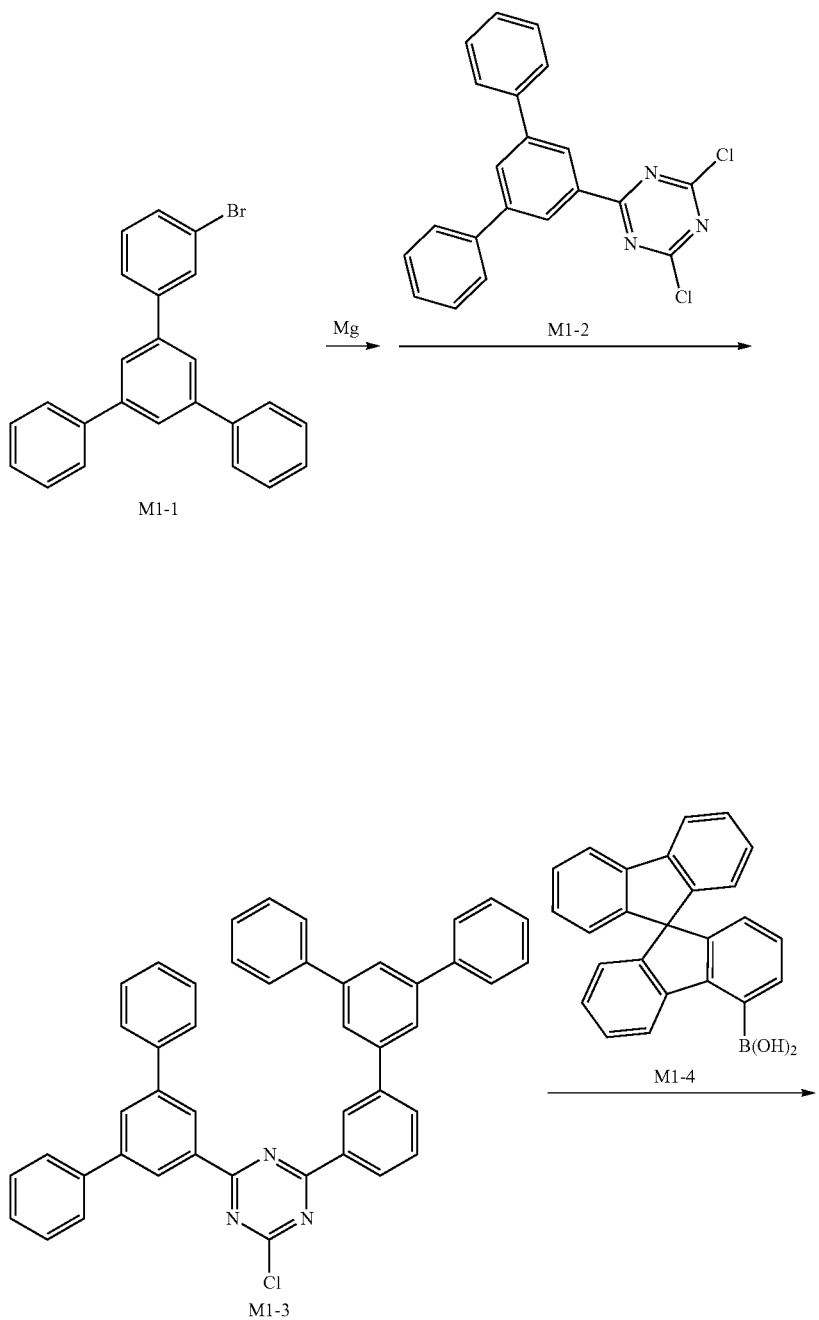

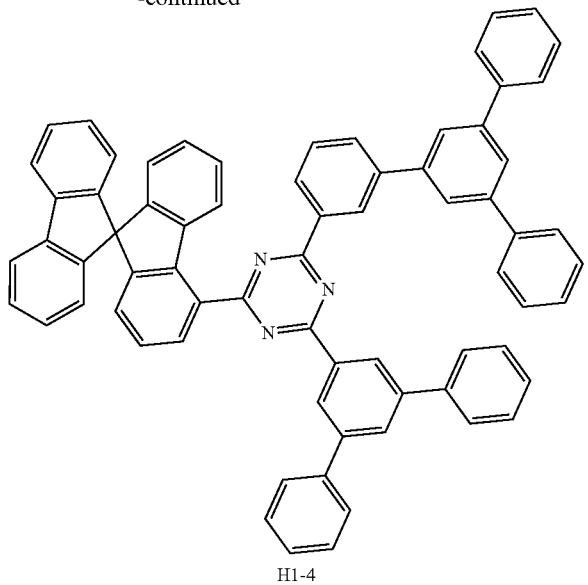

H1-4

Synthesis of intermediate M1-3: put magnesium chips (1.0 g) in a dry double-necked flask, add dry THF (40 ml), and add a small amount of iodine element. Under a nitrogen atmosphere, a THF solution of M1-1 (5.0 g) is slowly added dropwise to the double-necked flask, and the reaction is initiated and maintained by heating appropriately. When after a reaction between the magnesium chips and M1-1 to generate Grignard reagent is completed, the generated Grignard reagent is added dropwise to a THF solution of M1-2 (4.9 g) under the nitrogen atmosphere, and stirred at room temperature overnight. Then, water is added to the reaction to quench residual Grignard reagent, an appropriate amount of ethyl acetate is added for extraction, and the mixture is washed with water and separated. After drying the organic phase, the solvent is removed by rotary evaporation, and an intermediate M1-3 is obtained by beating with petroleum ether. MS(ASAP): 648.21.

Synthesis of H1-4: M1-3 (6.0 g), M1-4 (3.4 g), Pd(PPh$_3$)$_4$ (0.3 g), and potassium carbonate (2.0 g) are added to a 150 ml mixed solvent of 1,4-dioxane/water (volume ratio is 9:1), and then refluxed for 12 hours under the nitrogen atmosphere. After cooling, most of the solvent is distilled off under a reduced pressure, and the product is extracted with dichloromethane and washed with water for separation. After drying the organic phase, the solvent is removed by rotary evaporation, and then H1-4 is obtained by recrystallization. MS(ASAP): 928.15.

Synthesis Example 2

Synthesis of H3-4

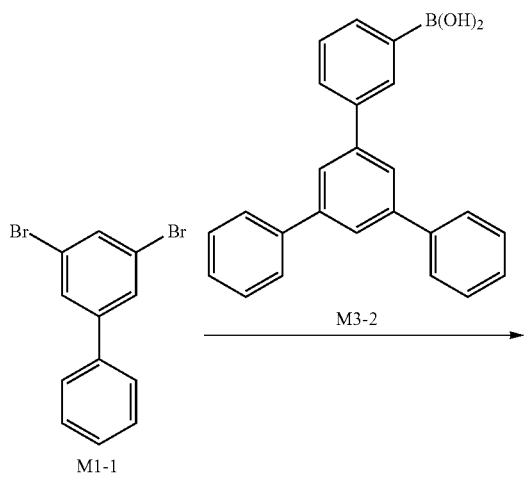

-continued

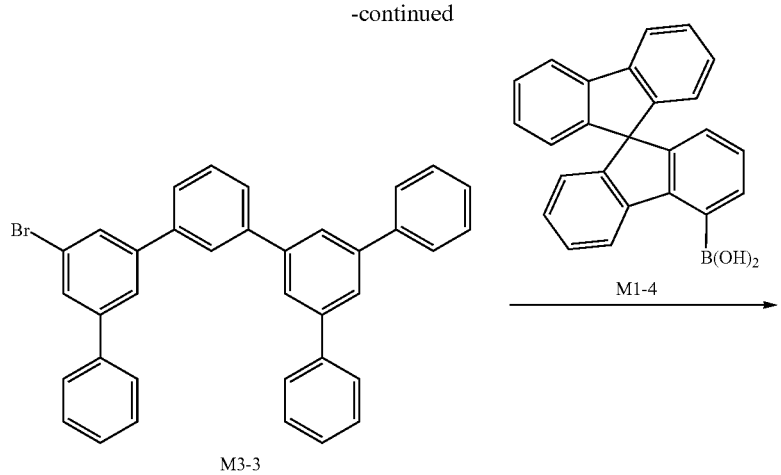

M3-3        M1-4

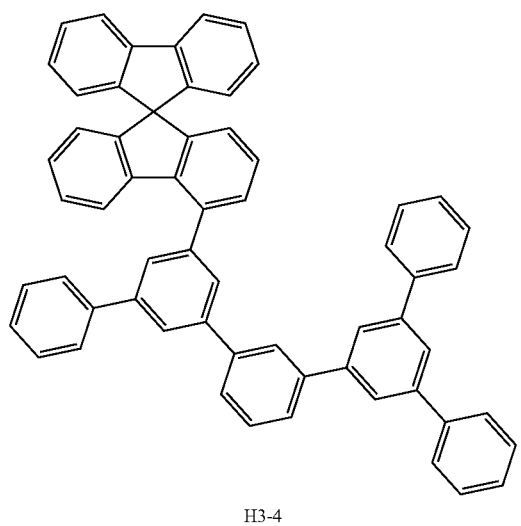

H3-4

Synthesis of an intermediate M3-3: M3-1 (8.0 g), M3-2 (8.9 g), Pd(PPh$_3$)$_4$ (0.3 g), and potassium carbonate (7.1 g) are added to a 200 ml mixed solvent of 1,4-dioxane/water (volume ratio is 9:1), and then refluxed for 12 hours under the nitrogen atmosphere. After cooling, most of the solvent is distilled off under the reduced pressure, and the product is extracted with dichloromethane and washed with water for separation. After drying the organic phase, the solvent is removed by rotary evaporation, and M3-3 is obtained by column chromatography. MS(ASAP): 537.50.

The synthesis of H3-4 can refer to the synthesis of M3-3, except that M3-1 is replaced by M3-3 and M3-2 is replaced by M1-4. MS(ASAP) of H3-4: 772.99.

Synthesis Example 3
Synthesis of H3-5
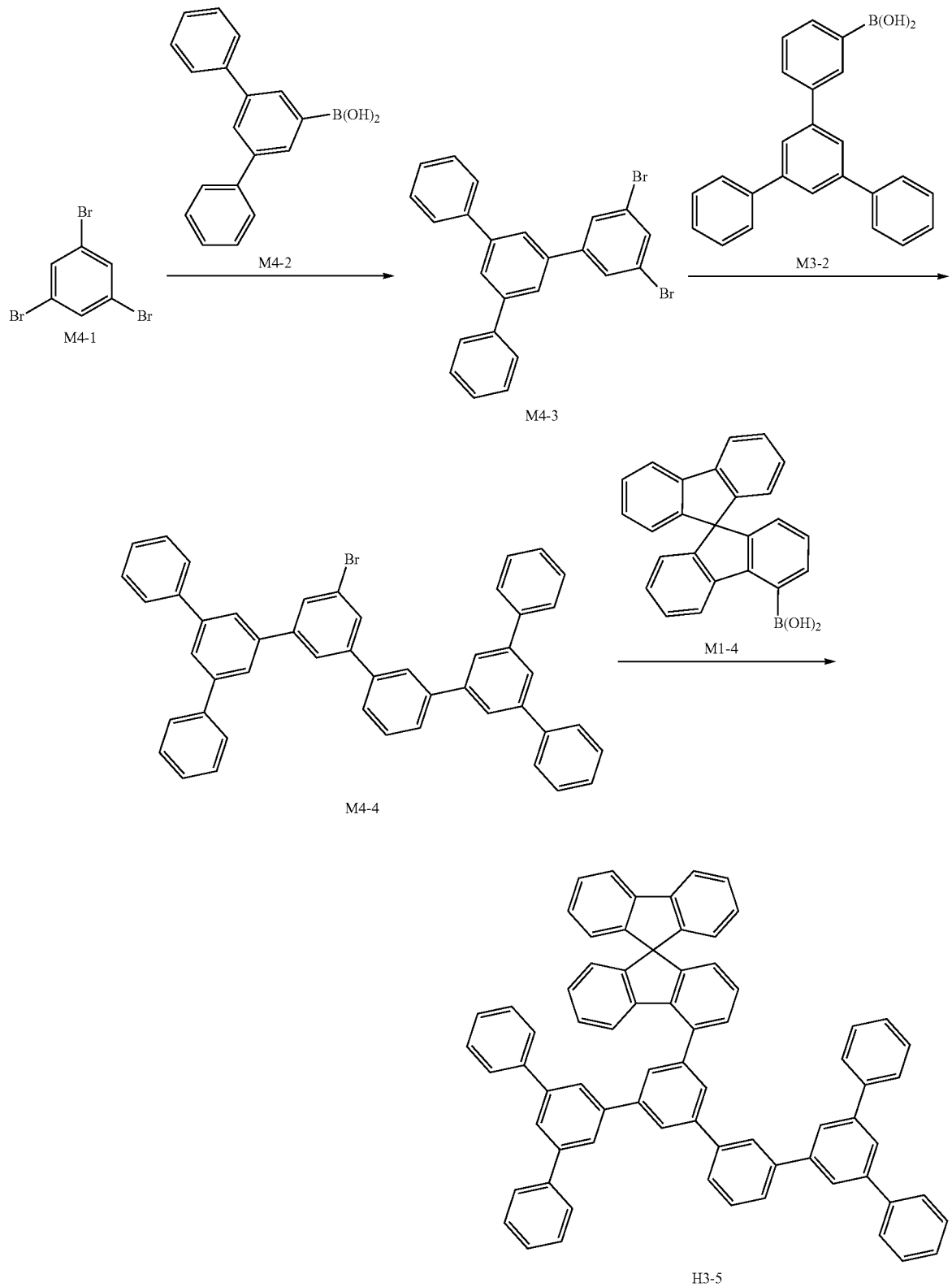

The synthesis of an intermediate M4-3 can refer to the synthesis of M3-3, except that M3-1 is replaced by M4-1 and M3-2 is replaced by M4-2. MS(ASAP): 464.20.

The synthesis of an intermediate M4-4 can refer to the synthesis of M3-3, except that M3-1 is replaced by M4-3. MS(ASAP): 689.70.

The synthesis of H3-5 can refer to the synthesis of M3-3, except that M3-1 is replaced by M4-4 and M3-2 is replaced by M1-4. MS(ASAP): 925.19.

Synthesis Example 4

Synthesis of H3-6

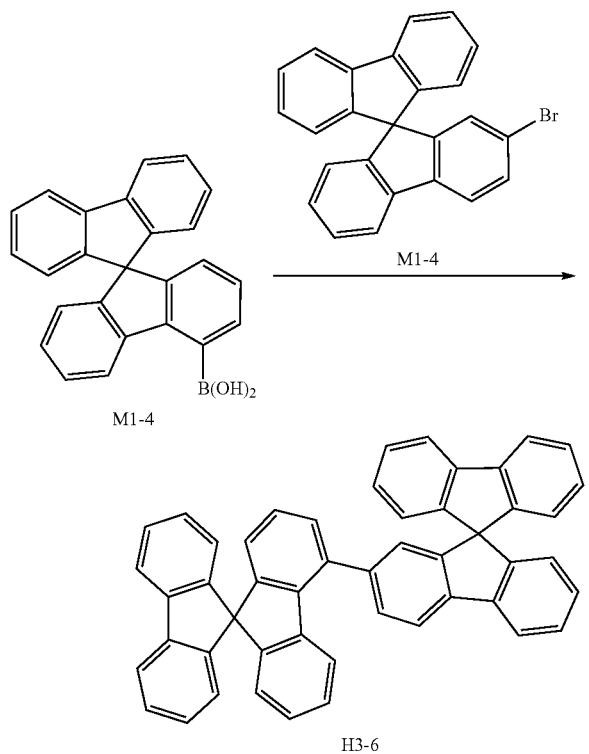

Synthesis of H3-6: M1-4 (7.5 g), M4-1 (8.2 g), Pd(PPh$_3$)$_4$ (0.3 g), and potassium carbonate (5.8 g) were added to a 150 ml mixed solvent of 1,4-dioxane/water (volume ratio is 9:1), and then refluxed for 12 hours under the nitrogen atmosphere. After cooling, most of the solvent is distilled off under the reduced pressure, and the product is extracted with dichloromethane and washed with water for separation. After drying the organic phase, the solvent is removed by rotary evaporation, and then H3-6 is obtained by column chromatography. MS(ASAP): 630.79.

2. Energy Level Structure Calculation

Energy levels of the organic compound materials can be obtained by quantum simulation calculation, such as using time-dependent density functional theory (TD-DFT) by Gaussian 09W (Gaussian Inc.), and a specific simulation method can refer to WO2011141110. First, a semi-empirical method "Ground State/Semi-empirical/Default Spin/AM1" (Charge 0/Spin Singlet) is used to optimize the molecular geometry, and then the energy structure of organic molecules is determined by the TD-DFT (time-dependent density functional theory) method to calculate and obtain "TD-SCF/DFT/Default Spin/B3PW91" and a basis set "6-31G (d)" (Charge 0/Spin Singlet). The HOMO and LUMO energy levels are calculated according to a calibration formula below, and S1, T1, and the resonance factor f(S1) are used directly.

HOMO(eV)=((HOMO(G)×27.212)−0.9899)/1.1206

LUMO(eV)=((LUMO(G)×27.212)−2.0041)/1.385

Wherein, HOMO(G) and LUMO(G) are direct calculation results from Gaussian 09W, and the unit thereof is Hartree. The result is shown in table 1:

TABLE 1

| material | HOMO [eV] | LUMO [eV] | $E_g$ [eV] | $T_1$ [eV] | $S_1$ [eV] |
|---|---|---|---|---|---|
| H1-1 | −5.68 | −2.93 | 2.76 | 2.74 | 2.80 |
| H1-2 | −5.54 | −2.89 | 2.65 | 2.67 | 2.81 |
| H1-3 | −6.00 | −2.84 | 3.16 | 2.95 | 3.26 |
| H1-4 | −6.05 | −2.85 | 3.19 | 2.94 | 3.41 |
| H2-1 | −5.44 | −2.22 | 3.22 | 2.92 | 3.12 |
| H2-2 | −5.50 | −2.25 | 3.25 | 2.88 | 3.27 |
| H2-3 | −5.33 | −2.20 | 3.12 | 2.72 | 3.28 |
| H2-4 | −5.40 | −2.29 | 3.11 | 2.75 | 3.48 |
| H2-5 | −5.73 | −2.41 | 3.32 | 2.95 | 3.44 |
| H3-1 | −6.01 | −2.19 | 3.81 | 2.94 | 3.70 |
| H3-2 | −6.14 | −2.22 | 3.87 | 2.94 | 3.08 |
| H3-3 | −6.16 | −2.21 | 3.94 | 2.96 | 3.18 |
| H3-4 | −5.99 | −2.22 | 3.77 | 2.92 | 4.13 |
| H3-5 | −5.81 | −2.28 | 3.54 | 2.80 | 3.92 |
| H3-6 | −5.93 | −2.28 | 3.65 | 2.87 | 4.00 |

3. Preparation of the Composition

A fourth organic functional material contained in the composition prepared in the examples is a metal complex E1 shown in the following formula to be a phosphorescent guest, and a synthesis thereof can refer to patent CN 102668152.

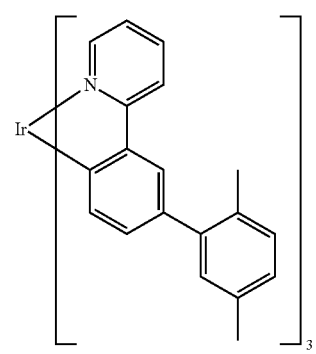

Compositions are prepared according to following constituents, and molar ratios of each organic functional material are also shown as follows.

| | H1 | molar ratio | H2 | molar ratio | H3 | molar ratio |
|---|---|---|---|---|---|---|
| Example 1 | H1-1 | 35 | H2-1 | 45 | H3-1 | 20 |
| Example 2 | H1-1 | 40 | H2-1 | 50 | H3-2 | 10 |
| Example 3 | H1-1 | 35 | H2-1 | 45 | H3-3 | 20 |

-continued

| | H1 | molar ratio | H2 | molar ratio | H3 | molar ratio |
|---|---|---|---|---|---|---|
| Example 4 | H1-1 | 35 | H2-1 | 45 | H3-4 | 20 |
| Example 5 | H1-1 | 35 | H2-2 | 45 | H3-1 | 20 |
| Example 6 | H1-1 | 35 | H2-2 | 45 | H3-2 | 20 |
| Example 7 | H1-1 | 35 | H2-2 | 45 | H3-3 | 20 |
| Example 8 | H1-1 | 35 | H2-2 | 45 | H3-4 | 20 |
| Example 9 | H1-1 | 35 | H2-3 | 45 | H3-1 | 20 |
| Example 10 | H1-1 | 35 | H2-4 | 45 | H3-4 | 20 |
| Example 11 | H1-1 | 35 | H2-4 | 45 | H3-5 | 20 |
| Example 12 | H1-1 | 35 | H2-4 | 45 | H3-6 | 20 |
| Example 13 | H1-1 | 35 | H2-5 | 45 | H3-4 | 20 |
| Example 14 | H1-2 | 35 | H2-1 | 45 | H3-1 | 20 |
| Example 15 | H1-2 | 40 | H2-1 | 50 | H3-2 | 10 |
| Example 16 | H1-2 | 35 | H2-1 | 45 | H3-3 | 20 |
| Example 17 | H1-2 | 35 | H2-1 | 45 | H3-4 | 20 |
| Example 18 | H1-2 | 35 | H2-2 | 45 | H3-1 | 20 |
| Example 19 | H1-2 | 35 | H2-2 | 45 | H3-4 | 20 |
| Example 20 | H1-2 | 35 | H2-3 | 45 | H3-1 | 20 |
| Example 21 | H1-2 | 35 | H2-4 | 45 | H3-4 | 20 |
| Example 22 | H1-2 | 35 | H2-4 | 45 | H3-5 | 20 |
| Example 23 | H1-2 | 35 | H2-4 | 45 | H3-6 | 20 |
| Example 24 | H1-3 | 35 | H2-1 | 45 | H3-1 | 20 |
| Example 25 | H1-3 | 35 | H2-1 | 45 | H3-2 | 20 |
| Example 26 | H1-3 | 35 | H2-1 | 45 | H3-3 | 20 |
| Example 27 | H1-3 | 35 | H2-2 | 45 | H3-1 | 20 |
| Example 28 | H1-3 | 35 | H2-3 | 45 | H3-1 | 20 |
| Example 29 | H1-3 | 35 | H2-4 | 45 | H3-1 | 20 |
| Example 30 | H1-3 | 35 | H2-5 | 45 | H3-1 | 20 |
| Example 31 | H1-4 | 35 | H2-1 | 45 | H3-1 | 20 |
| Example 32 | H1-4 | 35 | H2-2 | 45 | H3-1 | 20 |
| Example 33 | H1-4 | 35 | H2-3 | 45 | H3-1 | 20 |
| Example 34 | H1-4 | 35 | H2-4 | 45 | H3-1 | 20 |
| Example 35 | H1-4 | 35 | H2-5 | 45 | H3-1 | 20 |

Preparation method of the above compositions are as follows:

A stir bar is put in a vial, and they were cleaned and transferred to a glove box. 9.8 g of 3-phenoxytoluene solvent is prepared in the vial. 0.19 g of a mixture in examples 1 to 35 and 0.01 g of E1 were weighed in the glove box, added to a solvent system in the vial, and stirred to mix. The organic mixture is stirred at 60° C. until it is completely dissolved, and then cooled to room temperature. The obtained organic mixture solution is filtered through a 0.2 um PTFE filter, sealed, and saved.

Viscosity of the organic compositions were measured by a DV-I Prime Brookfield rheometer, and surface tensions of the organic composition were measured by a SITA bubble pressure tensiometer.

After the above tests, the viscosities of the organic compositions in examples 1 to 35 all range from 5.6±0.5 cPs to 6.3±0.5 cPs, and the surface tensions thereof all range from 32.1±0.5 dyne/cm to 34.2±0.5 dyne/cm.

In further experiments, the mixtures of examples 1 to 35 were used to prepare the compositions in the following solvents: 1-tetralone, 1-methoxynaphthalene, tetrahydronaphthalene, cyclohexylbenzene, chloronaphthalene, 1,4-dimethylnaphthalene, 3-isopropylbiphenyl, p-methylcumene, dipentylbenzene, o-diethylbenzene, p-diethylbenzene, 1,2,3,4-tetratoluene, 1,2,3,5-tetratoluene, 1,2,4,5-tetratoluene, dodecylbenzene, 1-methylnaphthalene, 4-isopropyl biphenyl, benzyl benzoate, 1,1-bis(3,4-dimethylphenyl)ethane, 2-isopropylnaphthalene, or dibenzyl ether. The compositions obtained has a viscosity ranging from 2 cPs to 20 cPs, and the viscosity can be further adjusted by combining solvents and other methods, thereby satisfying the needs of inkjet printing and other techniques.

Comparative Example 1

Preparation of the composition is basically same as the above example 1, and an only difference is that compound H1-1 is used to replace the combination of compounds H1-1, H2-1, and H3-1.

Comparative Example 2

Preparation of the composition is basically same as the above example 1, and an only difference is that compound H1-2 is used to replace the combination of compounds H1-1, H2-1, and H3-1.

Comparative Example 3

Preparation of the composition is basically same as the above example 1, and an only difference is that compounds H1-1 and H2-1 are used to replace the combination of compounds H1-1, H2-1, and H3-1.

Comparative Example 4

Preparation of the composition is basically same as the above example 1, and an only difference is that compounds H1-2 and H2-1 are used to replace the combination of compounds H1-1, H2-1, and H3-1.

Manufacture of OLED Devices

Preparation steps of OLED devices having a structure of ITO/HIL/HTL/EML (examples 1 to 35 or comparative example 1)/Al are as follows:

1) cleaning of ITO transparent electrode (anode) glass substrates: ultrasonic treatment with 5% Decon90 aqueous cleaning solution for 30 minutes, followed by ultrasonic cleaning with deionized water for several times, then ultrasonic cleaning with isopropanol, and nitrogen drying. After that, treating under oxygen plasma for 5 minutes to clean ITO surfaces and improve a work function thereof.
2) Preparation of HIL and HTL: spin-coating PEDOT:PSS (Clevios™ PEDOT:PSS Al4083) on oxygen plasma-treated glass substrates to obtain 80 nm of thin films. After spin-coating, annealed at 150° C. for 20 minutes in air, and then a 20 nm of poly-TFB film (CAS: 223569-31-1, purchased from Lumtec. Corp; 5 mg/mL toluene solution) is spin-coated on the PEDOT:PSS layer, followed by treating at 180° C. on a hot plate for 60 minutes.
3) Preparation of light-emitting layers: the compositions mentioned above are spin-coated on the HTL in the glove box at the nitrogen atmosphere to obtain 80 nm of thin films thereof, and then annealed at 120° C. for 10 minutes.
4) Preparation of cathodes: the spin-coated devices are put into a vacuum evaporation chamber, and sequentially evaporated 2 nm of barium and 100 nm of aluminum, thereby completing the light-emitting devices.
5) All devices are encapsulated with UV-curable resins and glass covers in the glove box at the nitrogen atmosphere.

Current-voltage (J-V) characteristics of each OLED device are characterized by a characterization equipment while recording important parameters such as efficiency, lifespan, and current efficiency. In table 2, all device data are relative values of comparative example 1. After testing, the luminous efficiency and lifespan of examples 1 to 35 are significantly improved compared with the comparative examples, especially the lifespan. Applicants think that in the composition, addition of a wide bandgap material (H3) may dilute concentrations of H1 and H2 in the composition, which is beneficial to reduce concentration quenching of excitons in the light-emitting layer (such as exciton quenching caused by triplet-triplet annihilation (TTA)), which can reduce roll-off of the device efficiency, thereby improving the lifespan of the electroluminescent devices.

TABLE 2

|  | host materials | | | current efficiency@ 1000 nits | T95@ 1000 nits |
|---|---|---|---|---|---|
| Example 1 | H1-1 | H2-1 | H3-1 | 1.42 | 2.73 |
| Example 2 | H1-1 | H2-1 | H3-2 | 1.38 | 2.49 |
| Example 3 | H1-1 | H2-1 | H3-3 | 1.27 | 2.16 |
| Example 4 | H1-1 | H2-1 | H3-4 | 1.32 | 2.20 |
| Example 5 | H1-1 | H2-2 | H3-1 | 1.36 | 2.52 |
| Example 6 | H1-1 | H2-2 | H3-2 | 1.31 | 2.29 |
| Example 7 | H1-1 | H2-2 | H3-3 | 1.28 | 2.25 |
| Example 8 | H1-1 | H2-2 | H3-4 | 1.23 | 2.06 |
| Example 9 | H1-1 | H2-3 | H3-1 | 1.35 | 2.31 |
| Example 10 | H1-1 | H2-4 | H3-4 | 1.33 | 2.23 |
| Example 11 | H1-1 | H2-4 | H3-5 | 1.24 | 2.16 |
| Example 12 | H1-1 | H2-4 | H3-6 | 1.19 | 2.07 |
| Example 13 | H1-1 | H2-5 | H3-4 | 1.25 | 2.00 |
| Example 14 | H1-2 | H2-1 | H3-1 | 1.36 | 2.35 |
| Example 15 | H1-2 | H2-1 | H3-2 | 1.34 | 2.40 |
| Example 16 | H1-2 | H2-1 | H3-3 | 1.27 | 2.49 |
| Example 17 | H1-2 | H2-1 | H3-4 | 1.23 | 2.32 |
| Example 18 | H1-2 | H2-2 | H3-1 | 1.30 | 2.37 |
| Example 19 | H1-2 | H2-2 | H3-4 | 1.35 | 2.26 |
| Example 20 | H1-2 | H2-3 | H3-1 | 1.29 | 2.17 |
| Example 21 | H1-2 | H2-4 | H3-4 | 1.22 | 2.08 |
| Example 22 | H1-2 | H2-4 | H3-5 | 1.20 | 2.14 |
| Example 23 | H1-2 | H2-4 | H3-6 | 1.14 | 2.01 |
| Example 24 | H1-3 | H2-1 | H3-1 | 1.29 | 2.17 |
| Example 25 | H1-3 | H2-1 | H3-2 | 1.23 | 2.10 |
| Example 26 | H1-3 | H2-1 | H3-3 | 1.14 | 2.13 |
| Example 27 | H1-3 | H2-2 | H3-1 | 1.31 | 2.04 |
| Example 28 | H1-3 | H2-3 | H3-1 | 1.18 | 2.11 |
| Example 29 | H1-3 | H2-4 | H3-1 | 1.20 | 2.01 |
| Example 30 | H1-3 | H2-5 | H3-1 | 1.23 | 2.04 |
| Example 31 | H1-4 | H2-1 | H3-1 | 1.27 | 2.31 |
| Example 32 | H1-4 | H2-2 | H3-1 | 1.24 | 2.18 |
| Example 33 | H1-4 | H2-3 | H3-1 | 1.16 | 2.05 |
| Example 34 | H1-4 | H2-4 | H3-1 | 1.21 | 2.17 |
| Example 35 | H1-4 | H2-5 | H3-1 | 1.27 | 2.15 |
| Comparative example 1 |  | H1-1 |  | 1 | 1 |
| Comparative example 2 |  | H1-2 |  | 0.95 | 1.08 |
| Comparative example 3 | H1-1 | H2-1 |  | 1.23 | 1.74 |
| Comparative example 4 | H1-2 | H2-1 |  | 1.27 | 1.61 |

The technical features of the above-described embodiments can be combined arbitrarily. For the sake of brevity, all possible combinations of the technical features in the above-described embodiments are not described. However, as long as there is no contradiction between the combinations of these technical features, all should be regarded as the scope described in the present disclosure.

The above-mentioned embodiments only express several implementations of the present disclosure, and the description thereof is more specific and detailed, but cannot be understood as a limitation on the scope of the present disclosure. It should be noted that for those having ordinary skills in the art, without departing from the concept of the present disclosure, several modifications and improvements can be made, and these all belong to the protection scope of the present disclosure. Therefore, the protection scope of the present disclosure shall be subject to the appended claims.

What is claimed is:

1. A composition, comprising at least three organic functional materials H1, H2, and H3, and at least one organic solvent;
   wherein 1) H1 and H2 form a type II semiconductor heterojunction structure, and min (LUMO(H1)-HOMO (H2), LUMO(H2)-HOMO(H1))≤min($E_T$(H1), $E_T$(H2))+0.1 eV; and 2) LUMO(H3)≥max(LUMO (H1), LUMO(H2)) and HOMO(H3)≤min (HOMO (H1), HOMO(H2));
   wherein LUMO(H1) represents a lowest unoccupied molecular orbital energy level of H1, HOMO(H1) represents a highest occupied molecular orbital energy level of H1, and $E_T$(H1) represents a triplet state energy level of H1; LUMO(H2) represents a lowest unoccupied molecular orbital energy level of H2, HOMO(H2) represents a highest occupied molecular orbital energy level of H2, and $E_T$(H2) represents a triplet state energy level of H2; and LUMO(H3) represents a lowest unoccupied molecular orbital energy level of H3, and HOMO(H3) represents a highest occupied molecular orbital energy level of H3.

2. The composition according to claim 1, wherein H1 is an electron transport material, and H2 is a hole transport material.

3. The composition according to claim 2, wherein H1 has a structure of a general formula (1):

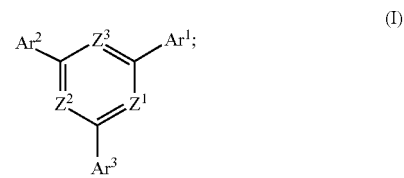

wherein $Ar^1$ to $Ar^3$ are independently selected from a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms;

each $Z^1$ to $Z^3$ is same or different and independently represents $CR_1$ or N, and at least one of $Z^1$ to $Z^3$ is N; and each $R_1$ is independently selected from the group consisting of H, D, a linear alkyl group with 1 to 20 carbon atoms, an alkoxy group with 1 to 20 carbon atoms, a thioalkoxy group with 1 to 20 carbon atoms, a branched alkyl group with 3 to 20 carbon atoms, a cyclic alkyl group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, $CF_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a heteroaryloxy group with 5 to 60 ring atoms, or a combination thereof.

4. The composition according to claim 3, wherein H1 has a structure selected from general formulas (1-1) to (1-4):

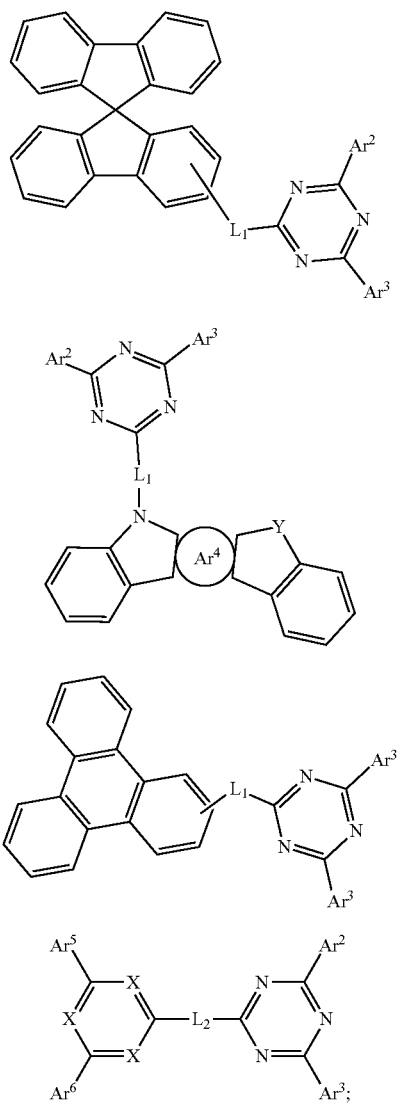

wherein each X independently represents CR$_2$ or N;
each Y independently represents CR$_3$R$_4$, NR$_3$, BR$_3$, O, S, SiR$_3$R$_4$, PR$_3$, P(=O)R$_3$, S=O, S(=O)$_2$, or C=O;
Ar$^4$ is independently a substituted or unsubstituted phenyl group;
Ar$^5$ and Ar$_6$ are independently selected from a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms;
wherein L$_1$ and L$_2$ are each independently selected from a single bond, a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms; and
R$_2$ to R$_4$ are each independently selected from the group consisting of H, D, a linear alkyl group with 1 to 20 carbon atoms, an alkoxy group with 1 to 20 carbon atoms, a thioalkoxy group with 1 to 20 carbon atoms, a branched alkyl group with 3 to 20 carbon atoms, a cyclic alkyl group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, CF$_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a heteroaryloxy group with 5 to 60 ring atoms, or a combination thereof.

5. The composition according to claim 3, wherein H2 has a structure selected from general formulas (2-1) to (2-4):

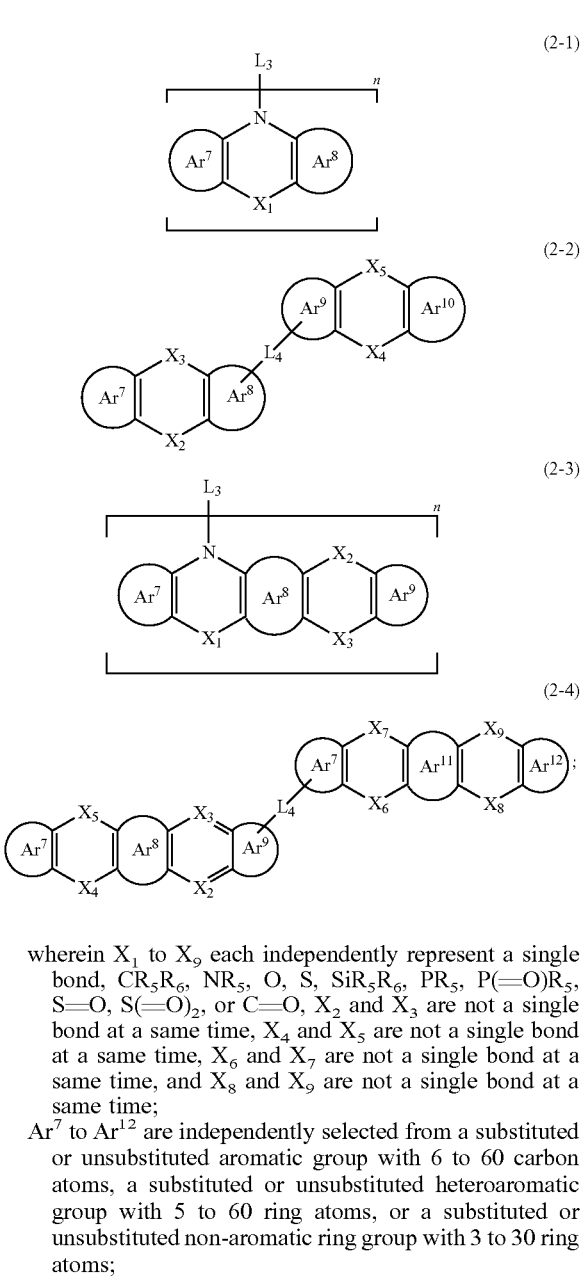

wherein X$_1$ to X$_9$ each independently represent a single bond, CR$_5$R$_6$, NR$_5$, O, S, SiR$_5$R$_6$, PR$_5$, P(=O)R$_5$, S=O, S(=O)$_2$, or C=O, X$_2$ and X$_3$ are not a single bond at a same time, X$_4$ and X$_5$ are not a single bond at a same time, X$_6$ and X$_7$ are not a single bond at a same time, and X$_8$ and X$_9$ are not a single bond at a same time;
Ar$^7$ to Ar$^{12}$ are independently selected from a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms;

wherein L₃ and L₄ are each independently selected from a single bond, a triarylamino group, a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms;

n is an integer ranging from 1 to 4; and

R₅ and R₆ are each independently selected from the group consisting of H, D, a linear alkyl group with 1 to 20 carbon atoms, an alkoxy group with 1 to 20 carbon atoms, a thioalkoxy group with 1 to 20 carbon atoms, a branched alkyl group with 3 to 20 carbon atoms, a cyclic alkyl group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, CF₃, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a heteroaryloxy group with 5 to 60 ring atoms, or a combination thereof; and H3 has a structure of a general formula (4):

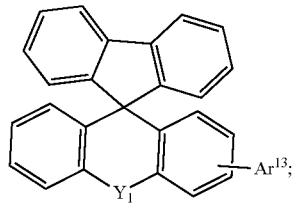

(4)

wherein each Y₁ independently represents nonexistence, a single bond, CR₉R₁₀, NR₉, O, S, SiR₉R₁₀, PR₉, P(=O)R₉, S=O, S(=O)₂, or C=O;

each Ar¹³ is independently selected from a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms; and R₉ to R₁₀ are each independently selected from the group consisting of H, D, a linear alkyl group with 1 to 20 carbon atoms, an alkoxy group with 1 to 20 carbon atoms, a thioalkoxy group with 1 to 20 carbon atoms, a branched alkyl group with 3 to 20 carbon atoms, a cyclic alkyl group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, CF₃, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a substituted or unsubstituted heteroaryloxy group with 5 to 60 ring atoms, or a combination thereof.

6. The composition according to claim 2, wherein H2 has a structure selected from general formulas (2-1) to (2-4):

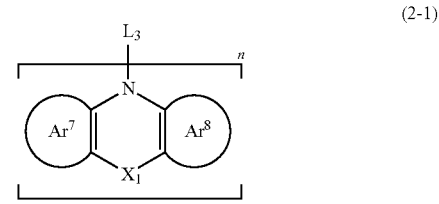

(2-1)

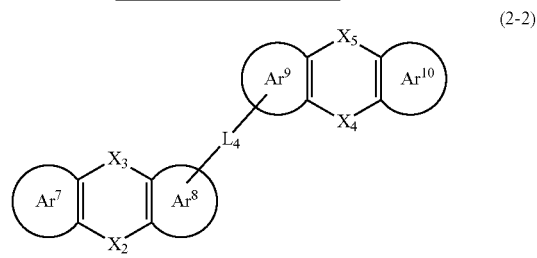

(2-2)

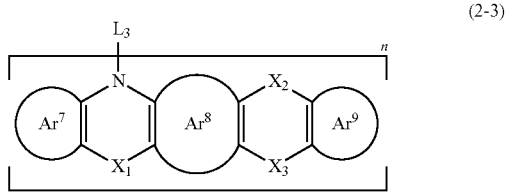

(2-3)

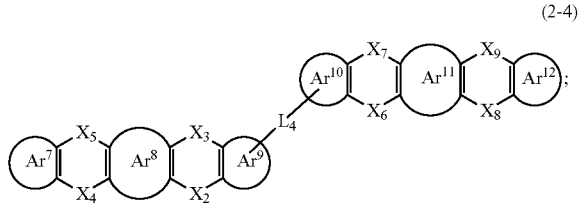

(2-4)

wherein X₁ to X₉ each independently represent a single bond, CR₅R₆, NR₅, O, S, SiR₅R₆, PR₅, P(=O)R₅, S=O, S(=O)₂, or C=O, X₂ and X₃ are not a single bond at a same time, X₄ and X₅ are not a single bond at a same time, X₆ and X₇ are not a single bond at a same time, and X₈ and X₉ are not a single bond at a same time;

Ar⁷ to Ar¹² are independently selected from a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms;

L₃ and L₄ are each independently selected from a single bond, a triarylamino group, a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms;

n is an integer ranging from 1 to 4; and

R₅ and R₆ are each independently selected from the group consisting of H, D, a linear alkyl group with 1 to 20 carbon atoms, an alkoxy group with 1 to 20 carbon atoms, a thioalkoxy group with 1 to 20 carbon atoms, a branched alkyl group with 3 to 20 carbon atoms, a cyclic alkyl group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, $CF_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a heteroaryloxy group with 5 to 60 ring atoms, or a combination thereof.

7. The composition according to claim 6, wherein H2 has a structure selected from general formulas (3-1) to (3-4):

a branched alkyl group with 3 to 20 carbon atoms, a cyclic alkyl group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, $CF_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a substituted or unsubstituted heteroaryloxy group with 5 to 60 ring atoms, or a combination thereof.

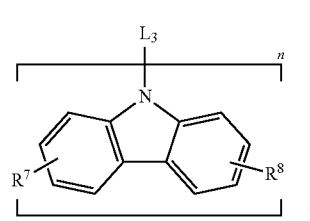

(3-1)

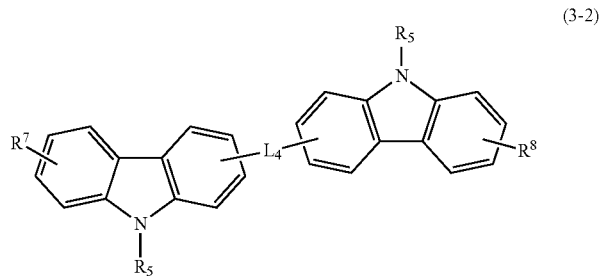

(3-2)

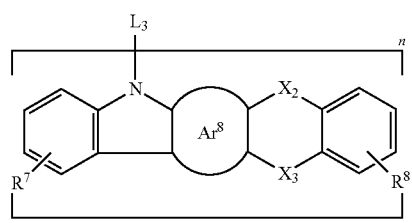

(3-3)

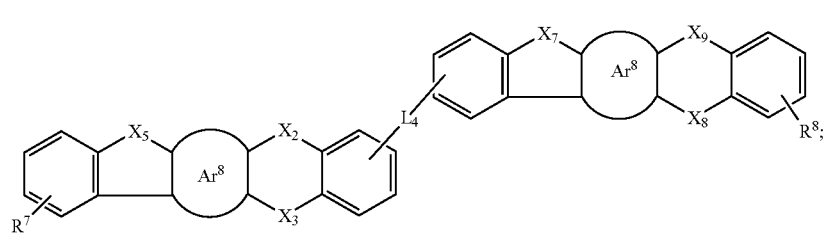

(3-4)

wherein $R^7$ to $R^8$ are each independently selected from the group consisting of H, D, a linear alkyl group with 1 to 20 carbon atoms, an alkoxy group with 1 to 20 carbon atoms, a thioalkoxy group with 1 to 20 carbon atoms, 8. The composition according to claim 7, wherein H1 has a structure selected from general formulas (1-1) or (1-2), H2 has a structure selected from general formulas (3-1) or (3-2), and H3 has a structure of a general formula (4);

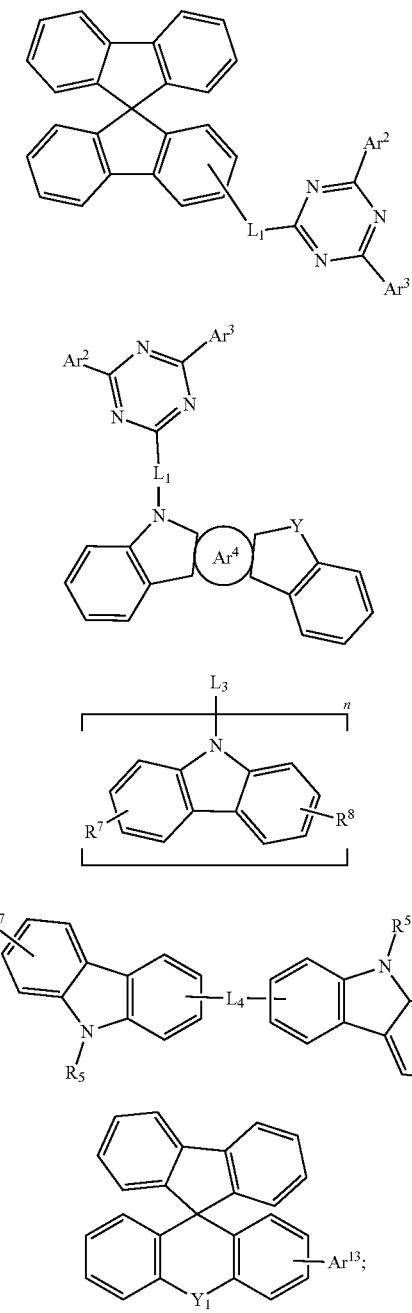

(1-1)

(1-2)

(3-1)

(3-2)

(4)

wherein each Y independently represents CR$_3$R$_4$, NR$_3$, BR$_3$, O, S, SiR$_3$R$_4$, PR$_3$, P(=O)R$_3$, S=O, S(=O)$_2$, or C=O;

Ar$^4$ is independently a substituted or unsubstituted phenyl group;

Ar$^2$ to Ar$^3$ are independently selected from a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms;

wherein L$_1$ is each independently selected from a single bond, a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms; and R$_3$ to R$_4$ are each independently selected from the group consisting of H, D, a linear alkyl group with 1 to 20 carbon atoms, an alkoxy group with 1 to 20 carbon atoms, a thioalkoxy group with 1 to 20 carbon atoms, a branched alkyl group with 3 to 20 carbon atoms, a cyclic alkyl group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, CF$_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a heteroaryloxy group with 5 to 60 ring atoms, or a combination thereof;

wherein each Y$_1$ independently represents nonexistence, a single bond, CR$_9$R$_{10}$, NR$_9$, O, S, SiR$_9$R$_{10}$, PR$_9$, P(=O)R$_9$, S=O, S(=O)$_2$, or C=O;

each Ar$^{13}$ is independently selected from a substituted or unsubstituted aromatic group with 6 to 60 carbon atoms, a heteroaromatic group with 5 to 60 ring atoms, or a non-aromatic ring group with 3 to 30 ring atoms; and R$_9$ to R$_{10}$ are each independently selected from the group consisting of H, D, a linear alkyl group with 1 to 20 carbon atoms, an alkoxy group with 1 to 20 carbon atoms, a thioalkoxy group with 1 to 20 carbon atoms, a branched alkyl group with 3 to 20 carbon atoms, a cyclic alkyl group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, CF$_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a substituted or unsubstituted heteroaryloxy group with 5 to 60 ring atoms, or a combination thereof.

9. The composition according to claim 8, wherein H3 has a structure selected from general formulas (B-1) or (B-2);

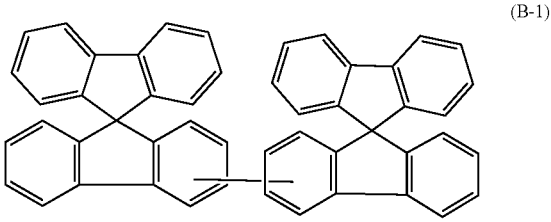

(B-1)

-continued (B-2)

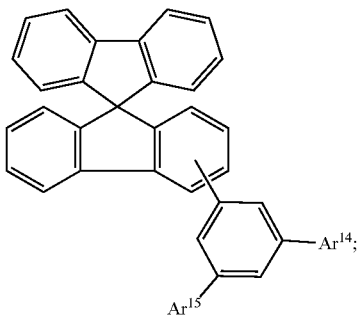

wherein Ar$^{14}$ and Ar$^{15}$ are each independently selected from a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms.

10. The composition according to claim 9, wherein H1 has the structure of the general formula (1-1), H2 has the structure selected from the general formulas (3-1) or (3-2), and H3 has the structure of the general formula (B-1).

11. The composition according to claim 9, wherein H1 has the structure of the general formula (1-2), H2 has the structure selected from the general formulas (3-1) or (3-2), and H3 has the structure of the general formula (B-1).

12. The composition according to claim 9, wherein H1 has the structure of the general formula (1-2), H2 has the structure selected from the general formulas (3-1) or (3-2), and H3 has the structure of the general formula (B-2).

13. The composition according to claim 1, wherein H3 has a structure of a general formula (4):

(4)

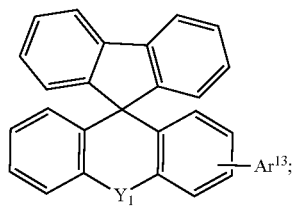

wherein each Y$_1$ independently represents nonexistence, a single bond, CR$_9$R$_{10}$, NR$_9$, O, S, SiR$_9$R$_{10}$, PR$_9$, P(=O)R$_9$, S=O, S(=O)$_2$, or C=O;
each Ar$^{13}$ is independently selected from a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms; and
R$_9$ to R$_{10}$ are each independently selected from the group consisting of H, D, a linear alkyl group with 1 to 20 carbon atoms, an alkoxy group with 1 to 20 carbon atoms, a thioalkoxy group with 1 to 20 carbon atoms, a branched alkyl group with 3 to 20 carbon atoms, a cyclic alkyl group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, CF$_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a substituted or unsubstituted heteroaryloxy group with 5 to 60 ring atoms, or a combination thereof.

14. The composition according to claim 13, wherein Ar$^{13}$ is independently selected from following groups:

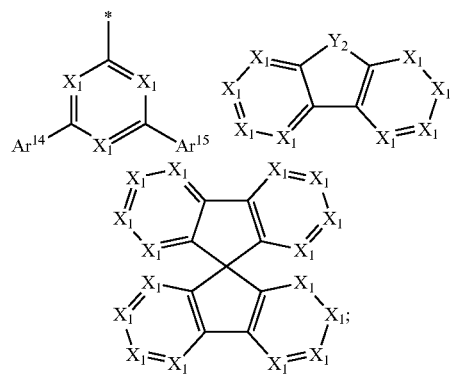

wherein each X$_1$ independently represents CR$_{11}$ or N;
each Y$_2$ independently represents CR$_{11}$R$_{12}$, NR$_{11}$, O, S, SiR$_{11}$R$_{12}$, PR$_{11}$, P(=O)R$_{11}$, S=O, S(=O)$_2$, or C=O;
Ar$^{14}$ and Ar$^{15}$ are each independently selected from a substituted or unsubstituted aromatic group with 6 to 60 carbon atoms, a substituted or unsubstituted heteroaromatic group with 5 to 60 ring atoms, or a substituted or unsubstituted non-aromatic ring group with 3 to 30 ring atoms; and
R$_{11}$ to R$_{12}$ are each independently selected from the group consisting of H, D, a linear alkyl group with 1 to 20 carbon atoms, an alkoxy group with 1 to 20 carbon atoms, a thioalkoxy group with 1 to 20 carbon atoms, a branched alkyl group with 3 to 20 carbon atoms, a cyclic alkyl group with 3 to 20 carbon atoms, a silyl group, a keto group with 1 to 20 carbon atoms, an alkoxycarbonyl group with 2 to 20 carbon atoms, an aryloxycarbonyl group with 7 to 20 carbon atoms, a cyano group, a carbamoyl group, a haloformyl group, a formyl group, an isocyano group, an isocyanate group, a thiocyanate group, an isothiocyanate group, a hydroxyl group, a nitro group, CF$_3$, Cl, Br, F, I, a crosslinkable group, a substituted or unsubstituted aromatic group with 5 to 60 ring atoms, a substituted or unsubstituted heteroaromatic group with 5 to 60 ring atoms, an aryloxy group with 5 to 60 ring atoms, a heteroaryloxy group with 5 to 60 ring atoms, or a combination thereof.

15. The composition according to claim 14, wherein H3 has a structure selected from following structures:

(B-1)

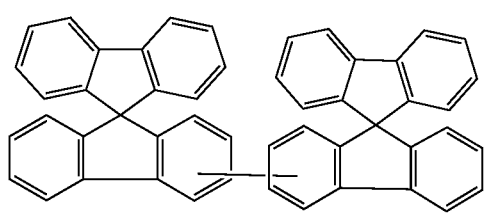

-continued

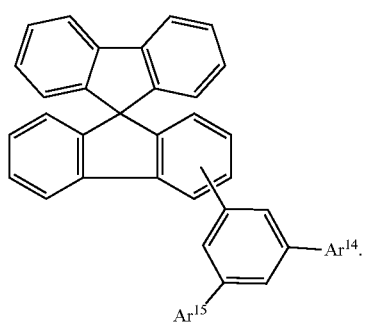

(B-2)

16. The composition according to claim 1, wherein the organic solvent is one or more selected from aromatic, heteroaromatic, ester, aromatic ketone, aromatic ether, aliphatic ketone, aliphatic ether, alicyclic compounds, olefin compound, borate ester, or phosphate ester compounds.

17. An organic electronic device, comprising a functional layer manufactured by the composition according to claim 1.

18. The composition according to claim 1, wherein H1 is selected from the following compounds:

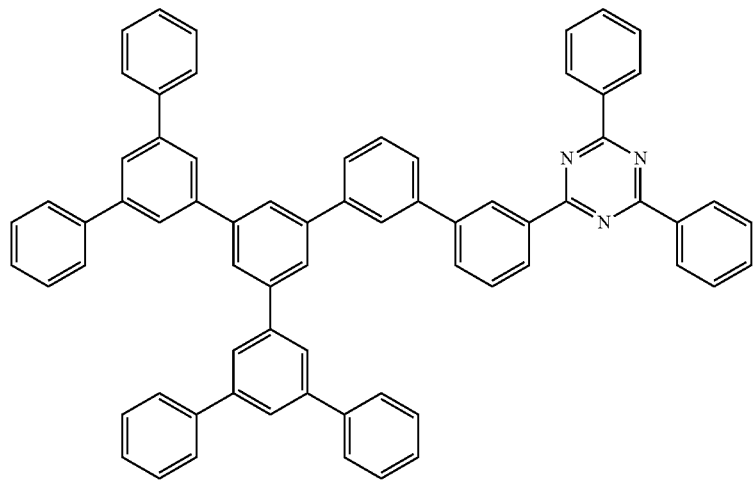

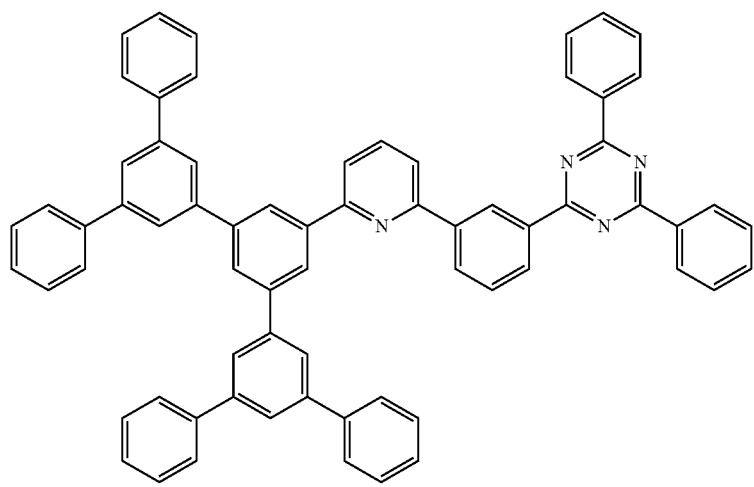

-continued
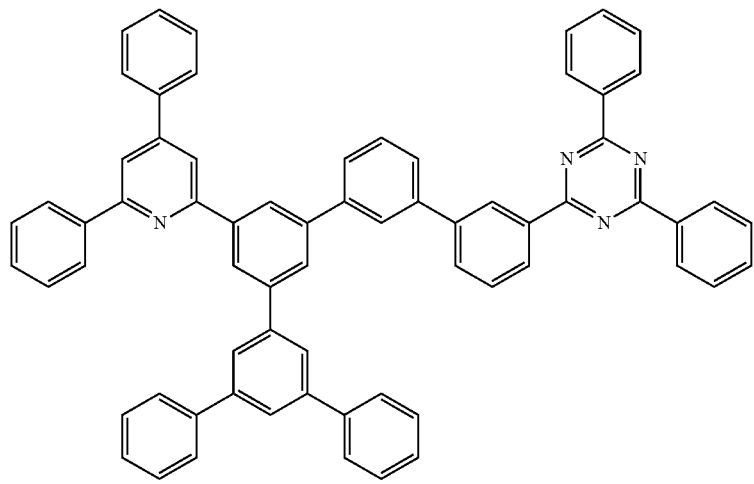
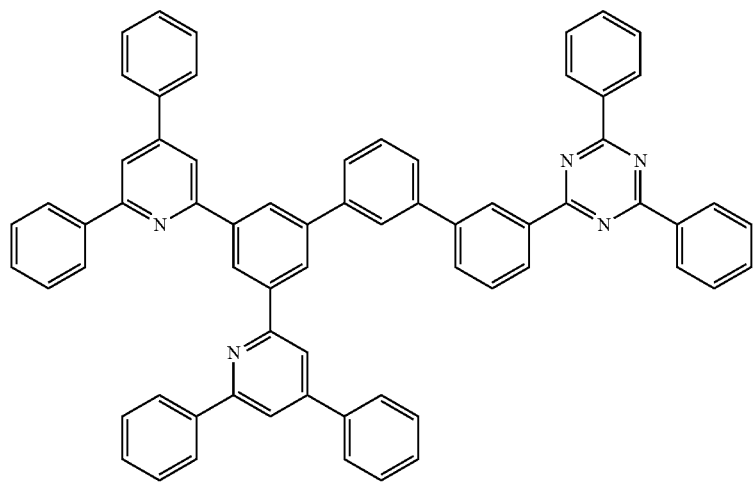
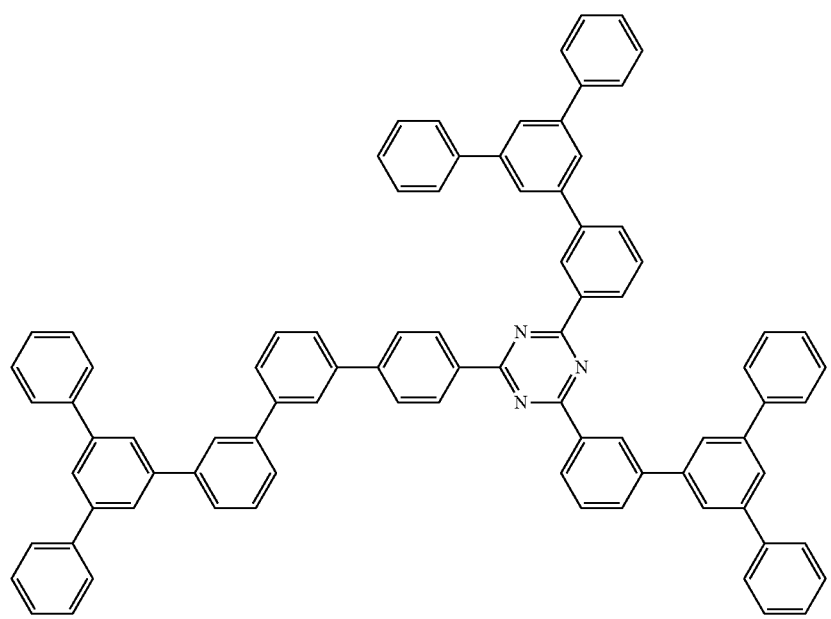

-continued
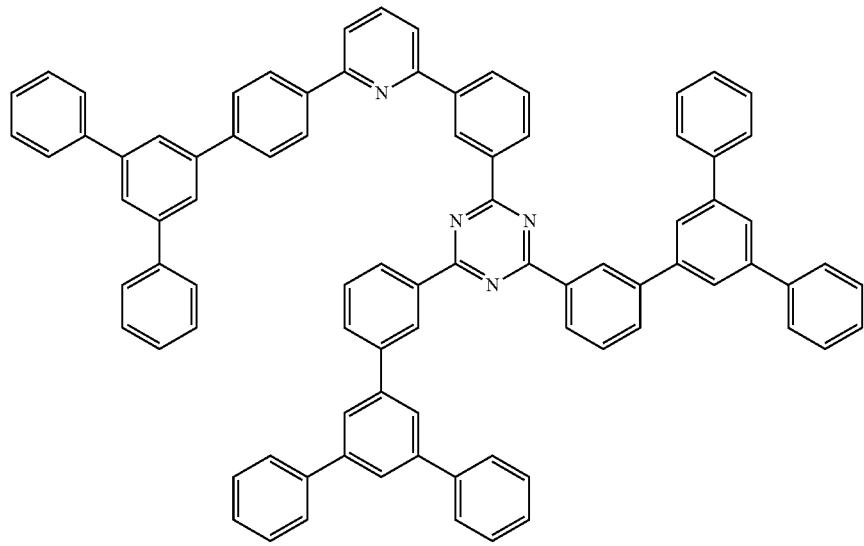
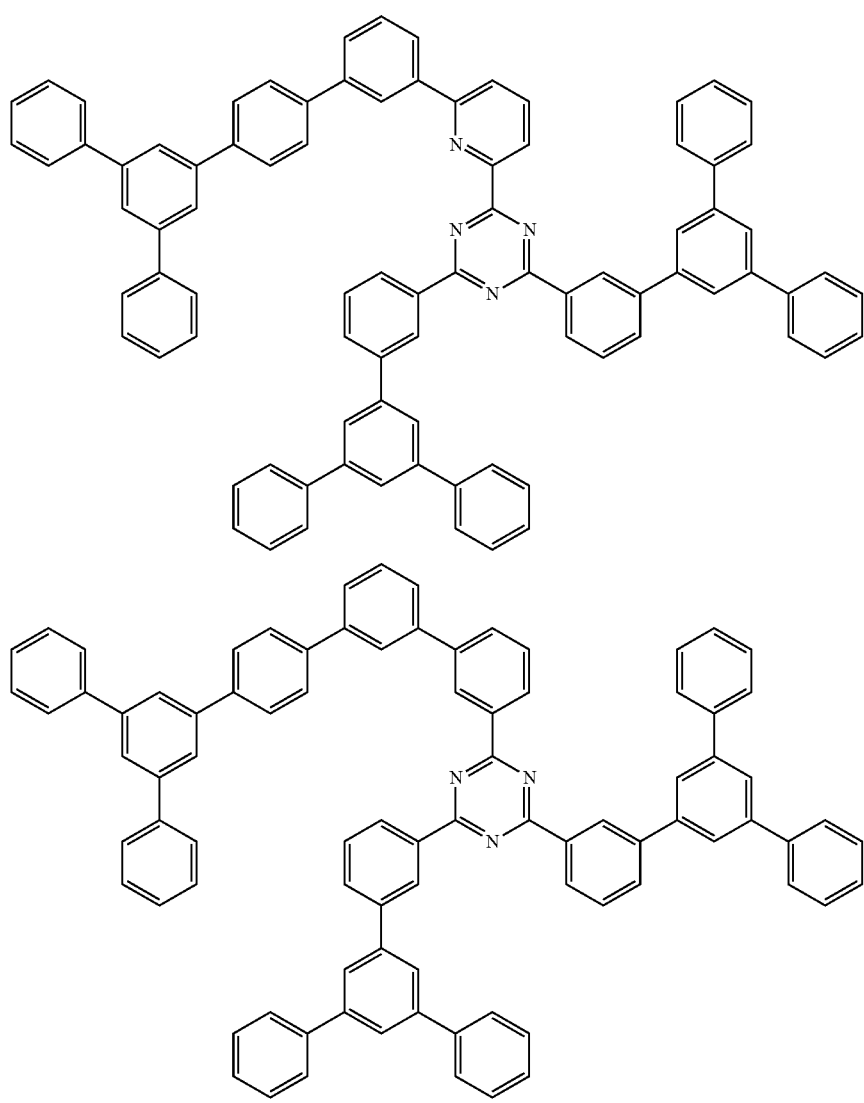

-continued
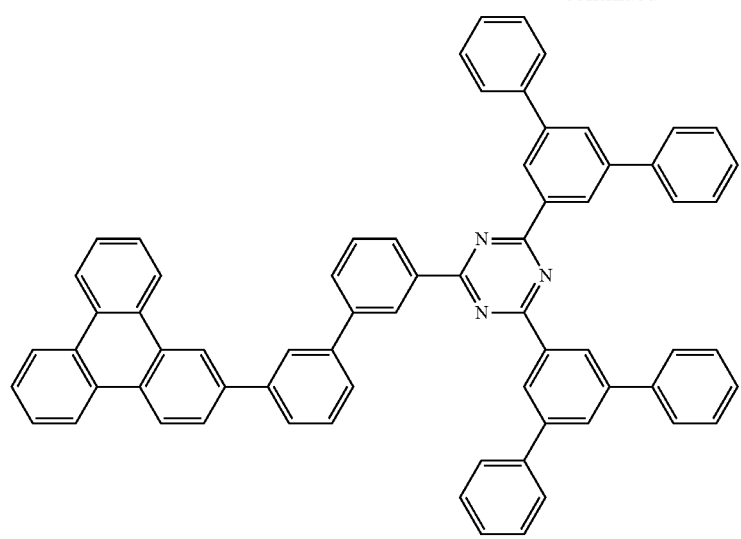
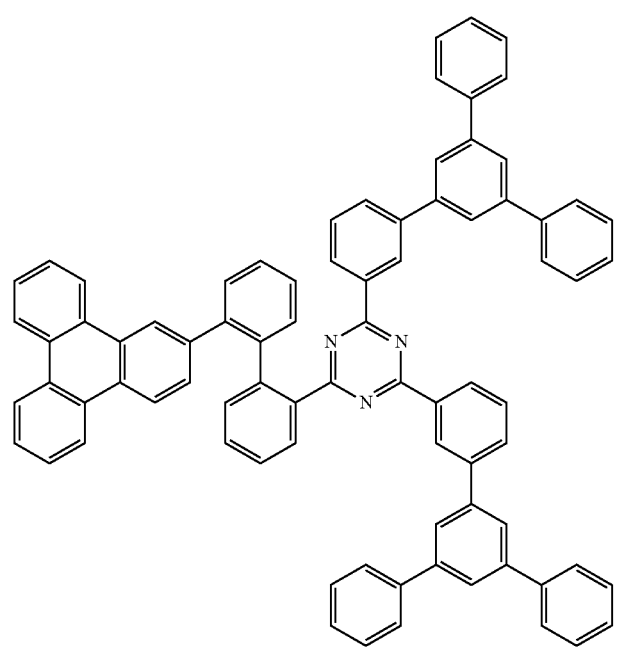

-continued
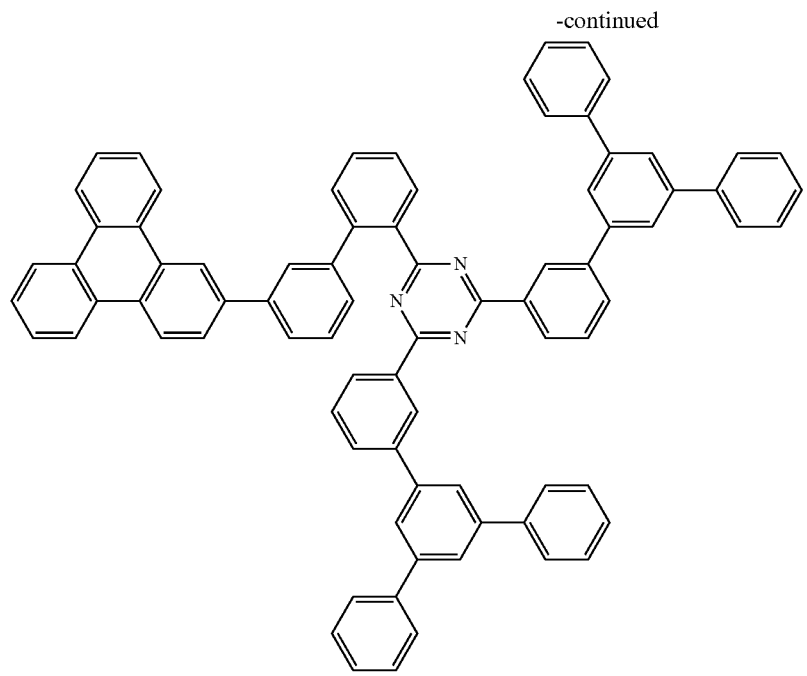
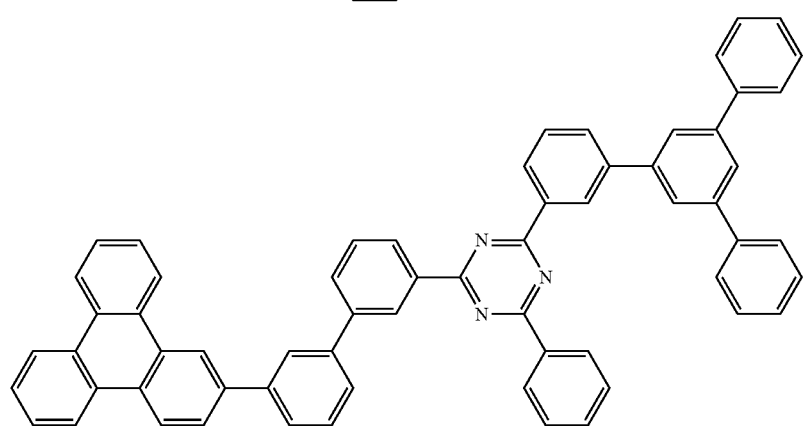
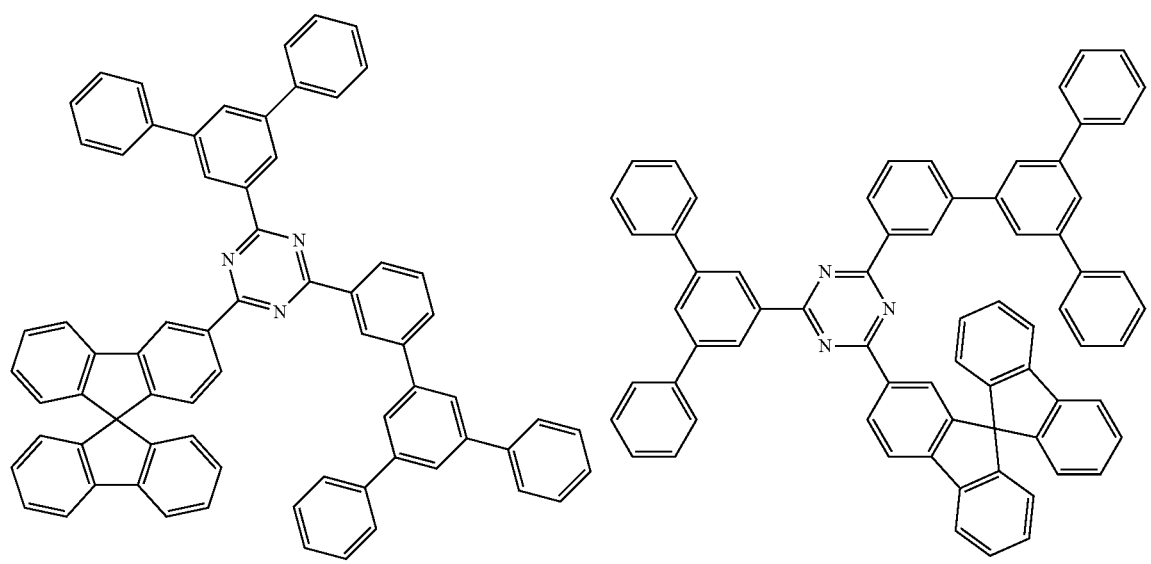

229 230
-continued
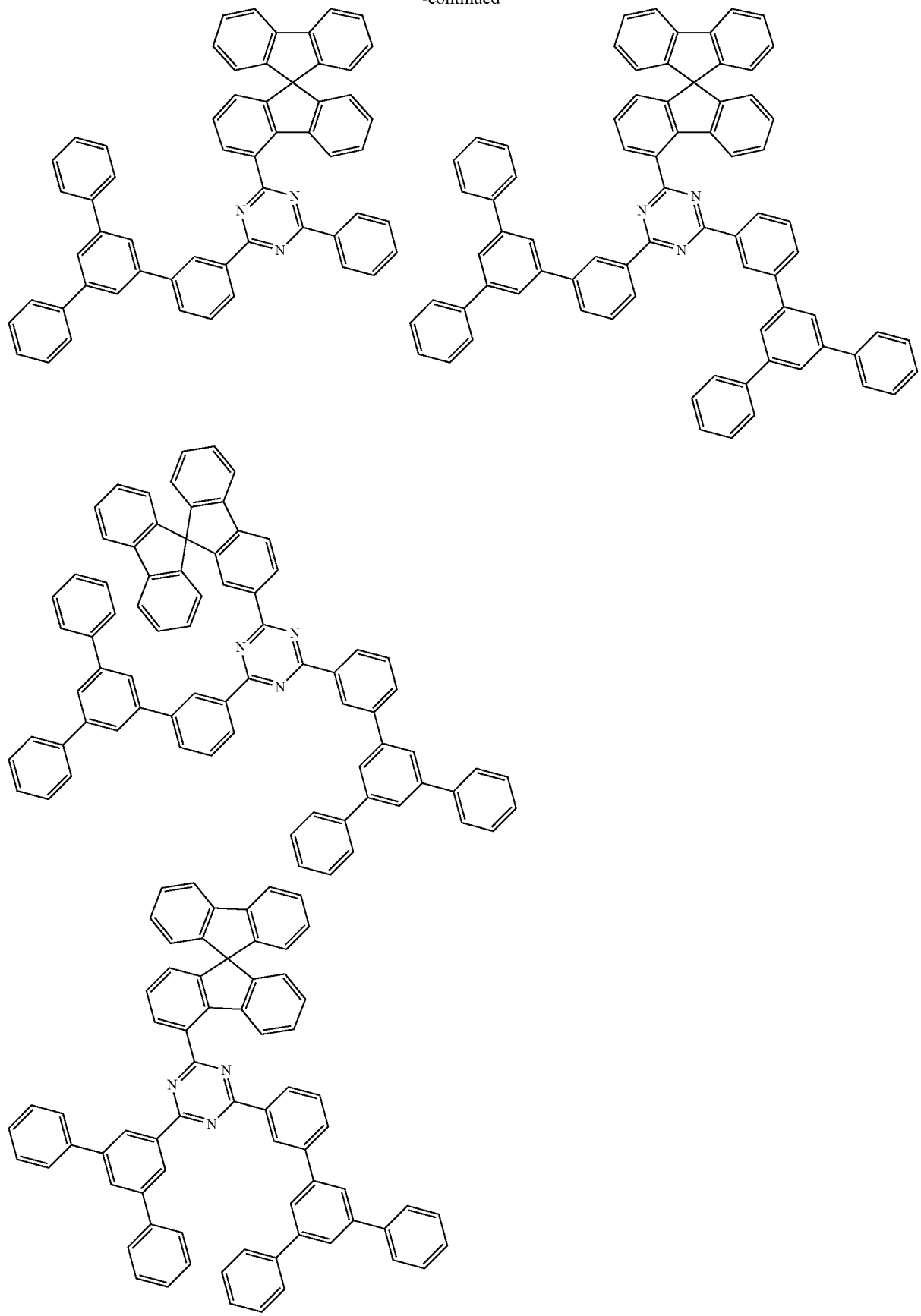

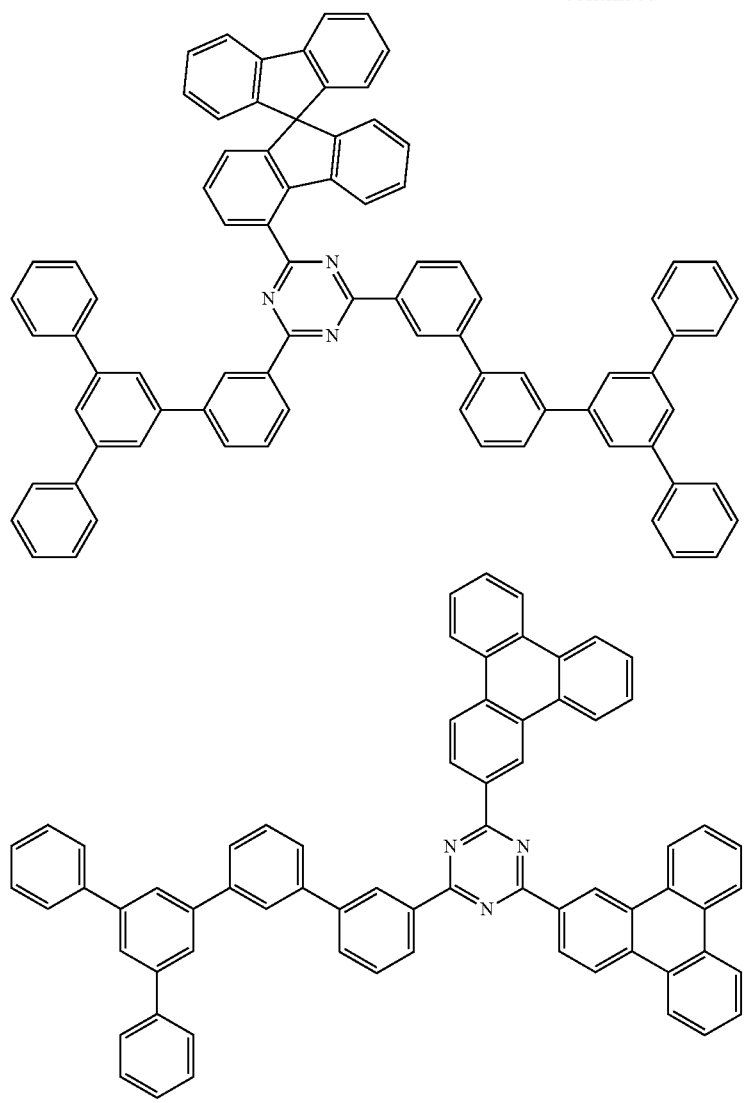
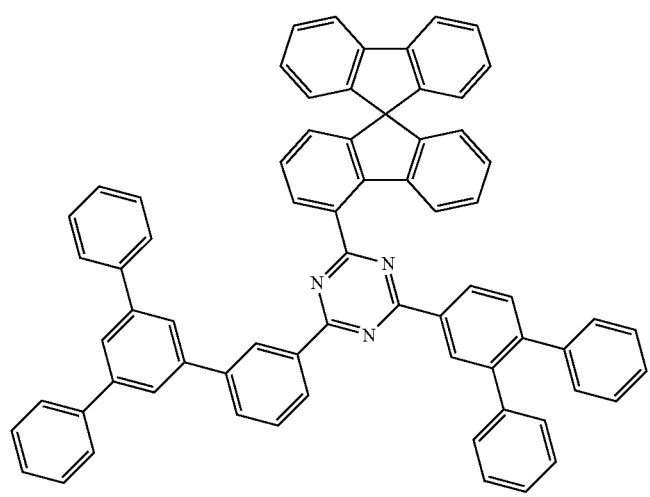

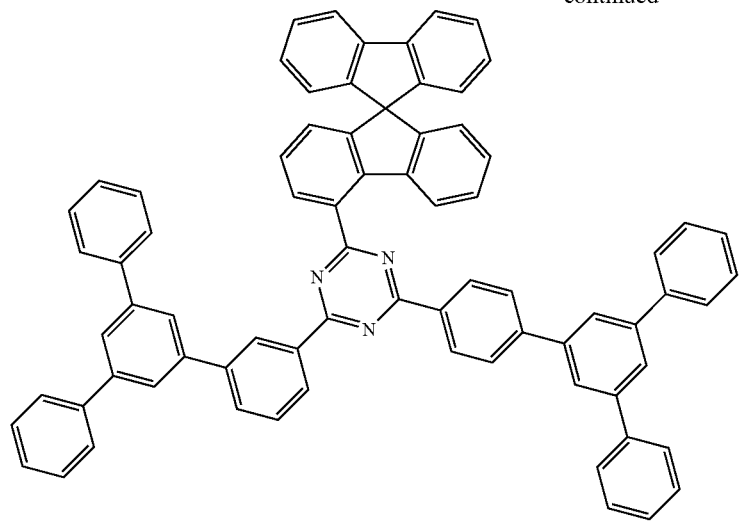
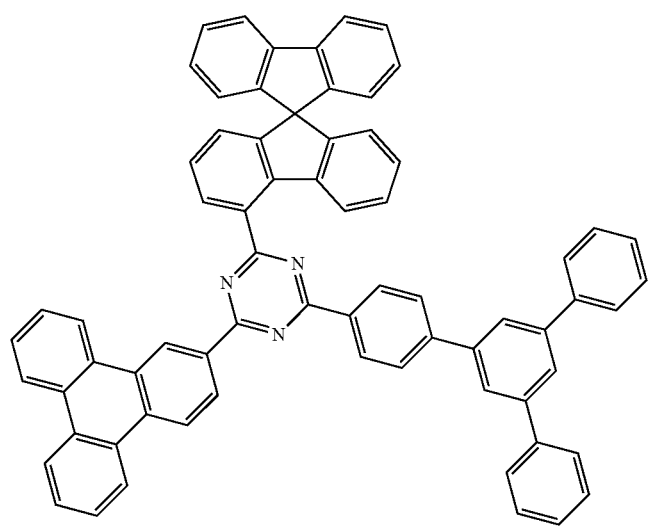
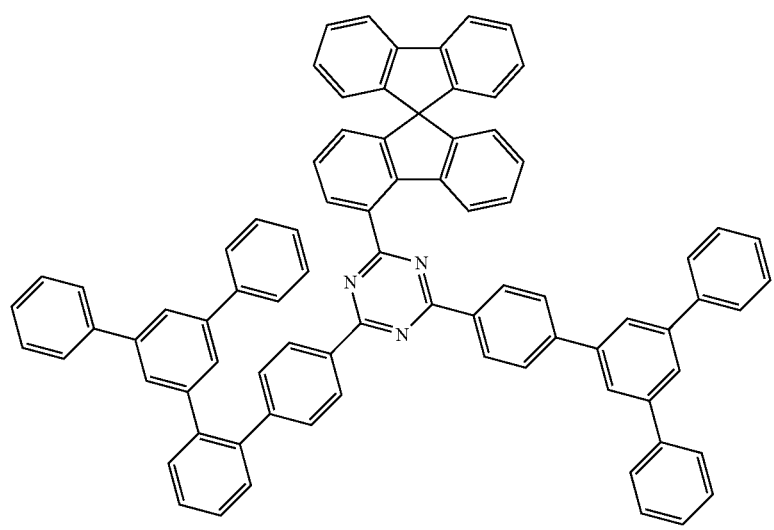

-continued
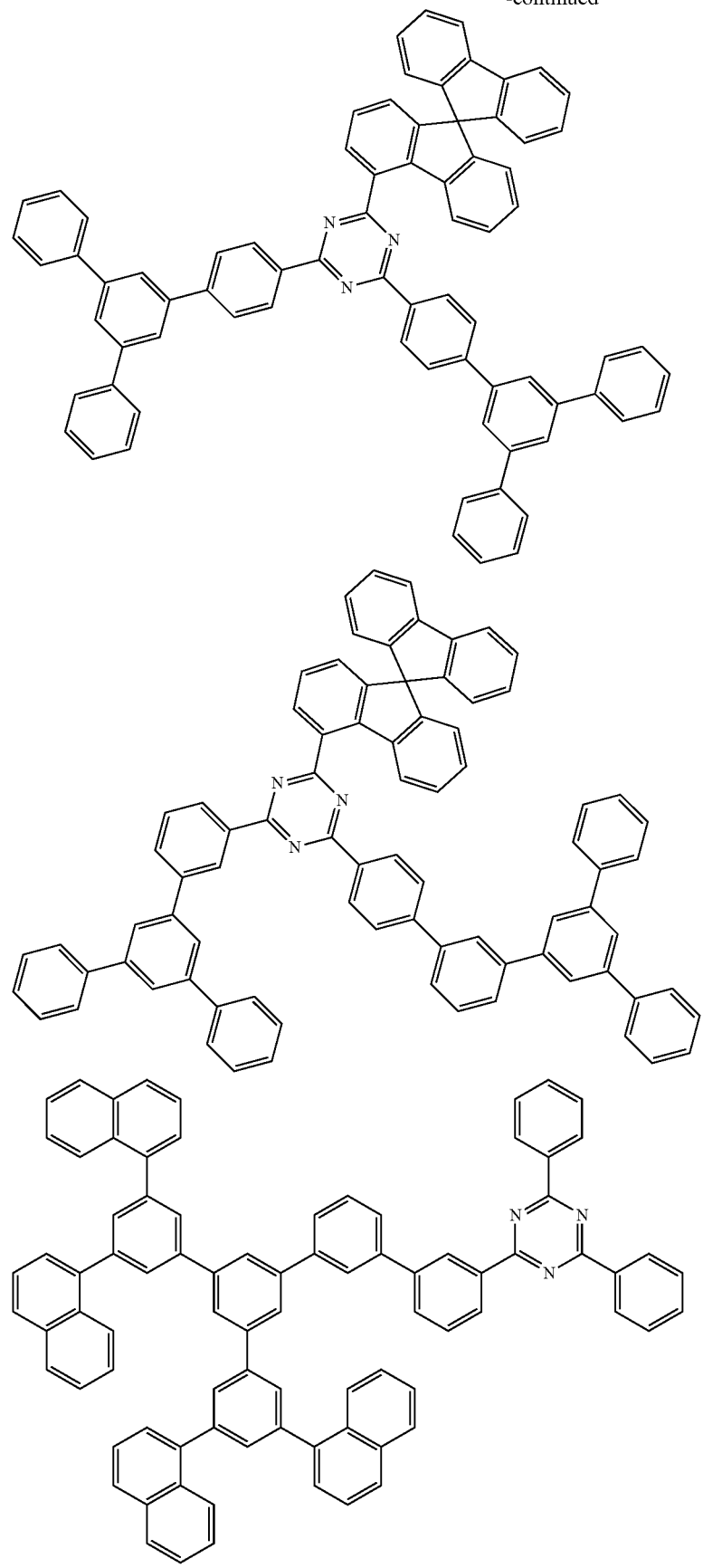

-continued
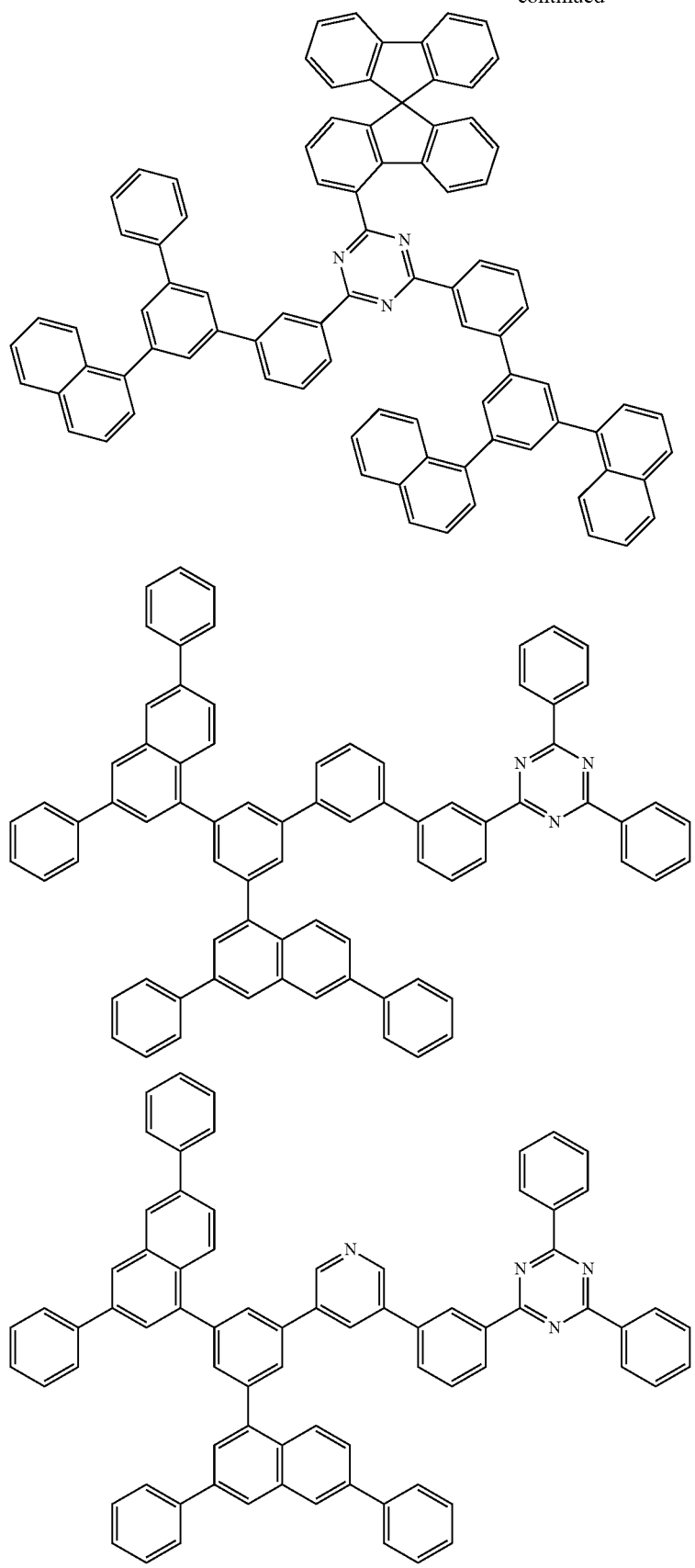

-continued
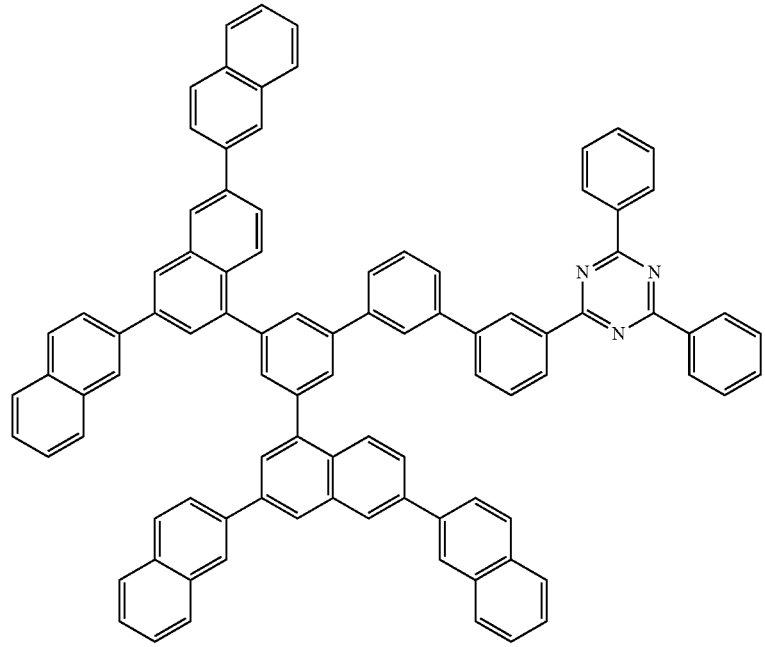
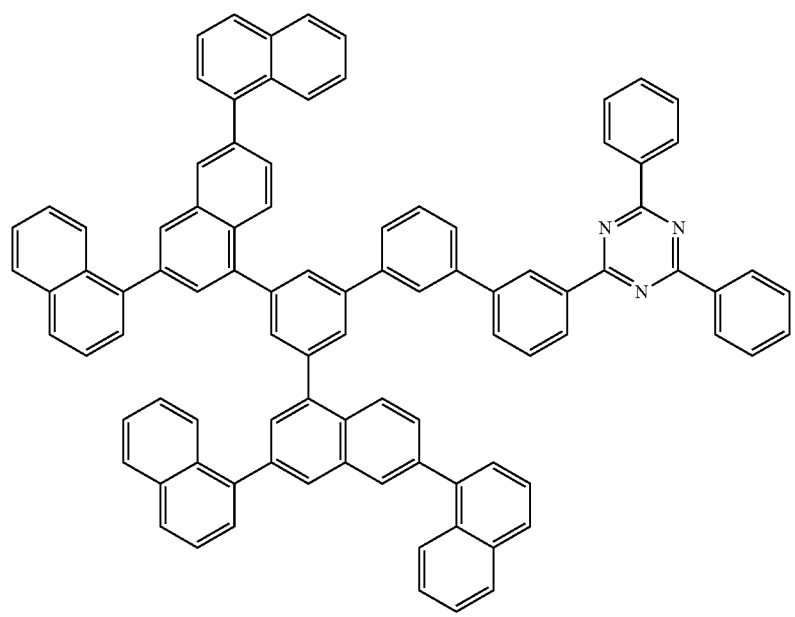

-continued
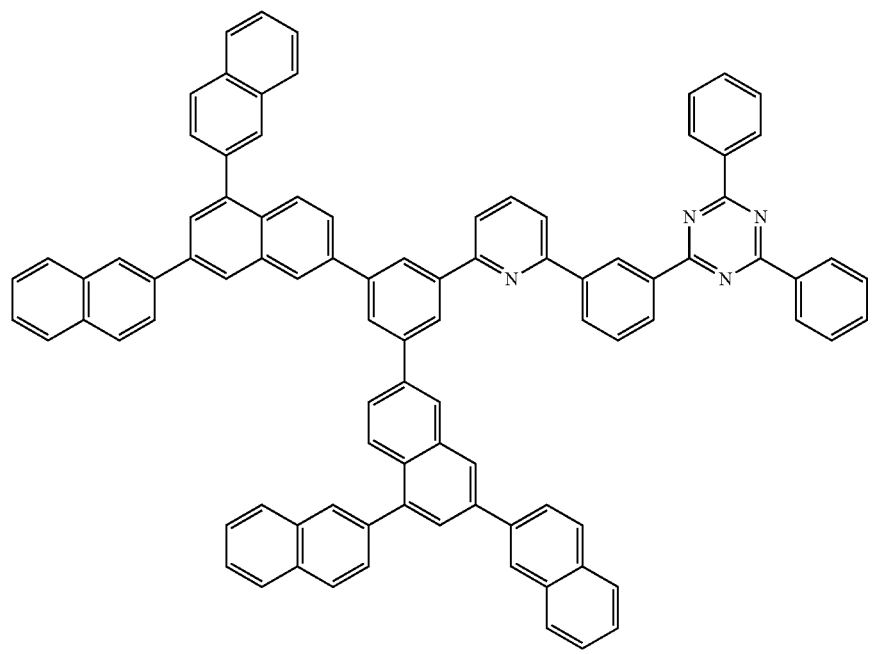
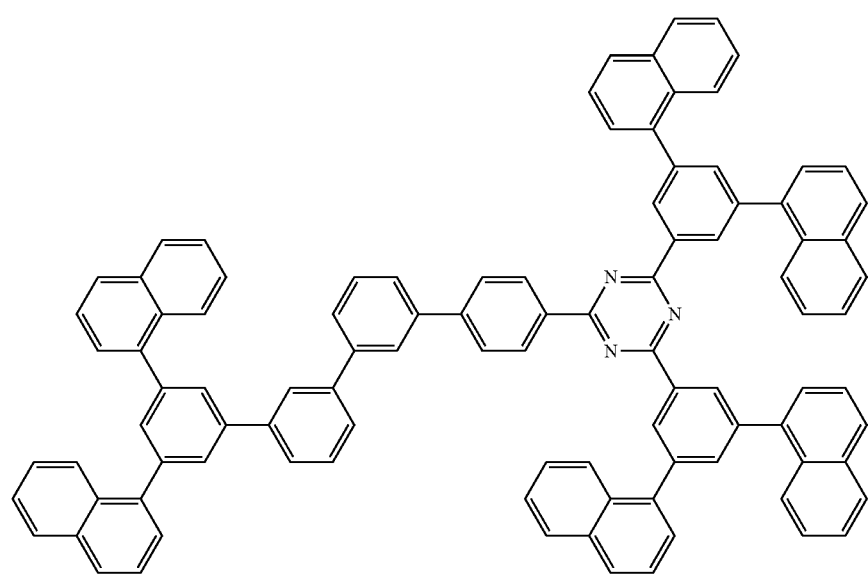

-continued
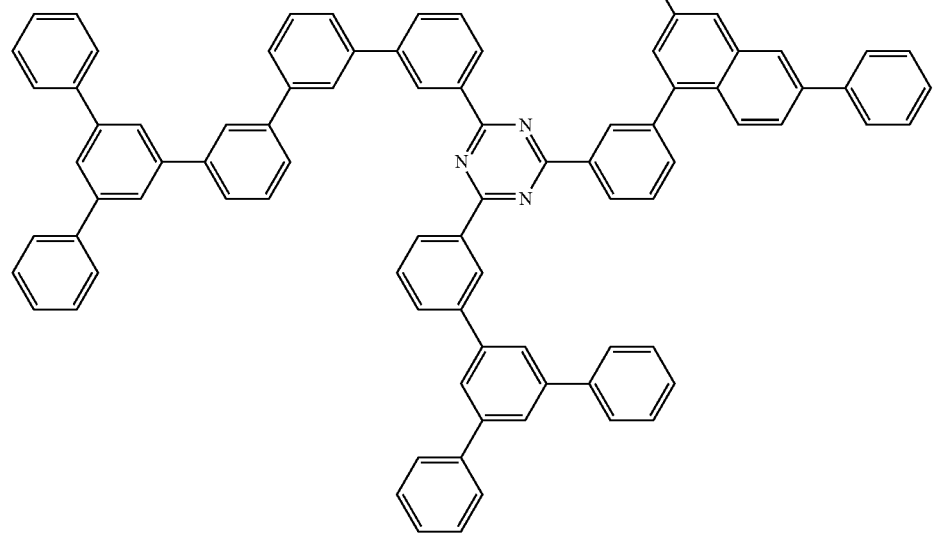
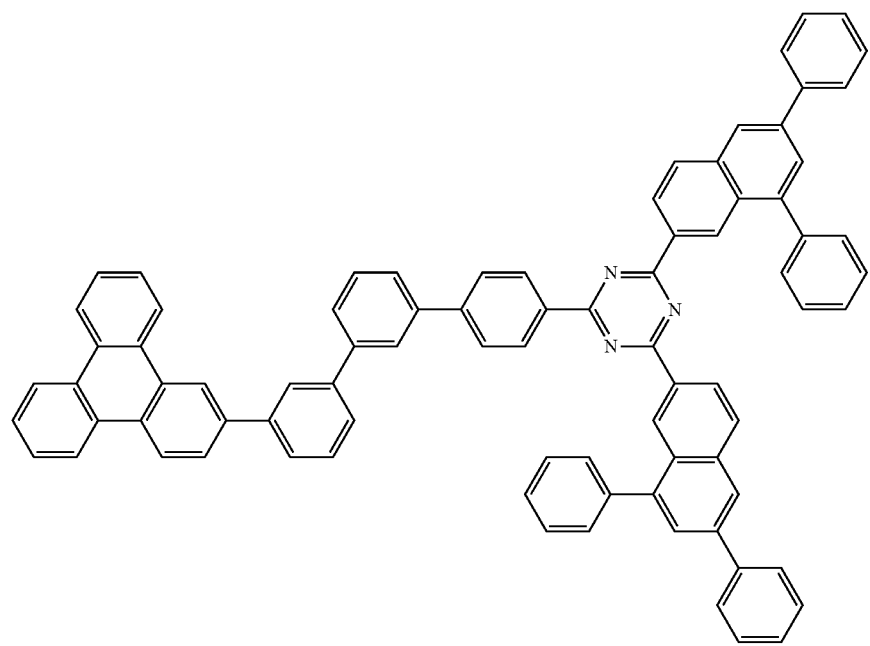

-continued
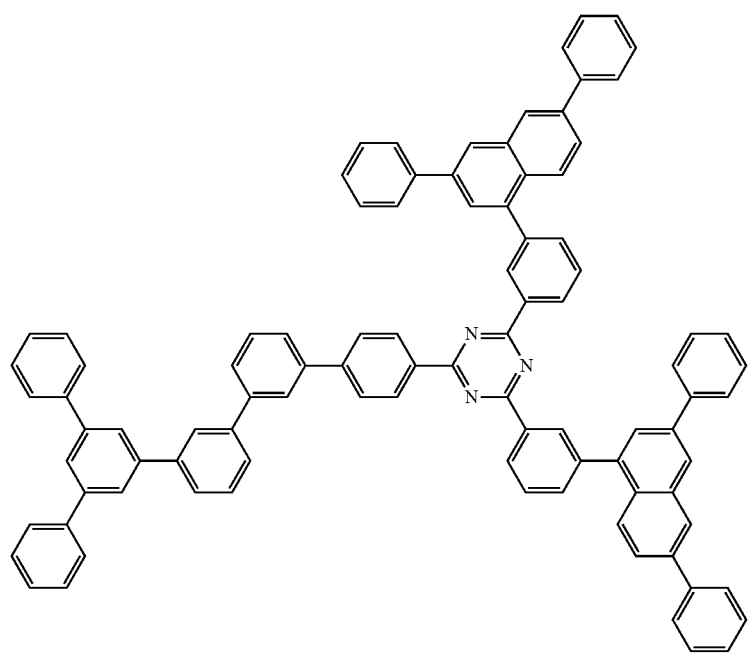
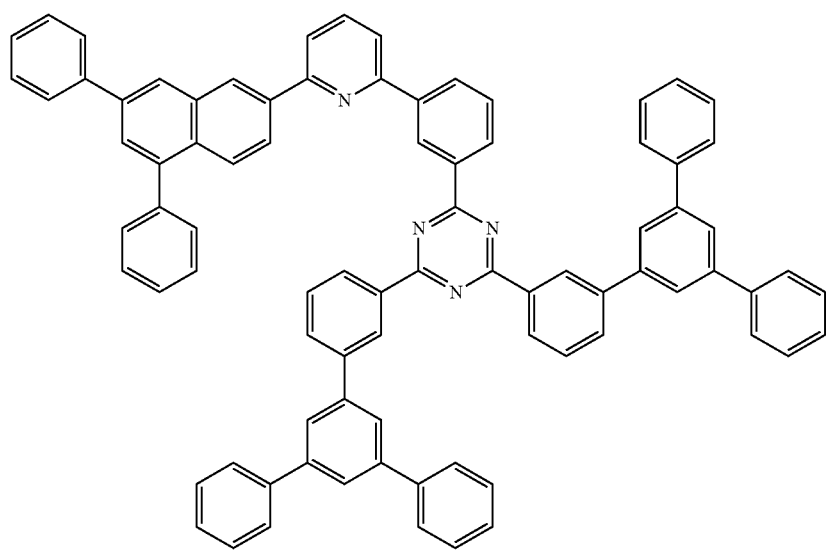

-continued
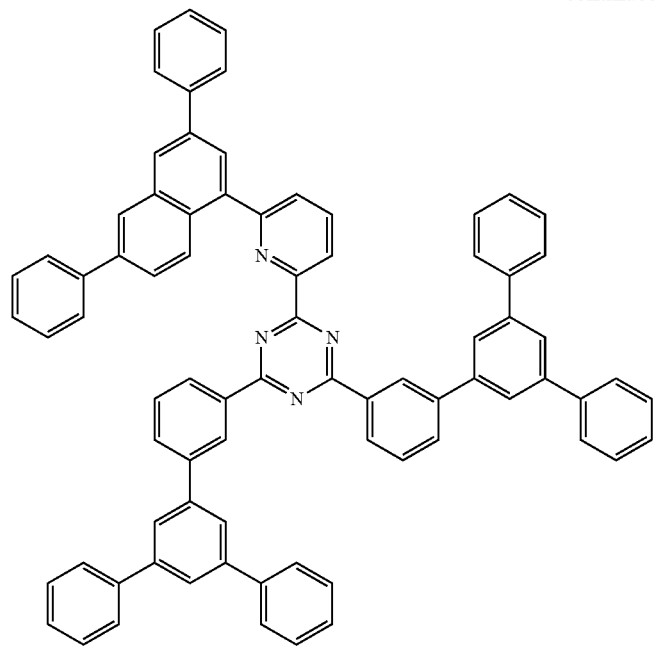
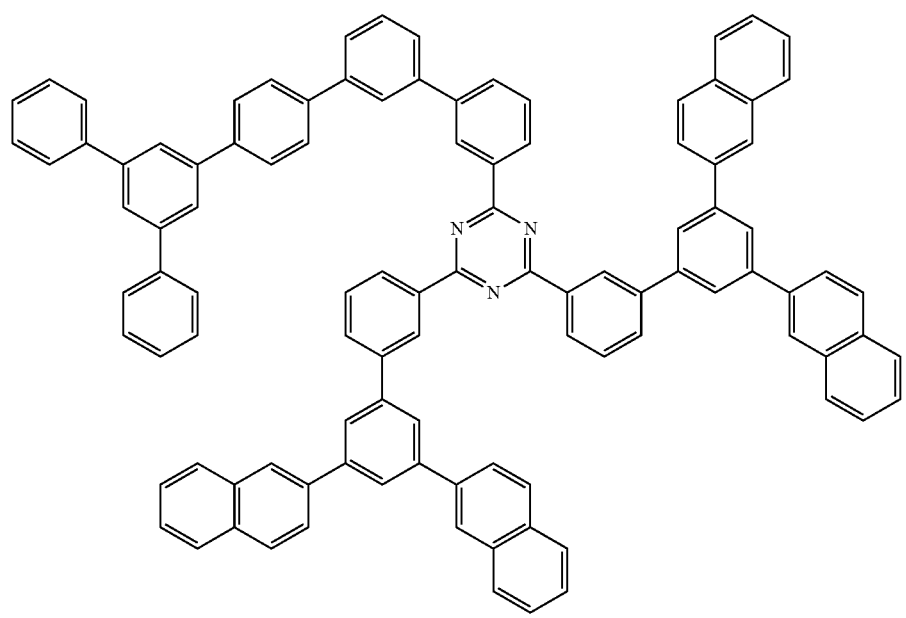

-continued
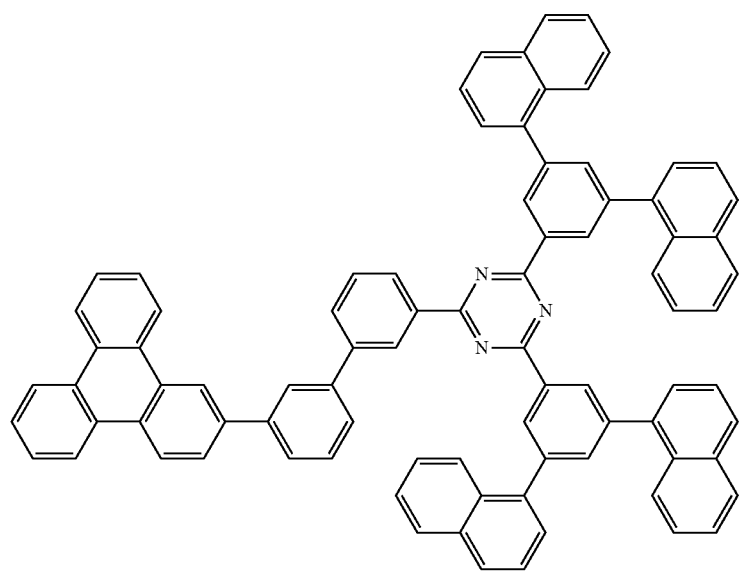
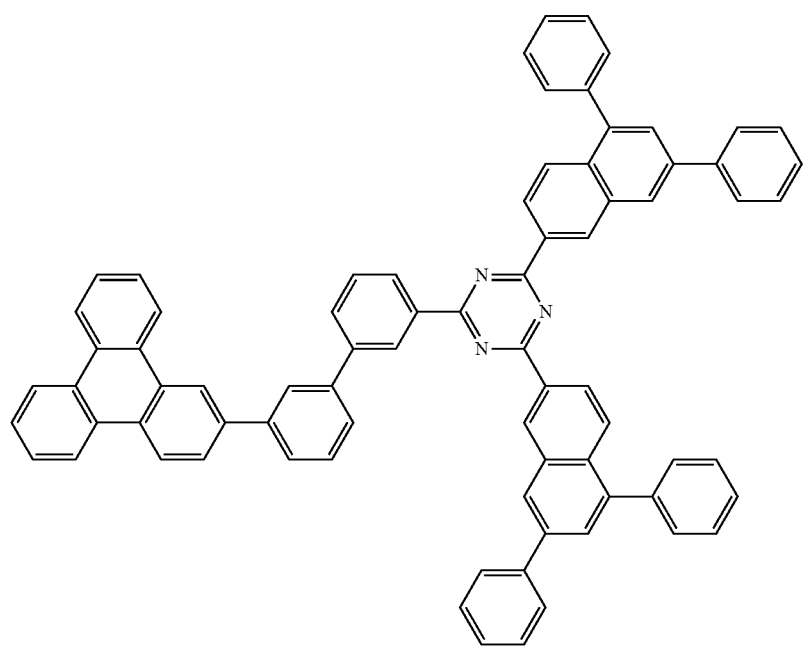

-continued
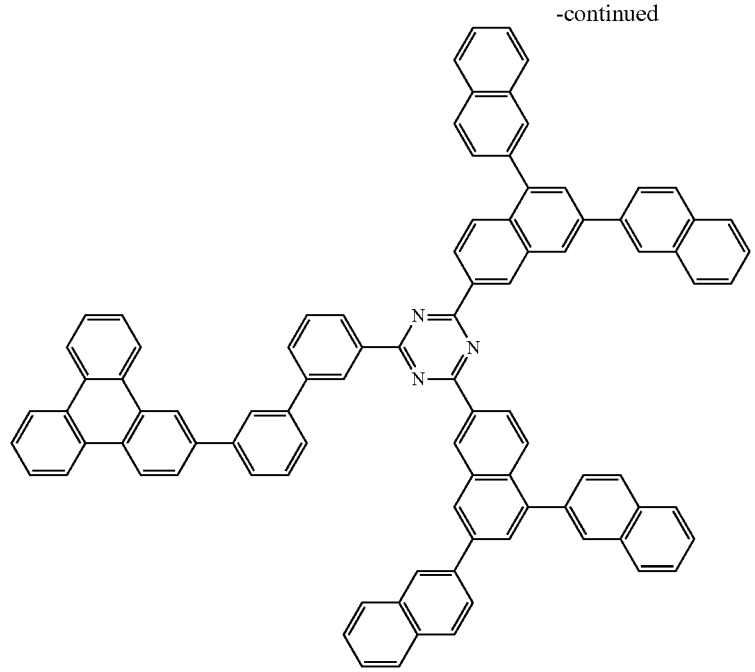
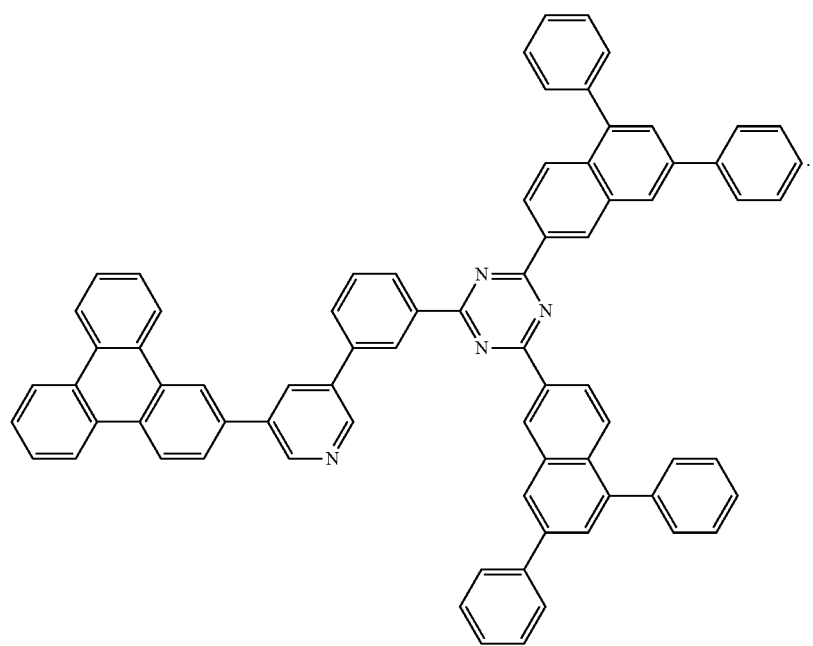

-continued
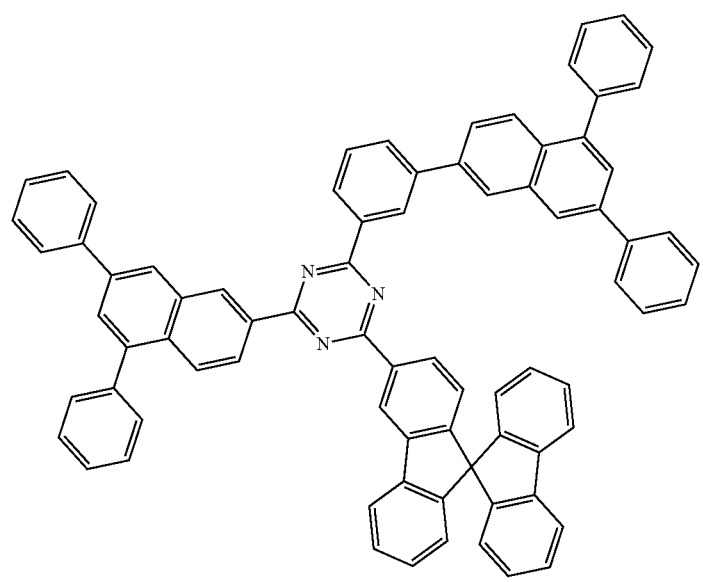
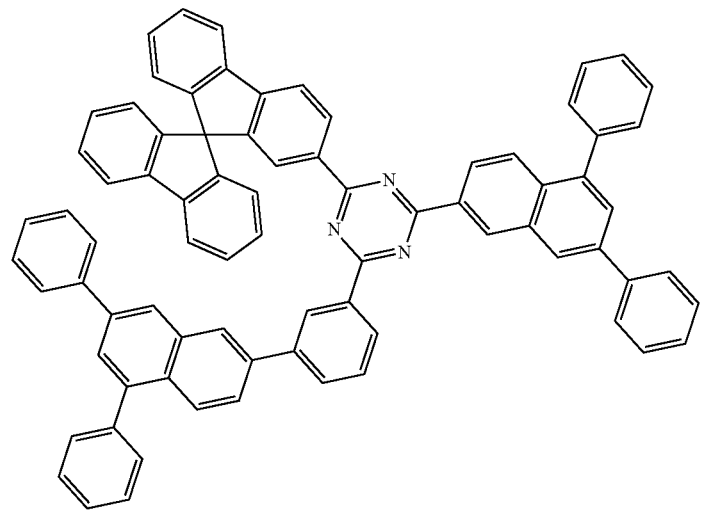
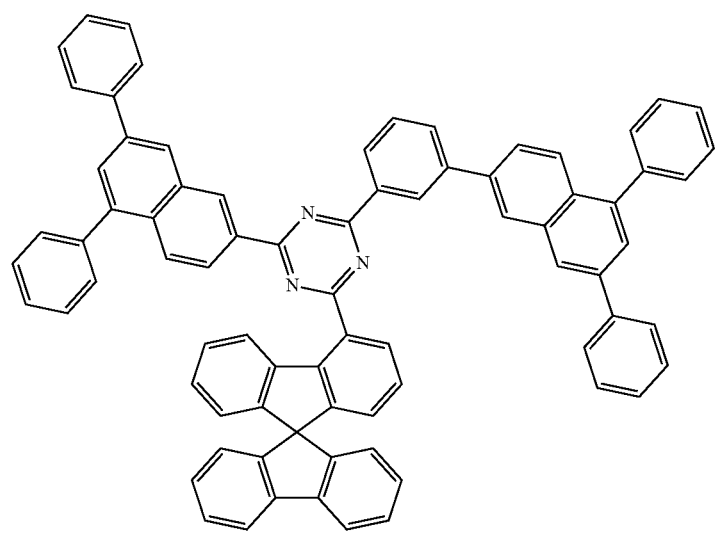

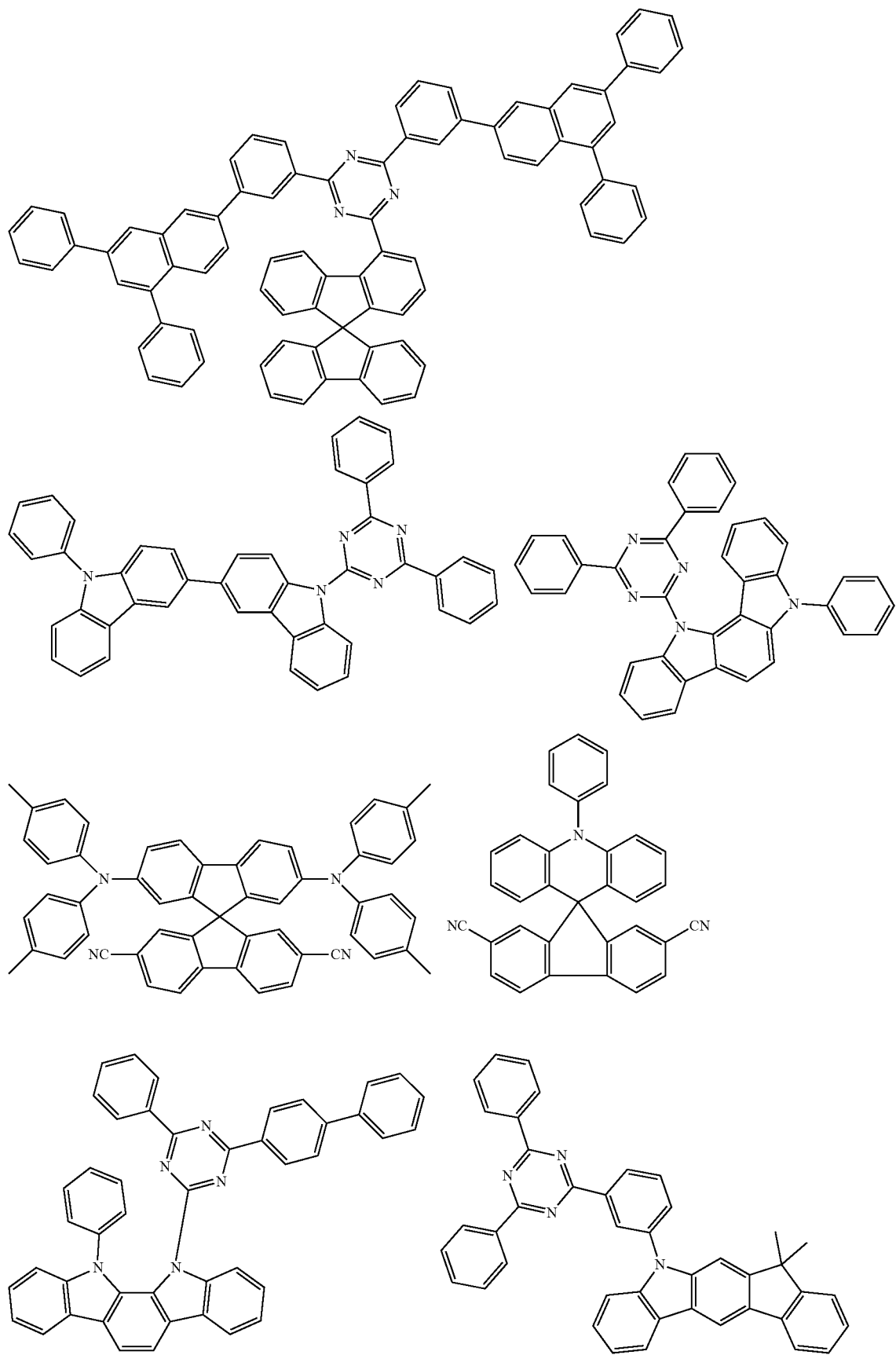

-continued
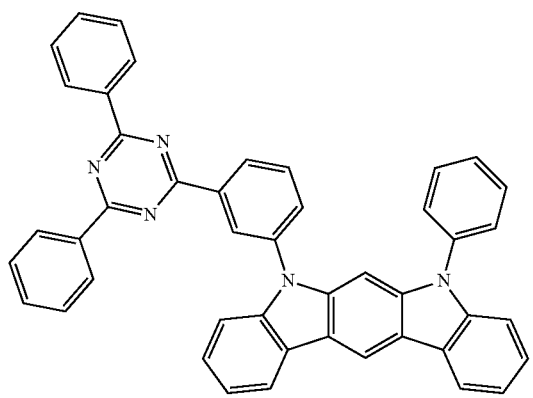
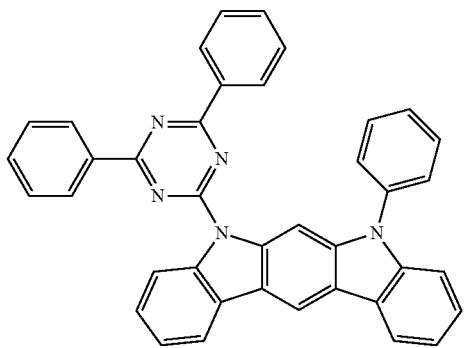
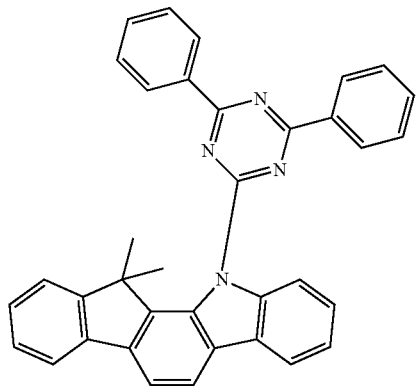
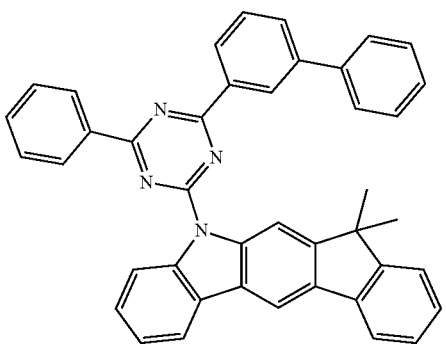
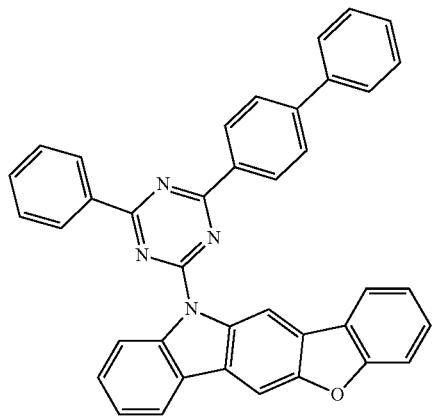
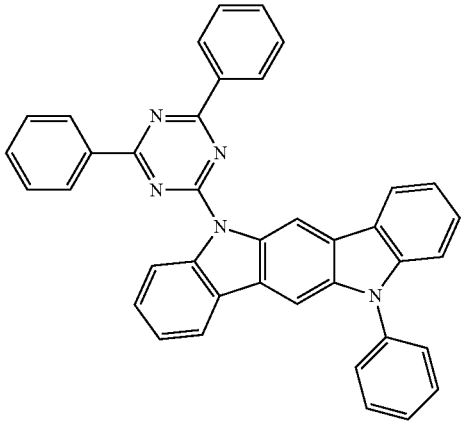
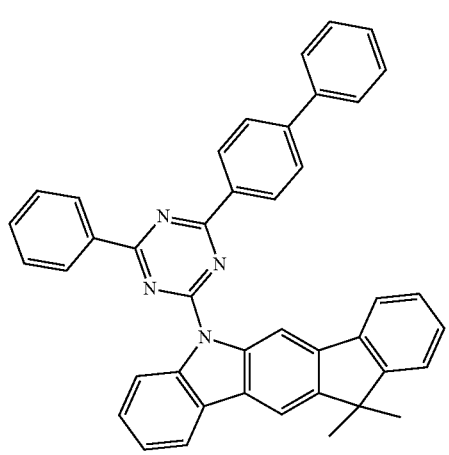
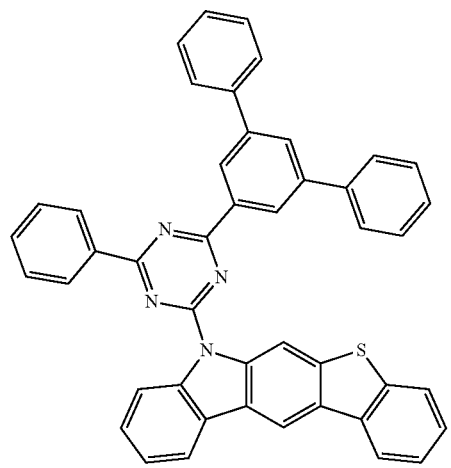

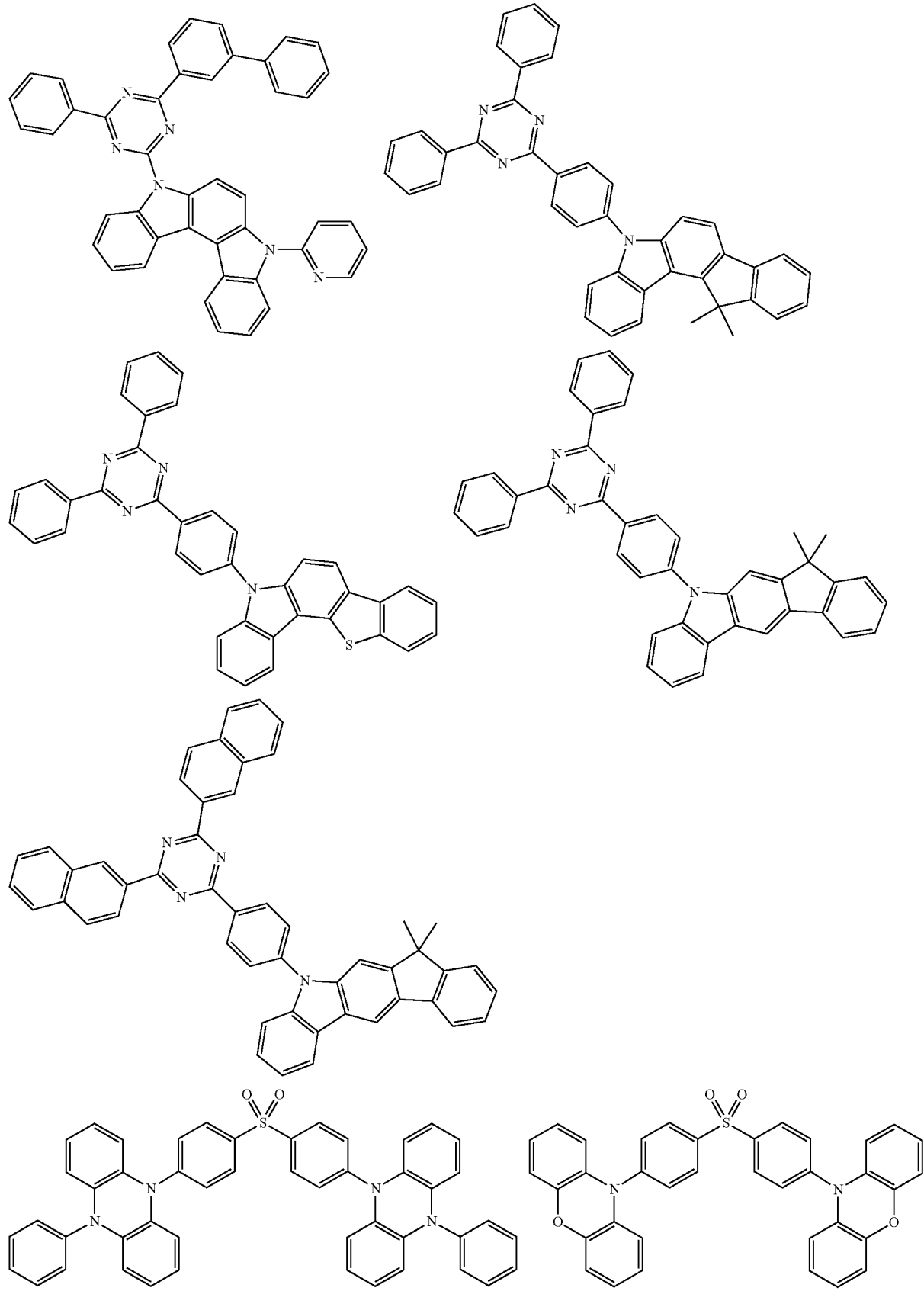

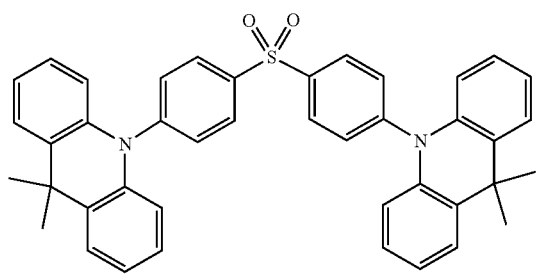
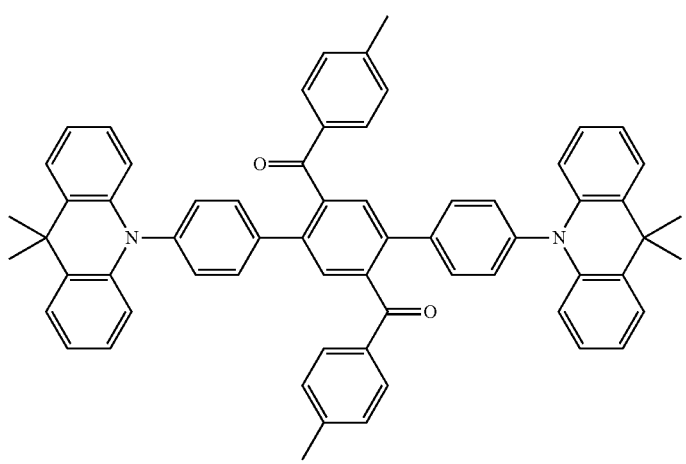
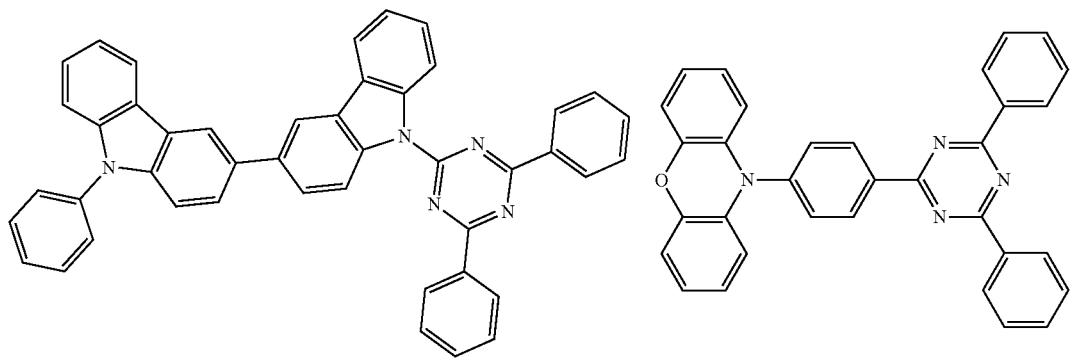
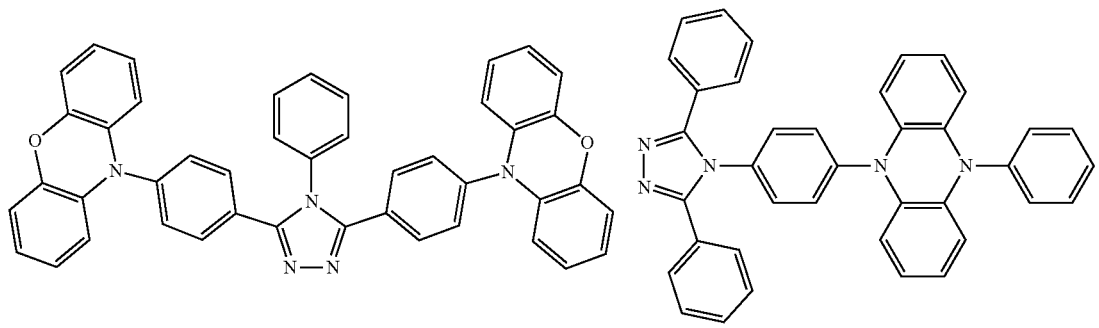

263
264
-continued
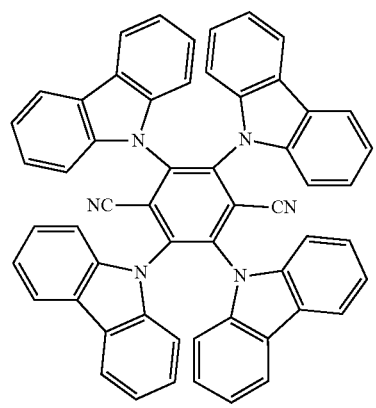
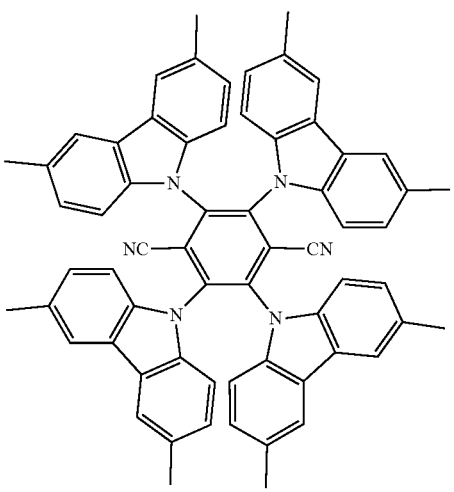
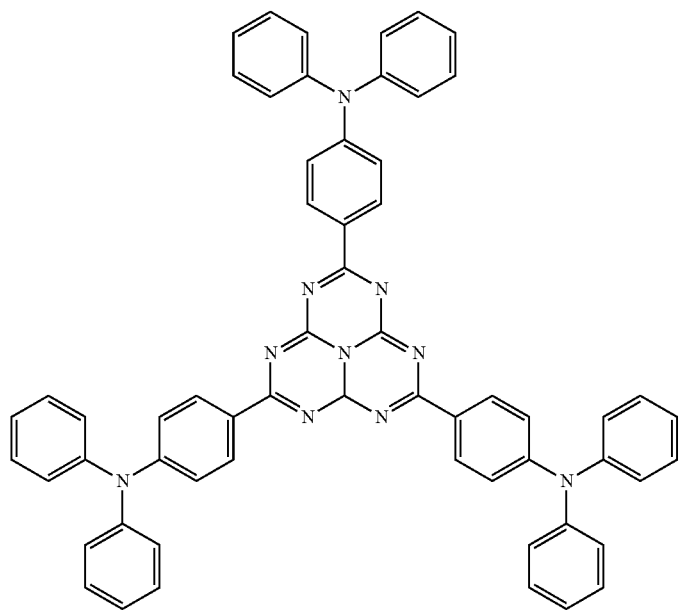
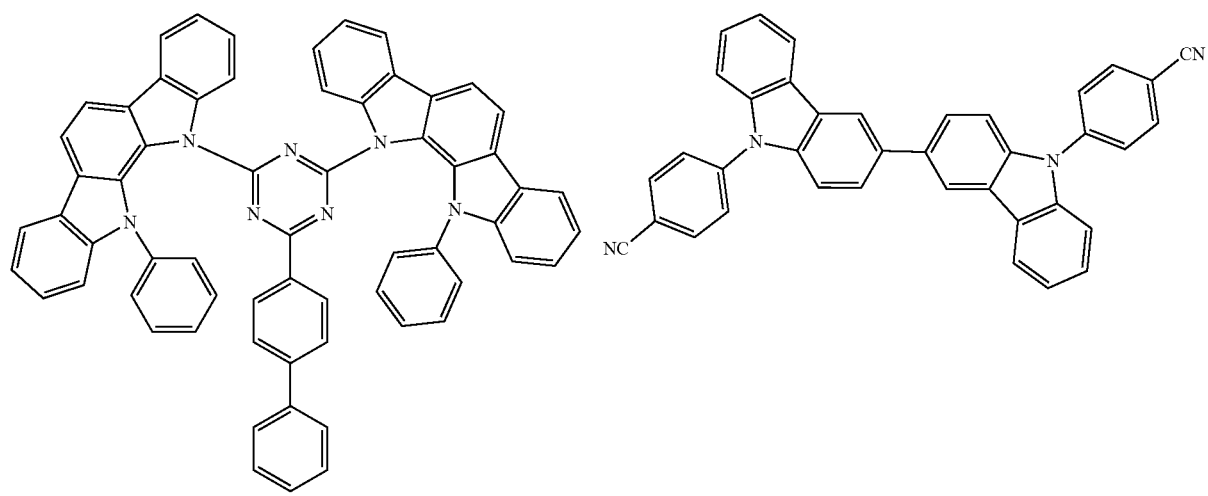

-continued
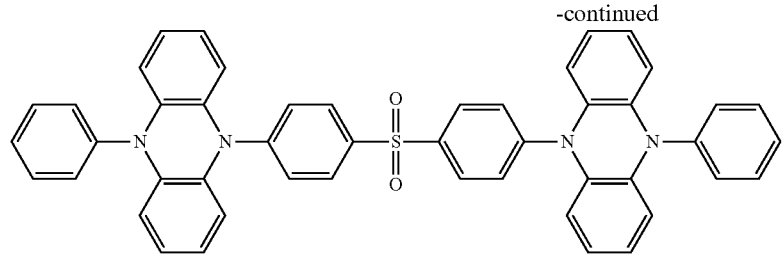
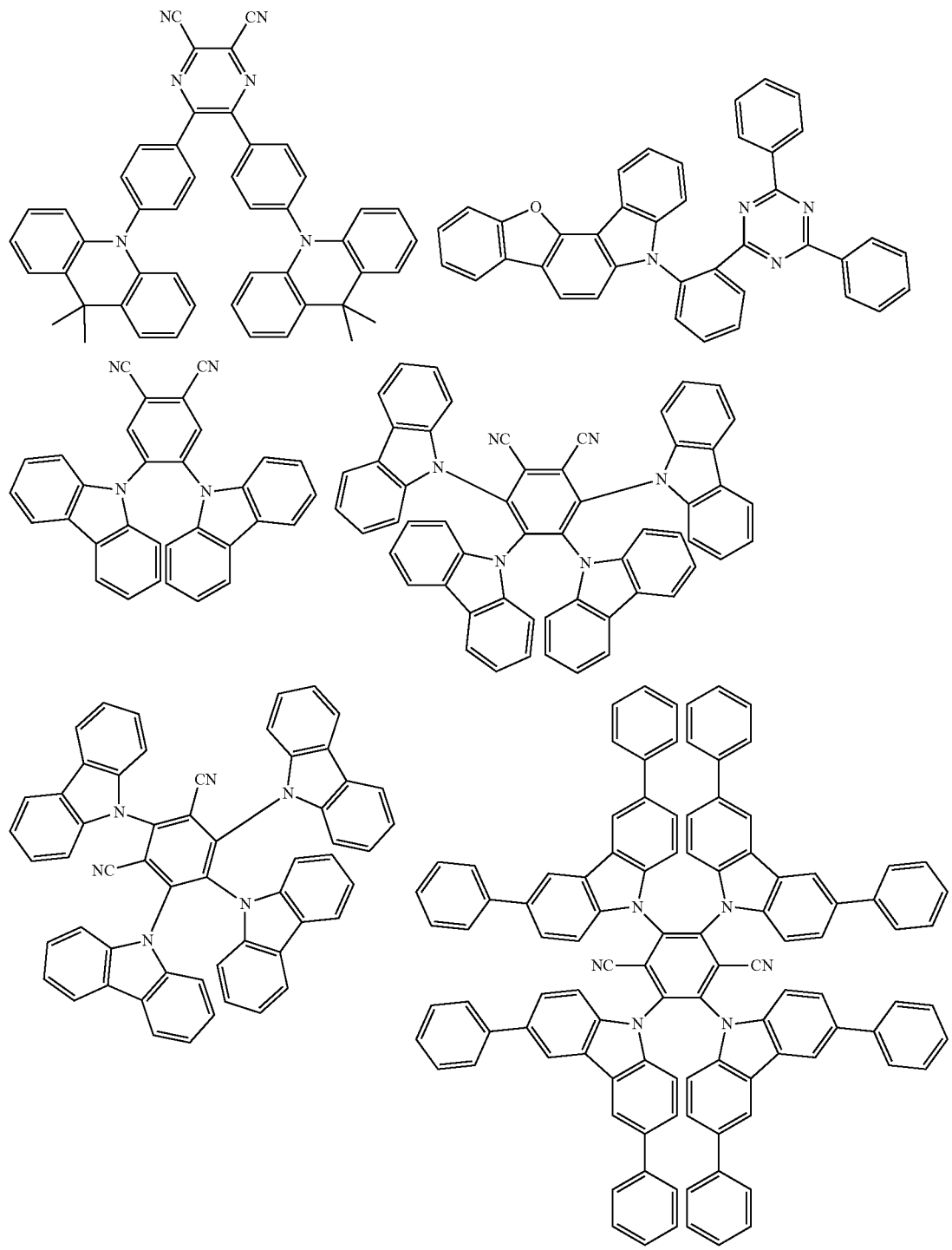

-continued
267
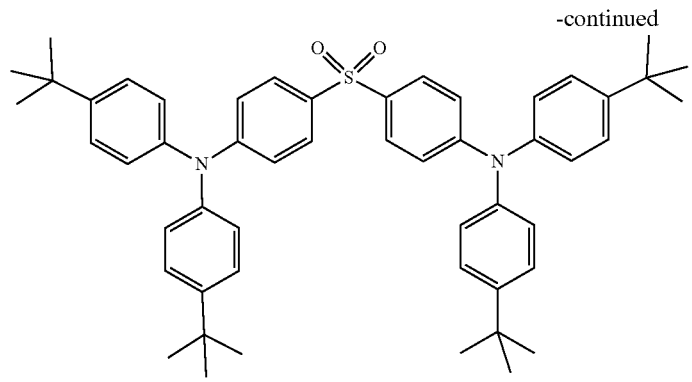
268
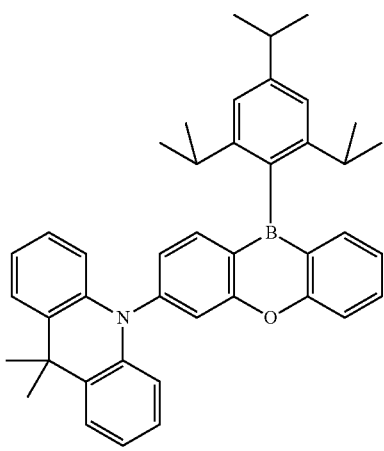
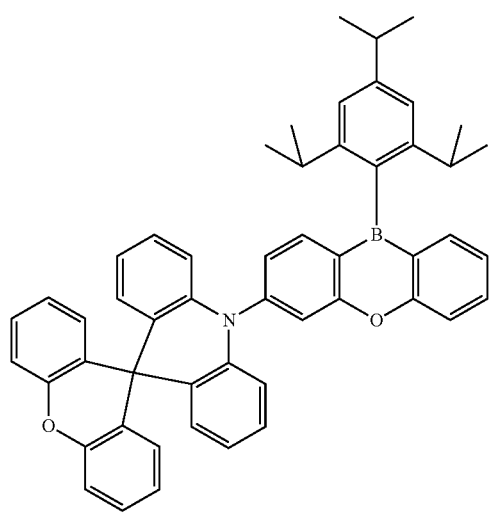
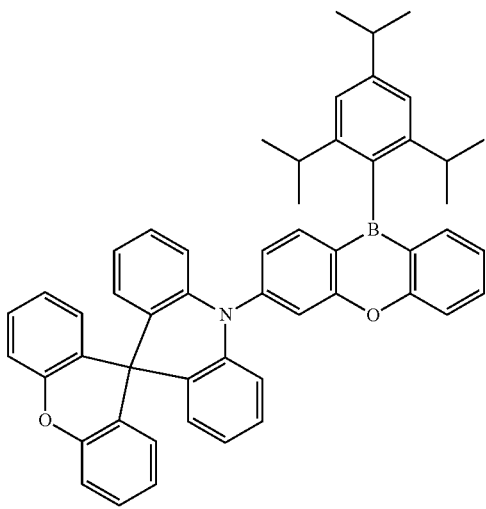
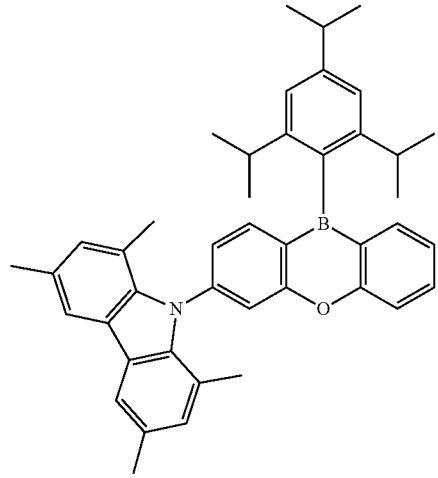
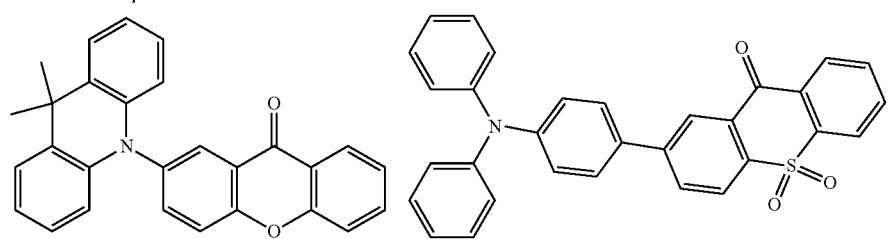

269    270
-continued
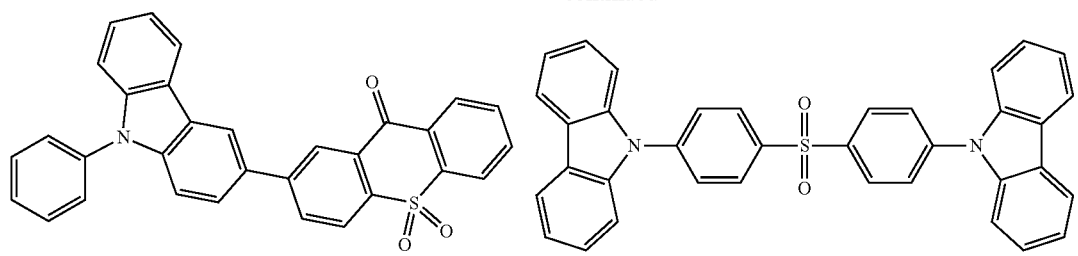
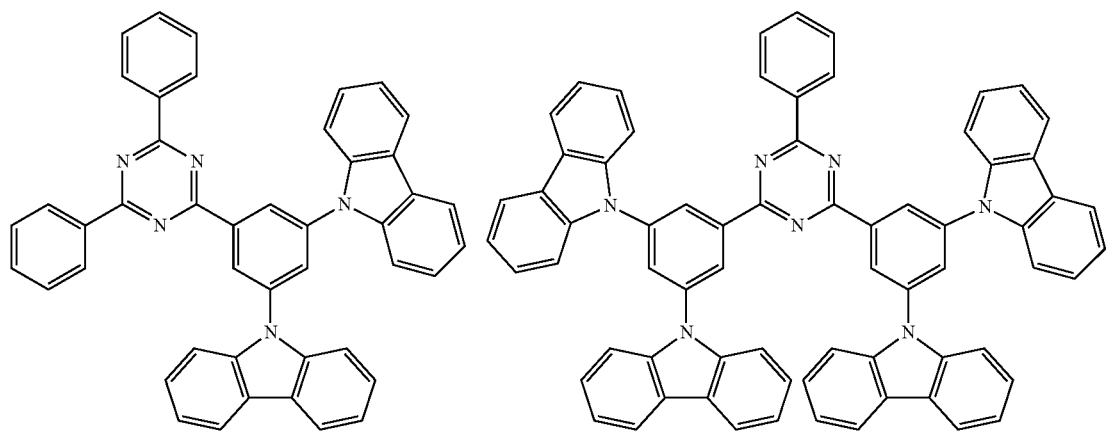
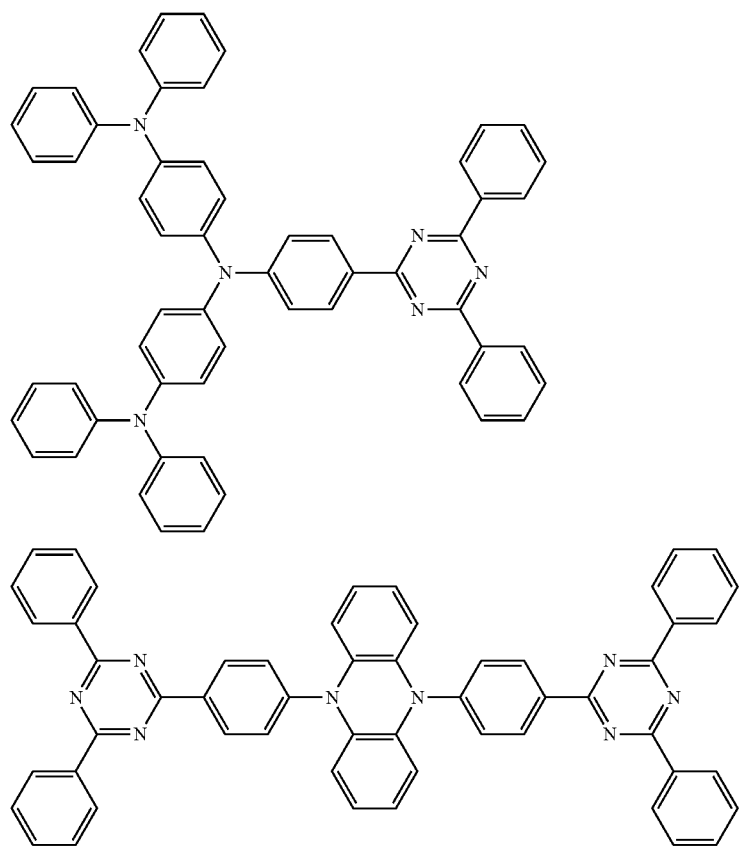

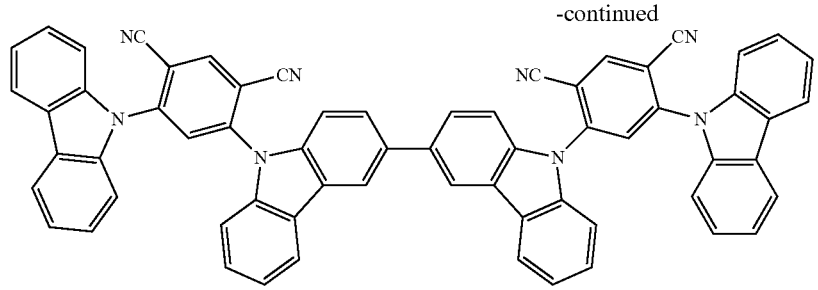
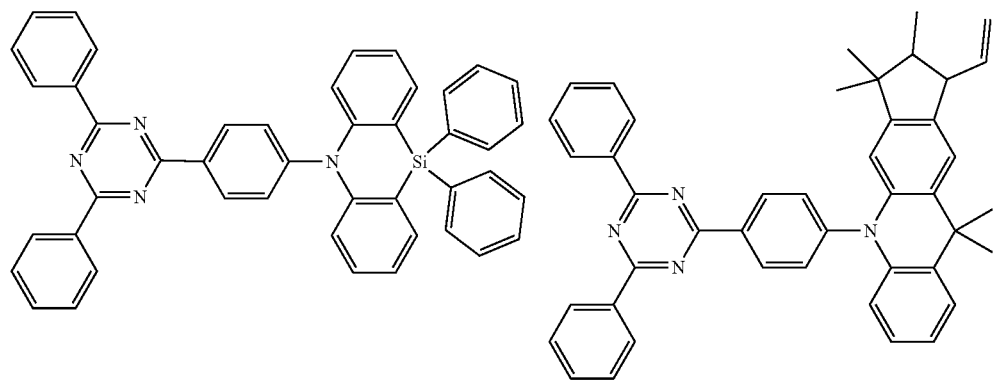
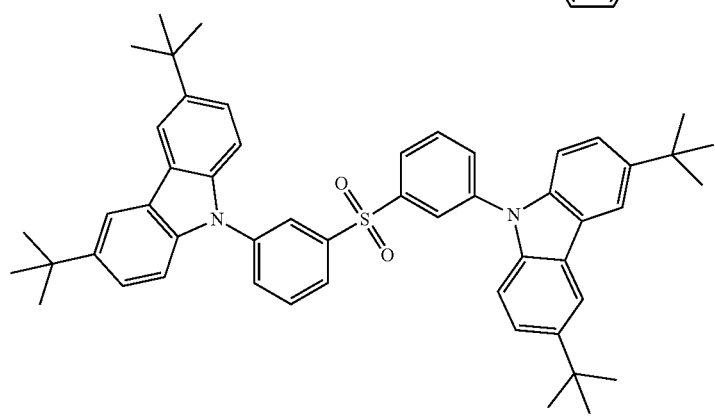
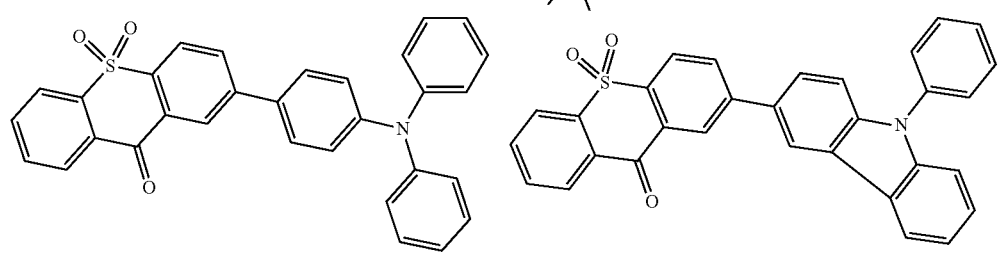
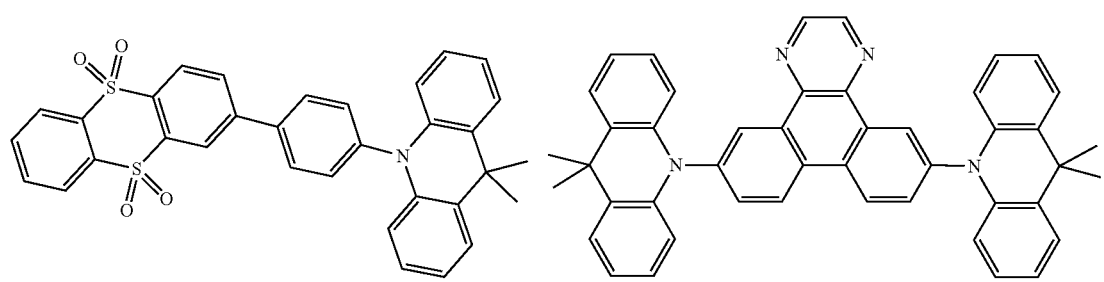

-continued
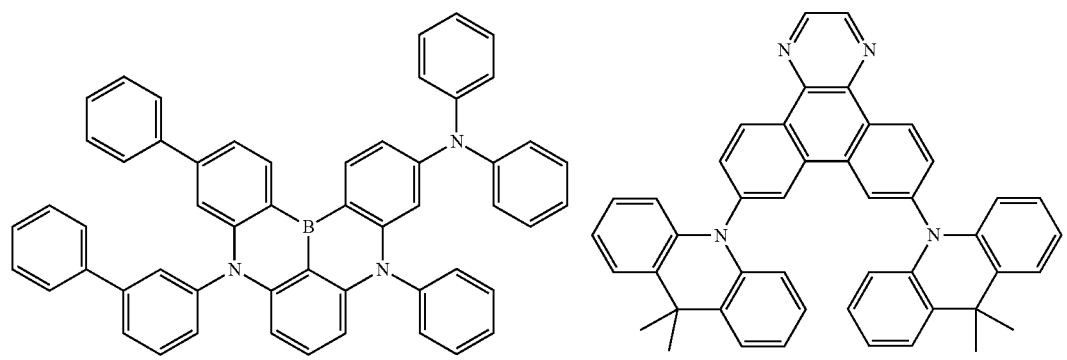
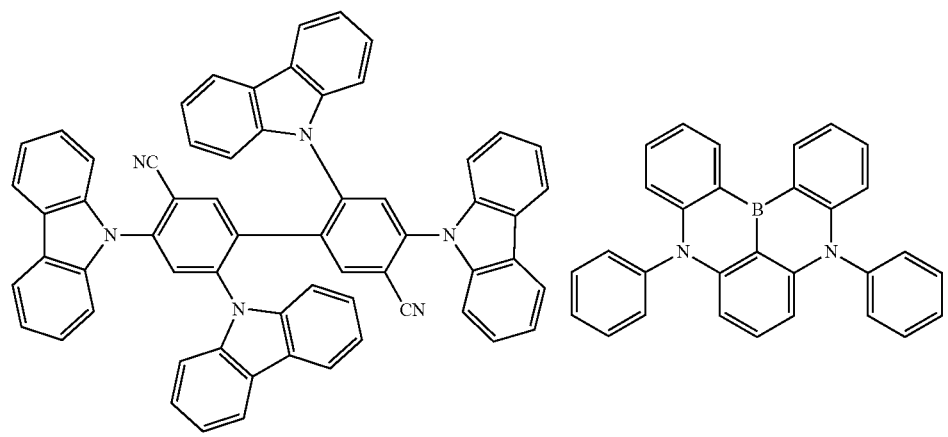
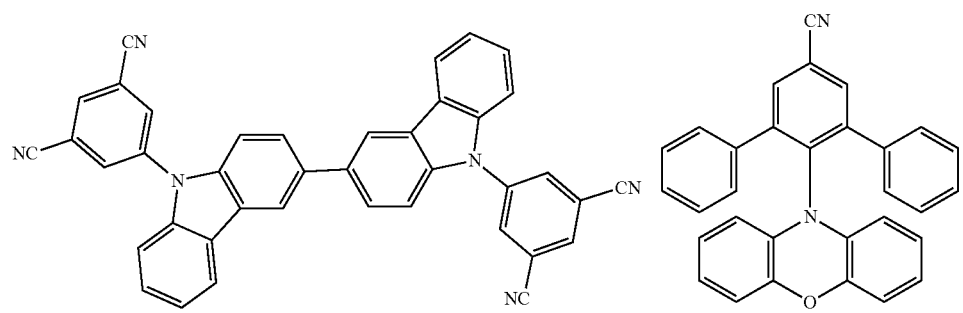
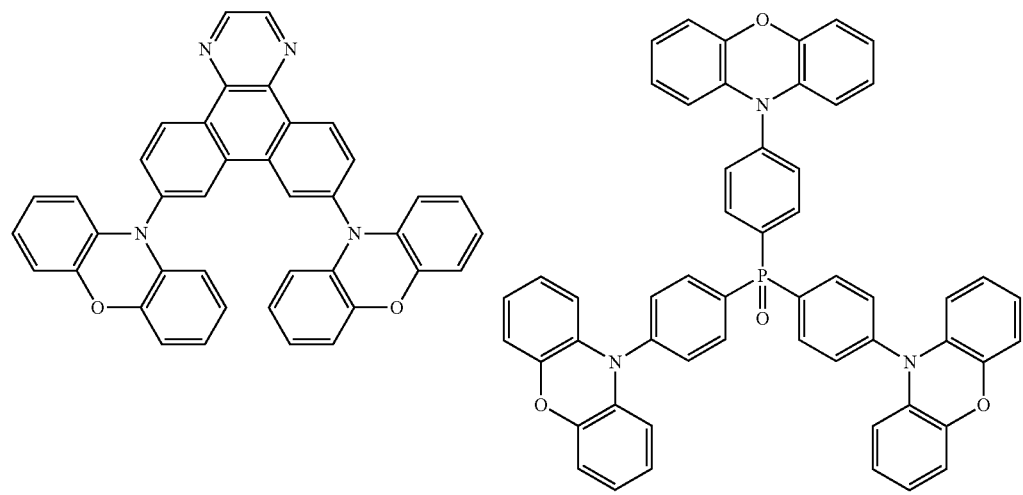

275
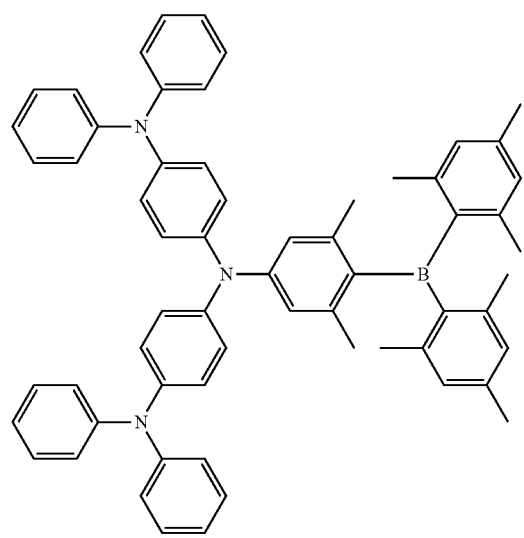
276
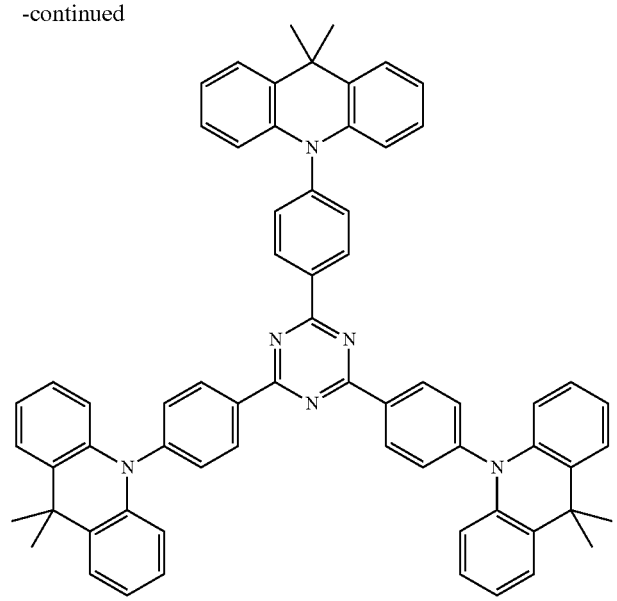
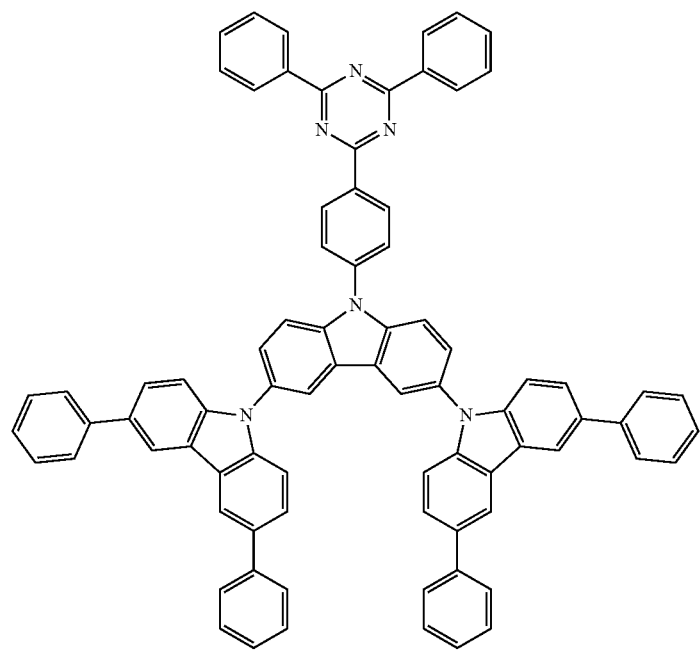

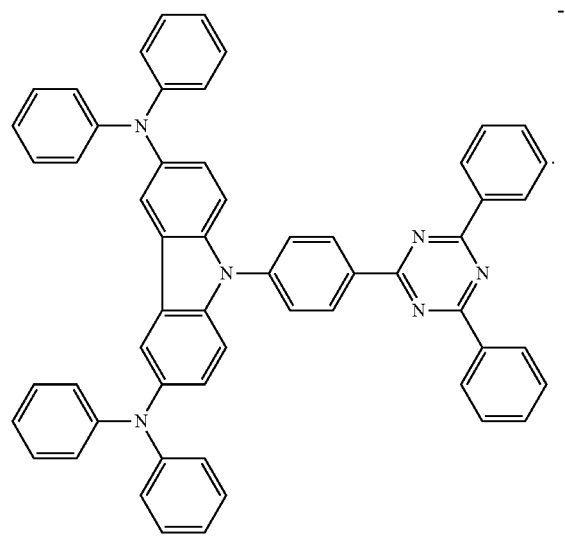 [SMILES: c1ccc(-c2nc(-c3ccccc3)nc(-c3ccc(-n4c5ccc(N(c6ccccc6)c6ccccc6)cc5c5cc(N(c6ccccc6)c6ccccc6)ccc54)cc3)n2)cc1]
19. The composition according to claim 1, wherein H1 is selected from the following compounds:
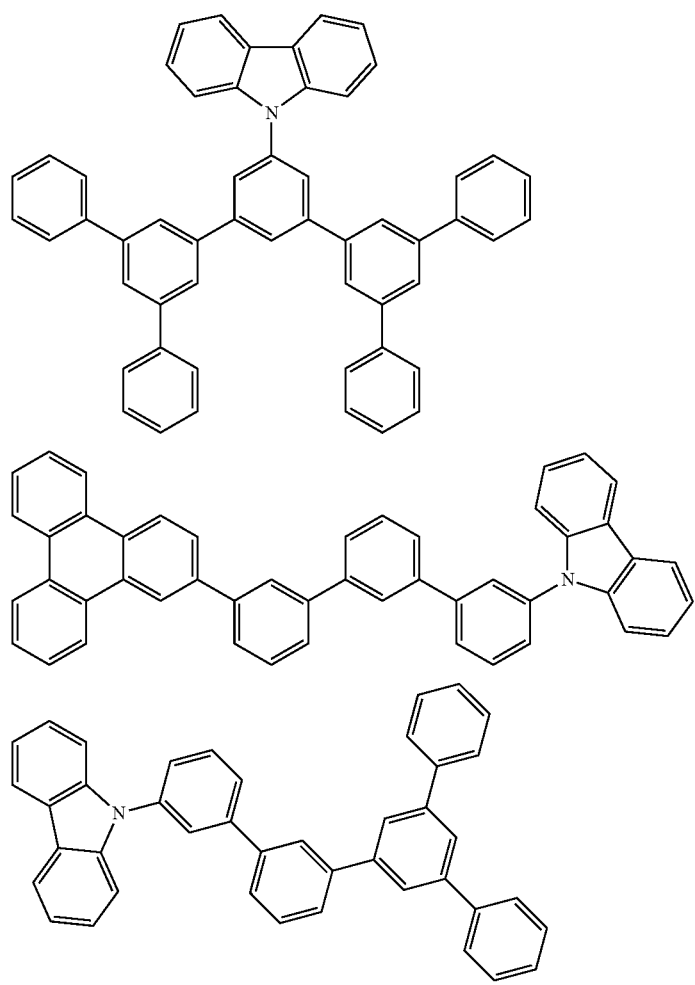

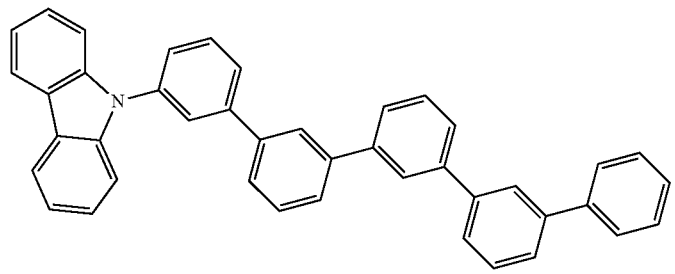
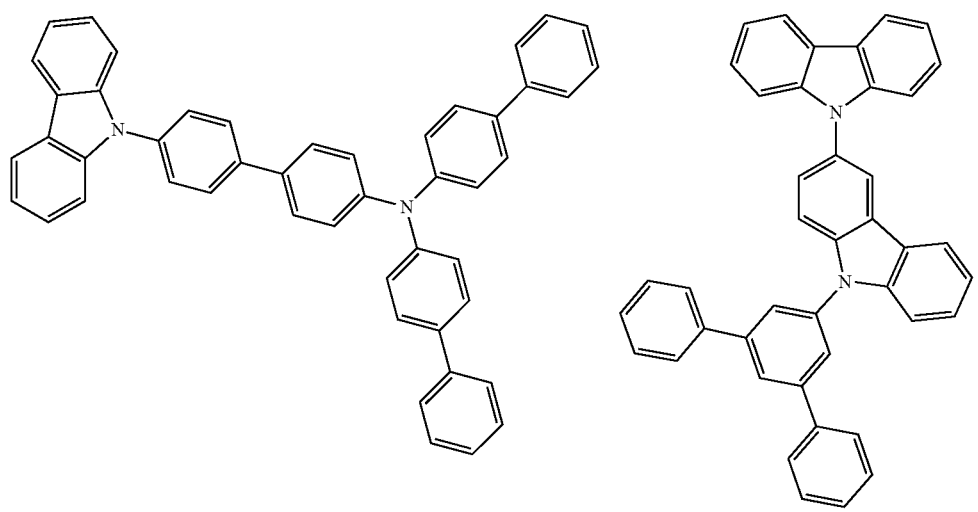
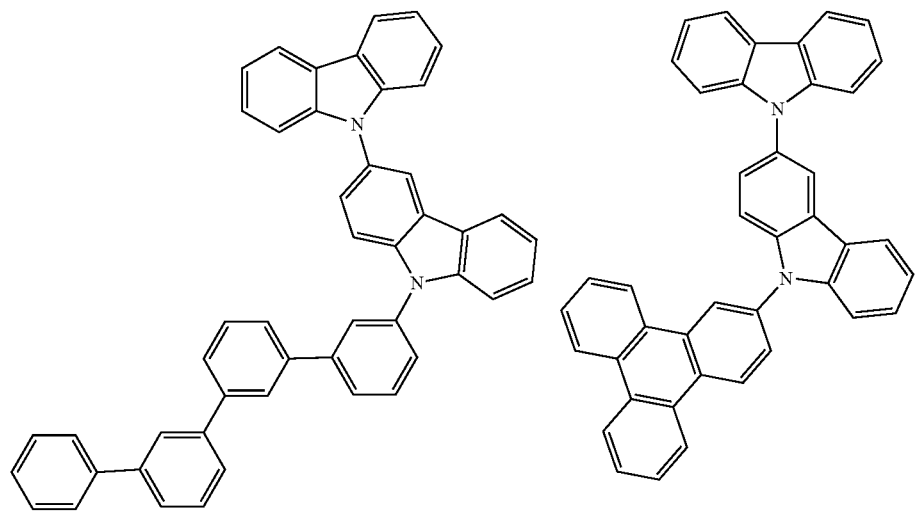

281 -continued 282
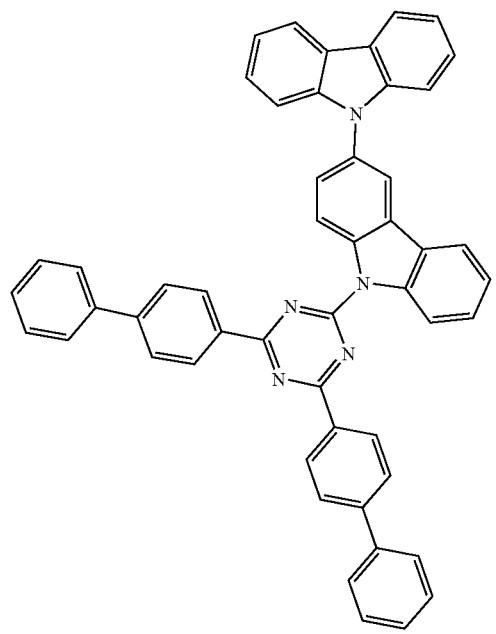 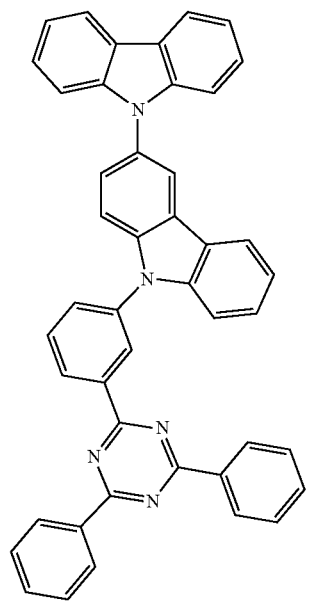 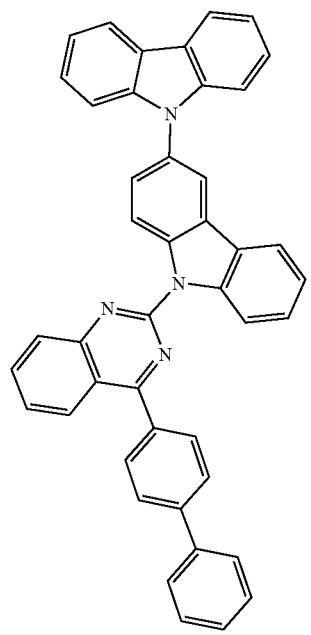
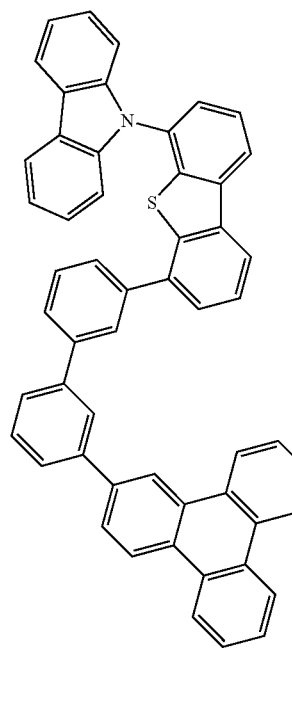 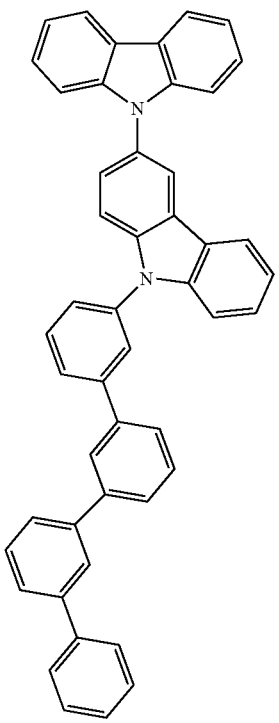 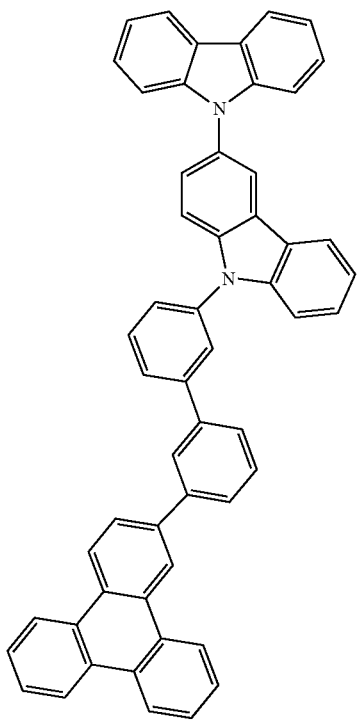

283
284
-continued
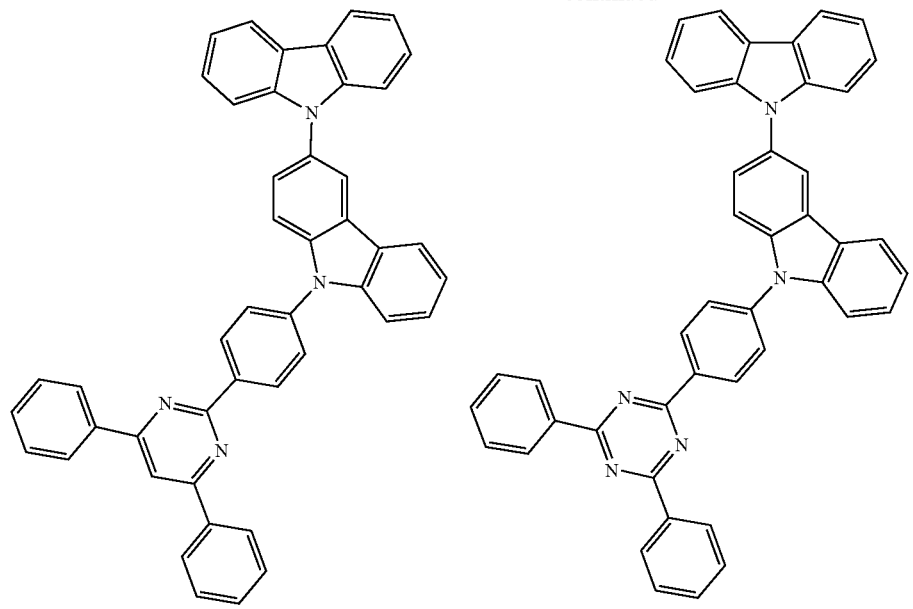
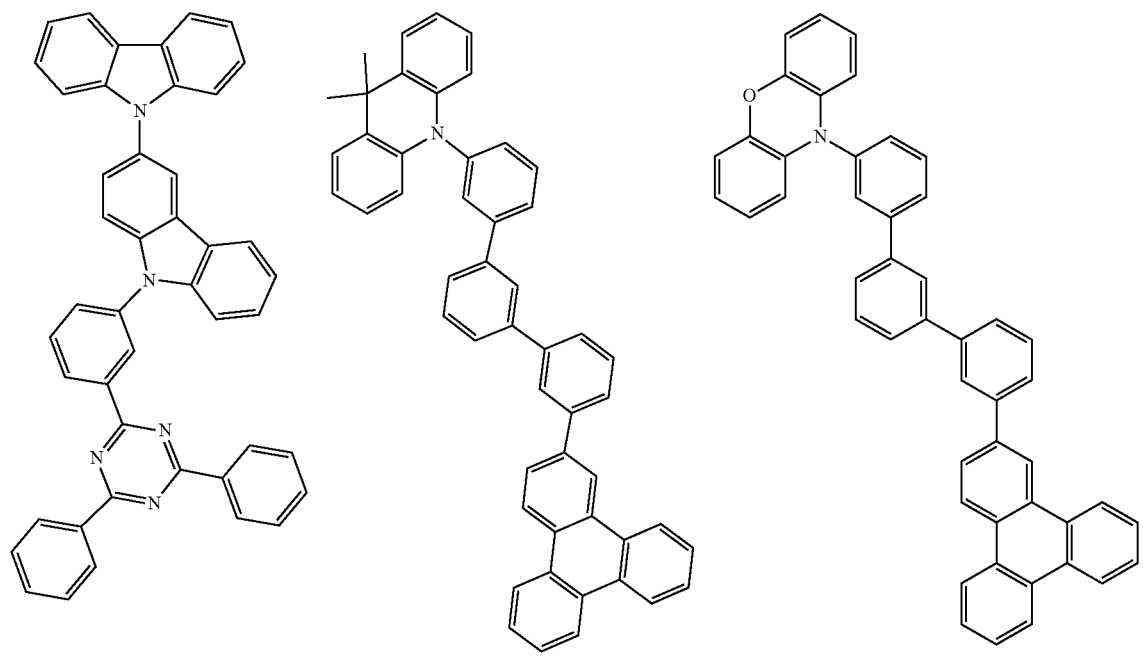

285
286
-continued
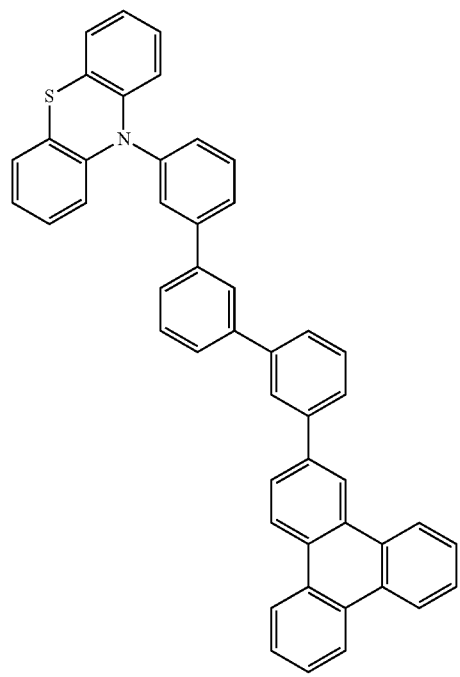
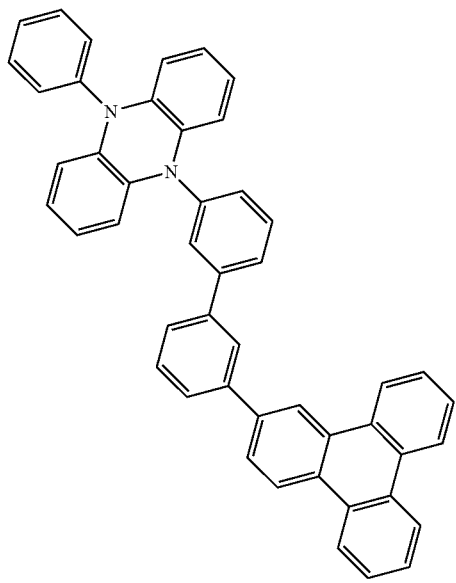
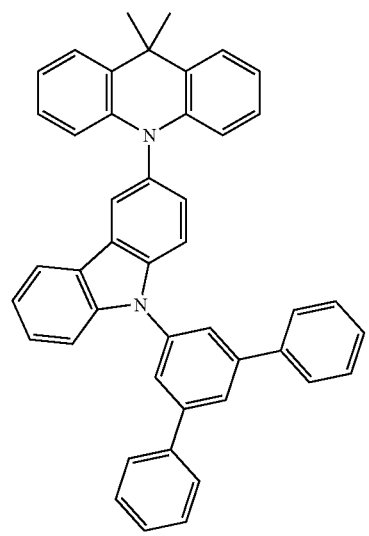
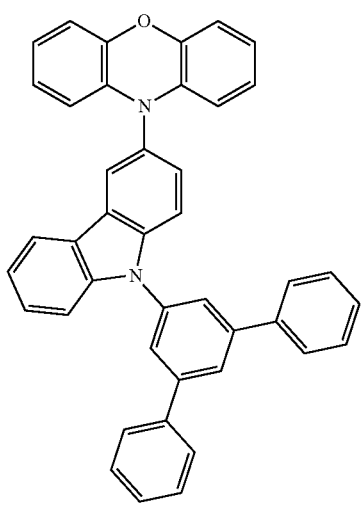
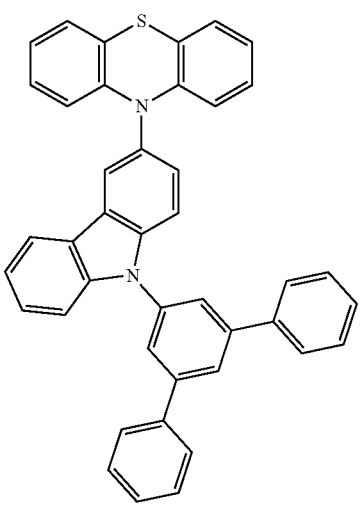

287
288
-continued
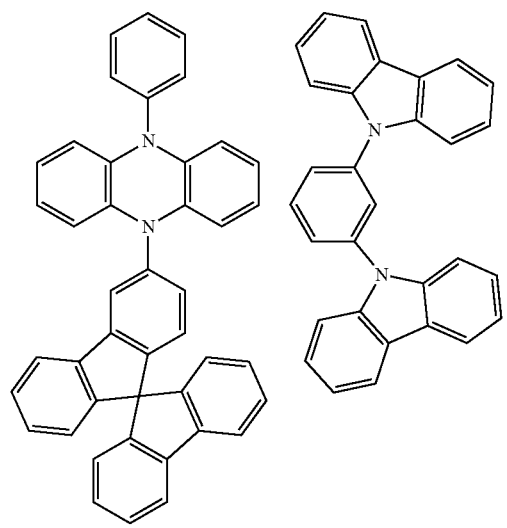
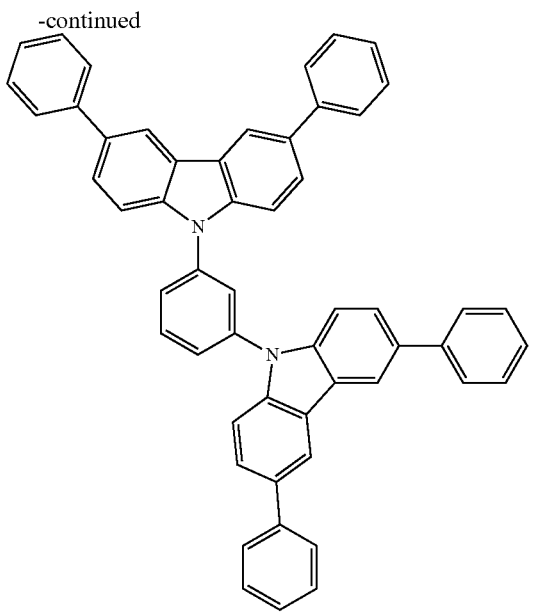
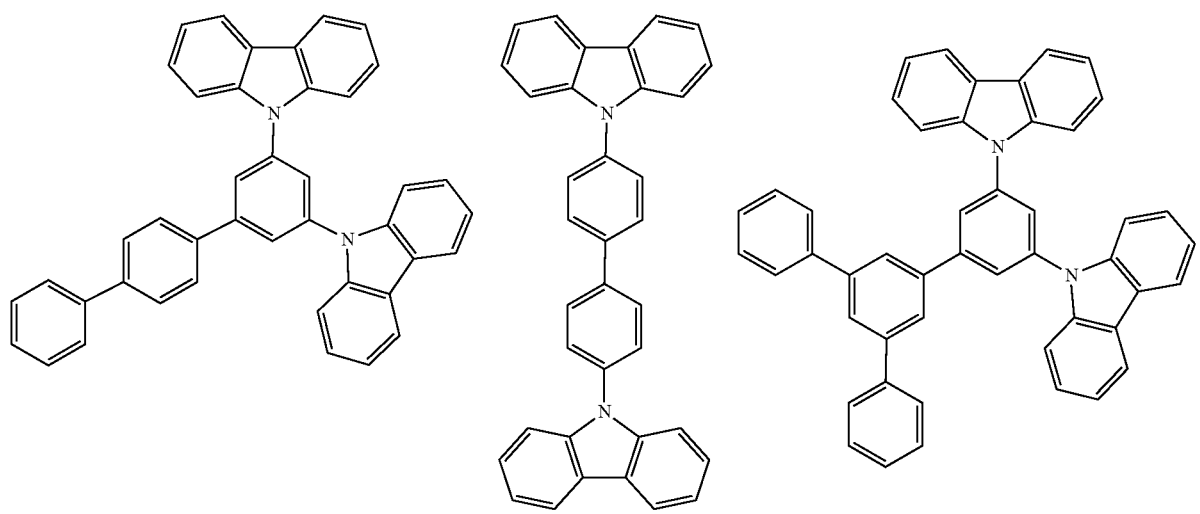
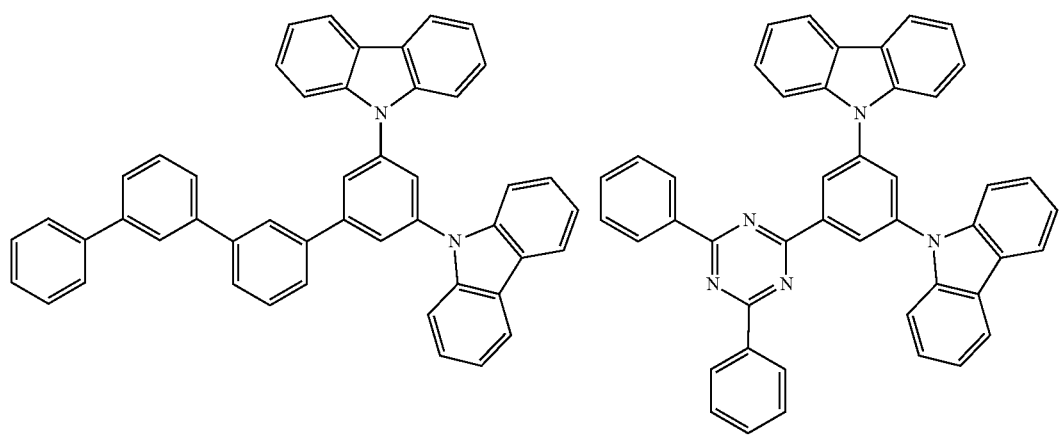

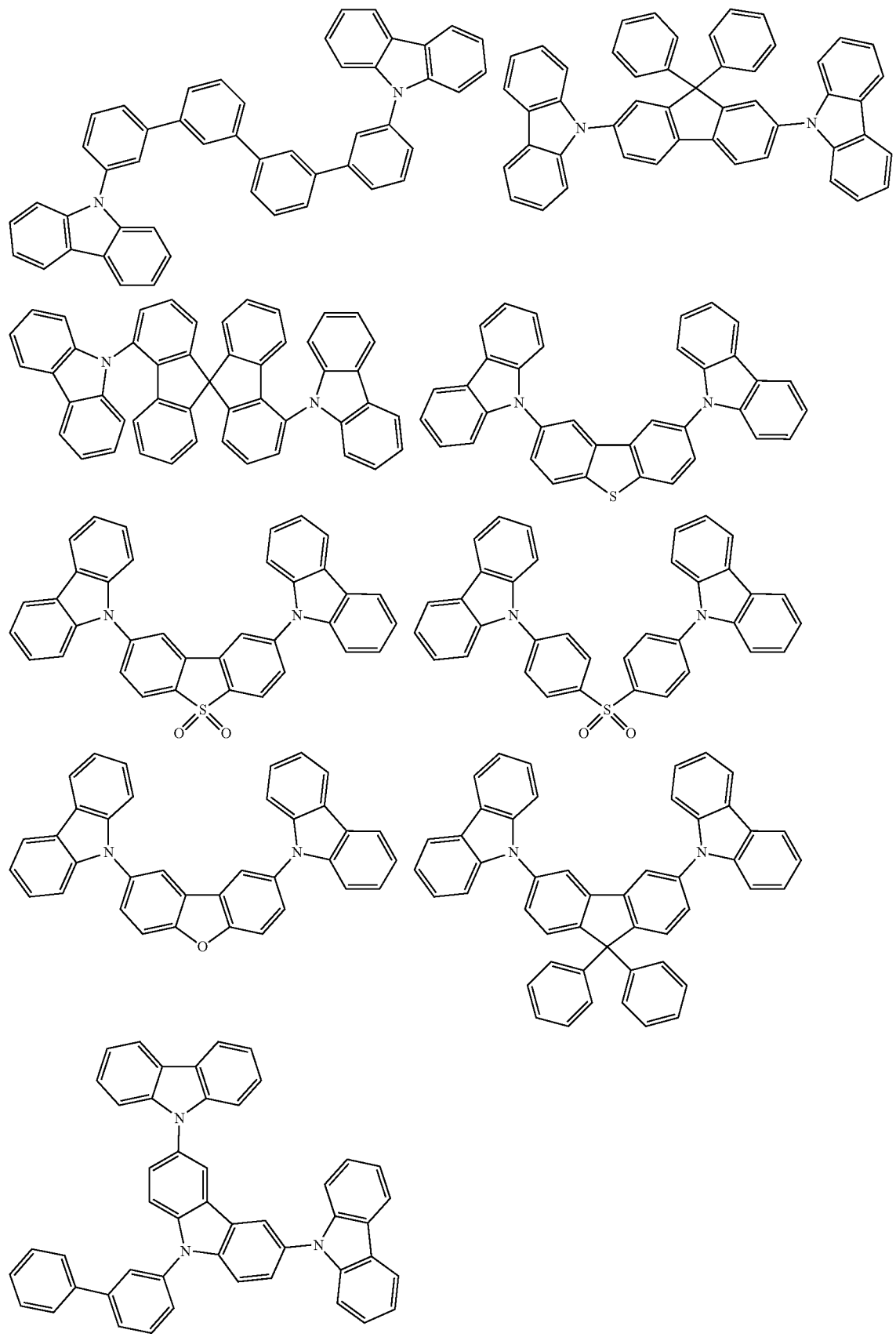

-continued
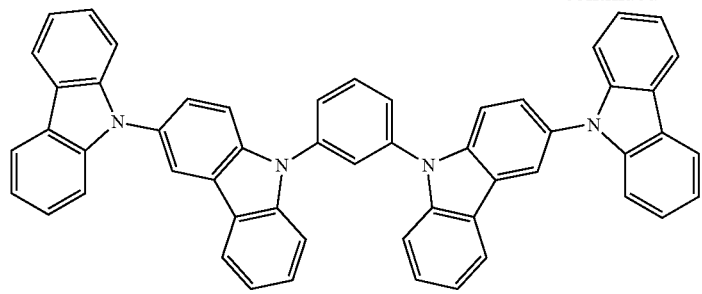
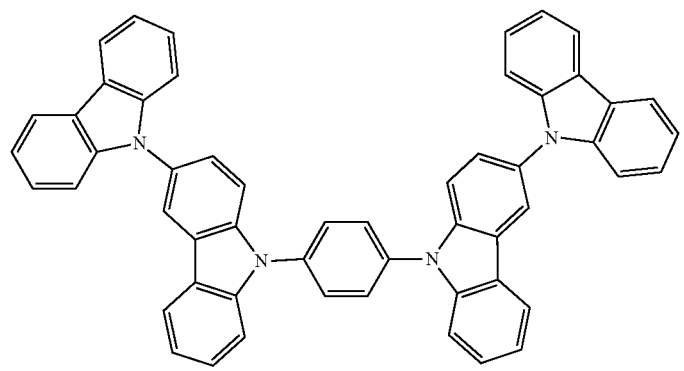
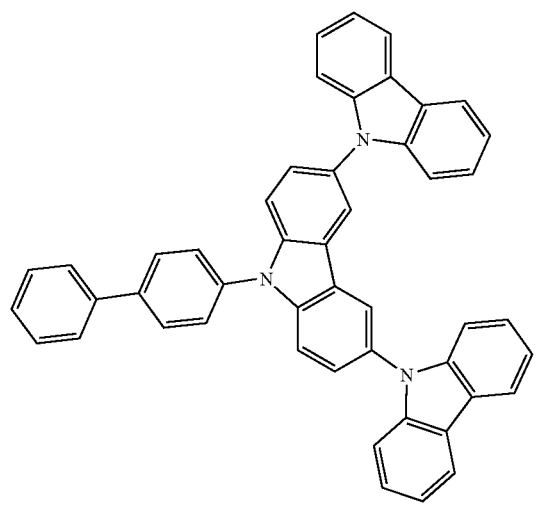
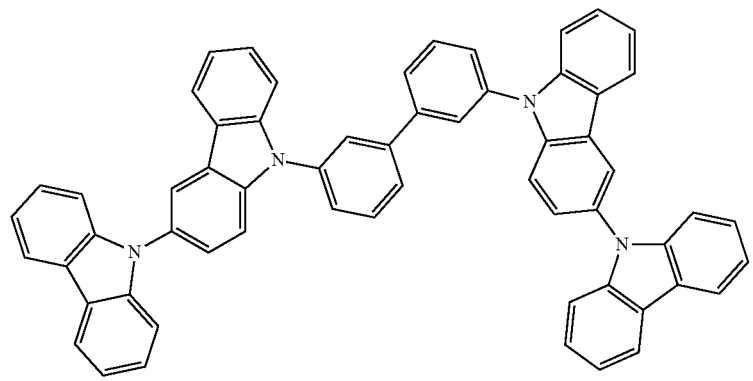

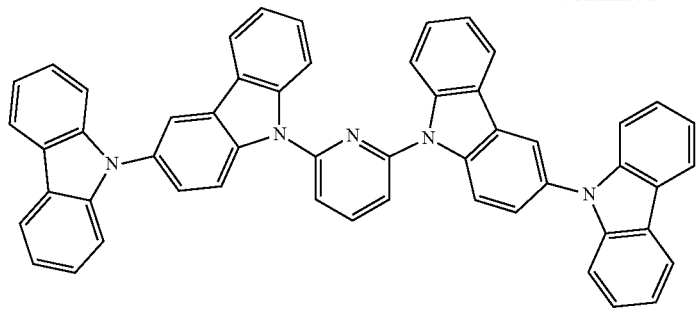
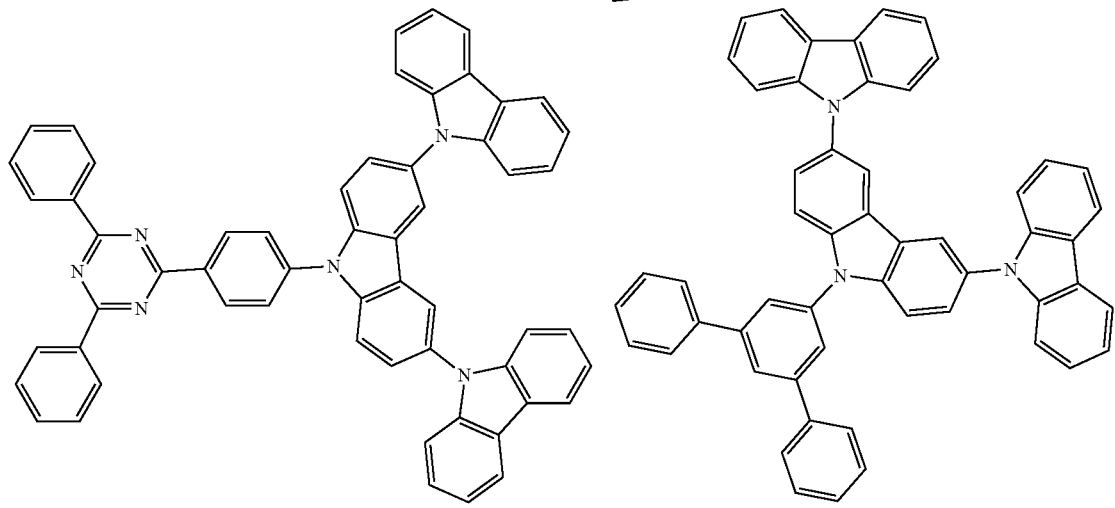
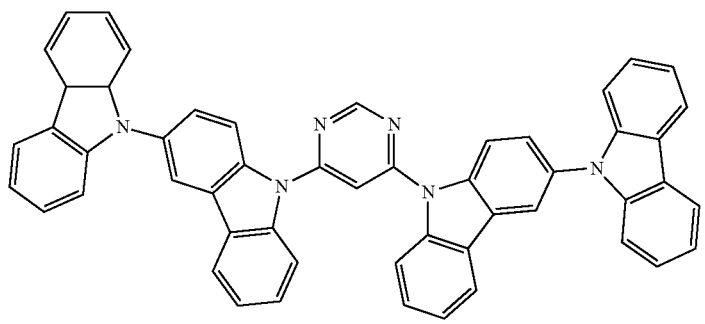
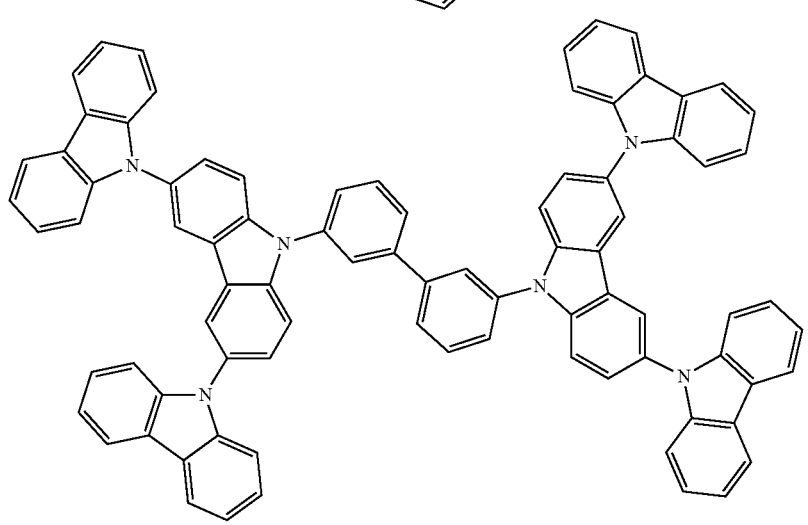

-continued
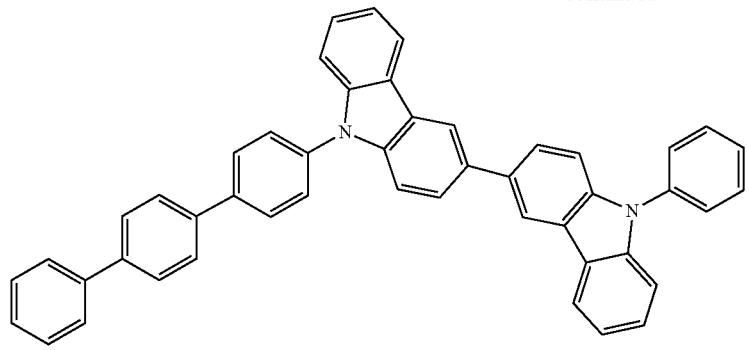
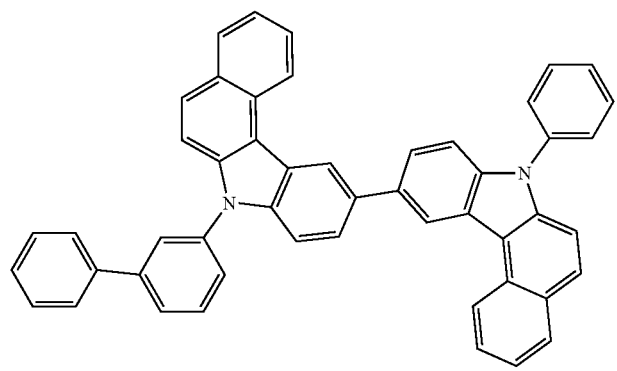
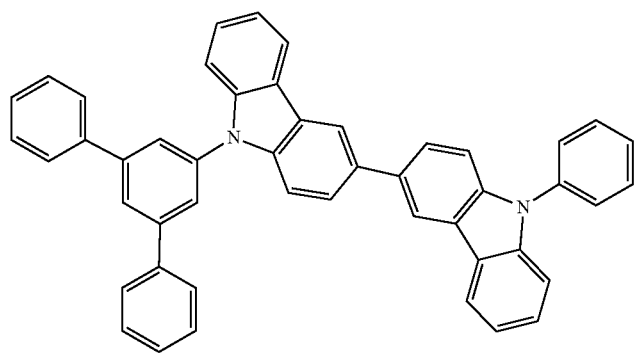
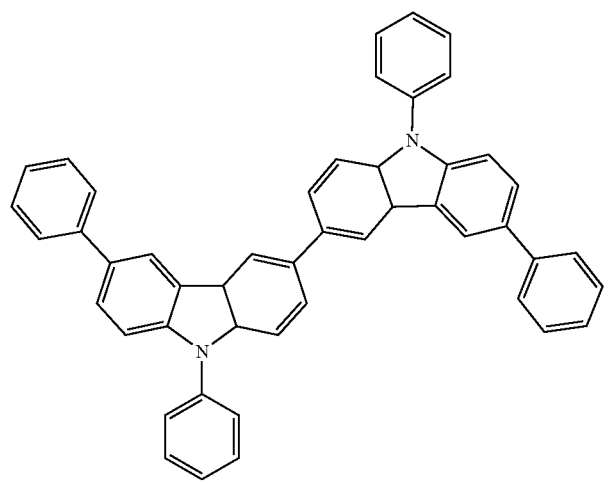

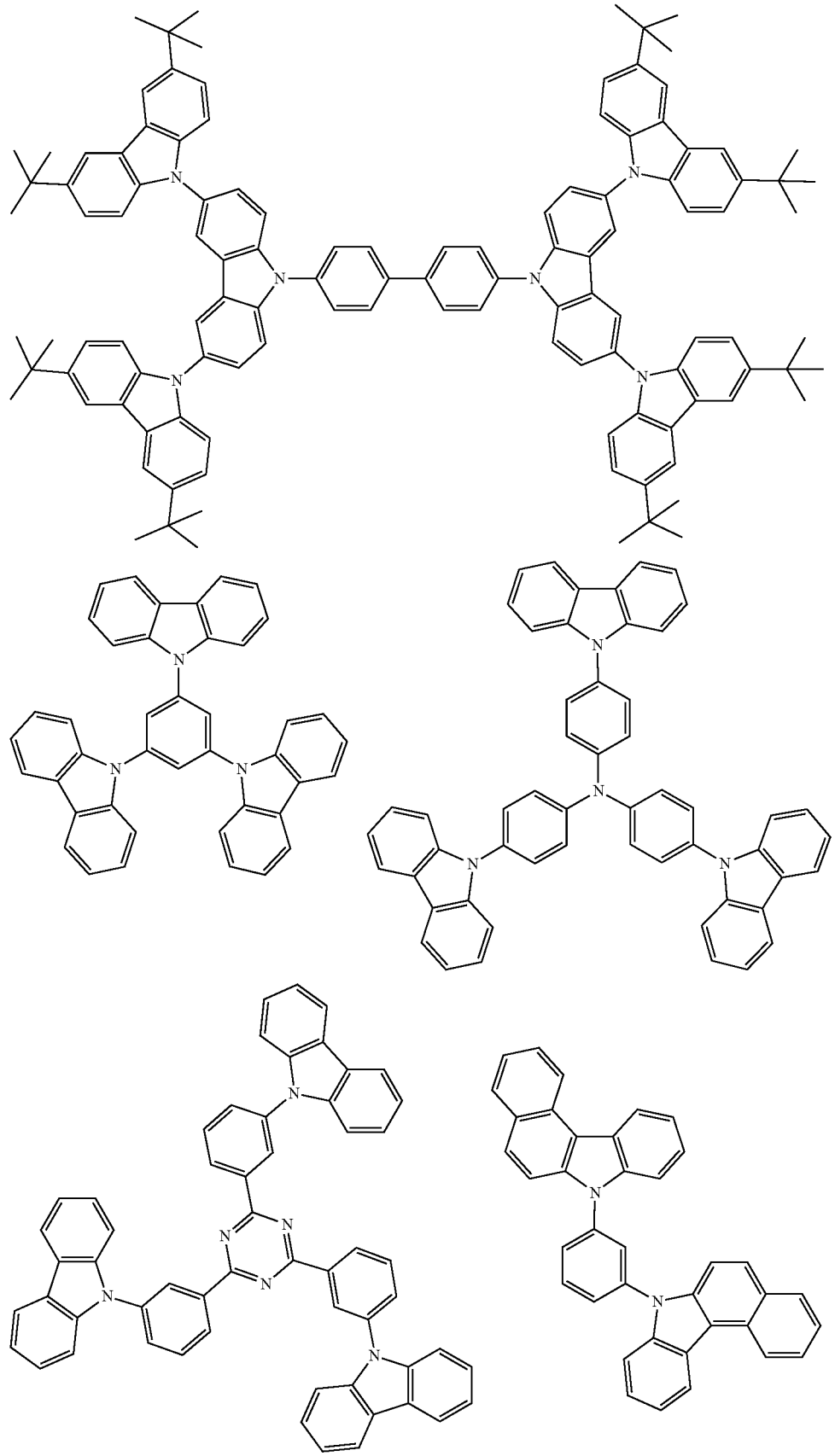

-continued
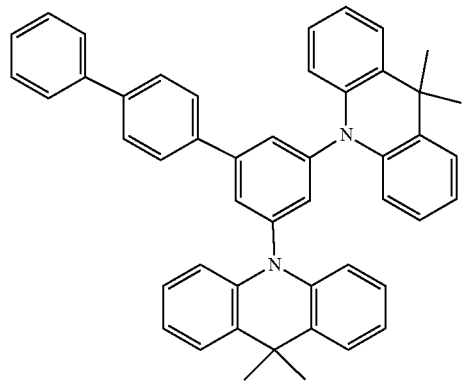
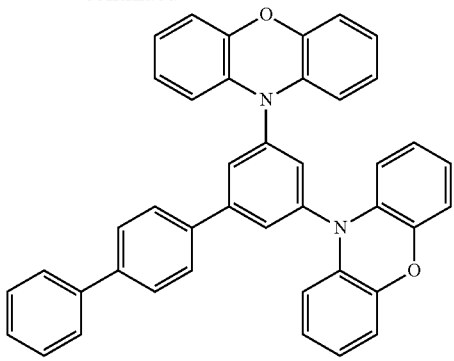
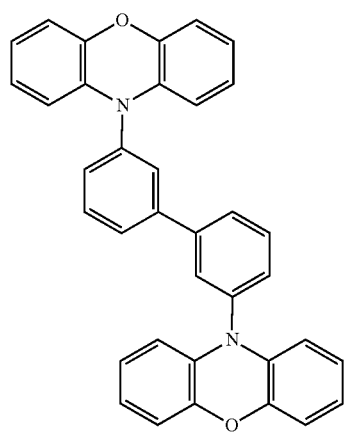
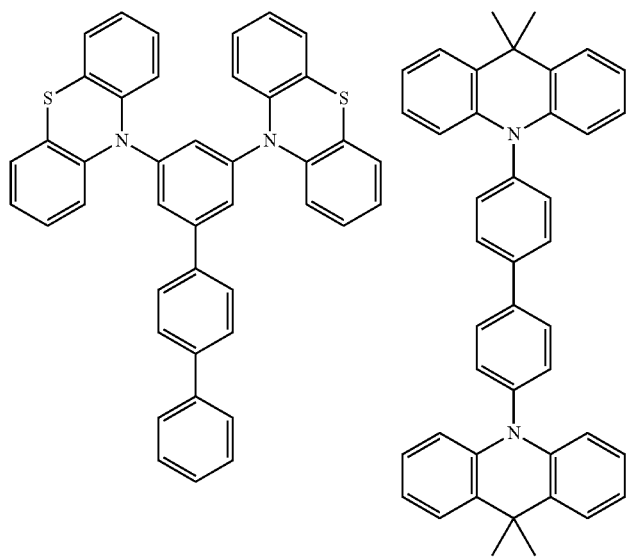
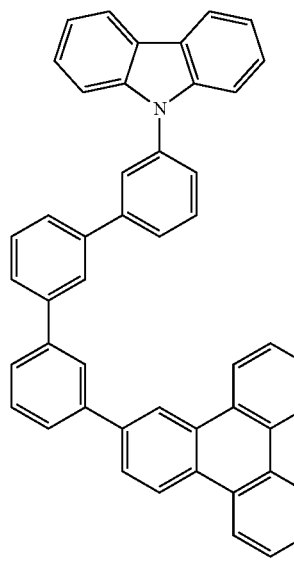
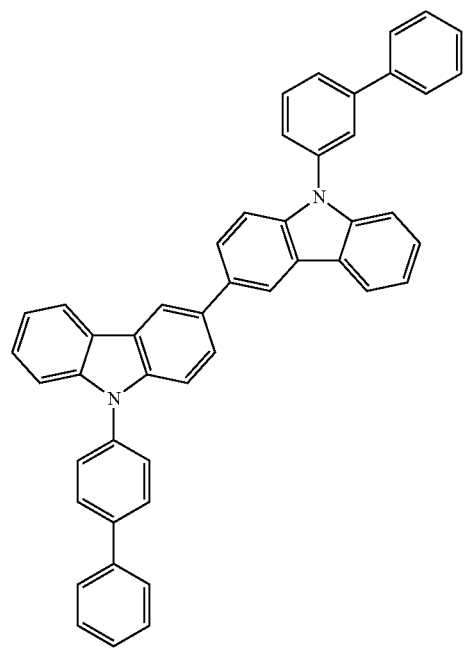

-continued
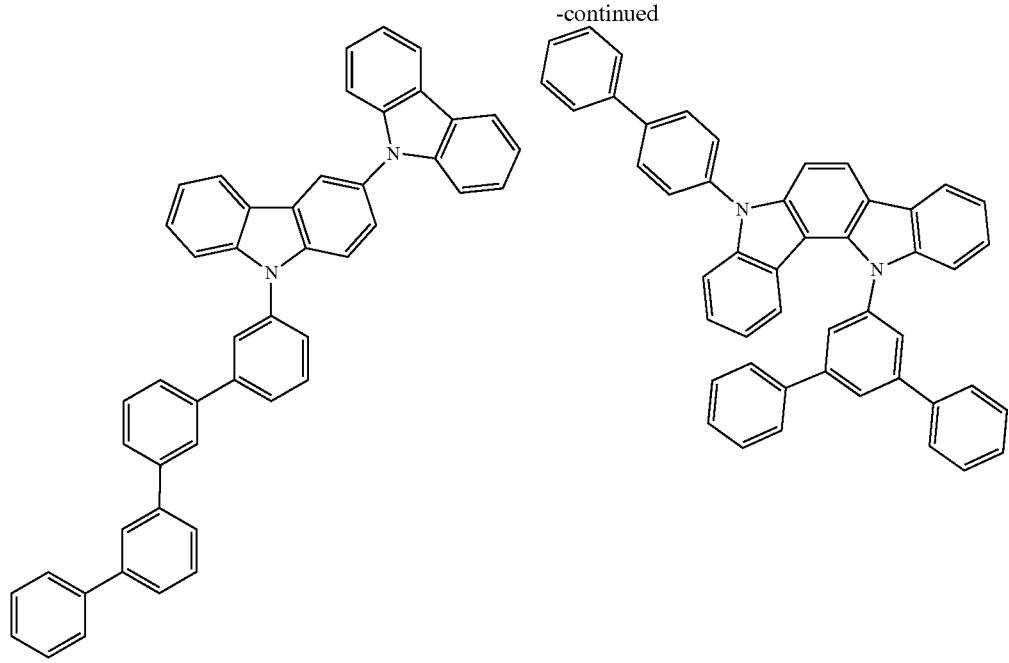
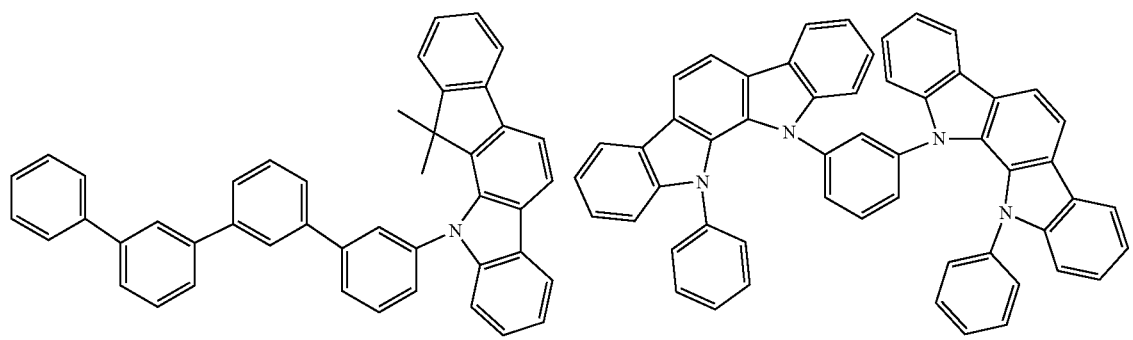
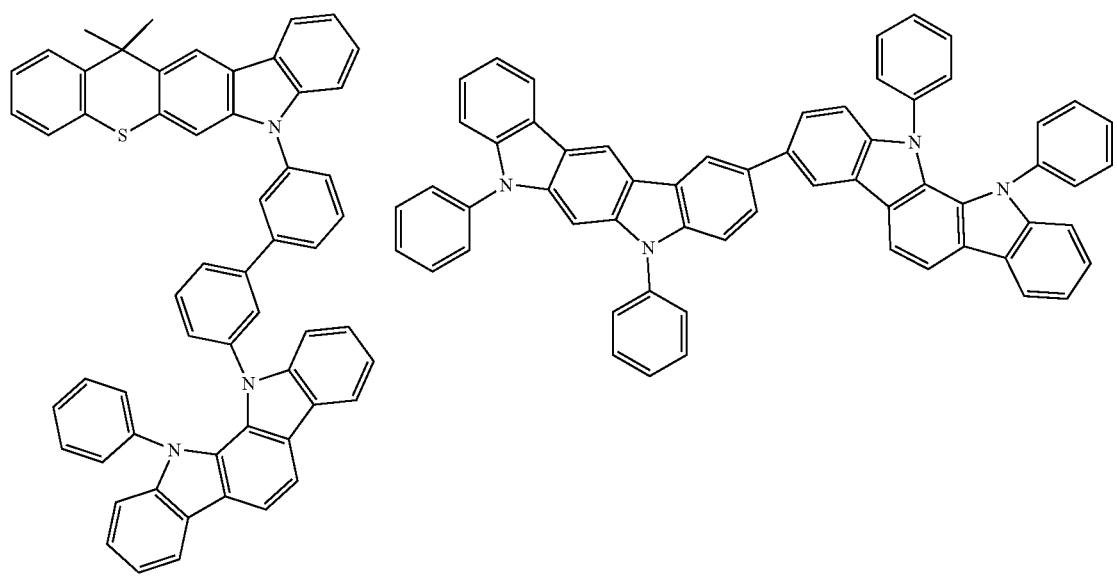

-continued
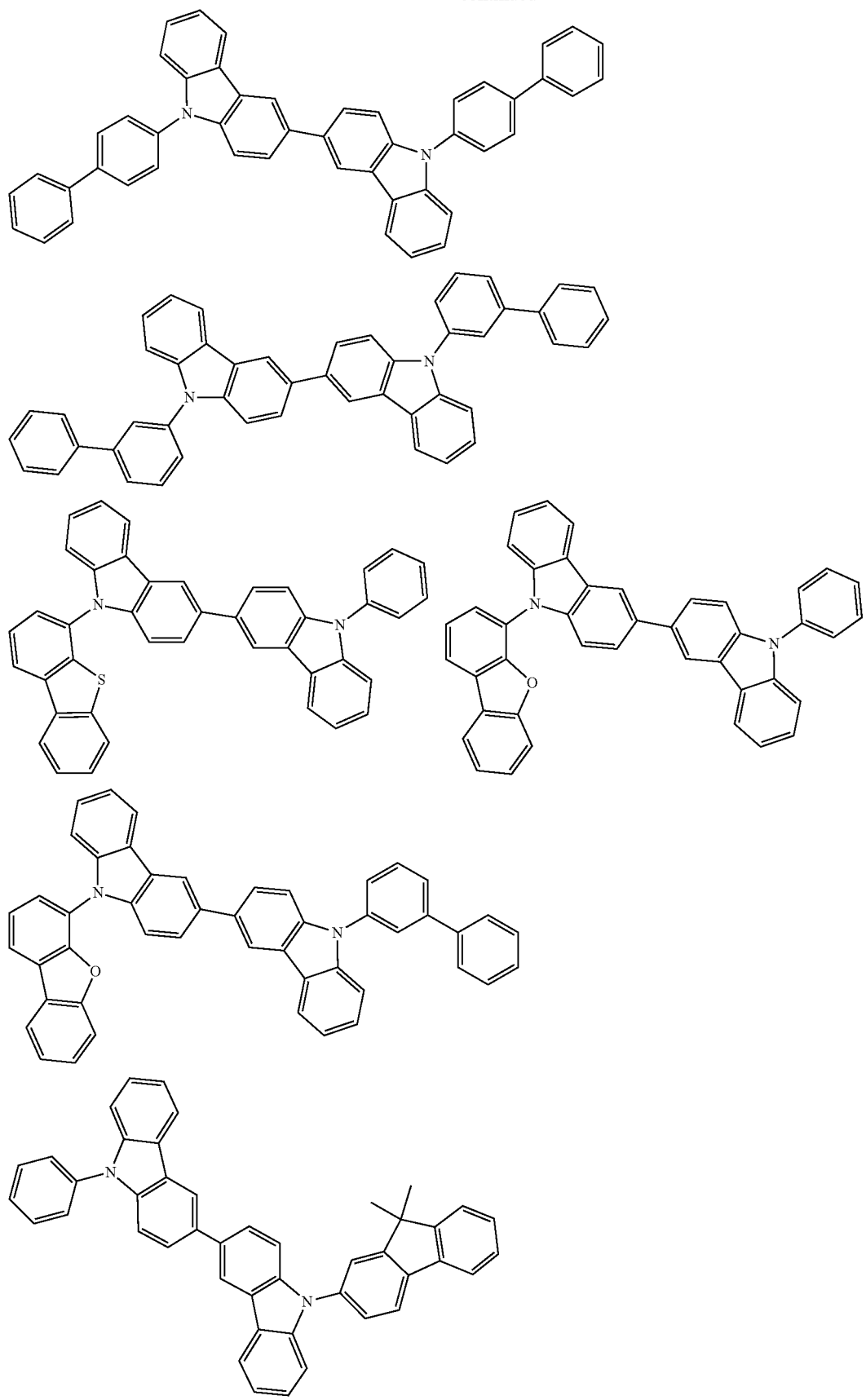

305
-continued
306
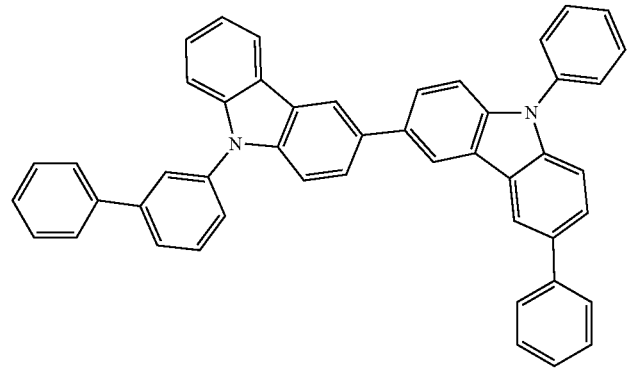
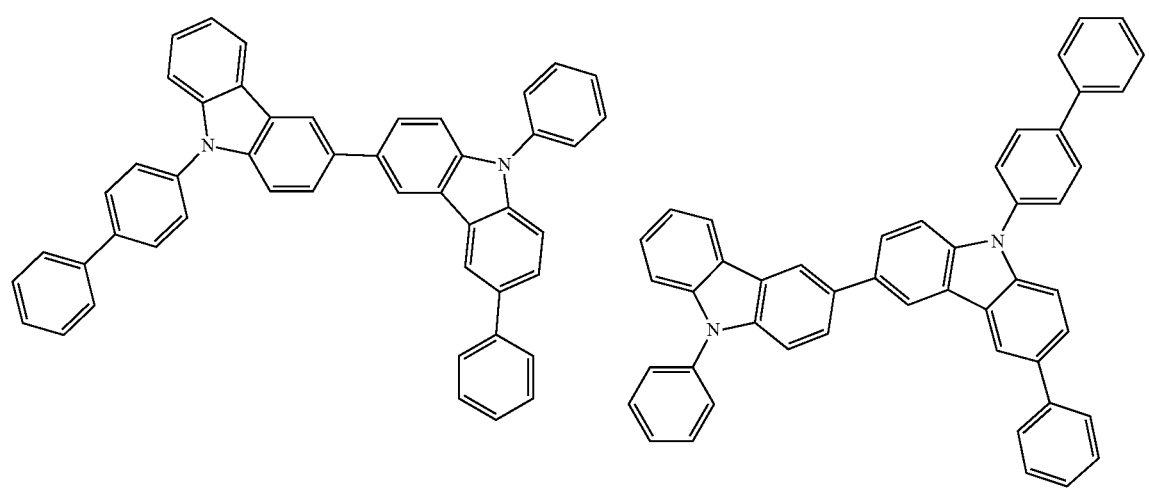
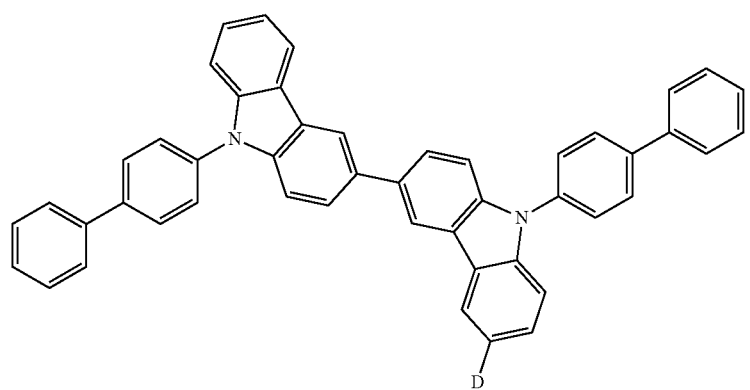
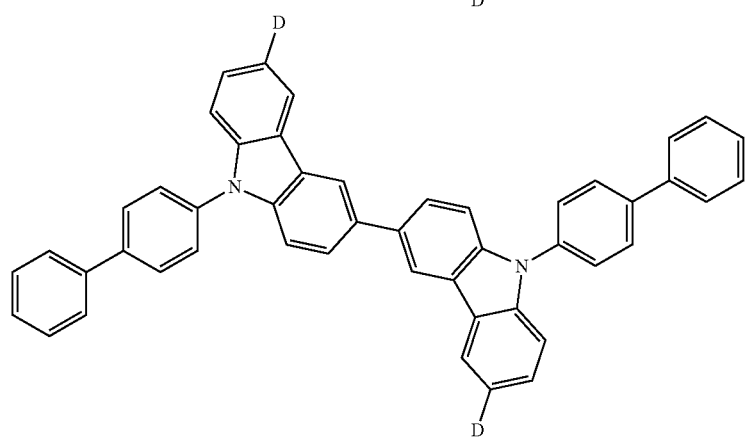

307
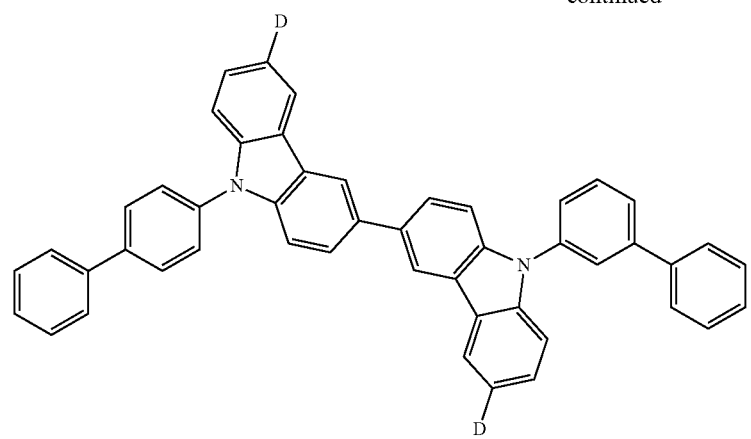
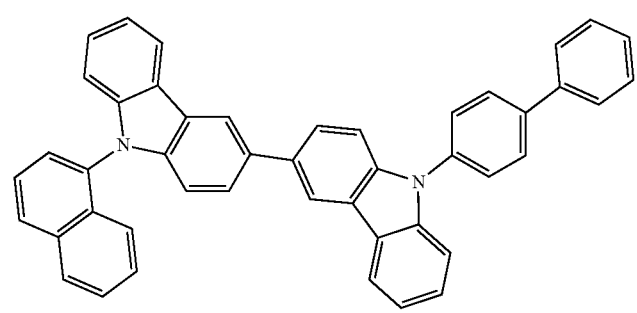
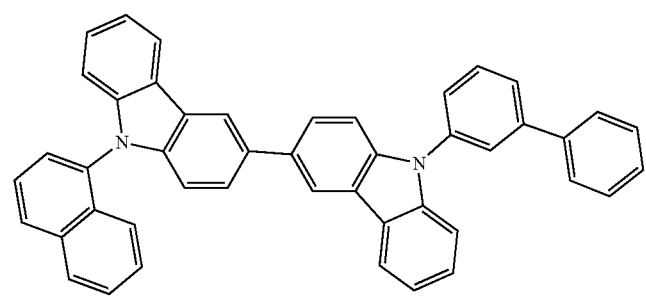
308
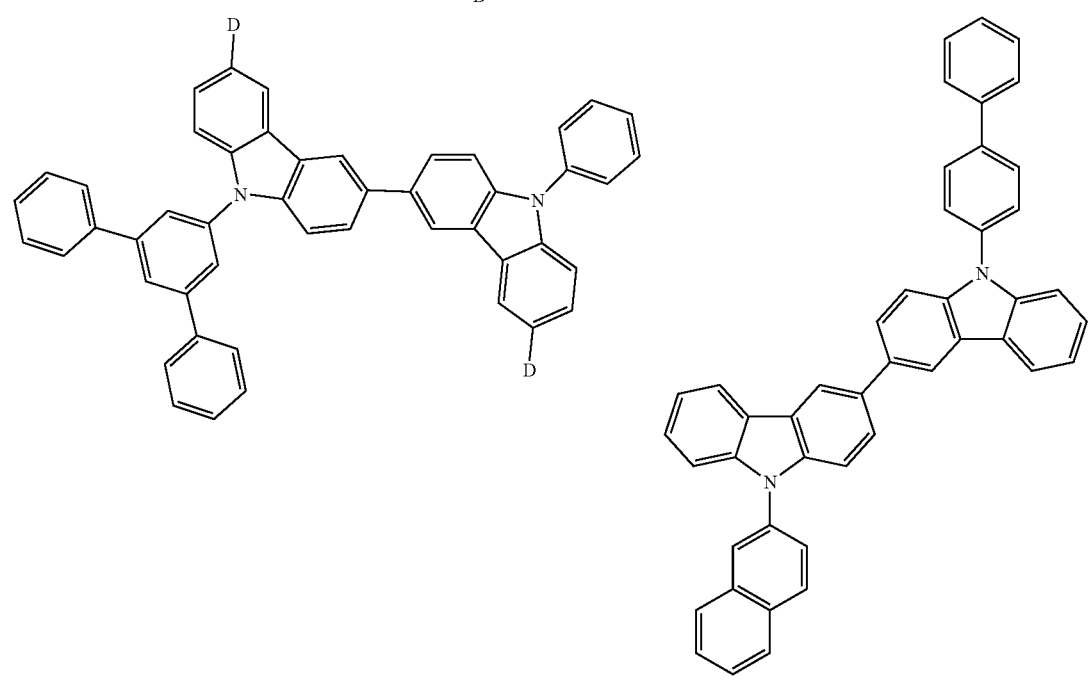

-continued
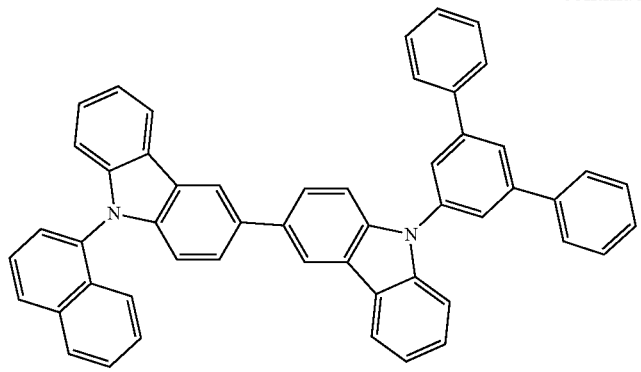
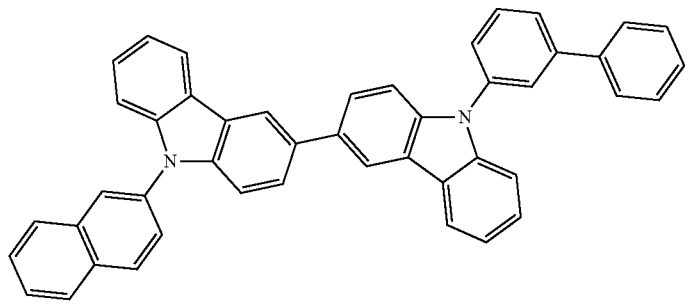
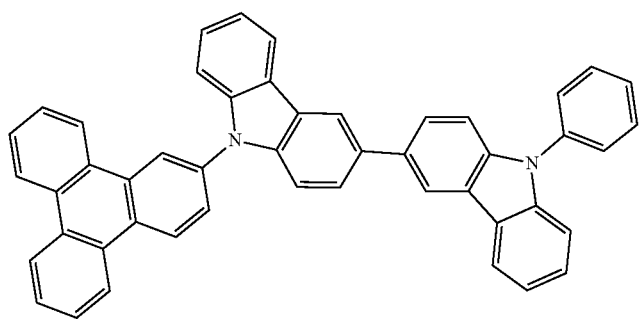
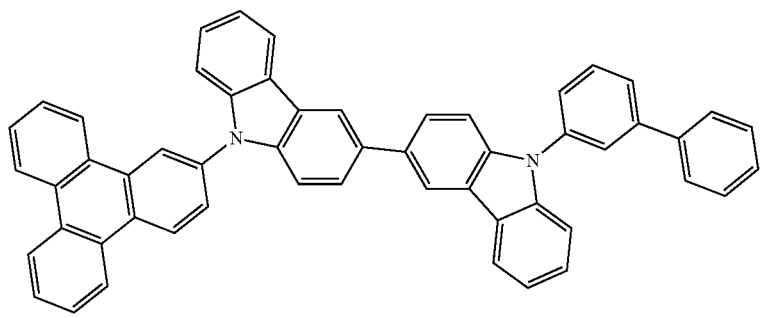
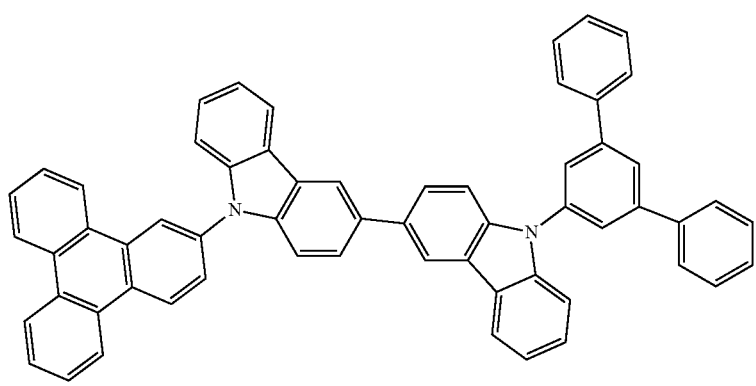

311
-continued
312
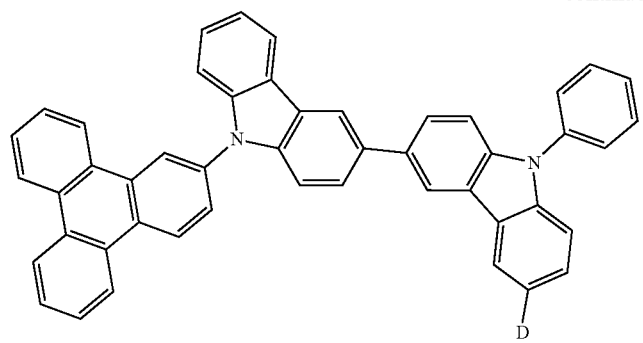
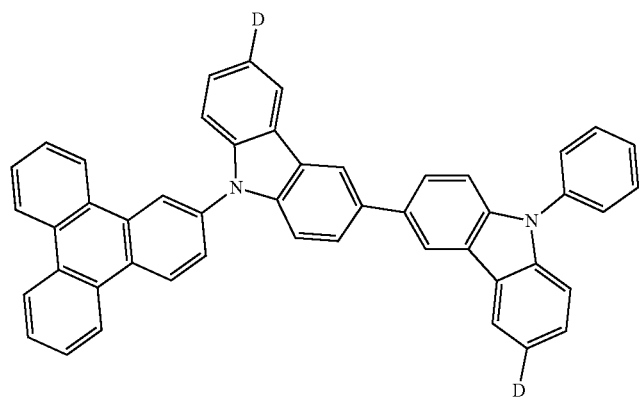
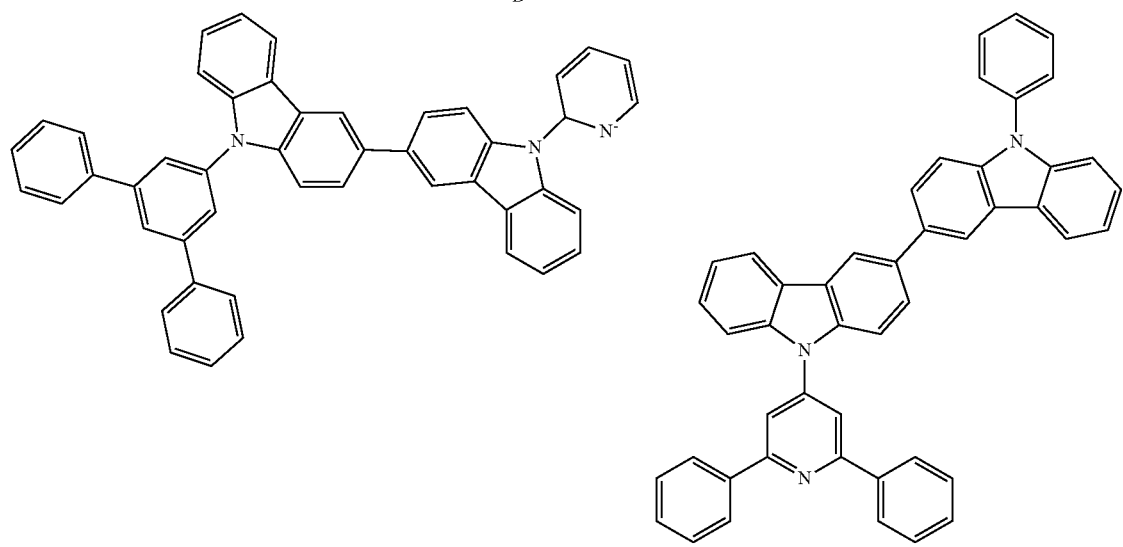
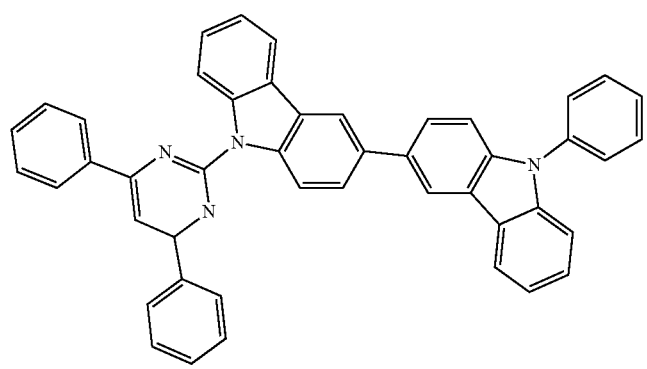

313
314
-continued
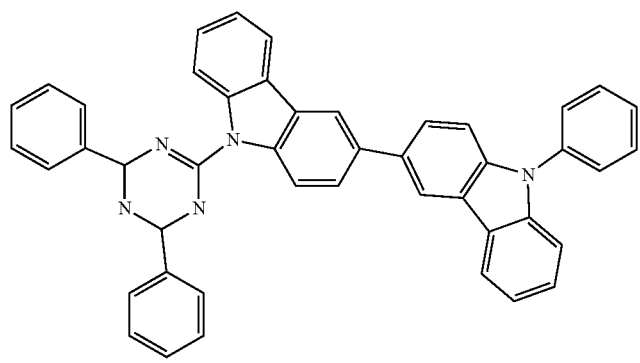
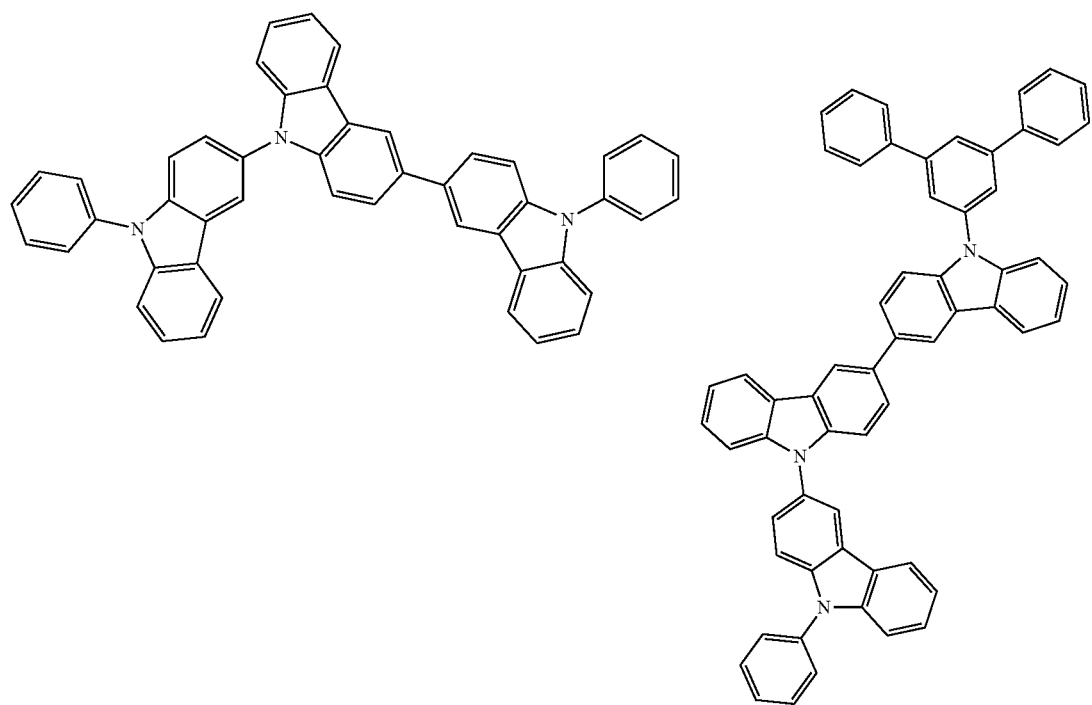
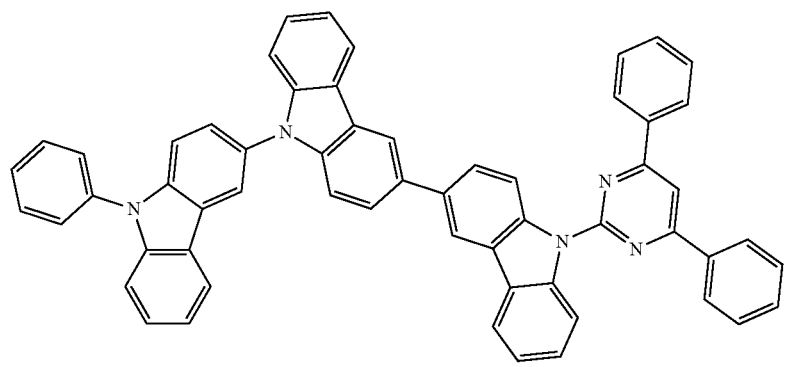

-continued
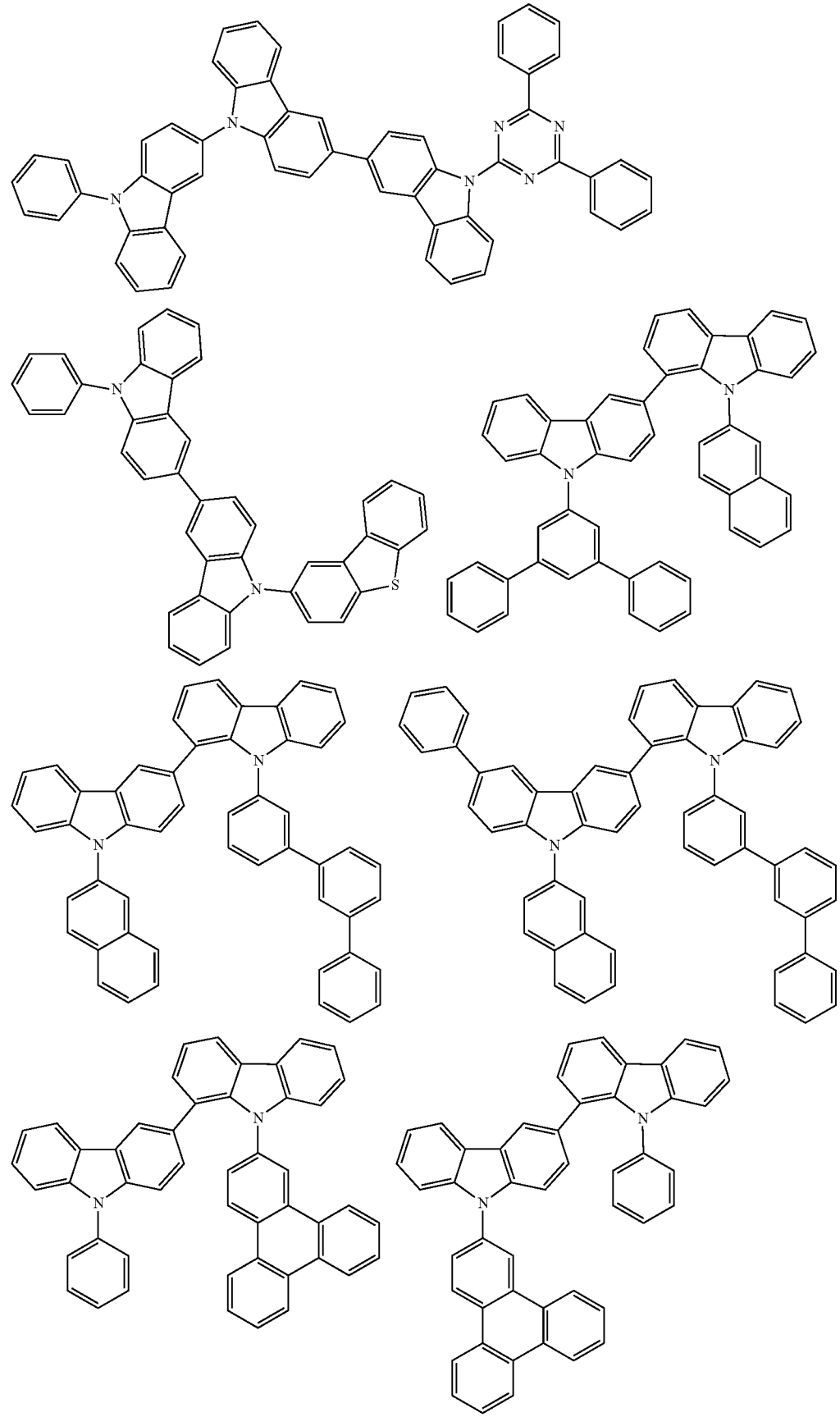

317
-continued
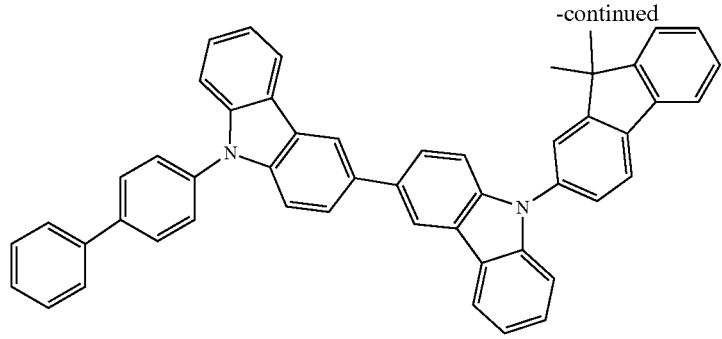
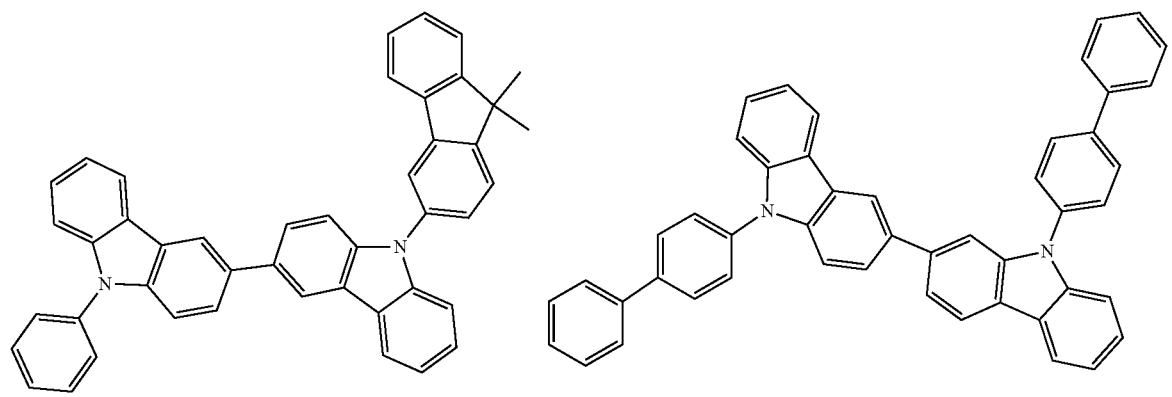
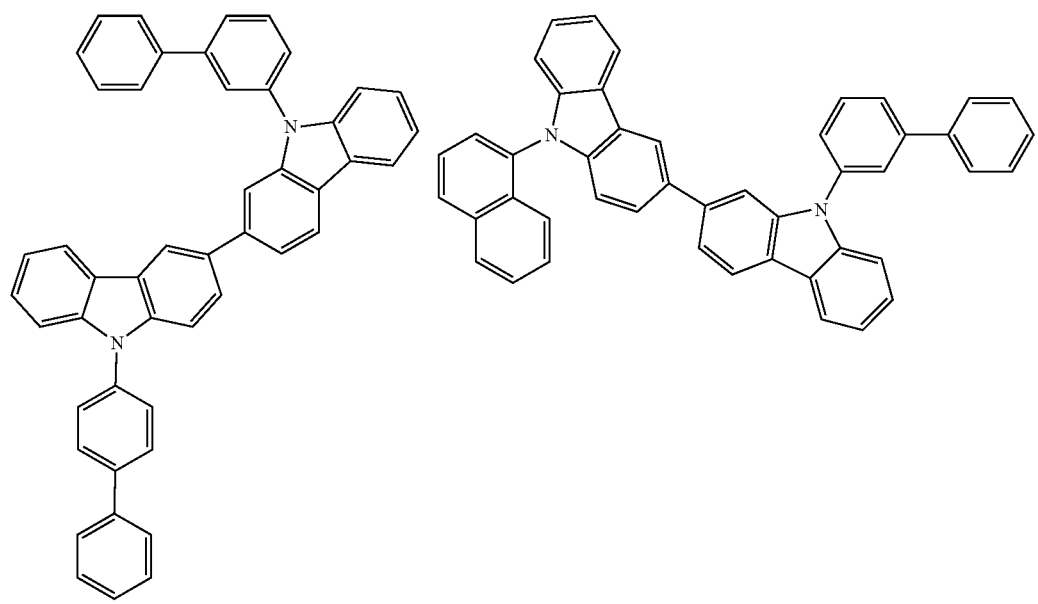
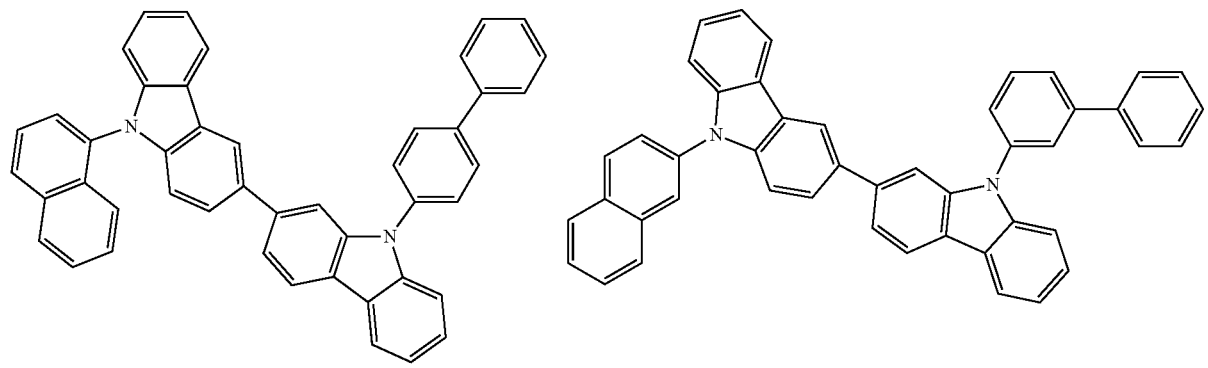
318

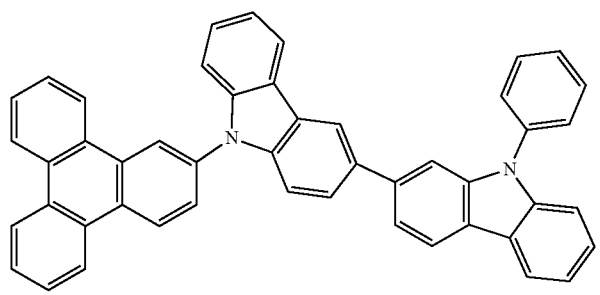
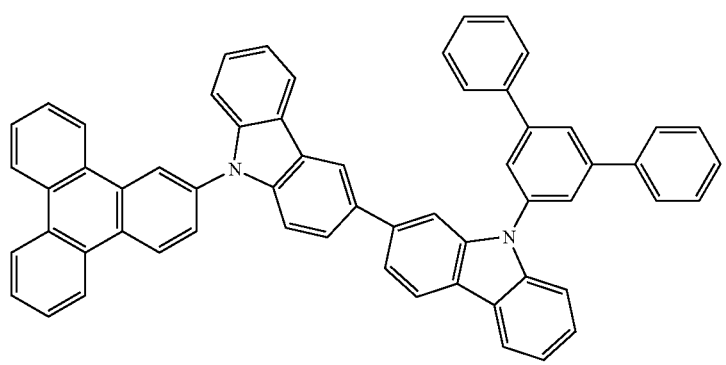
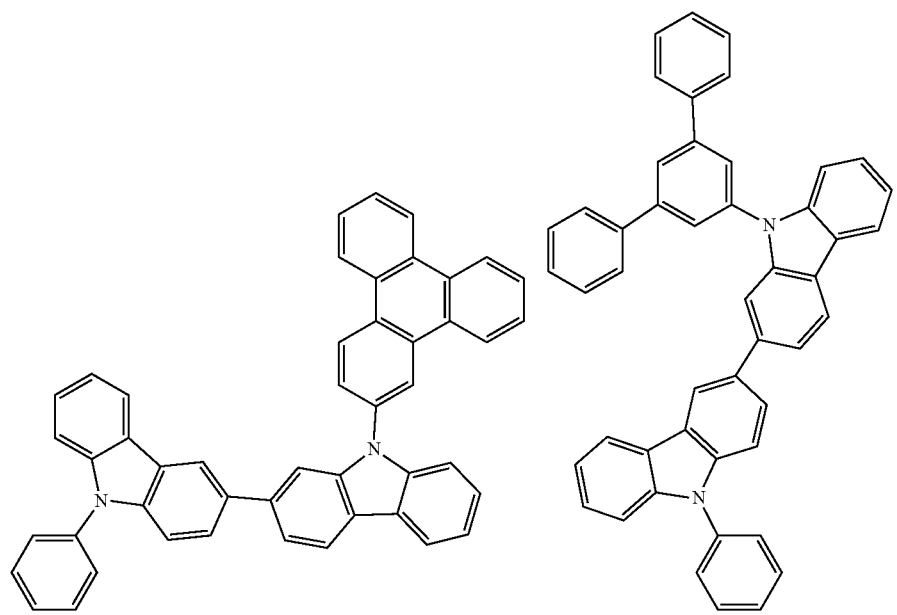
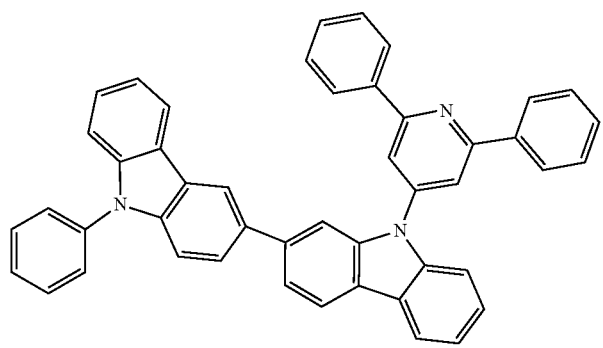

-continued
321
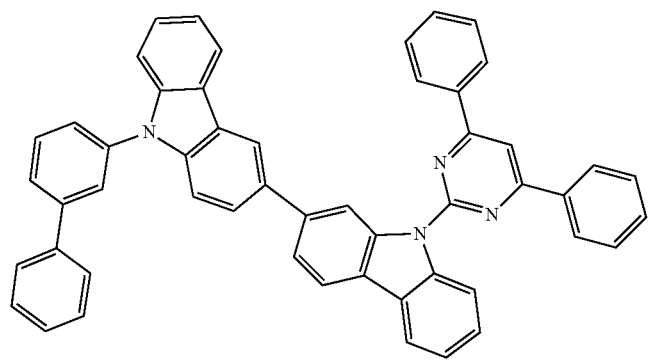
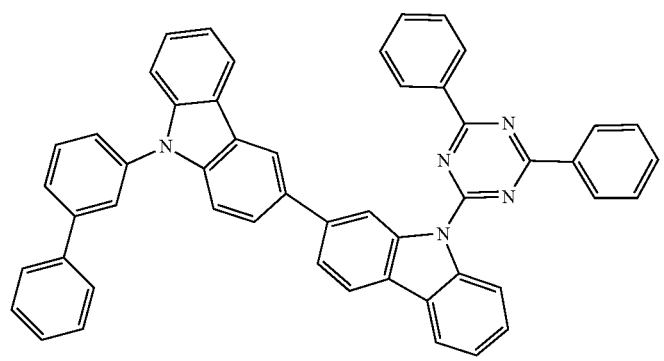
322
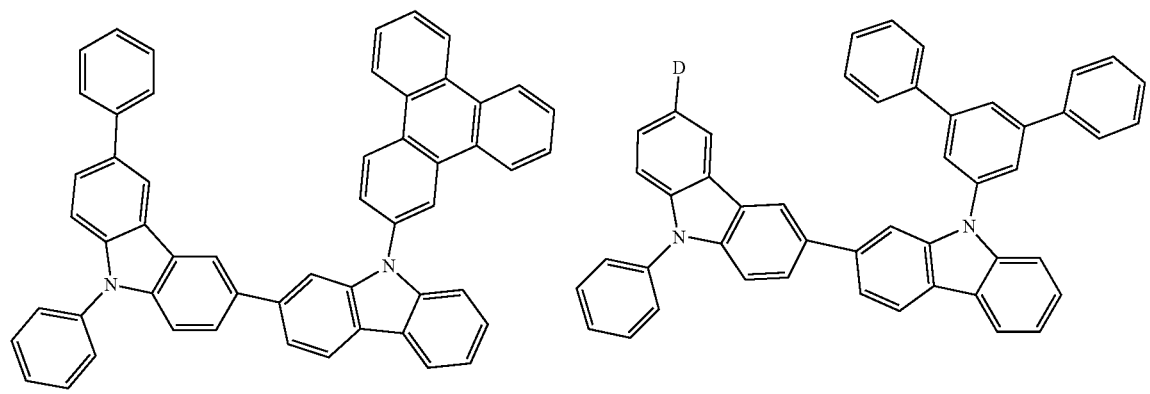

-continued
323
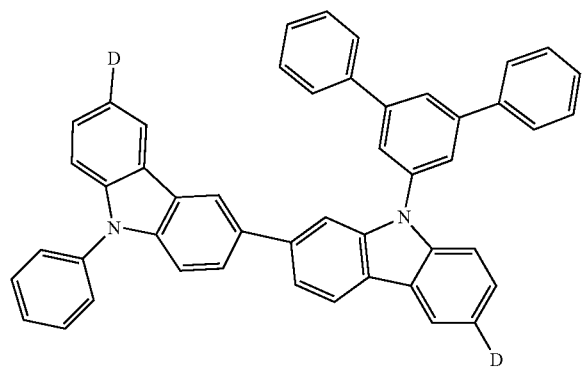
324
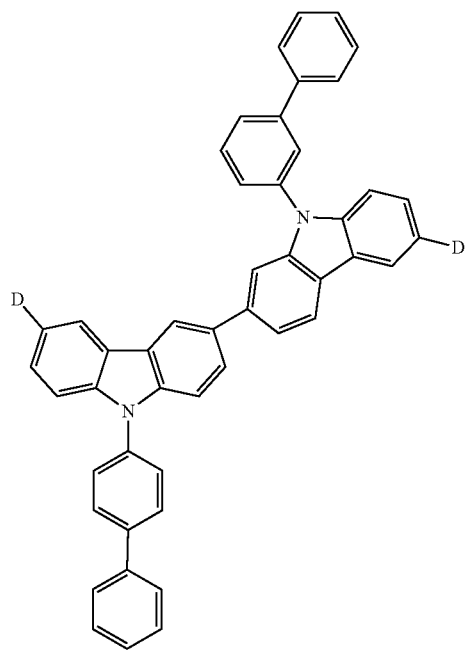
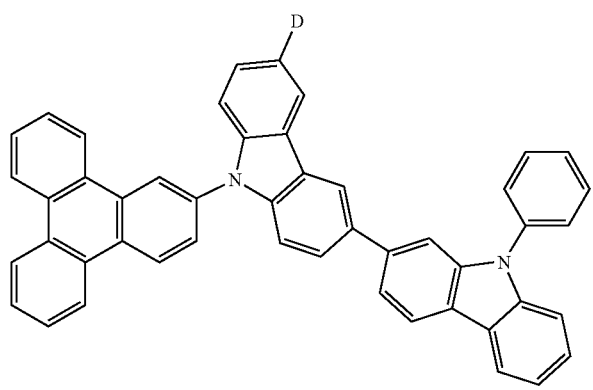
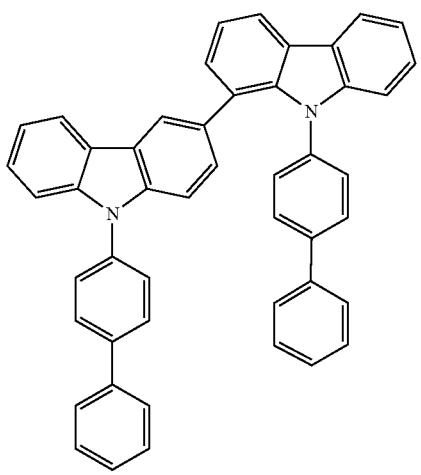
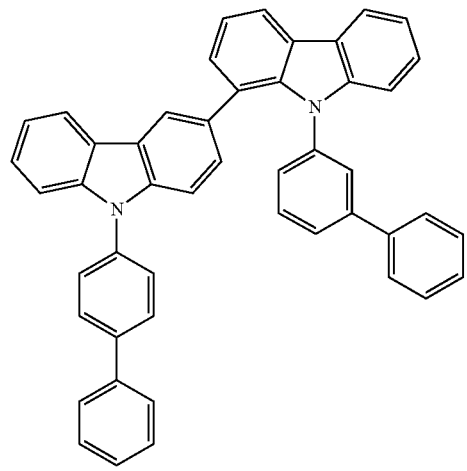
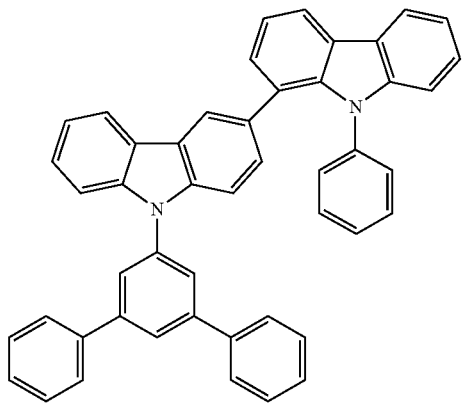

-continued
325
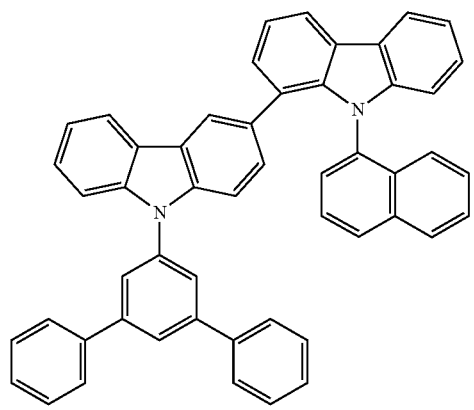
326
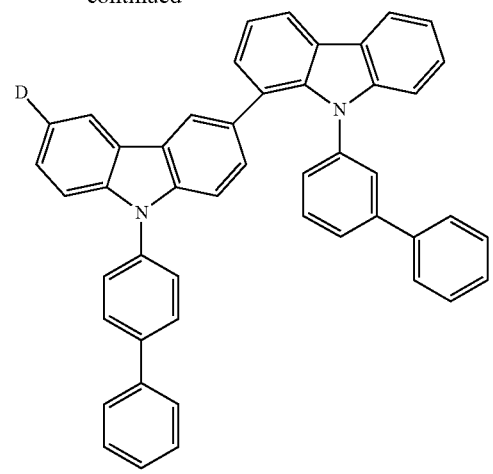
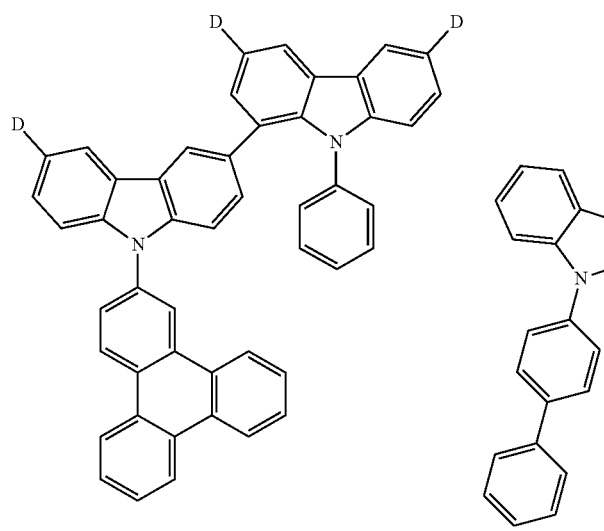
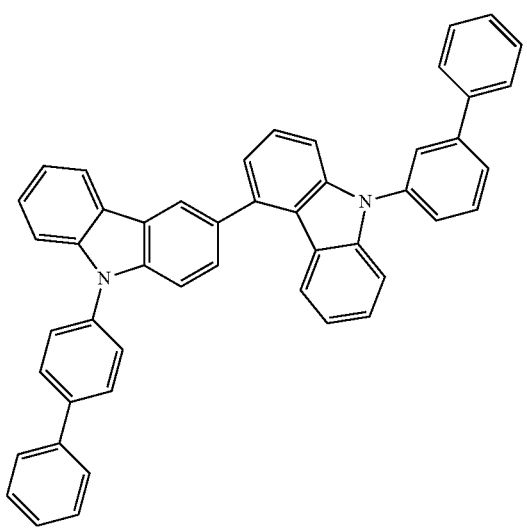
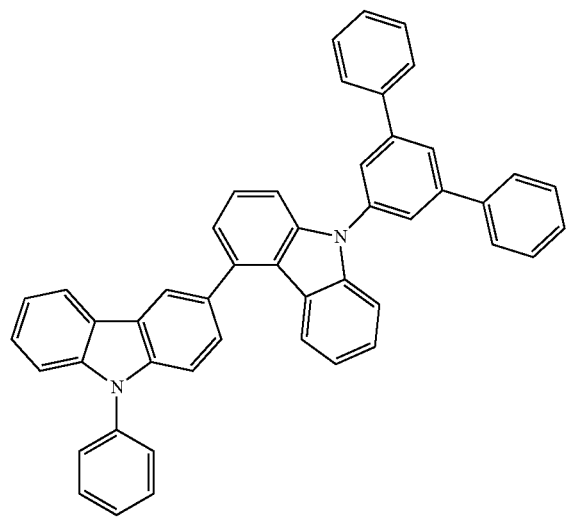
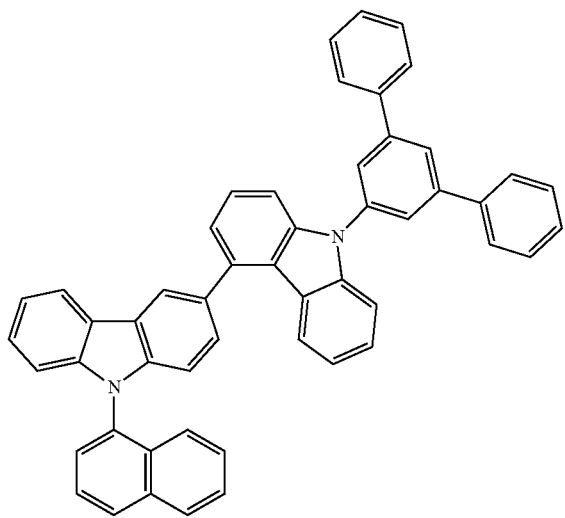

-continued
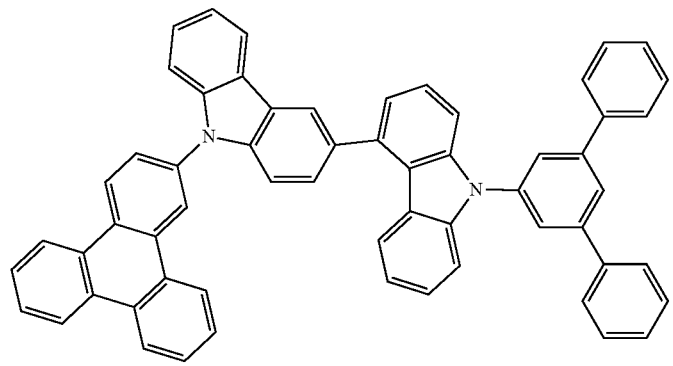
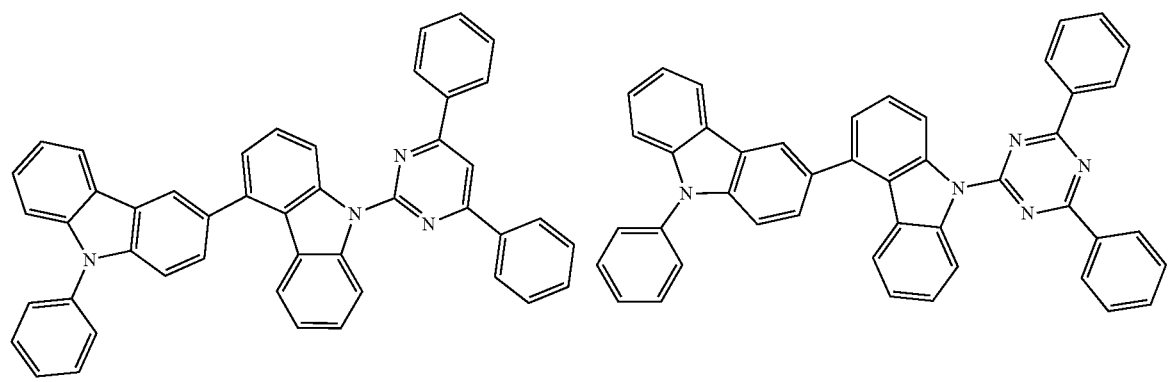
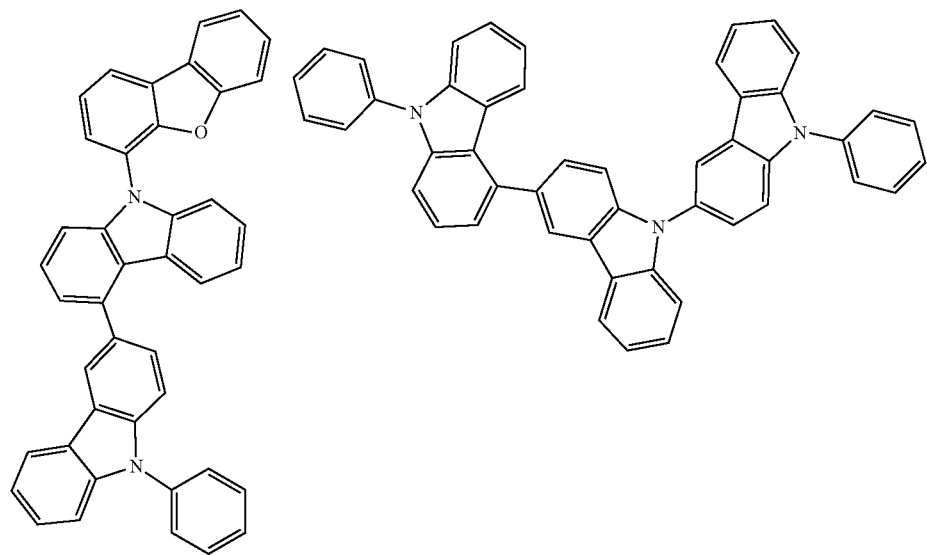

329 330
-continued
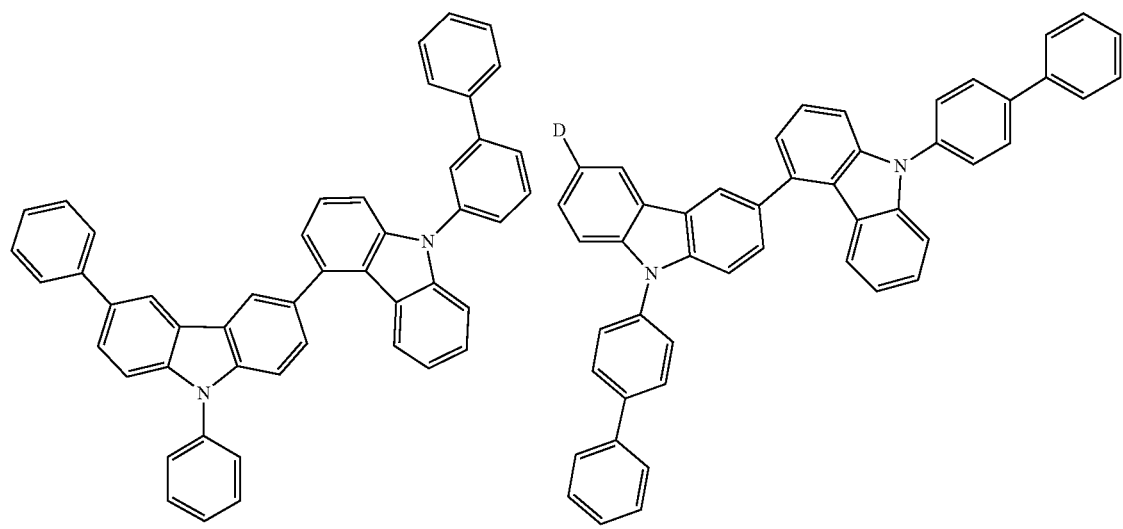
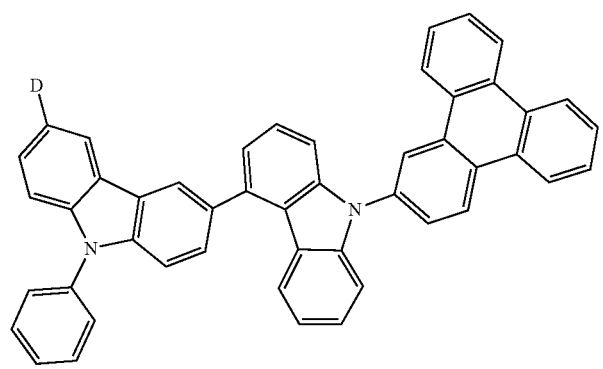
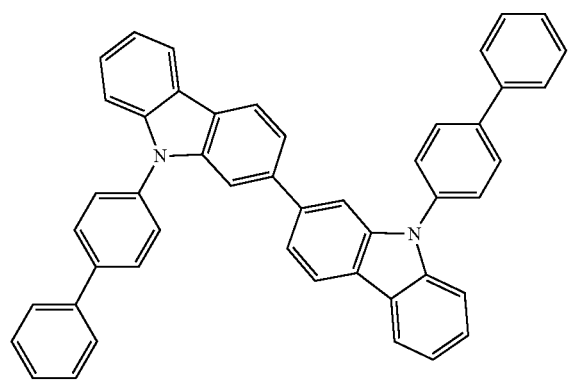

-continued
331
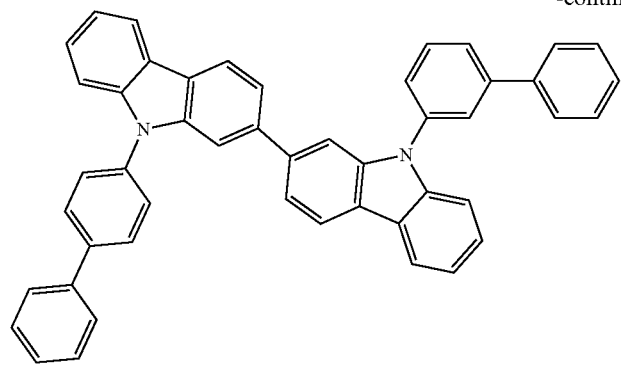
332
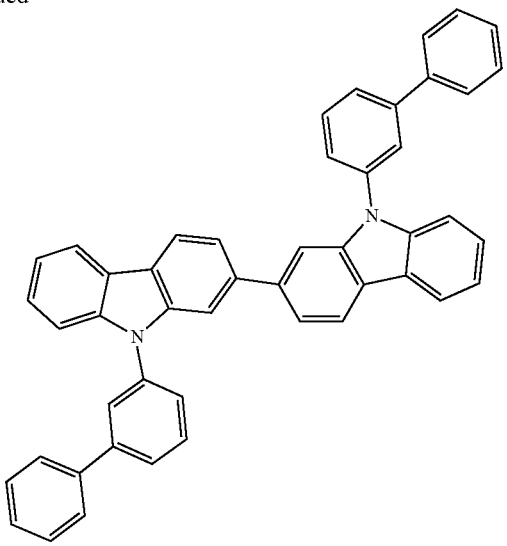
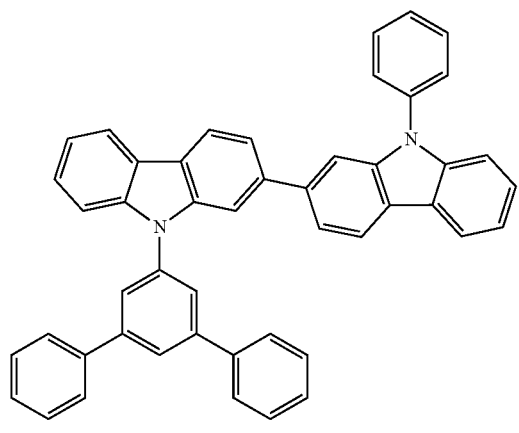
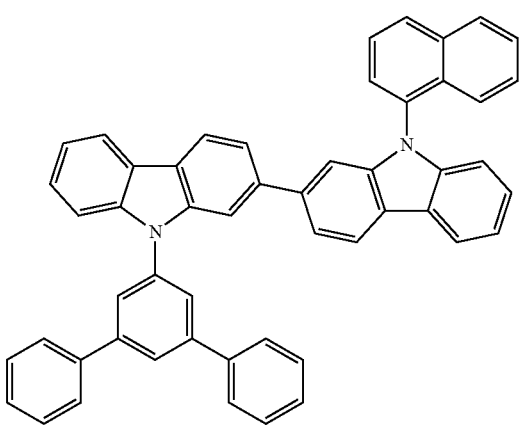
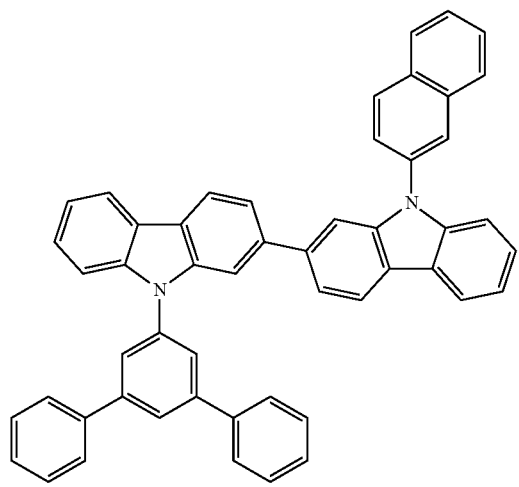

-continued
333
334
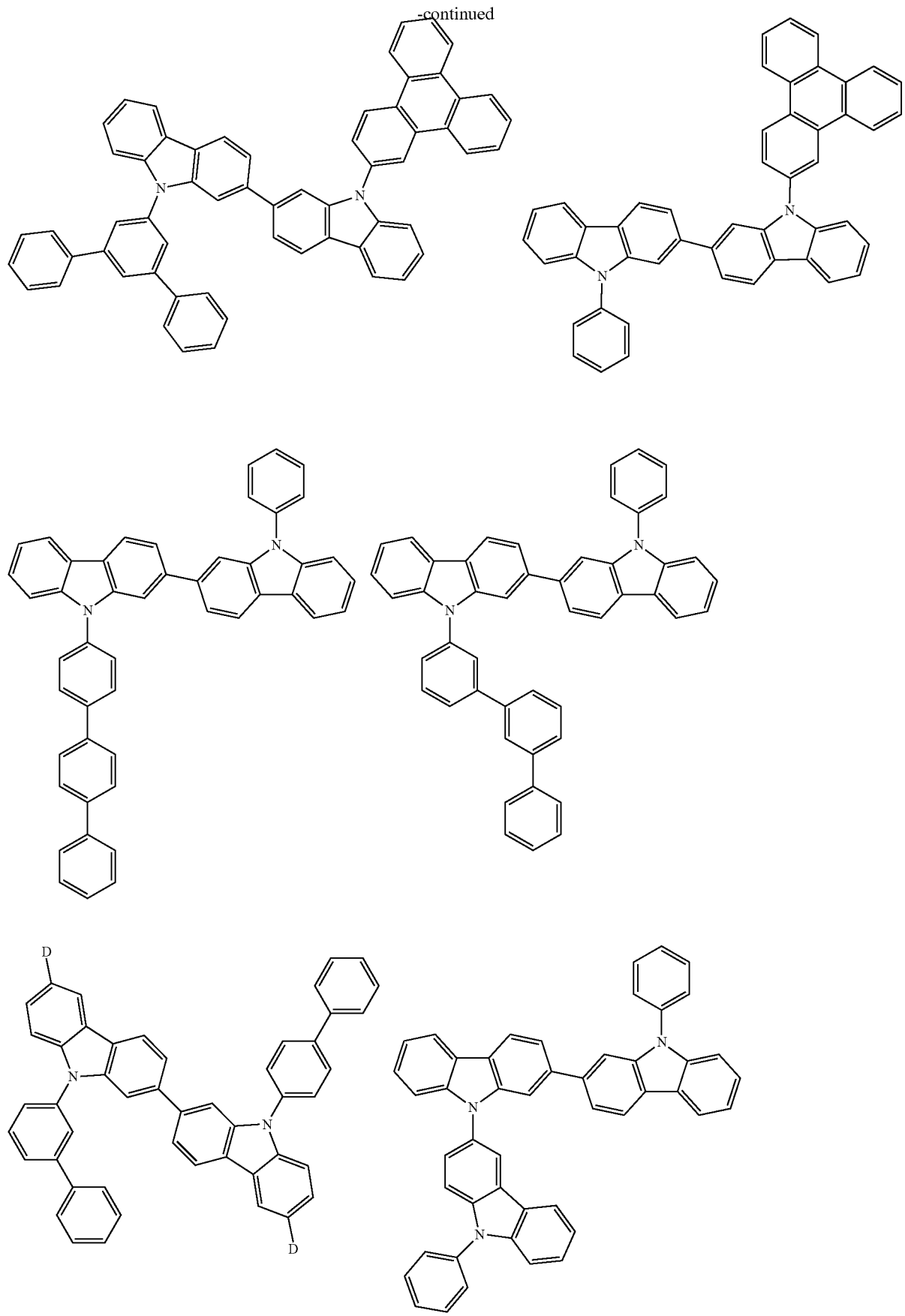

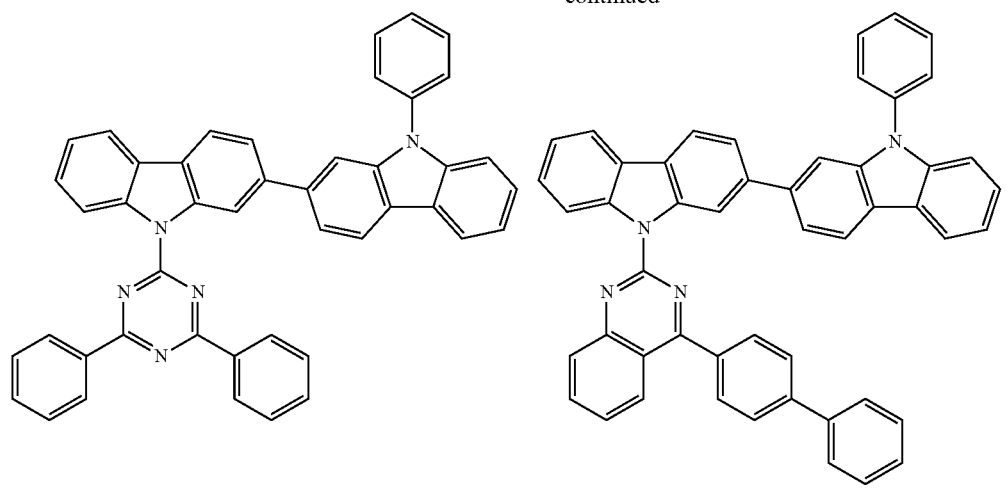
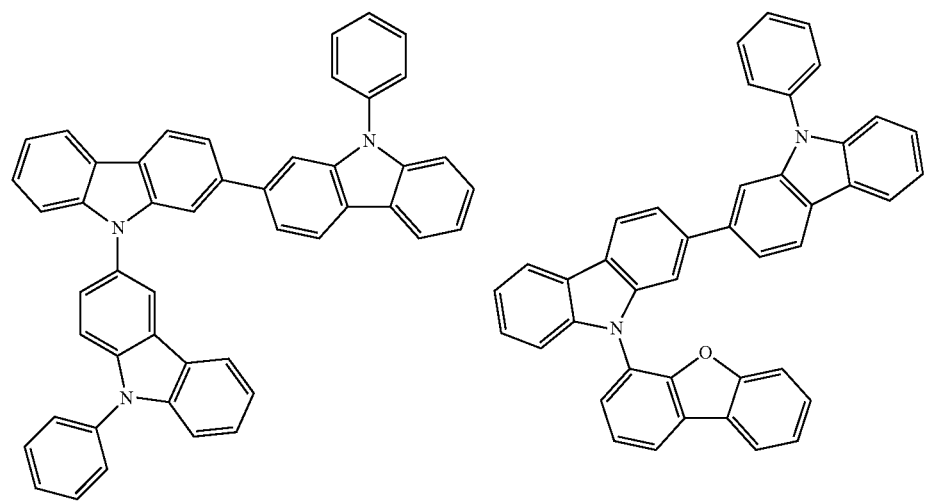
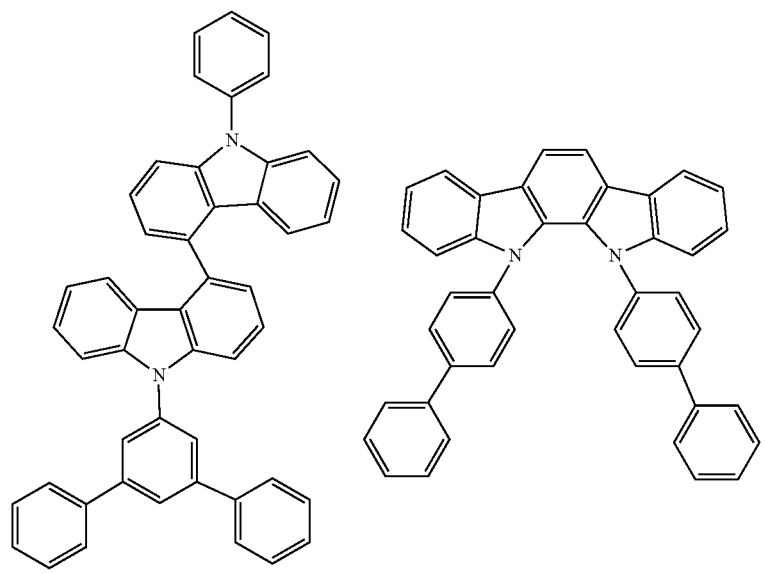

-continued
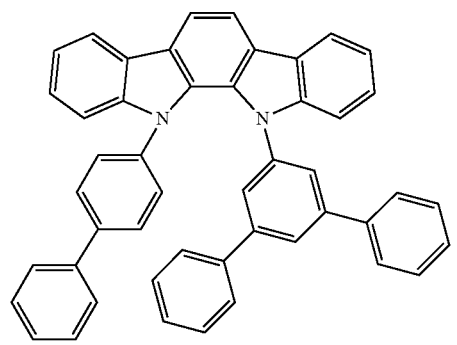
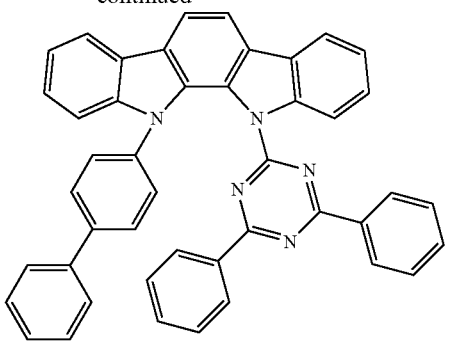
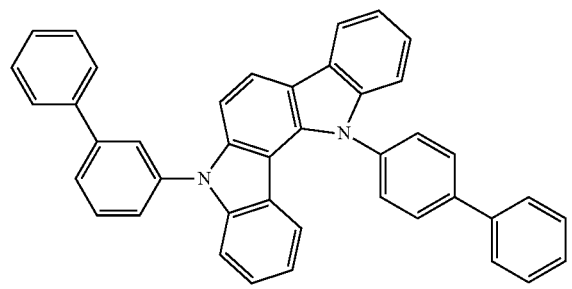
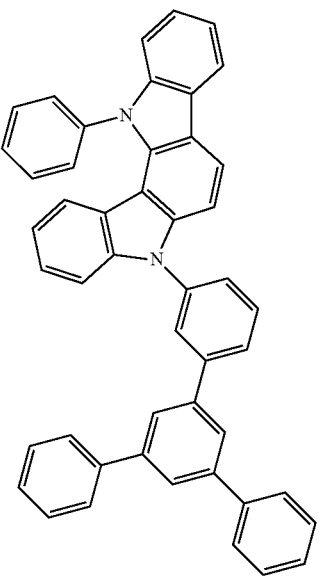
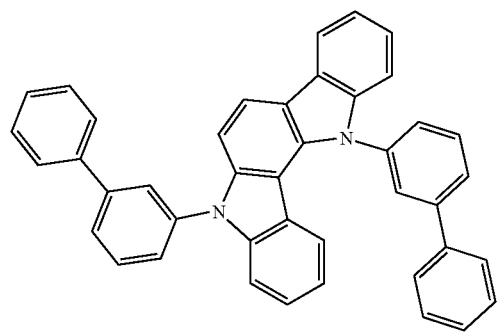
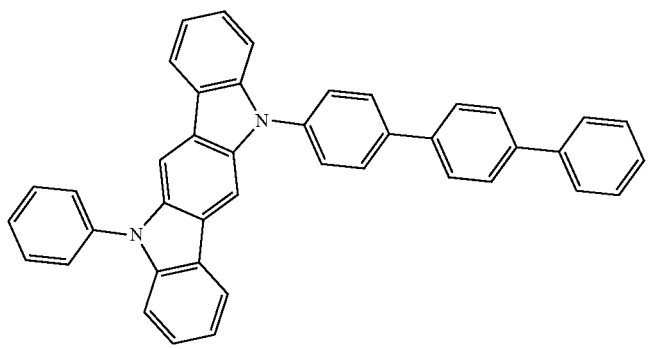
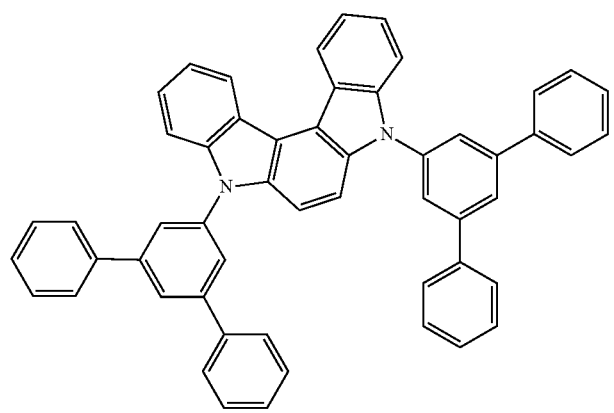
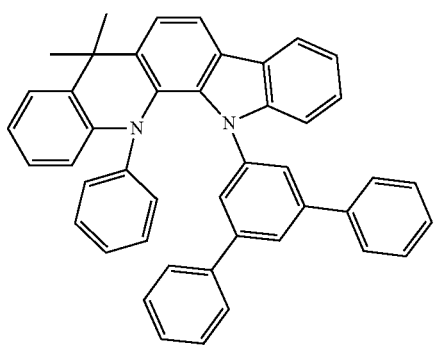

-continued
339
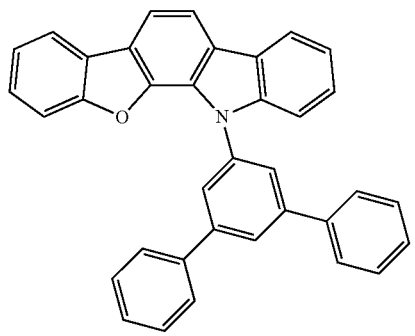
340
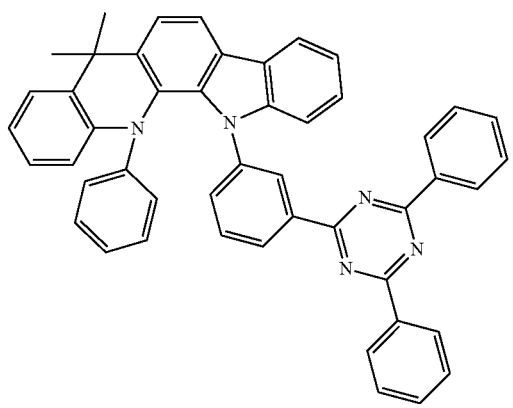
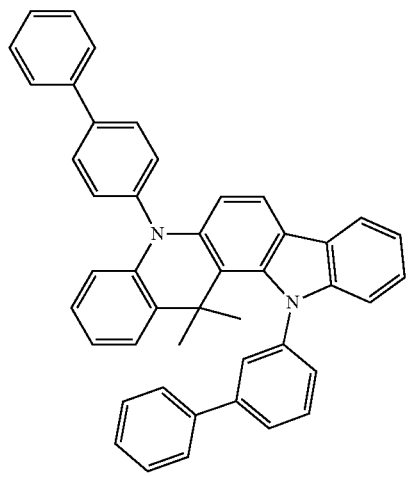
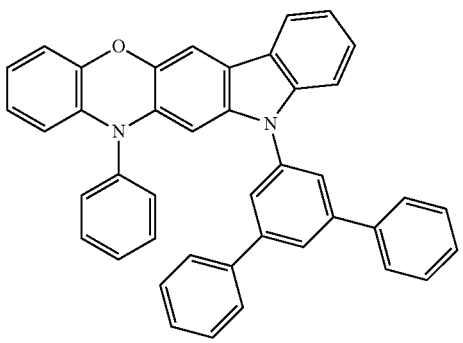
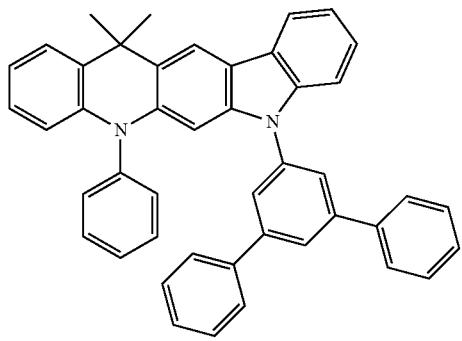
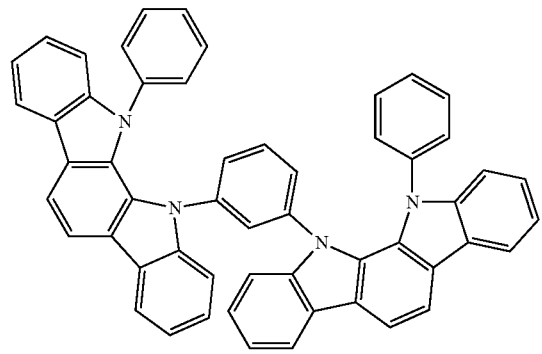

-continued
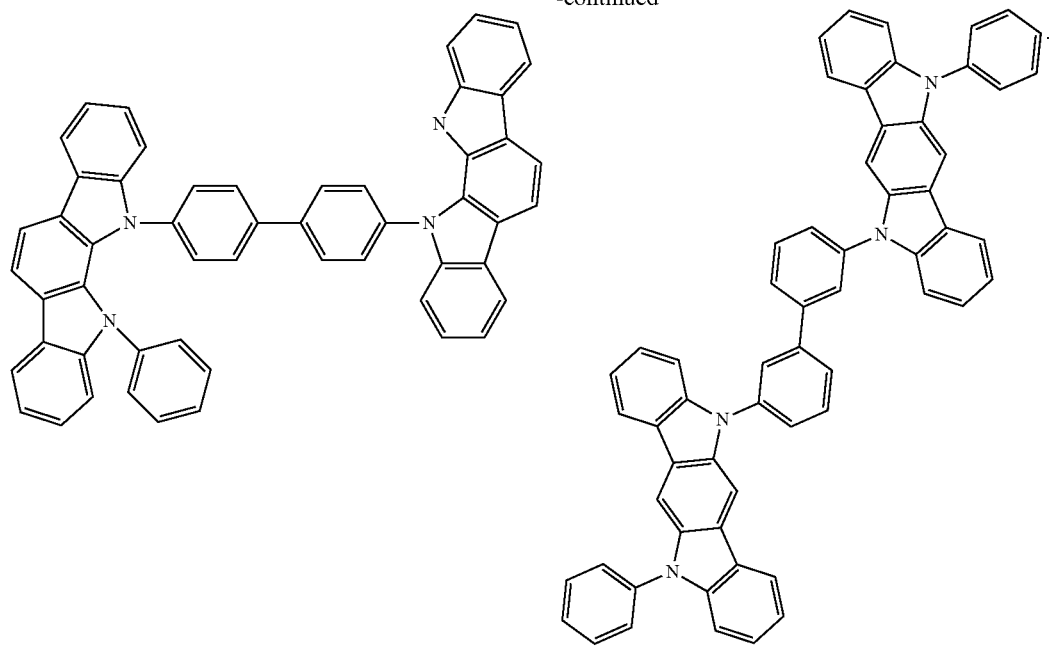
20. The composition according to claim 1, wherein H1 is selected from the following compounds:
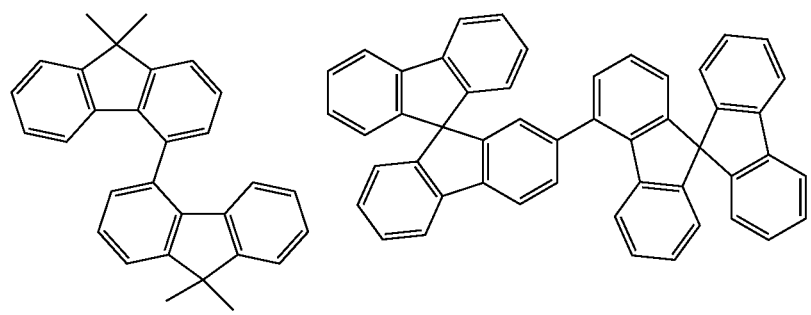
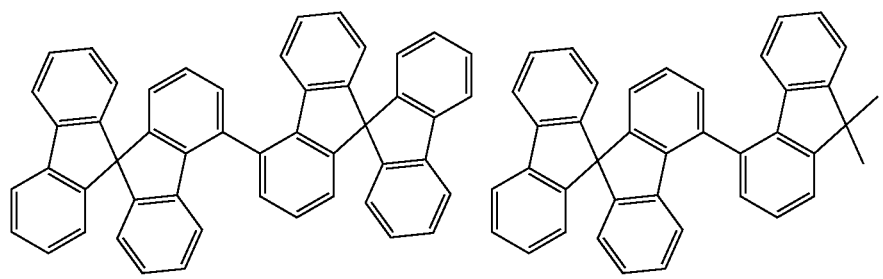

343 344
-continued
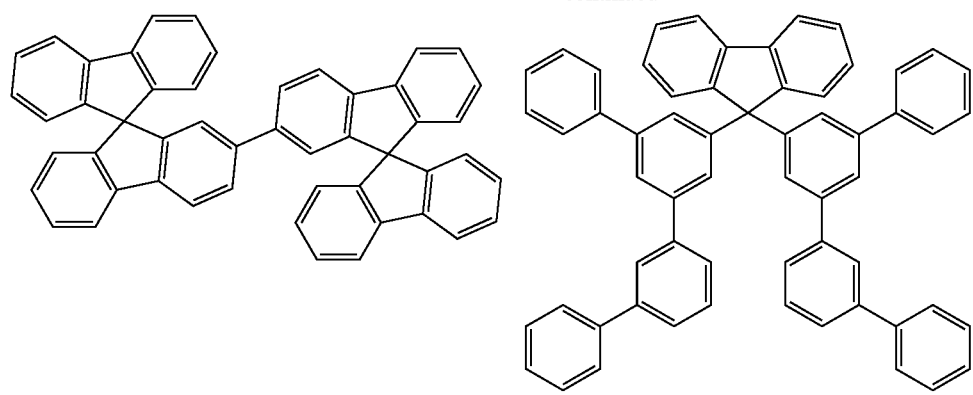
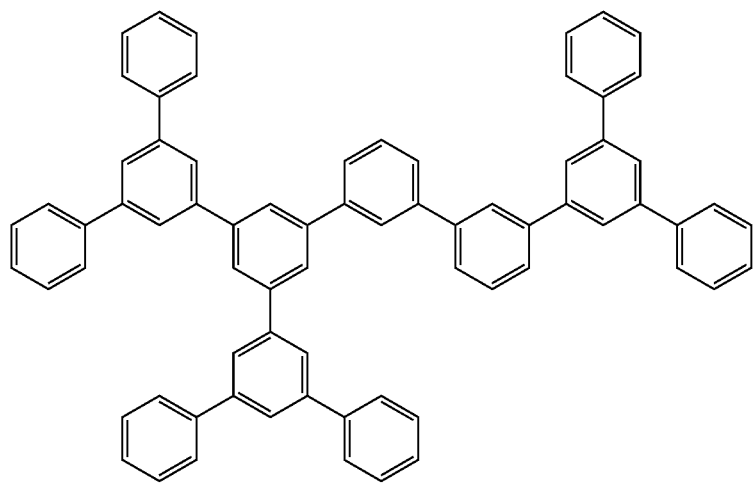
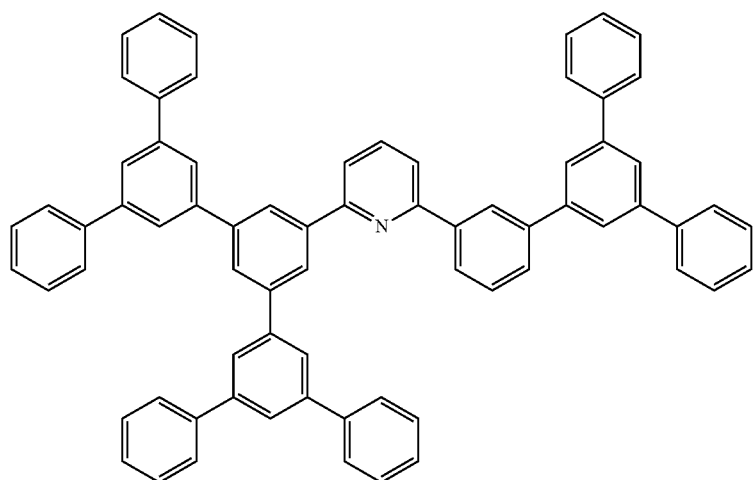

-continued
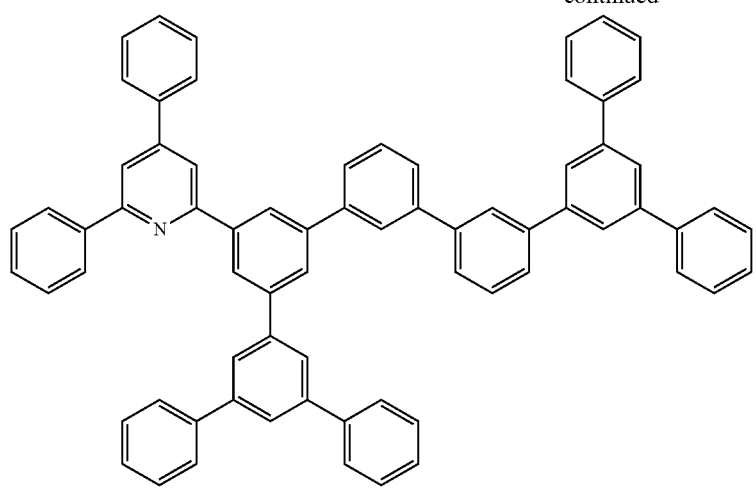
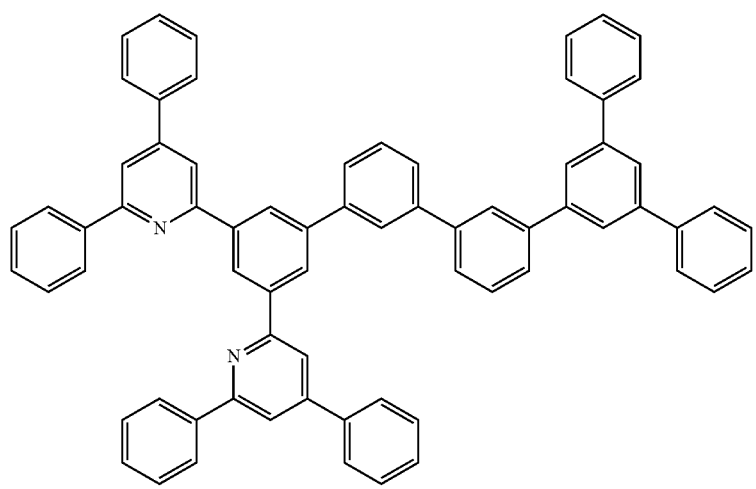
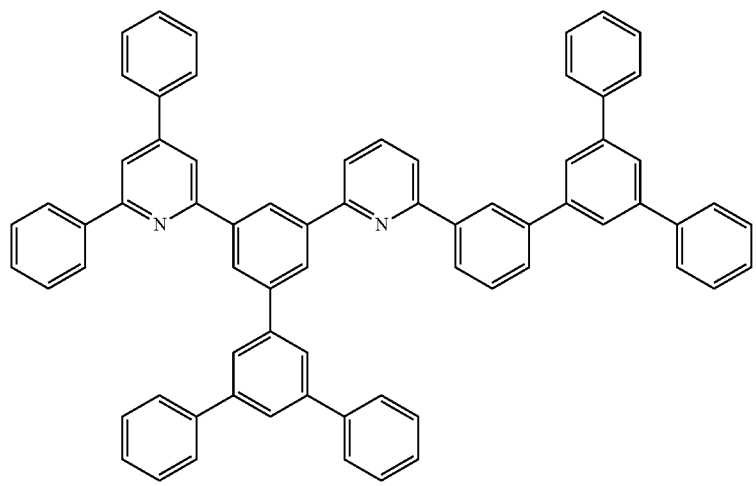

-continued
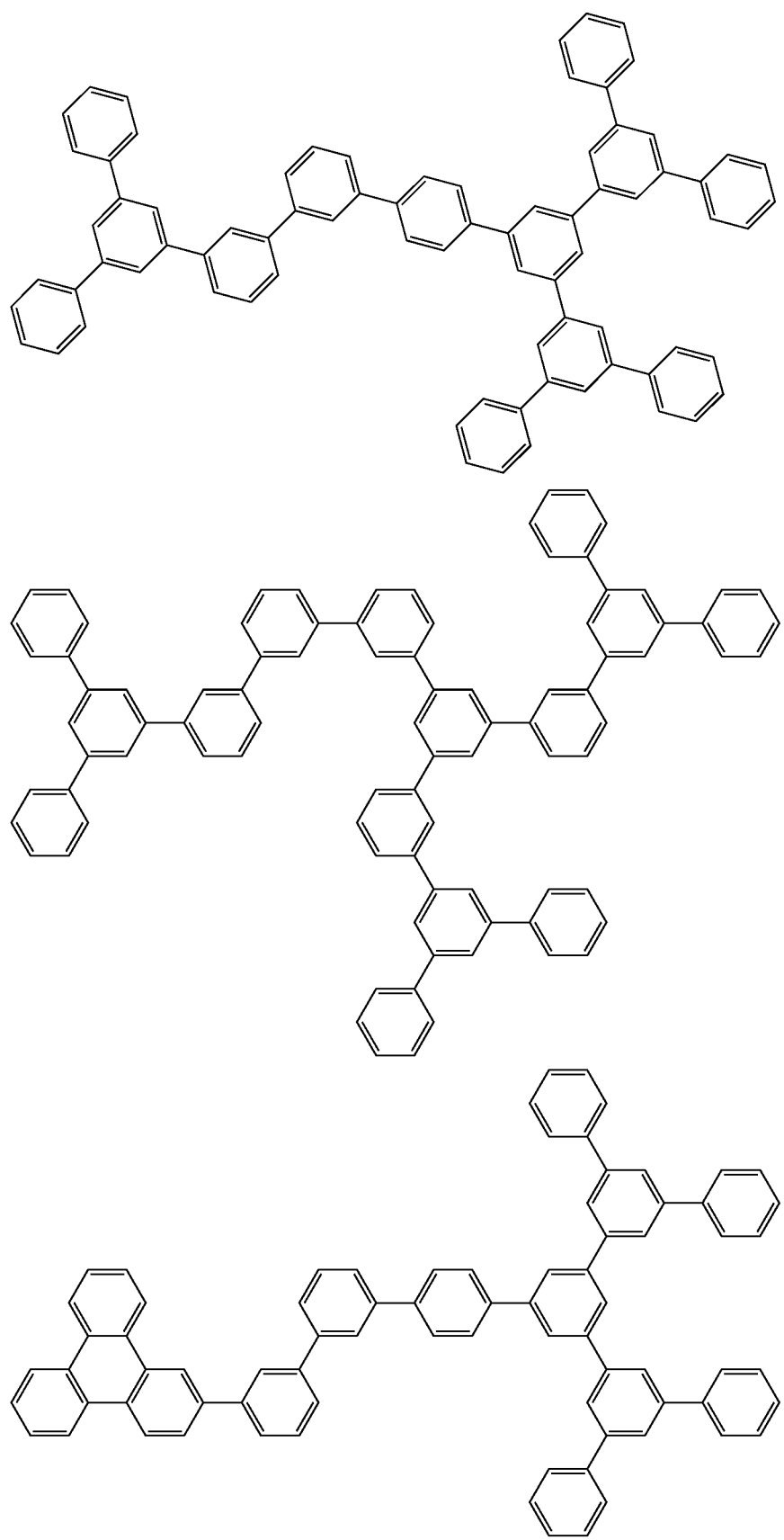

-continued
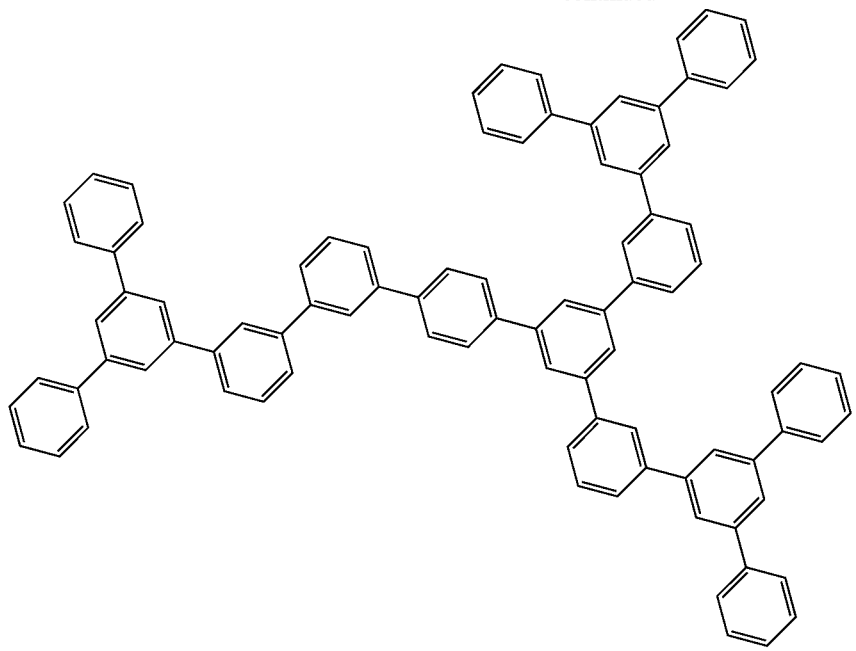
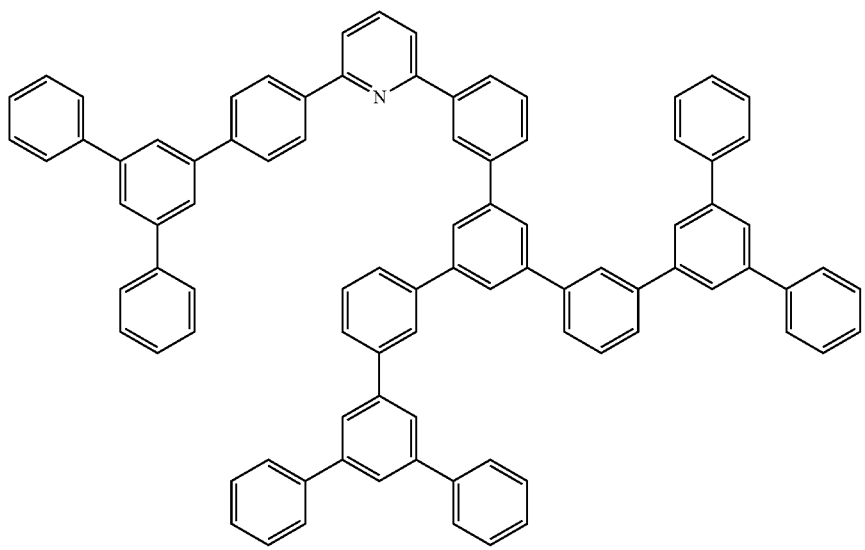

-continued
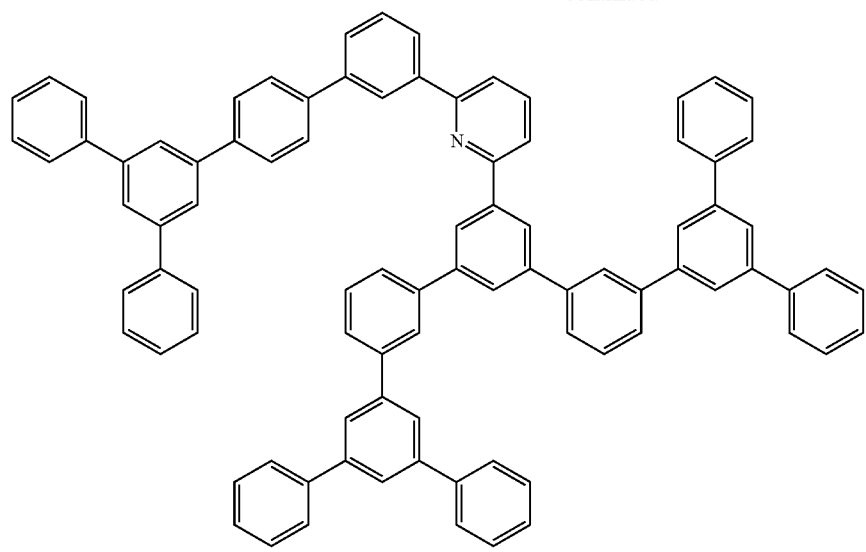
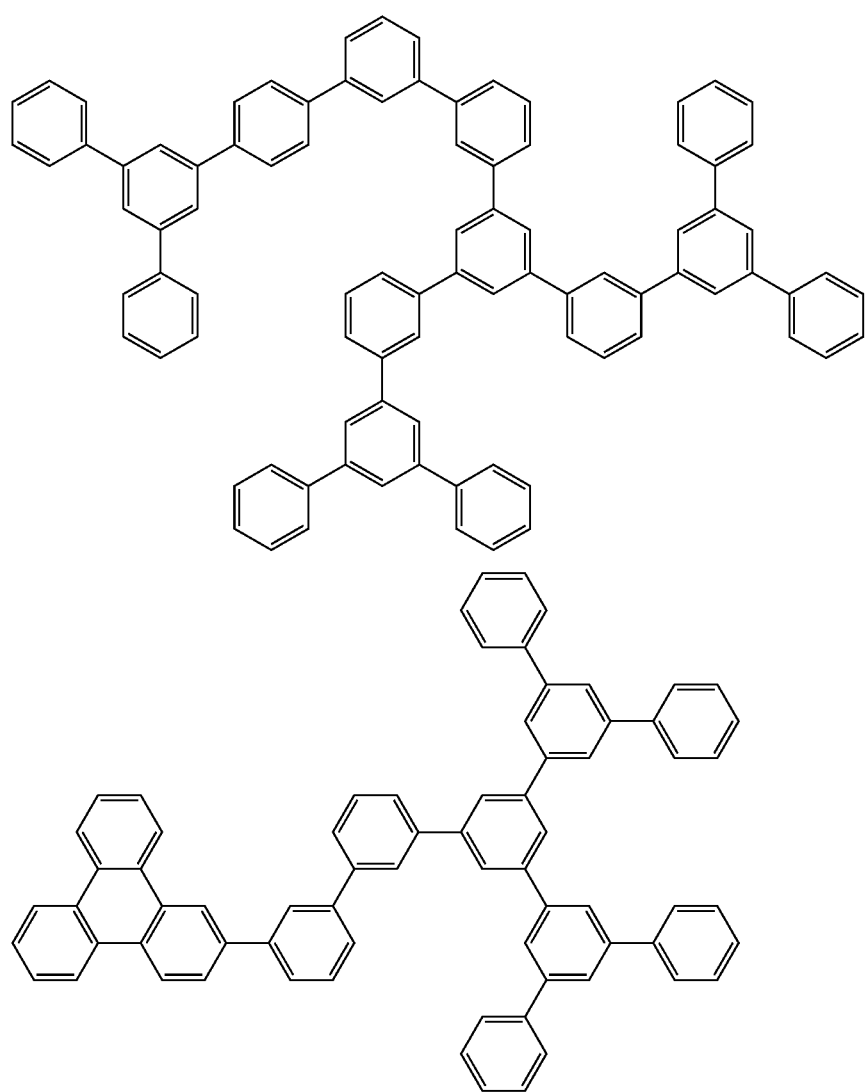

-continued
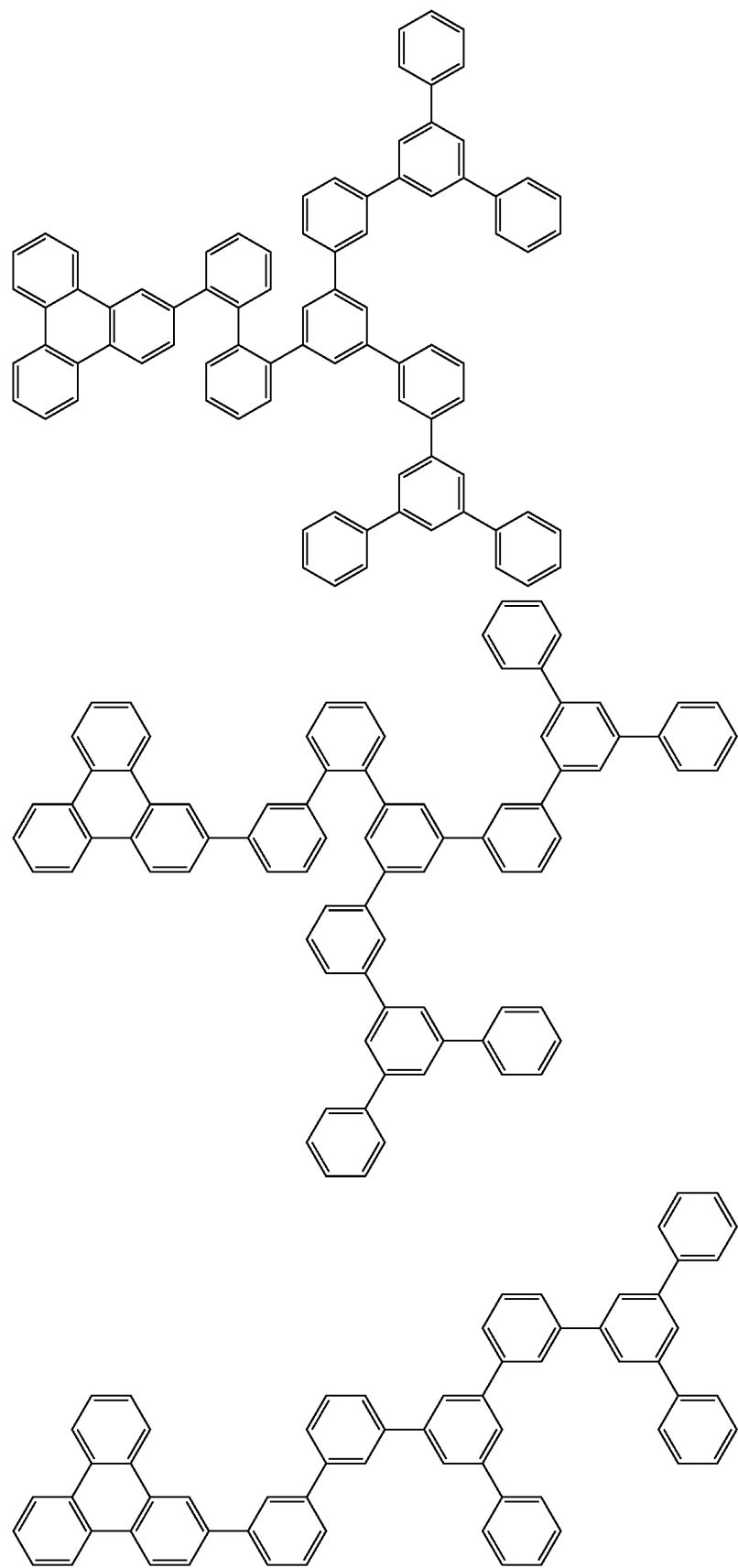

-continued
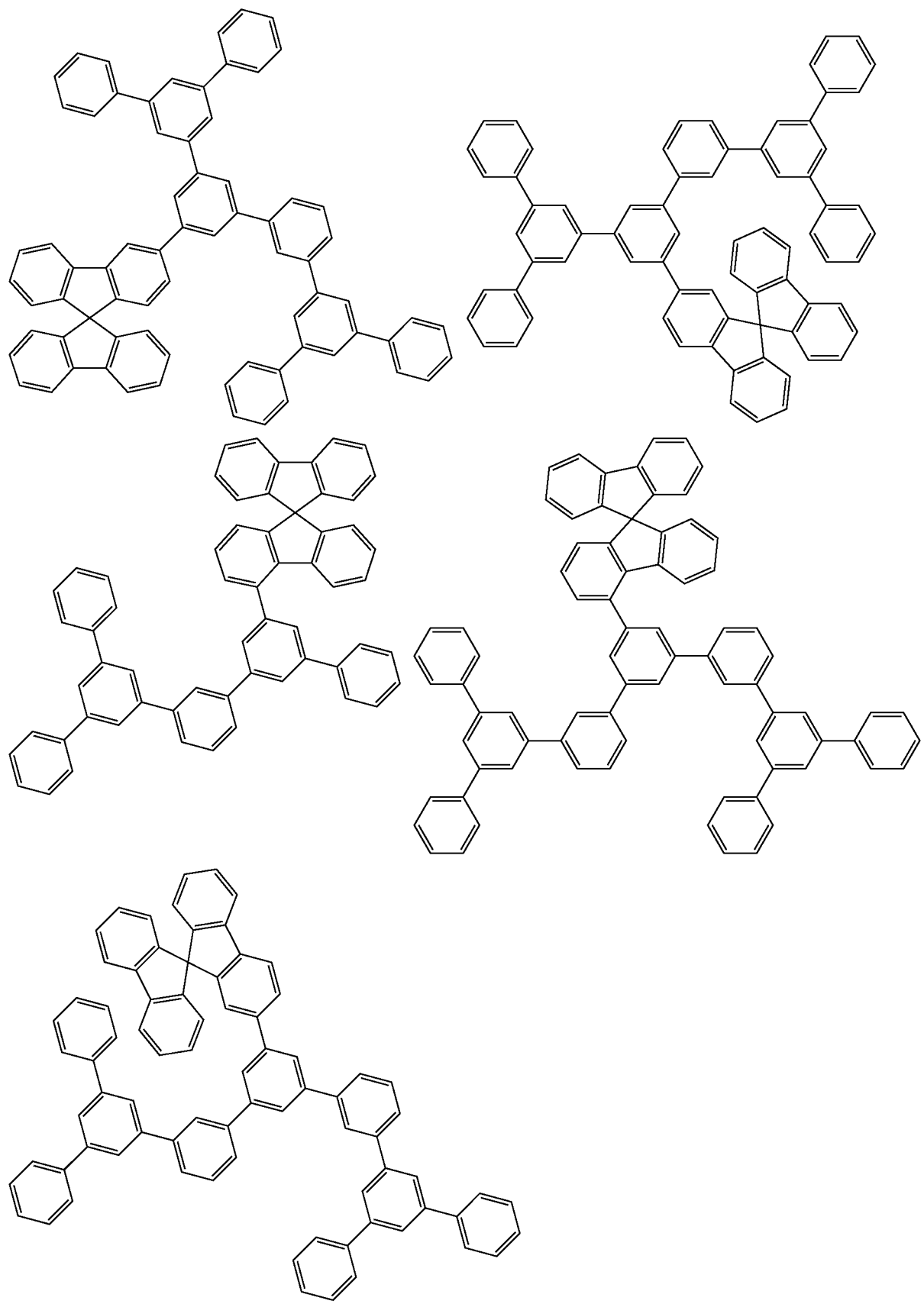

-continued
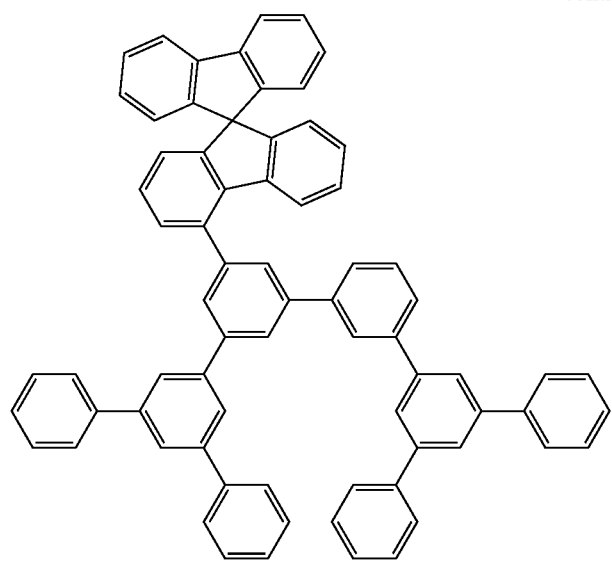
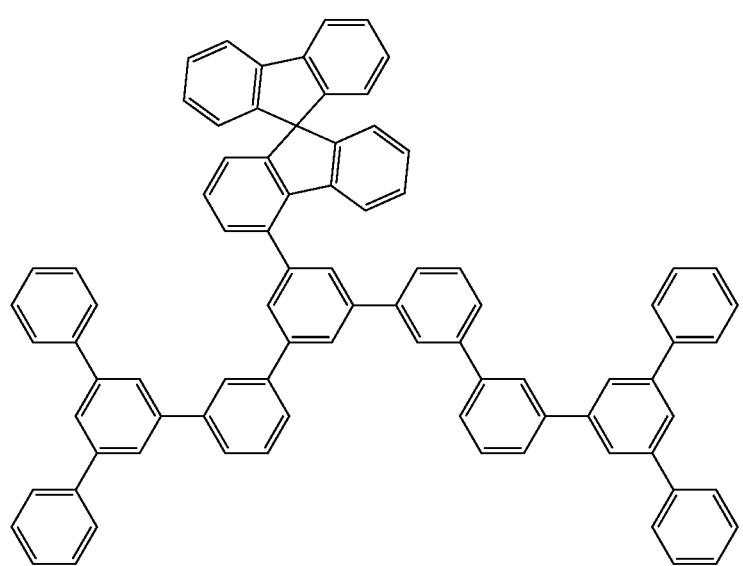

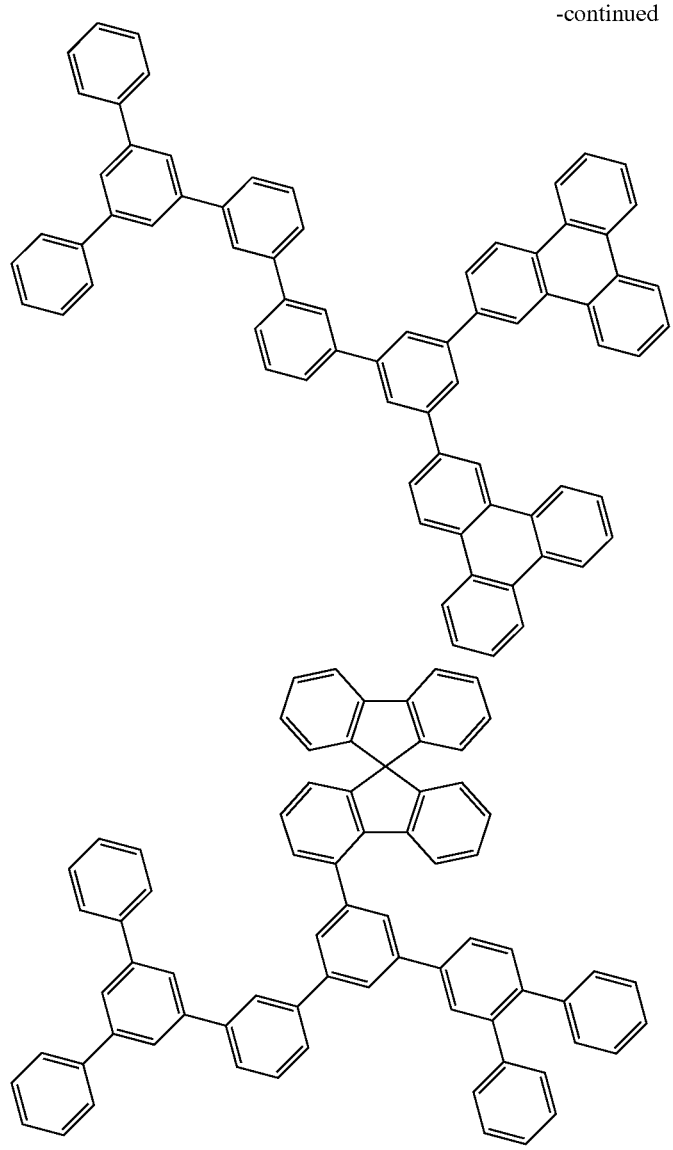
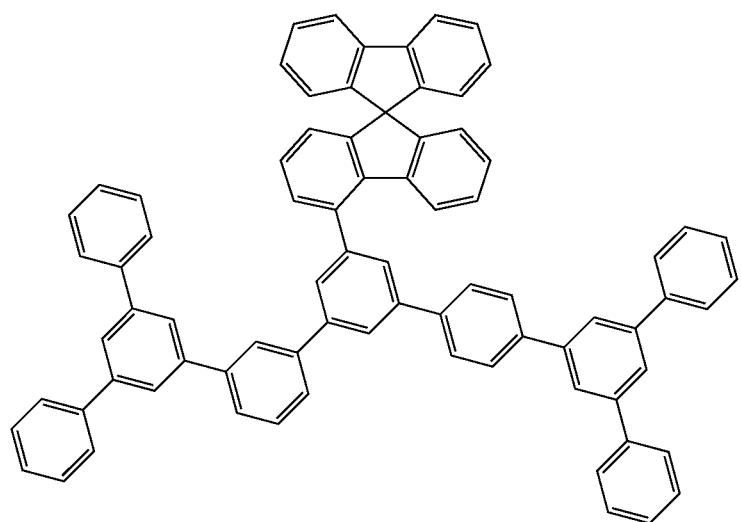

-continued
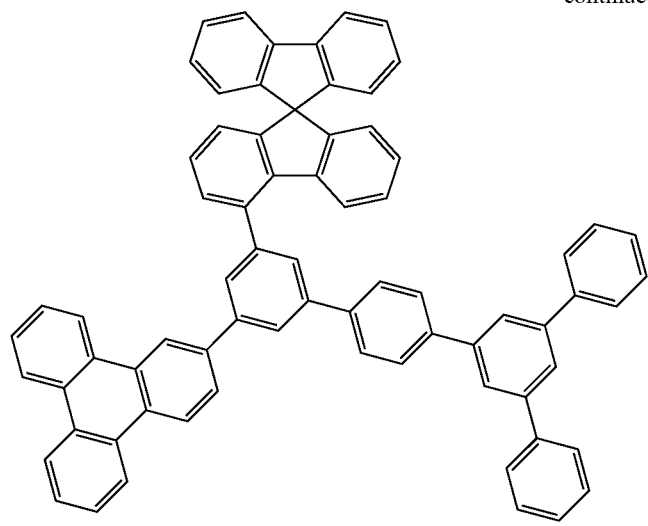
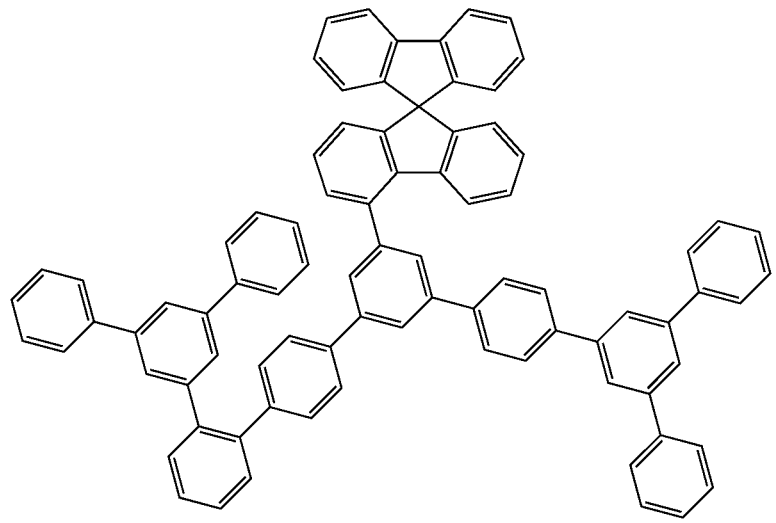
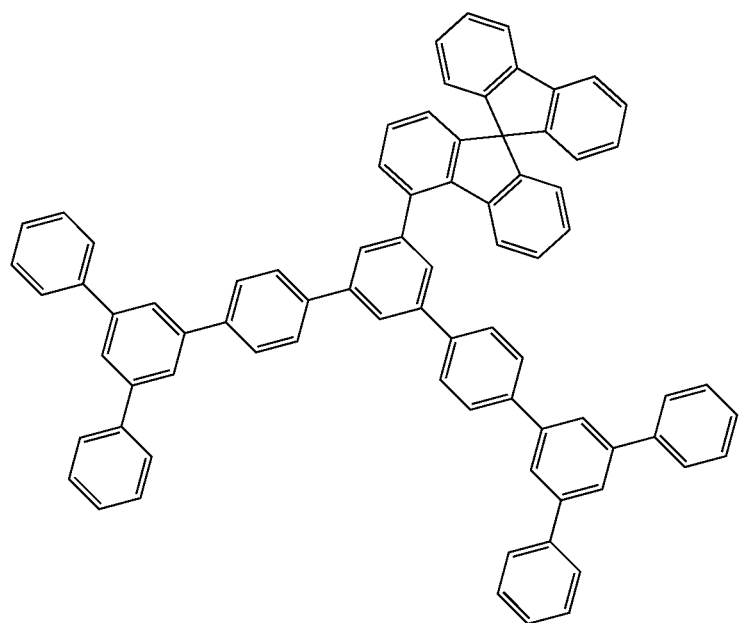

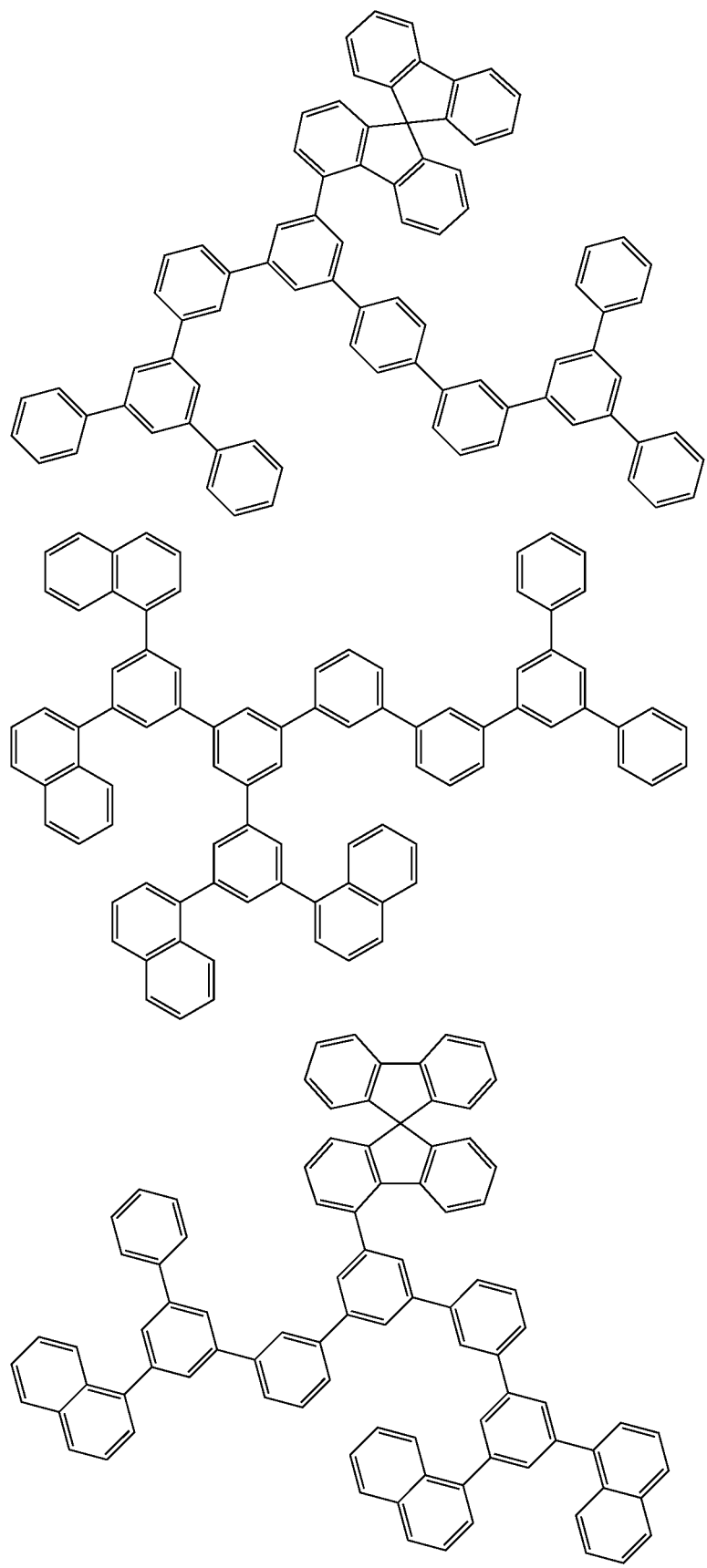

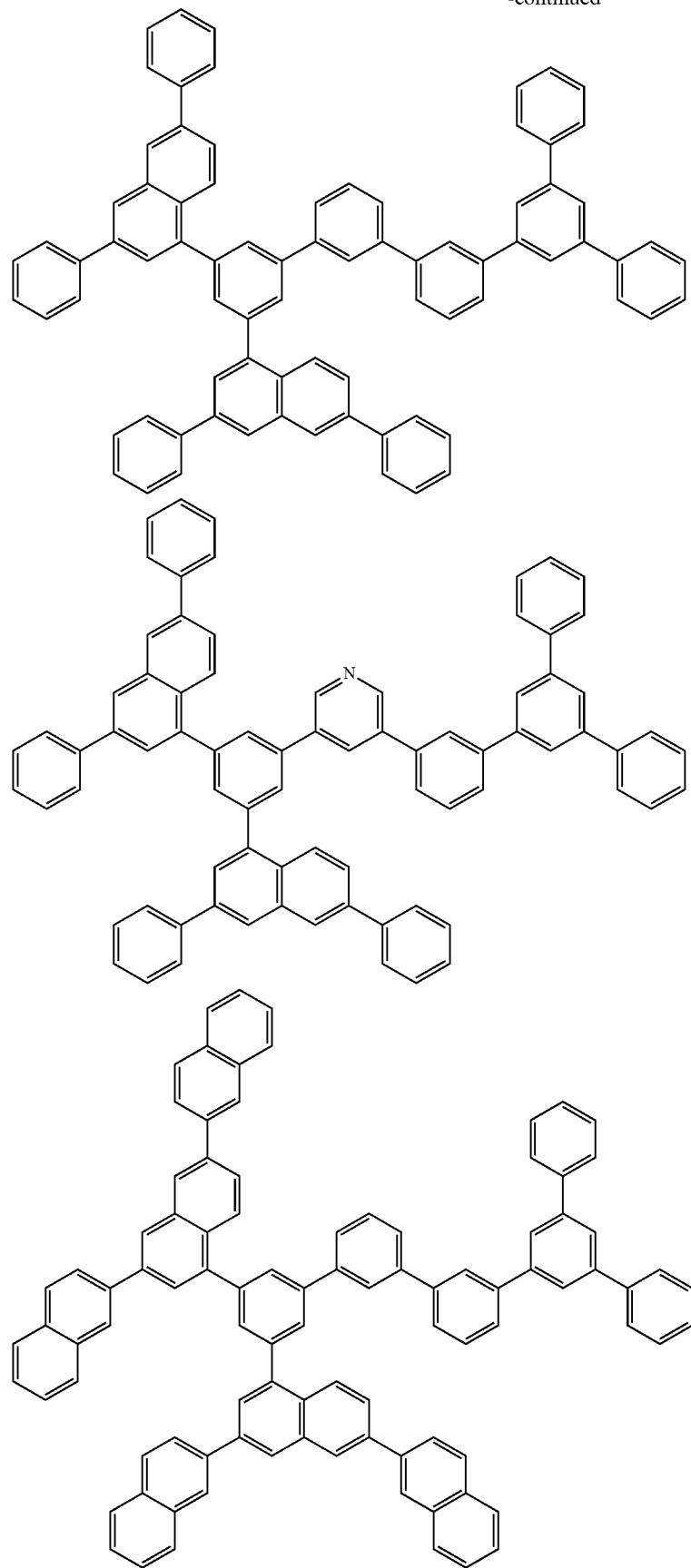
-continued

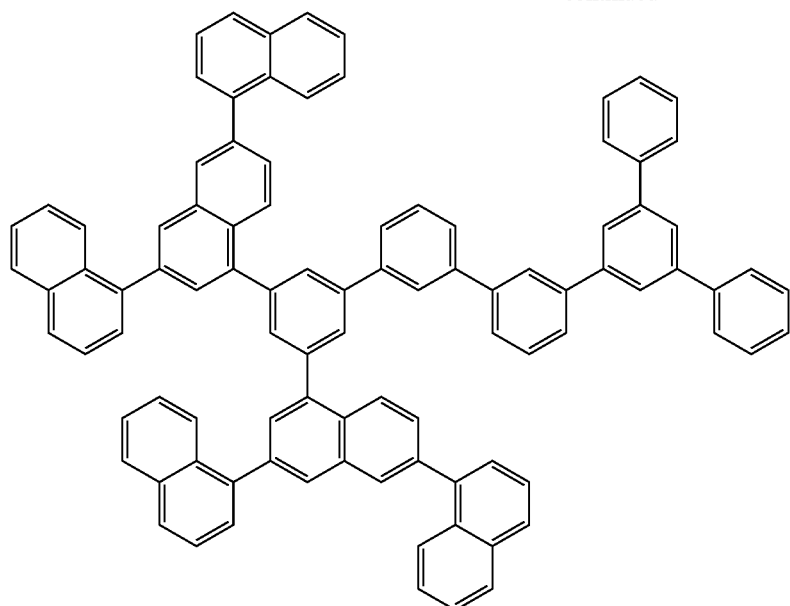
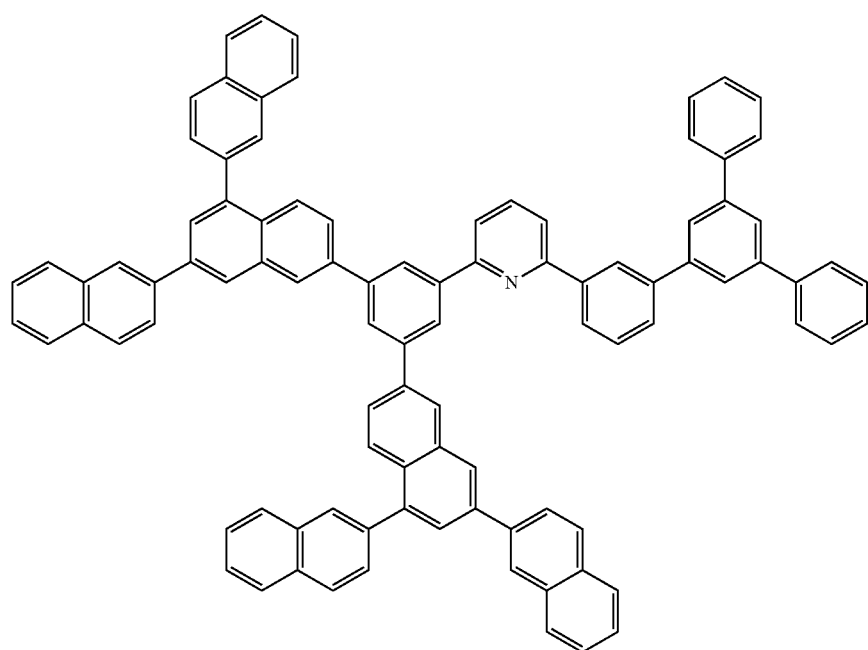

-continued
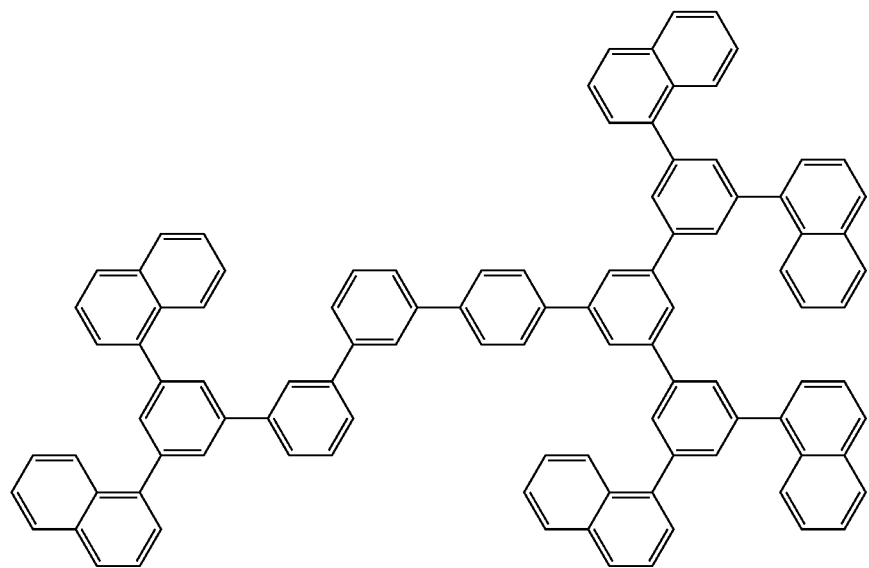
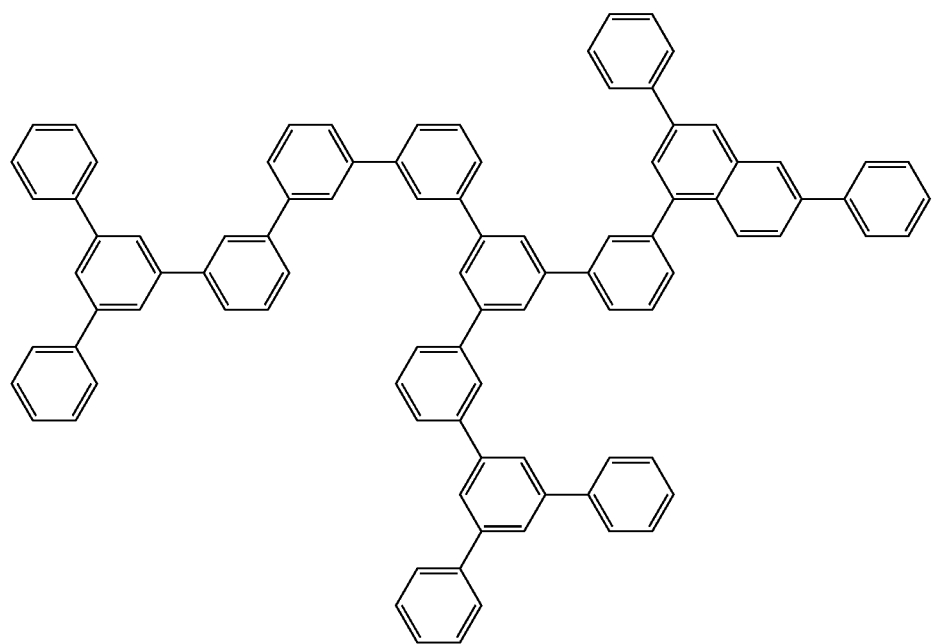

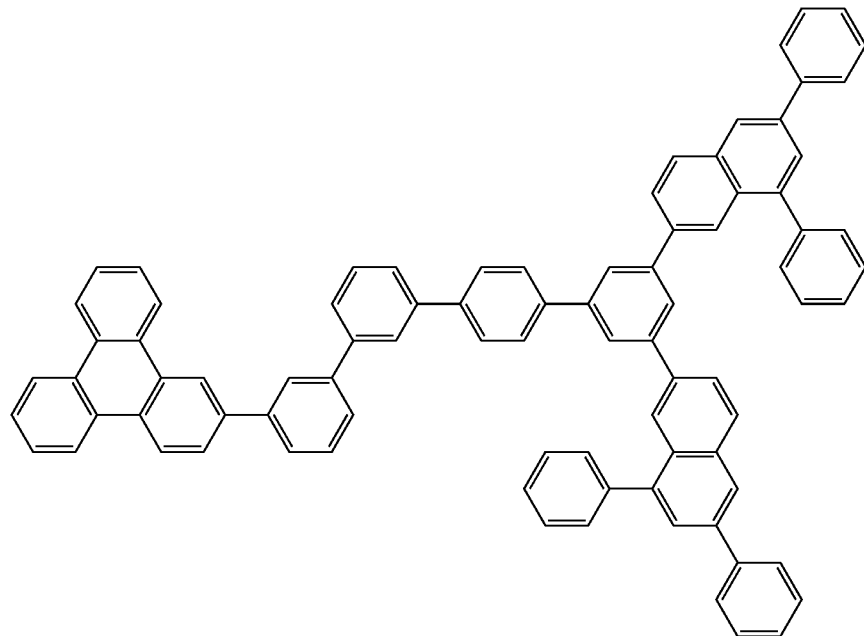
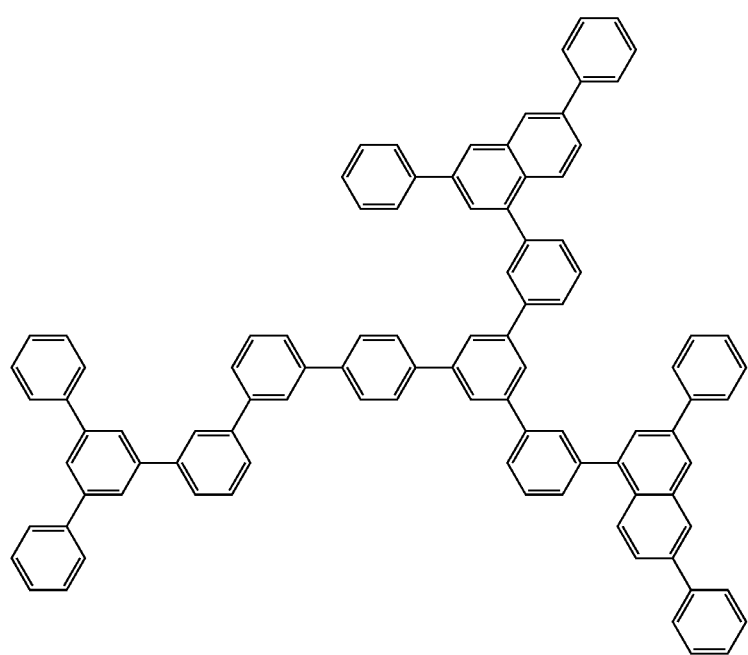

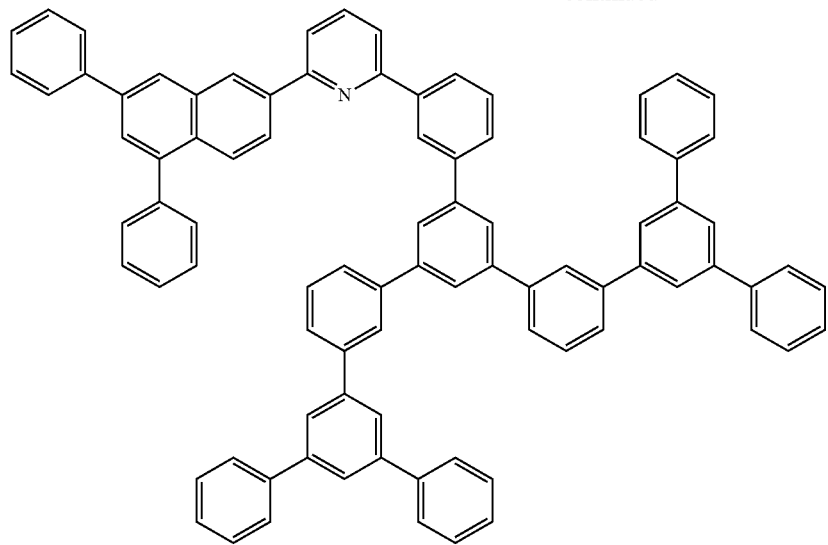
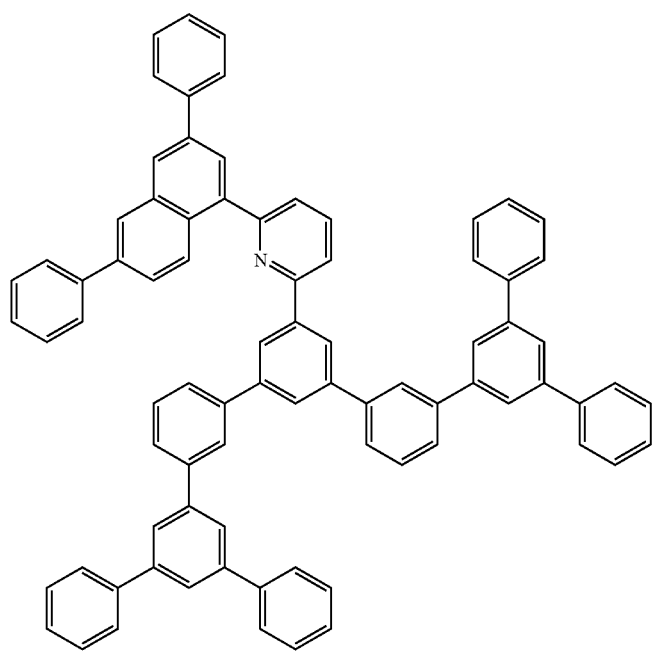

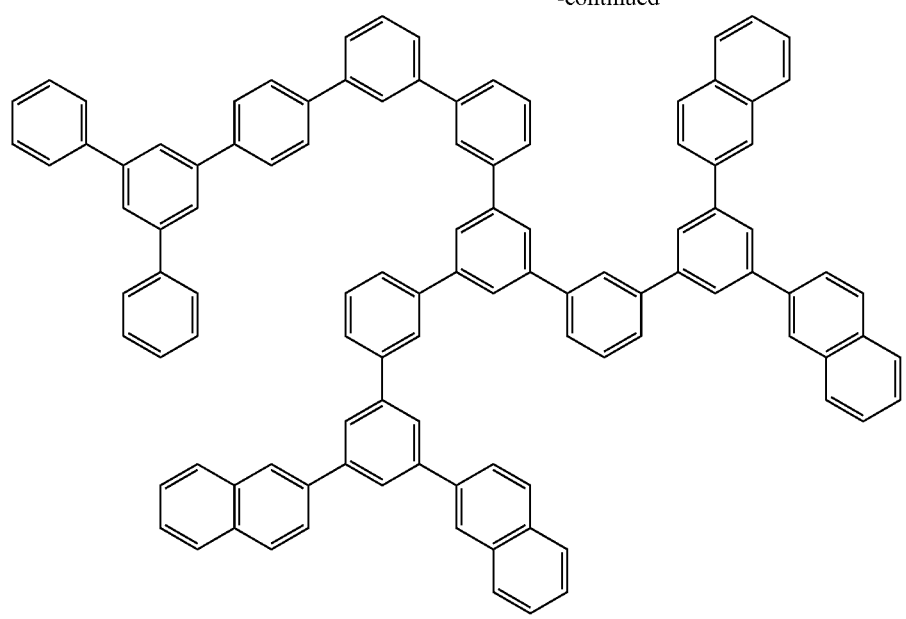
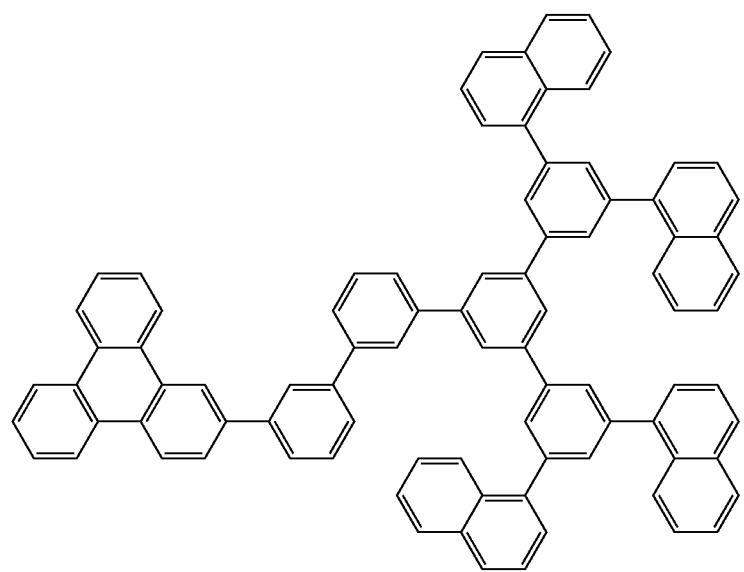

-continued
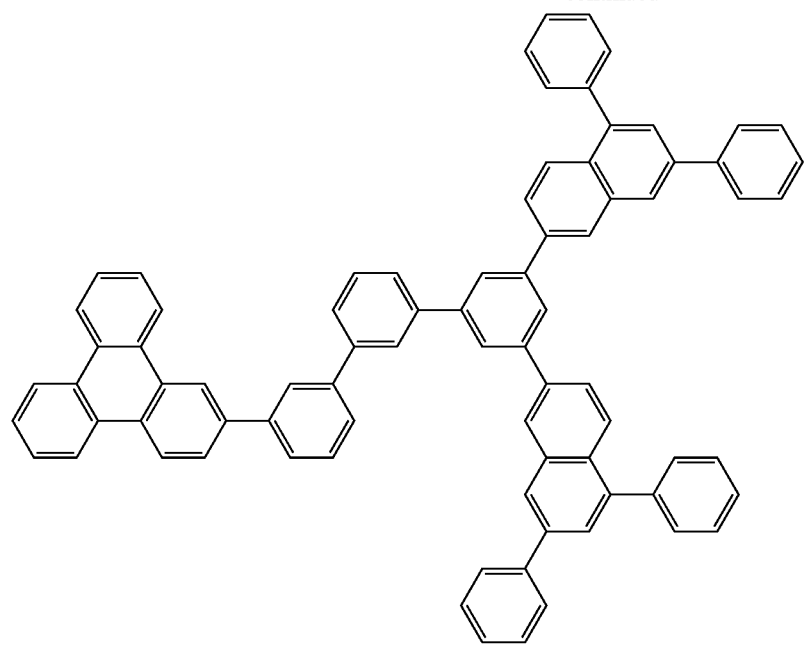
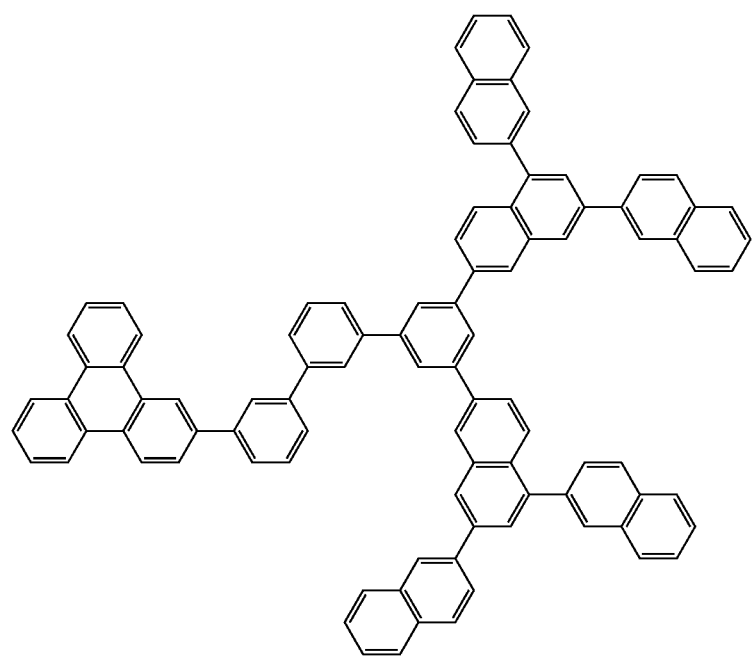

-continued
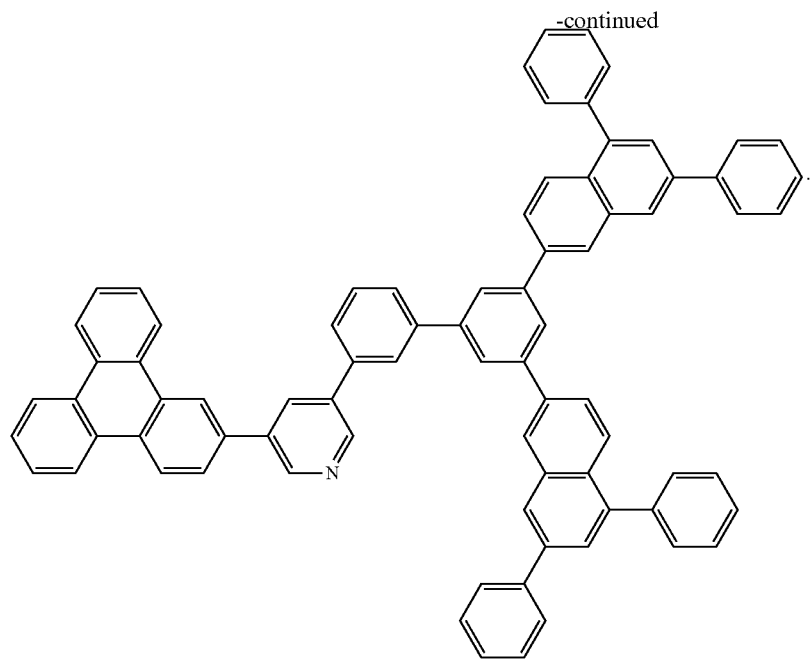
* * * * *